(12) United States Patent
Kontermann et al.

(10) Patent No.: US 11,008,402 B2
(45) Date of Patent: May 18, 2021

(54) ANTIGEN BINDING PROTEIN AGAINST HER3

(71) Applicant: UNIVERSITÄT STUTTGART, Stuttgart (DE)

(72) Inventors: Roland Kontermann, Nürtingen (DE); Lisa Schmitt, Stuttgart (DE); Meike Hutt, Stuttgart (DE); Oliver Seifert, Stuttgart (DE); Monilola Olayioye, Stuttgart (DE); Michael Hust, Braunschweig (DE); Stefan Dübel, Braunschweig (DE); Jonas Zantow, Braunschweig (DE)

(73) Assignee: UNIVERSITAT STUTTGART

( * ) Notice: Subject to any disclaimer, the term of this patent is extended or adjusted under 35 U.S.C. 154(b) by 171 days.

(21) Appl. No.: 16/326,864

(22) PCT Filed: Sep. 15, 2017

(86) PCT No.: PCT/EP2017/073328
§ 371 (c)(1),
(2) Date: Feb. 20, 2019

(87) PCT Pub. No.: WO2018/050848
PCT Pub. Date: Mar. 22, 2018

(65) Prior Publication Data
US 2019/0194350 A1 Jun. 27, 2019

(30) Foreign Application Priority Data
Sep. 15, 2016 (EP) ..................... 16188871

(51) Int. Cl.
*A61K 39/00* (2006.01)
*C07K 16/32* (2006.01)
*C07K 16/28* (2006.01)
*C07K 16/30* (2006.01)
*A61P 35/00* (2006.01)
*A61K 39/395* (2006.01)

(52) U.S. Cl.
CPC ........ *C07K 16/32* (2013.01); *A61K 39/39558* (2013.01); *A61P 35/00* (2018.01); *C07K 16/2809* (2013.01); *C07K 16/2863* (2013.01); *C07K 16/30* (2013.01); *A61K 2039/505* (2013.01); *C07K 2317/14* (2013.01); *C07K 2317/24* (2013.01); *C07K 2317/31* (2013.01); *C07K 2317/33* (2013.01); *C07K 2317/34* (2013.01); *C07K 2317/35* (2013.01); *C07K 2317/52* (2013.01); *C07K 2317/565* (2013.01); *C07K 2317/622* (2013.01); *C07K 2317/626* (2013.01); *C07K 2317/64* (2013.01); *C07K 2317/73* (2013.01); *C07K 2317/76* (2013.01); *C07K 2317/77* (2013.01); *C07K 2317/92* (2013.01); *C07K 2319/00* (2013.01); *C07K 2319/30* (2013.01)

(58) Field of Classification Search
CPC .... C07K 16/32; C07K 16/30; C07K 16/2863; C07K 2317/565; C07K 2317/76; C07K 2317/77; C07K 2317/92; A61P 35/00; A61K 39/39558; A61K 2039/505
See application file for complete search history.

(56) References Cited

U.S. PATENT DOCUMENTS

2014/0308287 A1* 10/2014 Bhatt .................... C07K 16/32
424/138.1

FOREIGN PATENT DOCUMENTS

| WO | 2011/060206 A2 | 5/2011 |
| WO | 2013/016714 A1 | 1/2013 |
| WO | 2013/084151 A1 | 6/2013 |
| WO | 2014/066530 A2 | 5/2014 |

OTHER PUBLICATIONS

George et al. (Circulation. 1998; 97: 900-906), (Year: 1998).*
Brown et al (J. Immunol. May 1996; 156(9):3285-3291 (Year: 1996).*
Vajdos et al (J. Mol. Biol. Jul. 5, 2002;320(2); 415-428) (Year: 2002).*
Paul, Fundamental Immunology, 3rd Edition, 1993, pp. 292-295 (Year: 1993).*

(Continued)

*Primary Examiner* — Sheela J. Huff
(74) *Attorney, Agent, or Firm* — McDonnell Boehnen Hulbert & Berghoff LLP

(57) ABSTRACT

The invention provides an antigen-binding protein that specifically binds to a conformational epitope formed by domain III & IV of human epidermal growth factor receptor 3 (HER3) and antigen-binding proteins which compete therewith for binding, as well as fusion protein or conjugate comprising these. The invention also provides nucleic acid molecule comprising a sequence encoding said antigen binding proteins, vectors comprising the nucleic acid, and cells and pharmaceuticals comprising the antigen binding protein, the fusion protein, the nucleic acid, or the vector. The invention also provides the antigen binding protein, the fusion protein or conjugate, the nucleic acid, the vector, the cell, or the pharmaceutical for use as a medicament. The invention further provides a method of inhibiting tumor growth or treating cancer, comprising administering a therapeutically effective amount of the antigen binding protein, the fusion protein or conjugate, the nucleic acid, the vector, the cell, or the pharmaceutical.

Figure 1:
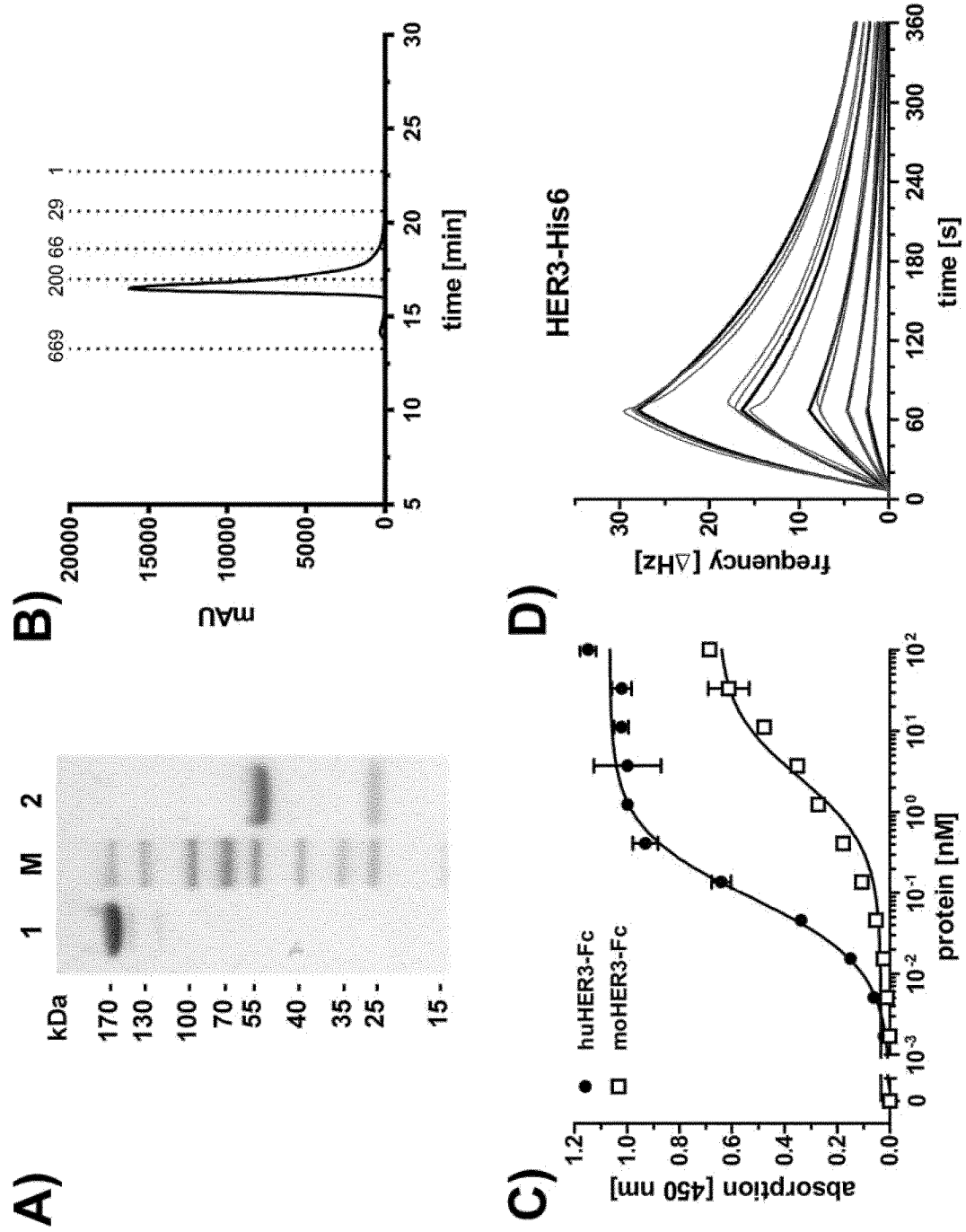

14 Claims, 34 Drawing Sheets
Specification includes a Sequence Listing.

(56) References Cited

OTHER PUBLICATIONS

Rudikoff et al(Proc. Natl. Acad. Sci. USA 1982 vol. 79: p. 1979). (Year: 1982).*
Pascalis et al (The Journal of Immunology (2002) 169, 3076-3084) (Year: 2002).*
Casset et al. (2003) BBRC 307, 198-205, (Year: 2003).*
Johnson et al, Cancer Treatment Reviews, vol. 2, p. 1 (1975) (Year: 1975).*
Strome et al., The Oncologist, 2007; 12:1084-95 (Year: 2007).*
Brand et al., Anticancer Res. 2006; 26:463-70 (Year: 2006).*
Kataja et al., Ann Oncol 2009; 20(sup 4): iv10-14 (Year: 2009).*
Nelson et al., Ann. Intern Med. 2009; 151:727-737 (Year: 2009).*
Balmana et al. Ann Oncol 2009; 20(supp 4):iv19-20 (Year: 2009).*
"Human epidermal growth factor receptor 3 (HER3) protein SEQ: 1." EBI accession No. BAP59392, Aug. 2013.
Schmitt, et al., "Inhibition of HER3 activation and tumor growth with a human antibody binding to a conserved epitope formed by domain III and IV," MABS, 9(5): 831-843, Jul. 2017.

* cited by examiner

A

B

C

D

E

F

G

A

B

C

D

E

A

B

C  D

E  F

SEQUENCE LISTING

<160> NUMBER OF SEQ ID NOS: 35

<210> SEQ ID NO 1
<211> LENGTH: 1342
<212> TYPE: PRT
<213> ORGANISM: Homo sapiens

<400> SEQUENCE: 1

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

-continued

```
Ile Val Leu Thr Gly His Asn Ala Asp Leu Ser Phe Leu Gln Trp Ile
 65                  70                  75                  80

Arg Glu Val Thr Gly Tyr Val Leu Val Ala Met Asn Glu Phe Ser Thr
                 85                  90                  95

Leu Pro Leu Pro Asn Leu Arg Val Val Arg Gly Thr Gln Val Tyr Asp
             100                 105                 110

Gly Lys Phe Ala Ile Phe Val Met Leu Asn Tyr Asn Thr Asn Ser Ser
         115                 120                 125

His Ala Leu Arg Gln Leu Arg Leu Thr Gln Leu Thr Glu Ile Leu Ser
     130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                 165                 170                 175

Lys Asp Asn Gly Arg Ser Cys Pro Pro Cys His Glu Val Cys Lys Gly
             180                 185                 190

Arg Cys Trp Gly Pro Gly Ser Glu Asp Cys Gln Thr Leu Thr Lys Thr
         195                 200                 205

Ile Cys Ala Pro Gln Cys Asn Gly His Cys Phe Gly Pro Asn Pro Asn
     210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                 245                 250                 255

Pro Arg Cys Pro Gln Pro Leu Val Tyr Asn Lys Leu Thr Phe Gln Leu
             260                 265                 270

Glu Pro Asn Pro His Thr Lys Tyr Gln Tyr Gly Gly Val Cys Val Ala
         275                 280                 285

Ser Cys Pro His Asn Phe Val Val Asp Gln Thr Ser Cys Val Arg Ala
     290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                 325                 330                 335

Gly Ser Arg Phe Gln Thr Val Asp Ser Ser Asn Ile Asp Gly Phe Val
             340                 345                 350

Asn Cys Thr Lys Ile Leu Gly Asn Leu Asp Phe Leu Ile Thr Gly Leu
         355                 360                 365

Asn Gly Asp Pro Trp His Lys Ile Pro Ala Leu Asp Pro Glu Lys Leu
     370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                 405                 410                 415

Thr Ile Gly Gly Arg Ser Leu Tyr Asn Arg Gly Phe Ser Leu Leu Ile
             420                 425                 430

Met Lys Asn Leu Asn Val Thr Ser Leu Gly Phe Arg Ser Leu Lys Glu
         435                 440                 445

Ile Ser Ala Gly Arg Ile Tyr Ile Ser Ala Asn Arg Gln Leu Cys Tyr
     450                 455                 460

His His Ser Leu Asn Trp Thr Lys Val Leu Arg Gly Pro Thr Glu Glu
465                 470                 475                 480
```

```
Arg Leu Asp Ile Lys His Asn Arg Pro Arg Arg Asp Cys Val Ala Glu
            485                 490                 495
Gly Lys Val Cys Asp Pro Leu Cys Ser Ser Gly Gly Cys Trp Gly Pro
        500                 505                 510
Gly Pro Gly Gln Cys Leu Ser Cys Arg Asn Tyr Ser Arg Gly Gly Val
    515                 520                 525
Cys Val Thr His Cys Asn Phe Leu Asn Gly Glu Pro Arg Glu Phe Ala
530                 535                 540
His Glu Ala Glu Cys Phe Ser Cys His Pro Glu Cys Gln Pro Met Glu
545                 550                 555                 560
Gly Thr Ala Thr Cys Asn Gly Ser Gly Ser Asp Thr Cys Ala Gln Cys
                565                 570                 575
Ala His Phe Arg Asp Gly Pro His Cys Val Ser Ser Cys Pro His Gly
            580                 585                 590
Val Leu Gly Ala Lys Gly Pro Ile Tyr Lys Tyr Pro Asp Val Gln Asn
        595                 600                 605
Glu Cys Arg Pro Cys His Glu Asn Cys Thr Gln Gly Cys Lys Gly Pro
    610                 615                 620
Glu Leu Gln Asp Cys Leu Gly Gln Thr Leu Val Leu Ile Gly Lys Thr
625                 630                 635                 640
His Leu Thr Met Ala Leu Thr Val Ile Ala Gly Leu Val Val Ile Phe
                645                 650                 655
Met Met Leu Gly Gly Thr Phe Leu Tyr Trp Arg Gly Arg Arg Ile Gln
            660                 665                 670
Asn Lys Arg Ala Met Arg Arg Tyr Leu Glu Arg Gly Glu Ser Ile Glu
        675                 680                 685
Pro Leu Asp Pro Ser Glu Lys Ala Asn Lys Val Leu Ala Arg Ile Phe
    690                 695                 700
Lys Glu Thr Glu Leu Arg Lys Leu Lys Val Leu Gly Ser Gly Val Phe
705                 710                 715                 720
Gly Thr Val His Lys Gly Val Trp Ile Pro Glu Gly Glu Ser Ile Lys
                725                 730                 735
Ile Pro Val Cys Ile Lys Val Ile Glu Asp Lys Ser Gly Arg Gln Ser
            740                 745                 750
Phe Gln Ala Val Thr Asp His Met Leu Ala Ile Gly Ser Leu Asp His
        755                 760                 765
Ala His Ile Val Arg Leu Leu Gly Leu Cys Pro Gly Ser Ser Leu Gln
    770                 775                 780
Leu Val Thr Gln Tyr Leu Pro Leu Gly Ser Leu Leu Asp His Val Arg
785                 790                 795                 800
Gln His Arg Gly Ala Leu Gly Pro Gln Leu Leu Leu Asn Trp Gly Val
                805                 810                 815
Gln Ile Ala Lys Gly Met Tyr Tyr Leu Glu Glu His Gly Met Val His
            820                 825                 830
Arg Asn Leu Ala Ala Arg Asn Val Leu Leu Lys Ser Pro Ser Gln Val
        835                 840                 845
Gln Val Ala Asp Phe Gly Val Ala Asp Leu Leu Pro Pro Asp Asp Lys
    850                 855                 860
Gln Leu Leu Tyr Ser Glu Ala Lys Thr Pro Ile Lys Trp Met Ala Leu
865                 870                 875                 880
Glu Ser Ile His Phe Gly Lys Tyr Thr His Gln Ser Asp Val Trp Ser
                885                 890                 895
Tyr Gly Val Thr Val Trp Glu Leu Met Thr Phe Gly Ala Glu Pro Tyr
```

```
                    900             905             910
Ala Gly Leu Arg Leu Ala Glu Val Pro Asp Leu Leu Glu Lys Gly Glu
            915             920             925

Arg Leu Ala Gln Pro Gln Ile Cys Thr Ile Asp Val Tyr Met Val Met
        930             935             940

Val Lys Cys Trp Met Ile Asp Glu Asn Ile Arg Pro Thr Phe Lys Glu
945             950             955             960

Leu Ala Asn Glu Phe Thr Arg Met Ala Arg Asp Pro Pro Arg Tyr Leu
            965             970             975

Val Ile Lys Arg Glu Ser Gly Pro Gly Ile Ala Pro Gly Pro Glu Pro
        980             985             990

His Gly Leu Thr Asn Lys Lys Leu Glu Glu Val Glu Leu Glu Pro Glu
    995             1000            1005

Leu Asp Leu Asp Leu Asp Leu Glu Ala Glu Glu Asp Asn Leu Ala
    1010            1015            1020

Thr Thr Thr Leu Gly Ser Ala Leu Ser Leu Pro Val Gly Thr Leu
    1025            1030            1035

Asn Arg Pro Arg Gly Ser Gln Ser Leu Leu Ser Pro Ser Ser Gly
    1040            1045            1050

Tyr Met Pro Met Asn Gln Gly Asn Leu Gly Glu Ser Cys Gln Glu
    1055            1060            1065

Ser Ala Val Ser Gly Ser Ser Glu Arg Cys Pro Arg Pro Val Ser
    1070            1075            1080

Leu His Pro Met Pro Arg Gly Cys Leu Ala Ser Glu Ser Ser Glu
    1085            1090            1095

Gly His Val Thr Gly Ser Glu Ala Glu Leu Gln Glu Lys Val Ser
    1100            1105            1110

Met Cys Arg Ser Arg Ser Arg Ser Arg Ser Pro Arg Pro Arg Gly
    1115            1120            1125

Asp Ser Ala Tyr His Ser Gln Arg His Ser Leu Leu Thr Pro Val
    1130            1135            1140

Thr Pro Leu Ser Pro Pro Gly Leu Glu Glu Glu Asp Val Asn Gly
    1145            1150            1155

Tyr Val Met Pro Asp Thr His Leu Lys Gly Thr Pro Ser Ser Arg
    1160            1165            1170

Glu Gly Thr Leu Ser Ser Val Gly Leu Ser Ser Val Leu Gly Thr
    1175            1180            1185

Glu Glu Glu Asp Glu Asp Glu Glu Tyr Glu Tyr Met Asn Arg Arg
    1190            1195            1200

Arg Arg His Ser Pro Pro His Pro Pro Arg Pro Ser Ser Leu Glu
    1205            1210            1215

Glu Leu Gly Tyr Glu Tyr Met Asp Val Gly Ser Asp Leu Ser Ala
    1220            1225            1230

Ser Leu Gly Ser Thr Gln Ser Cys Pro Leu His Pro Val Pro Ile
    1235            1240            1245

Met Pro Thr Ala Gly Thr Thr Pro Asp Glu Asp Tyr Glu Tyr Met
    1250            1255            1260

Asn Arg Gln Arg Asp Gly Gly Gly Pro Gly Gly Asp Tyr Ala Ala
    1265            1270            1275

Met Gly Ala Cys Pro Ala Ser Glu Gln Gly Tyr Glu Glu Met Arg
    1280            1285            1290

Ala Phe Gln Gly Pro Gly His Gln Ala Pro His Val His Tyr Ala
    1295            1300            1305
```

```
Arg Leu Lys Thr Leu Arg Ser Leu Glu Ala Thr Asp Ser Ala Phe
    1310            1315                1320

Asp Asn Pro Asp Tyr Trp His Ser Arg Leu Phe Pro Lys Ala Asn
    1325            1330                1335

Ala Gln Arg Thr
    1340

<210> SEQ ID NO 2
<211> LENGTH: 123
<212> TYPE: PRT
<213> ORGANISM: Artificial Sequence
<220> FEATURE:
<223> OTHER INFORMATION: variable domain heavy chain of 3-43

<400> SEQUENCE: 2

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Arg Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Gln Ser Leu Lys Ser Arg Ile Thr Ile Asn Pro Asp Thr Pro Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Gly Gln Leu Gly Leu Asp Ala Leu Asp Ile
            100                 105                 110

Trp Gly Gln Gly Thr Met Val Thr Val Ser Ser
        115                 120

<210> SEQ ID NO 3
<211> LENGTH: 109
<212> TYPE: PRT
<213> ORGANISM: Artificial Sequence
<220> FEATURE:
<223> OTHER INFORMATION: variable domain light chain of 3-43

<400> SEQUENCE: 3

Gln Ala Gly Leu Thr Gln Pro Pro Ala Val Ser Val Ala Pro Gly Gln
1               5                   10                  15

Thr Ala Ser Ile Thr Cys Gly Arg Asp Asn Ile Gly Ser Arg Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ala Gly Ile Pro Glu Arg Phe Ser Gly Ser
    50                  55                  60

Asn Tyr Glu Asn Thr Ala Thr Leu Thr Ile Ser Arg Val Glu Ala Gly
65                  70                  75                  80

Asp Glu Ala Asp Tyr Tyr Cys Gln Val Trp Gly Ile Thr Ser Asp His
                85                  90                  95

Val Val Phe Gly Gly Gly Thr Lys Leu Thr Val Leu Gly
            100                 105

<210> SEQ ID NO 4
<211> LENGTH: 473
<212> TYPE: PRT
```

<213> ORGANISM: Artificial Sequence
<220> FEATURE:
<223> OTHER INFORMATION: IgK leader - IgG 3-43 HC

<400> SEQUENCE: 4

```
Met Glu Thr Asp Thr Leu Leu Leu Trp Val Leu Leu Leu Trp Val Pro
1               5                   10                  15

Gly Ser Thr Gly Gln Val Gln Leu Gln Gln Ser Gly Pro Gly Leu Val
            20                  25                  30

Lys Pro Ser Gln Thr Leu Ser Leu Thr Cys Ala Ile Ser Gly Asp Ser
        35                  40                  45

Val Ser Ser Asn Arg Ala Ala Trp Asn Trp Ile Arg Gln Ser Pro Ser
50                  55                  60

Arg Gly Leu Glu Trp Leu Gly Arg Thr Tyr Tyr Arg Ser Lys Trp Tyr
65                  70                  75                  80

Asn Asp Tyr Ala Gln Ser Leu Lys Ser Arg Ile Thr Ile Asn Pro Asp
                85                  90                  95

Thr Pro Lys Asn Gln Phe Ser Leu Gln Leu Asn Ser Val Thr Pro Glu
            100                 105                 110

Asp Thr Ala Val Tyr Tyr Cys Ala Arg Asp Gly Gln Leu Gly Leu Asp
        115                 120                 125

Ala Leu Asp Ile Trp Gly Gln Gly Thr Met Val Thr Val Ser Ser Ala
130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Asp Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Glu Glu Lys Thr Ile Ser Lys Ala Lys Gly Gln
        355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
```

```
385                 390                 395                 400
Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
                420                 425                 430

Tyr Ser Lys Leu Thr Val Asp Lys Ser Arg Trp Gln Gln Gly Asn Val
                435                 440                 445

Phe Ser Cys Ser Val Met His Glu Ala Leu His Asn His Tyr Thr Gln
                450                 455                 460

Lys Ser Leu Ser Leu Ser Pro Gly Lys
465                 470

<210> SEQ ID NO 5
<211> LENGTH: 235
<212> TYPE: PRT
<213> ORGANISM: Artificial Sequence
<220> FEATURE:
<223> OTHER INFORMATION: IgK leader - IgG 3-43 LC

<400> SEQUENCE: 5

Met Glu Thr Asp Thr Leu Leu Leu Trp Val Leu Leu Leu Trp Val Pro
1               5                   10                  15

Gly Ser Thr Gly Gln Ala Gly Leu Thr Gln Pro Pro Ala Val Ser Val
                20                  25                  30

Ala Pro Gly Gln Thr Ala Ser Ile Thr Cys Gly Arg Asp Asn Ile Gly
                35                  40                  45

Ser Arg Ser Val His Trp Tyr Gln Gln Lys Pro Gly Gln Ala Pro Val
        50                  55                  60

Leu Val Val Tyr Asp Asp Ser Asp Arg Pro Ala Gly Ile Pro Glu Arg
65              70                  75                  80

Phe Ser Gly Ser Asn Tyr Glu Asn Thr Ala Thr Leu Thr Ile Ser Arg
                85                  90                  95

Val Glu Ala Gly Asp Glu Ala Asp Tyr Tyr Cys Gln Val Trp Gly Ile
                100                 105                 110

Thr Ser Asp His Val Val Phe Gly Gly Gly Thr Lys Leu Thr Val Leu
                115                 120                 125

Cys Gly Gln Pro Lys Ala Ala Pro Ser Val Thr Leu Phe Pro Pro Ser
        130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
                180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
        210                 215                 220

Val Glu Lys Thr Val Ala Pro Thr Glu Cys Ser
225                 230                 235

<210> SEQ ID NO 6
<211> LENGTH: 247
<212> TYPE: PRT
<213> ORGANISM: Artificial Sequence
<220> FEATURE:
<223> OTHER INFORMATION: scFv 3-43
```

<400> SEQUENCE: 6

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Arg Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Gln Ser Leu Lys Ser Arg Ile Thr Ile Asn Pro Asp Thr Pro Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Gly Gln Leu Gly Leu Asp Ala Leu Asp Ile
            100                 105                 110

Trp Gly Gln Gly Thr Met Val Thr Val Ser Ser Gly Gly Gly Gly Ser
        115                 120                 125

Gly Gly Gly Gly Ser Gly Gly Gly Ser Gln Ala Gly Leu Thr Gln
    130                 135                 140

Pro Pro Ala Val Ser Val Ala Pro Gly Gln Thr Ala Ser Ile Thr Cys
145                 150                 155                 160

Gly Arg Asp Asn Ile Gly Ser Arg Ser Val His Trp Tyr Gln Gln Lys
                165                 170                 175

Pro Gly Gln Ala Pro Val Leu Val Val Tyr Asp Asp Ser Asp Arg Pro
            180                 185                 190

Ala Gly Ile Pro Glu Arg Phe Ser Gly Ser Asn Tyr Glu Asn Thr Ala
        195                 200                 205

Thr Leu Thr Ile Ser Arg Val Glu Ala Gly Asp Glu Ala Asp Tyr Tyr
    210                 215                 220

Cys Gln Val Trp Gly Ile Thr Ser Asp His Val Val Phe Gly Gly Gly
225                 230                 235                 240

Thr Lys Leu Thr Val Leu Gly
                245
```

<210> SEQ ID NO 7
<211> LENGTH: 310
<212> TYPE: PRT
<213> ORGANISM: Artificial Sequence
<220> FEATURE:
<223> OTHER INFORMATION: PelB leader - scFv 3-43 - c-myc - his

<400> SEQUENCE: 7

```
Met Lys Tyr Leu Leu Pro Thr Ala Ala Gly Leu Leu Leu Leu Ala
1               5                   10                  15

Ala Gln Pro Ala Met Ala Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Arg Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Gln Ser Leu Lys Ser Arg Ile Thr Ile Asn
                85                  90                  95
```

Pro Asp Thr Pro Lys Asn Gln Phe Ser Leu Gln Leu Asn Ser Val Thr
            100                 105                 110

Pro Glu Asp Thr Ala Val Tyr Tyr Cys Ala Arg Asp Gly Gln Leu Gly
        115                 120                 125

Leu Asp Ala Leu Asp Ile Trp Gly Gln Gly Thr Met Val Thr Val Ser
130                 135                 140

Ser Gly Ser Ala Ser Ala Pro Lys Leu Glu Glu Gly Glu Phe Ser Glu
145                 150                 155                 160

Ala Arg Val Gln Ala Gly Leu Thr Gln Pro Ala Val Ser Val Ala
                165                 170                 175

Pro Gly Gln Thr Ala Ser Ile Thr Cys Gly Arg Asp Asn Ile Gly Ser
                180                 185                 190

Arg Ser Val His Trp Tyr Gln Gln Lys Pro Gly Gln Ala Pro Val Leu
        195                 200                 205

Val Val Tyr Asp Asp Ser Asp Arg Pro Ala Gly Ile Pro Glu Arg Phe
    210                 215                 220

Ser Gly Ser Asn Tyr Glu Asn Thr Ala Thr Leu Thr Ile Ser Arg Val
225                 230                 235                 240

Glu Ala Gly Asp Glu Ala Asp Tyr Tyr Cys Gln Val Trp Gly Ile Thr
                245                 250                 255

Ser Asp His Val Val Phe Gly Gly Gly Thr Lys Leu Thr Val Leu Gly
            260                 265                 270

Gln Pro Lys Ala Ala Pro Ser Val Thr Leu Phe Pro Pro Ser Ser Ala
        275                 280                 285

Ala Ala Glu Gln Lys Leu Ile Ser Glu Glu Asp Leu Asn Gly Ala Ala
    290                 295                 300

His His His His His His
305                 310

<210> SEQ ID NO 8
<211> LENGTH: 738
<212> TYPE: PRT
<213> ORGANISM: Artificial Sequence
<220> FEATURE:
<223> OTHER INFORMATION: IgK leader - scDb hu225x3-43-Fc

<400> SEQUENCE: 8

Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Ser
        35                  40                  45

Leu Thr Asn Tyr Gly Val His Trp Val Arg Gln Ala Pro Gly Lys Gly
    50                  55                  60

Leu Glu Trp Leu Gly Val Ile Trp Ser Gly Gly Asn Thr Asp Tyr Asn
65                  70                  75                  80

Thr Pro Phe Thr Ser Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ala Leu Thr Tyr Tyr Asp Tyr Glu Phe Ala Tyr
        115                 120                 125

Trp Gly Gln Gly Thr Thr Val Thr Val Ser Ser Gly Gly Gly Gly Ser
    130                 135                 140

Gln Ala Gly Leu Thr Gln Pro Pro Ala Val Ser Val Ala Pro Gly Gln
145                 150                 155                 160

Thr Ala Ser Ile Thr Cys Gly Arg Asp Asn Ile Gly Ser Arg Ser Val
                165                 170                 175

His Trp Tyr Gln Gln Lys Pro Gly Gln Ala Pro Val Leu Val Val Tyr
            180                 185                 190

Asp Asp Ser Asp Arg Pro Ala Gly Ile Pro Glu Arg Phe Ser Gly Ser
        195                 200                 205

Asn Tyr Glu Asn Thr Ala Thr Leu Thr Ile Ser Arg Val Glu Ala Gly
    210                 215                 220

Asp Glu Ala Asp Tyr Tyr Cys Gln Val Trp Gly Ile Thr Ser Asp His
225                 230                 235                 240

Val Val Phe Gly Gly Gly Thr Lys Leu Thr Val Leu Gly Gly Gly Gly
                245                 250                 255

Ser Gly Gly Arg Ala Ser Gly Gly Gly Ser Gln Val Gln Leu Gln
            260                 265                 270

Gln Ser Gly Pro Gly Leu Val Lys Pro Ser Gln Thr Leu Ser Leu Thr
    275                 280                 285

Cys Ala Ile Ser Gly Asp Ser Val Ser Ser Asn Arg Ala Ala Trp Asn
    290                 295                 300

Trp Ile Arg Gln Ser Pro Ser Arg Gly Leu Glu Trp Leu Gly Arg Thr
305                 310                 315                 320

Tyr Tyr Arg Ser Lys Trp Tyr Asn Asp Tyr Ala Gln Ser Leu Lys Ser
                325                 330                 335

Arg Ile Thr Ile Asn Pro Asp Thr Pro Lys Asn Gln Phe Ser Leu Gln
            340                 345                 350

Leu Asn Ser Val Thr Pro Glu Asp Thr Ala Val Tyr Tyr Cys Ala Arg
        355                 360                 365

Asp Gly Gln Leu Gly Leu Asp Ala Leu Asp Ile Trp Gly Gln Gly Thr
    370                 375                 380

Met Val Thr Val Ser Ser Gly Gly Gly Ser Asp Ile Gln Leu Thr
385                 390                 395                 400

Gln Ser Pro Ser Phe Leu Ser Ala Ser Val Gly Asp Arg Val Thr Ile
                405                 410                 415

Thr Cys Arg Ala Ser Gln Ser Ile Gly Thr Asn Ile His Trp Tyr Gln
            420                 425                 430

Gln Lys Pro Gly Lys Ala Pro Lys Leu Leu Ile Lys Tyr Ala Ser Glu
        435                 440                 445

Ser Ile Ser Gly Val Pro Ser Arg Phe Ser Gly Ser Gly Ser Gly Thr
    450                 455                 460

Glu Phe Thr Leu Thr Ile Ser Ser Leu Gln Pro Glu Asp Phe Ala Thr
465                 470                 475                 480

Tyr Tyr Cys Gln Gln Asn Asn Asn Trp Pro Thr Thr Phe Gly Ala Gly
                485                 490                 495

Thr Lys Leu Glu Ile Lys Arg Ala Ala Ala Gly Gly Gly Gly Ser Asp
            500                 505                 510

Lys Thr His Thr Cys Pro Pro Cys Pro Ala Pro Glu Leu Leu Gly Gly
        515                 520                 525

Pro Ser Val Phe Leu Phe Pro Pro Lys Pro Lys Asp Thr Leu Met Ile
    530                 535                 540

Ser Arg Thr Pro Glu Val Thr Cys Val Val Val Asp Val Ser His Glu
545                 550                 555                 560

Asp Pro Glu Val Lys Phe Asn Trp Tyr Val Asp Gly Val Glu Val His

```
                   565                 570                 575

Asn Ala Lys Thr Lys Pro Arg Glu Glu Gln Tyr Asn Ser Thr Tyr Arg
                580                 585                 590

Val Val Ser Val Leu Thr Val Leu His Gln Asp Trp Leu Asn Gly Lys
                595                 600                 605

Glu Tyr Lys Cys Lys Val Ser Asn Lys Ala Leu Pro Ala Pro Ile Glu
                610                 615                 620

Lys Thr Ile Ser Lys Ala Lys Gly Gln Pro Arg Glu Pro Gln Val Tyr
625                 630                 635                 640

Thr Leu Pro Pro Ser Arg Asp Glu Leu Thr Lys Asn Gln Val Ser Leu
                645                 650                 655

Thr Cys Leu Val Lys Gly Phe Tyr Pro Ser Asp Ile Ala Val Glu Trp
                660                 665                 670

Glu Ser Asn Gly Gln Pro Glu Asn Asn Tyr Lys Thr Thr Pro Pro Val
                675                 680                 685

Leu Asp Ser Asp Gly Ser Phe Phe Leu Tyr Ser Lys Leu Thr Val Asp
                690                 695                 700

Lys Ser Arg Trp Gln Gln Gly Asn Val Phe Ser Cys Ser Val Met His
705                 710                 715                 720

Glu Ala Leu His Asn His Tyr Thr Gln Lys Ser Leu Ser Leu Ser Pro
                725                 730                 735

Gly Lys

<210> SEQ ID NO 9
<211> LENGTH: 744
<212> TYPE: PRT
<213> ORGANISM: Artificial Sequence
<220> FEATURE:
<223> OTHER INFORMATION: IgK leader 2-35 x 3-43 scDb-Fc

<400> SEQUENCE: 9

Met Glu Thr Asp Thr Leu Leu Leu Trp Val Leu Leu Leu Trp Val Pro
1               5                   10                  15

Gly Ser Thr Gly Gln Met Gln Leu Val Gln Ser Gly Ala Glu Val Lys
                20                  25                  30

Lys Pro Gly Glu Ser Leu Lys Ile Ser Cys Lys Gly Ser Gly Tyr Ser
                35                  40                  45

Phe Thr Ser Tyr Trp Ile Gly Trp Val Arg Gln Met Pro Gly Lys Gly
                50                  55                  60

Leu Glu Trp Met Gly Ile Ile Tyr Pro Gly Asp Ser Asp Thr Arg Tyr
65                  70                  75                  80

Ser Pro Ser Phe Gln Gly Gln Val Thr Ile Ser Ala Asp Lys Ser Ile
                85                  90                  95

Ser Thr Ala Tyr Leu Gln Trp Ser Ser Leu Lys Ala Ser Asp Thr Ala
                100                 105                 110

Met Tyr Tyr Cys Ala Arg Leu Gly Arg Ser Gly Ser Tyr Tyr Asn Tyr
                115                 120                 125

Gly Met Asp Val Trp Gly Gln Gly Thr Thr Val Thr Val Ser Ser Gly
                130                 135                 140

Gly Gly Gly Ser Gln Ala Gly Leu Thr Gln Pro Pro Ala Val Ser Val
145                 150                 155                 160

Ala Pro Gly Gln Thr Ala Ser Ile Thr Cys Gly Arg Asp Asn Ile Gly
                165                 170                 175

Ser Arg Ser Val His Trp Tyr Gln Gln Lys Pro Gly Gln Ala Pro Val
                180                 185                 190
```

-continued

```
Leu Val Val Tyr Asp Asp Ser Asp Arg Pro Ala Gly Ile Pro Glu Arg
        195                 200                 205

Phe Ser Gly Ser Asn Tyr Glu Asn Thr Ala Thr Leu Thr Ile Ser Arg
    210                 215                 220

Val Glu Ala Gly Asp Glu Ala Asp Tyr Tyr Cys Gln Val Trp Gly Ile
225                 230                 235                 240

Thr Ser Asp His Val Val Phe Gly Gly Gly Thr Lys Leu Thr Val Leu
                245                 250                 255

Gly Gly Gly Gly Ser Gly Gly Arg Ala Ser Gly Gly Gly Gly Ser Gln
            260                 265                 270

Val Gln Leu Gln Gln Ser Gly Pro Gly Leu Val Lys Pro Ser Gln Thr
        275                 280                 285

Leu Ser Leu Thr Cys Ala Ile Ser Gly Asp Ser Val Ser Ser Asn Arg
    290                 295                 300

Ala Ala Trp Asn Trp Ile Arg Gln Ser Pro Ser Arg Gly Leu Glu Trp
305                 310                 315                 320

Leu Gly Arg Thr Tyr Tyr Arg Ser Lys Trp Tyr Asn Asp Tyr Ala Gln
                325                 330                 335

Ser Leu Lys Ser Arg Ile Thr Ile Asn Pro Asp Thr Pro Lys Asn Gln
            340                 345                 350

Phe Ser Leu Gln Leu Asn Ser Val Thr Pro Glu Asp Thr Ala Val Tyr
        355                 360                 365

Tyr Cys Ala Arg Asp Gly Gln Leu Gly Leu Asp Ala Leu Asp Ile Trp
    370                 375                 380

Gly Gln Gly Thr Met Val Thr Val Ser Ser Gly Gly Gly Gly Ser Gln
385                 390                 395                 400

Ala Val Val Thr Gln Glu Pro Ser Phe Ser Val Ser Pro Gly Gly Thr
                405                 410                 415

Val Thr Leu Thr Cys Gly Leu Ser Ser Gly Ser Val Ser Ser Ser Tyr
            420                 425                 430

Tyr Pro Ser Trp Tyr Gln Gln Thr Ser Gly Gln Pro Pro Arg Thr Leu
        435                 440                 445

Ile Tyr Ser Thr Asp Thr Arg Ser Ser Gly Val Pro Asp Arg Phe Ser
    450                 455                 460

Gly Ser Ile Leu Gly Asp Lys Ala Ala Leu Thr Ile Thr Gly Ala Gln
465                 470                 475                 480

Ala Asp Asp Glu Ser Asp Tyr Tyr Cys Met Leu Tyr Met Gly Ser Gly
                485                 490                 495

Ile Ser Val Phe Gly Gly Gly Thr Lys Leu Ala Val Leu Ala Ala Ala
            500                 505                 510

Gly Gly Ser Gly Gly Asp Lys Thr His Thr Cys Pro Pro Cys Pro Ala
        515                 520                 525

Pro Glu Leu Leu Gly Gly Pro Ser Val Phe Leu Phe Pro Pro Lys Pro
    530                 535                 540

Lys Asp Thr Leu Met Ile Ser Arg Thr Pro Glu Val Thr Cys Val Val
545                 550                 555                 560

Val Asp Val Ser His Glu Asp Pro Glu Val Lys Phe Asn Trp Tyr Val
                565                 570                 575

Asp Gly Val Glu Val His Asn Ala Lys Thr Lys Pro Arg Glu Glu Gln
            580                 585                 590

Tyr Asn Ser Thr Tyr Arg Val Val Ser Val Leu Thr Val Leu His Gln
        595                 600                 605
```

Asp Trp Leu Asn Gly Lys Glu Tyr Lys Cys Lys Val Ser Asn Lys Ala
            610                 615                 620

Leu Pro Ala Pro Ile Glu Lys Thr Ile Ser Lys Ala Lys Gly Gln Pro
625                 630                 635                 640

Arg Glu Pro Gln Val Tyr Thr Leu Pro Pro Ser Arg Asp Glu Leu Thr
                645                 650                 655

Lys Asn Gln Val Ser Leu Thr Cys Leu Val Lys Gly Phe Tyr Pro Ser
            660                 665                 670

Asp Ile Ala Val Glu Trp Glu Ser Asn Gly Gln Pro Glu Asn Asn Tyr
        675                 680                 685

Lys Thr Thr Pro Pro Val Leu Asp Ser Asp Gly Ser Phe Phe Leu Tyr
690                 695                 700

Ser Lys Leu Thr Val Asp Lys Ser Arg Trp Gln Gln Gly Asn Val Phe
705                 710                 715                 720

Ser Cys Ser Val Met His Glu Ala Leu His Asn His Tyr Thr Gln Lys
                725                 730                 735

Ser Leu Ser Leu Ser Pro Gly Lys
            740

<210> SEQ ID NO 10
<211> LENGTH: 744
<212> TYPE: PRT
<213> ORGANISM: Artificial Sequence
<220> FEATURE:
<223> OTHER INFORMATION: IgK leader - scDb 4D5x3-43-LL-Fc

<400> SEQUENCE: 10

Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Asn
        35                  40                  45

Ile Lys Asp Thr Tyr Ile His Trp Val Arg Gln Ala Pro Gly Lys Gly
    50                  55                  60

Leu Glu Trp Val Ala Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Ala Tyr Leu Gln Met Asn Ser Leu Arg Ala Glu Asp Thr Ala
            100                 105                 110

Val Tyr Tyr Cys Ser Arg Trp Gly Gly Asp Gly Phe Tyr Ala Met Asp
        115                 120                 125

Tyr Trp Gly Gln Gly Thr Leu Val Thr Val Ser Ser Gly Gly Gly Gly
    130                 135                 140

Ser Gln Ala Gly Leu Thr Gln Pro Ala Val Ser Val Ala Pro Gly
145                 150                 155                 160

Gln Thr Ala Ser Ile Thr Cys Gly Arg Asp Asn Ile Gly Ser Arg Ser
                165                 170                 175

Val His Trp Tyr Gln Gln Lys Pro Gly Gln Ala Pro Val Leu Val Val
            180                 185                 190

Tyr Asp Asp Ser Asp Arg Pro Ala Gly Ile Pro Glu Arg Phe Ser Gly
        195                 200                 205

Ser Asn Tyr Glu Asn Thr Ala Thr Leu Thr Ile Ser Arg Val Glu Ala
    210                 215                 220

```
Gly Asp Glu Ala Asp Tyr Tyr Cys Gln Val Trp Gly Ile Thr Ser Asp
225                 230                 235                 240

His Val Val Phe Gly Gly Thr Lys Leu Thr Val Leu Gly Gly Gly Gly
            245                 250                 255

Gly Ser Gly Gly Arg Ala Ser Gly Gly Gly Ser Gly Gly Gly Gly Gly
        260                 265                 270

Ser Gln Val Gln Leu Gln Gln Ser Gly Pro Gly Leu Val Lys Pro Ser
    275                 280                 285

Gln Thr Leu Ser Leu Thr Cys Ala Ile Ser Gly Asp Ser Val Ser Ser
    290                 295                 300

Asn Arg Ala Ala Trp Asn Trp Ile Arg Gln Ser Pro Ser Arg Gly Leu
305                 310                 315                 320

Glu Trp Leu Gly Arg Thr Tyr Tyr Arg Ser Lys Trp Tyr Asn Asp Tyr
            325                 330                 335

Ala Gln Ser Leu Lys Ser Arg Ile Thr Ile Asn Pro Asp Thr Pro Lys
            340                 345                 350

Asn Gln Phe Ser Leu Gln Leu Asn Ser Val Thr Pro Glu Asp Thr Ala
    355                 360                 365

Val Tyr Tyr Cys Ala Arg Asp Gly Gln Leu Gly Leu Asp Ala Leu Asp
370                 375                 380

Ile Trp Gly Gln Gly Thr Met Val Thr Val Ser Ser Gly Gly Gly Gly
385                 390                 395                 400

Ser Asp Ile Gln Met Thr Gln Ser Pro Ser Ser Leu Ser Ala Ser Val
            405                 410                 415

Gly Asp Arg Val Thr Ile Thr Cys Arg Ala Ser Gln Asp Val Asn Thr
        420                 425                 430

Ala Val Ala Trp Tyr Gln Gln Lys Pro Gly Lys Ala Pro Lys Leu Leu
            435                 440                 445

Ile Tyr Ser Ala Ser Phe Leu Tyr Ser Gly Val Pro Ser Arg Phe Ser
        450                 455                 460

Gly Ser Arg Ser Gly Thr Asp Phe Thr Leu Thr Ile Ser Ser Leu Gln
465                 470                 475                 480

Pro Glu Asp Phe Ala Thr Tyr Tyr Cys Gln Gln His Tyr Thr Thr Pro
            485                 490                 495

Pro Thr Phe Gly Gln Gly Thr Lys Val Glu Ile Lys Arg Ala Ala Ala
        500                 505                 510

Gly Gly Ser Gly Gly Asp Lys Thr His Thr Cys Pro Pro Cys Pro Ala
        515                 520                 525

Pro Glu Leu Leu Gly Gly Pro Ser Val Phe Leu Phe Pro Pro Lys Pro
        530                 535                 540

Lys Asp Thr Leu Met Ile Ser Arg Thr Pro Glu Val Thr Cys Val Val
545                 550                 555                 560

Val Asp Val Ser His Glu Asp Pro Glu Val Lys Phe Asn Trp Tyr Val
            565                 570                 575

Asp Gly Val Glu Val His Asn Ala Lys Thr Lys Pro Arg Glu Glu Gln
        580                 585                 590

Tyr Asn Ser Thr Tyr Arg Val Val Ser Val Leu Thr Val Leu His Gln
    595                 600                 605

Asp Trp Leu Asn Gly Lys Glu Tyr Lys Cys Lys Val Ser Asn Lys Ala
    610                 615                 620

Leu Pro Ala Pro Ile Glu Lys Thr Ile Ser Lys Ala Lys Gly Gln Pro
625                 630                 635                 640

Arg Glu Pro Gln Val Tyr Thr Leu Pro Pro Ser Arg Asp Glu Leu Thr
```

-continued

```
                645                 650                 655
Lys Asn Gln Val Ser Leu Thr Cys Leu Val Lys Gly Phe Tyr Pro Ser
                660                 665                 670

Asp Ile Ala Val Glu Trp Glu Ser Asn Gly Gln Pro Glu Asn Asn Tyr
            675                 680                 685

Lys Thr Thr Pro Pro Val Leu Asp Ser Asp Gly Ser Phe Phe Leu Tyr
        690                 695                 700

Ser Lys Leu Thr Val Asp Lys Ser Arg Trp Gln Gln Gly Asn Val Phe
705                 710                 715                 720

Ser Cys Ser Val Met His Glu Ala Leu His Asn His Tyr Thr Gln Lys
                725                 730                 735

Ser Leu Ser Leu Ser Pro Gly Lys
                740
```

<210> SEQ ID NO 11
<211> LENGTH: 1020
<212> TYPE: PRT
<213> ORGANISM: Artificial Sequence
<220> FEATURE:
<223> OTHER INFORMATION: IgK leader - FLAG - linker - scFv3-43-Fc-scTRAIL

<400> SEQUENCE: 11

```
Met Glu Thr Asp Thr Leu Leu Leu Trp Val Leu Leu Leu Trp Val Pro
1               5                   10                  15

Gly Ser Thr Gly Asp Tyr Lys Asp Asp Asp Lys Gly Gly Gly Gly Gly
            20                  25                  30

Ser Gly Thr Gln Val Gln Leu Gln Gln Ser Gly Pro Gly Leu Val Lys
        35                  40                  45

Pro Ser Gln Thr Leu Ser Leu Thr Cys Ala Ile Ser Gly Asp Ser Val
    50                  55                  60

Ser Ser Asn Arg Ala Ala Trp Asn Trp Ile Arg Gln Ser Pro Ser Arg
65                  70                  75                  80

Gly Leu Glu Trp Leu Gly Arg Thr Tyr Tyr Arg Ser Lys Trp Tyr Asn
                85                  90                  95

Asp Tyr Ala Gln Ser Leu Lys Ser Arg Ile Thr Ile Asn Pro Asp Thr
            100                 105                 110

Pro Lys Asn Gln Phe Ser Leu Gln Leu Asn Ser Val Thr Pro Glu Asp
        115                 120                 125

Thr Ala Val Tyr Tyr Cys Ala Arg Asp Gly Gln Leu Gly Leu Asp Ala
    130                 135                 140

Leu Asp Ile Trp Gly Gln Gly Thr Met Val Thr Val Ser Ser Gly Gly
145                 150                 155                 160

Gly Gly Ser Gly Gly Gly Gly Ser Gly Gly Gly Gly Ser Gln Ala Gly
                165                 170                 175

Leu Thr Gln Pro Pro Ala Val Ser Val Ala Pro Gly Gln Thr Ala Ser
            180                 185                 190

Ile Thr Cys Gly Arg Asp Asn Ile Gly Ser Arg Ser Val His Trp Tyr
        195                 200                 205

Gln Gln Lys Pro Gly Gln Ala Pro Val Leu Val Val Tyr Asp Asp Ser
    210                 215                 220

Asp Arg Pro Ala Gly Ile Pro Glu Arg Phe Ser Gly Ser Asn Tyr Glu
225                 230                 235                 240

Asn Thr Ala Thr Leu Thr Ile Ser Arg Val Glu Ala Gly Asp Glu Ala
                245                 250                 255
```

```
Asp Tyr Tyr Cys Gln Val Trp Gly Ile Thr Ser Asp His Val Val Phe
            260                 265                 270

Gly Gly Gly Thr Lys Leu Thr Val Leu Ala Ala Ala Gly Gly Ser Gly
        275                 280                 285

Gly Asp Lys Thr His Thr Cys Pro Pro Cys Pro Ala Pro Glu Leu Leu
    290                 295                 300

Gly Gly Pro Ser Val Phe Leu Phe Pro Pro Lys Pro Lys Asp Thr Leu
305                 310                 315                 320

Met Ile Ser Arg Thr Pro Glu Val Thr Cys Val Val Val Asp Val Ser
            325                 330                 335

His Glu Asp Pro Glu Val Lys Phe Asn Trp Tyr Val Asp Gly Val Glu
            340                 345                 350

Val His Asn Ala Lys Thr Lys Pro Arg Glu Glu Gln Tyr Asn Ser Thr
        355                 360                 365

Tyr Arg Val Val Ser Val Leu Thr Val Leu His Gln Asp Trp Leu Asn
    370                 375                 380

Gly Lys Glu Tyr Lys Cys Lys Val Ser Asn Lys Ala Leu Pro Ala Pro
385                 390                 395                 400

Ile Glu Lys Thr Ile Ser Lys Ala Lys Gly Gln Pro Arg Glu Pro Gln
            405                 410                 415

Val Tyr Thr Leu Pro Pro Ser Arg Asp Glu Leu Thr Lys Asn Gln Val
            420                 425                 430

Ser Leu Thr Cys Leu Val Lys Gly Phe Tyr Pro Ser Asp Ile Ala Val
        435                 440                 445

Glu Trp Glu Ser Asn Gly Gln Pro Glu Asn Asn Tyr Lys Thr Thr Pro
450                 455                 460

Pro Val Leu Asp Ser Asp Gly Ser Phe Phe Leu Tyr Ser Lys Leu Thr
465                 470                 475                 480

Val Asp Lys Ser Arg Trp Gln Gln Gly Asn Val Phe Ser Cys Ser Val
            485                 490                 495

Met His Glu Ala Leu His Asn His Tyr Thr Gln Lys Ser Leu Ser Leu
        500                 505                 510

Ser Pro Gly Gln Gly Gly Ser Gly Gly Ser Ser Gly Gly Gly Pro
    515                 520                 525

Gln Arg Val Ala Ala His Ile Thr Gly Thr Arg Gly Arg Ser Asn Thr
530                 535                 540

Leu Ser Ser Pro Asn Ser Lys Asn Glu Lys Ala Leu Gly Arg Lys Ile
545                 550                 555                 560

Asn Ser Trp Glu Ser Ser Arg Ser Gly His Ser Phe Leu Ser Asn Leu
            565                 570                 575

His Leu Arg Asn Gly Glu Leu Val Ile His Glu Lys Gly Phe Tyr Tyr
        580                 585                 590

Ile Tyr Ser Gln Thr Tyr Phe Arg Phe Gln Glu Glu Ile Lys Glu Asn
    595                 600                 605

Thr Lys Asn Asp Lys Gln Met Val Gln Tyr Ile Tyr Lys Tyr Thr Ser
    610                 615                 620

Tyr Pro Asp Pro Ile Leu Leu Met Lys Ser Ala Arg Asn Ser Cys Trp
625                 630                 635                 640

Ser Lys Asp Ala Glu Tyr Gly Leu Tyr Ser Ile Tyr Gln Gly Gly Ile
            645                 650                 655

Phe Glu Leu Lys Glu Asn Asp Arg Ile Phe Val Ser Val Thr Asn Glu
            660                 665                 670

His Leu Ile Asp Met Asp His Glu Ala Ser Phe Phe Gly Ala Phe Leu
```

```
            675                 680                 685
Val Gly Gly Pro Gln Arg Val Ala Ala His Ile Thr Gly Thr Arg
        690                 695                 700

Gly Arg Ser Asn Thr Leu Ser Ser Pro Asn Ser Lys Asn Glu Lys Ala
705                 710                 715                 720

Leu Gly Arg Lys Ile Asn Ser Trp Glu Ser Arg Ser Gly His Ser
                725                 730                 735

Phe Leu Ser Asn Leu His Leu Arg Asn Gly Glu Leu Val Ile His Glu
                740                 745                 750

Lys Gly Phe Tyr Tyr Ile Tyr Ser Gln Thr Tyr Phe Arg Phe Gln Glu
                755                 760                 765

Glu Ile Lys Glu Asn Thr Lys Asn Asp Lys Gln Met Val Gln Tyr Ile
770                 775                 780

Tyr Lys Tyr Thr Ser Tyr Pro Asp Pro Ile Leu Leu Met Lys Ser Ala
785                 790                 795                 800

Arg Asn Ser Cys Trp Ser Lys Asp Ala Glu Tyr Gly Leu Tyr Ser Ile
                805                 810                 815

Tyr Gln Gly Gly Ile Phe Glu Leu Lys Glu Asn Asp Arg Ile Phe Val
                820                 825                 830

Ser Val Thr Asn Glu His Leu Ile Asp Met Asp His Glu Ala Ser Phe
                835                 840                 845

Phe Gly Ala Phe Leu Val Gly Gly Pro Gln Arg Val Ala Ala His
                850                 855                 860

Ile Thr Gly Thr Arg Gly Arg Ser Asn Thr Leu Ser Ser Pro Asn Ser
865                 870                 875                 880

Lys Asn Glu Lys Ala Leu Gly Arg Lys Ile Asn Ser Trp Glu Ser Ser
                885                 890                 895

Arg Ser Gly His Ser Phe Leu Ser Asn Leu His Leu Arg Asn Gly Glu
                900                 905                 910

Leu Val Ile His Glu Lys Gly Phe Tyr Tyr Ile Tyr Ser Gln Thr Tyr
                915                 920                 925

Phe Arg Phe Gln Glu Glu Ile Lys Glu Asn Thr Lys Asn Asp Lys Gln
            930                 935                 940

Met Val Gln Tyr Ile Tyr Lys Tyr Thr Ser Tyr Pro Asp Pro Ile Leu
945                 950                 955                 960

Leu Met Lys Ser Ala Arg Asn Ser Cys Trp Ser Lys Asp Ala Glu Tyr
                965                 970                 975

Gly Leu Tyr Ser Ile Tyr Gln Gly Gly Ile Phe Glu Leu Lys Glu Asn
                980                 985                 990

Asp Arg Ile Phe Val Ser Val Thr  Asn Glu His Leu Ile  Asp Met Asp
            995                 1000                1005

His Glu  Ala Ser Phe Phe Gly  Ala Phe Leu Val Gly
    1010                1015                1020

<210> SEQ ID NO 12
<211> LENGTH: 515
<212> TYPE: PRT
<213> ORGANISM: Artificial Sequence
<220> FEATURE:
<223> OTHER INFORMATION: IgK leader - scDb 3-43xCD3 - His

<400> SEQUENCE: 12

Met Glu Thr Asp Thr Leu Leu Leu Trp Val Leu Leu Leu Trp Val Pro
1               5                   10                  15

Gly Ser Thr Gly Gln Val Gln Leu Gln Gln Ser Gly Pro Gly Leu Val
```

```
               20                  25                  30
Lys Pro Ser Gln Thr Leu Ser Leu Thr Cys Ala Ile Ser Gly Asp Ser
                35                  40                  45

Val Ser Ser Asn Arg Ala Ala Trp Asn Trp Ile Arg Gln Ser Pro Ser
         50                  55                  60

Arg Gly Leu Glu Trp Leu Gly Arg Thr Tyr Tyr Arg Ser Lys Trp Tyr
 65                  70                  75                  80

Asn Asp Tyr Ala Gln Ser Leu Lys Ser Arg Ile Thr Ile Asn Pro Asp
                 85                  90                  95

Thr Pro Lys Asn Gln Phe Ser Leu Gln Leu Asn Ser Val Thr Pro Glu
                100                 105                 110

Asp Thr Ala Val Tyr Tyr Cys Ala Arg Asp Gly Gln Leu Gly Leu Asp
                115                 120                 125

Ala Leu Asp Ile Trp Gly Gln Gly Thr Met Val Thr Val Ser Ser Gly
            130                 135                 140

Gly Gly Gly Ser Asp Ile Gln Met Thr Gln Ser Pro Ser Ser Leu Ser
145                 150                 155                 160

Ala Ser Val Gly Asp Arg Val Thr Ile Thr Cys Arg Ala Ser Gln Asp
                165                 170                 175

Ile Arg Asn Tyr Leu Asn Trp Tyr Gln Gln Lys Pro Gly Lys Ala Pro
                180                 185                 190

Lys Leu Leu Ile Tyr Tyr Thr Ser Arg Leu His Ser Gly Val Pro Ser
            195                 200                 205

Arg Phe Ser Gly Ser Gly Ser Gly Thr Asp Phe Thr Phe Thr Ile Ser
            210                 215                 220

Ser Leu Gln Pro Glu Asp Ile Ala Thr Tyr Tyr Cys Gln Gln Gly Asn
225                 230                 235                 240

Thr Leu Pro Trp Thr Phe Gly Gln Gly Thr Lys Leu Glu Ile Lys Arg
                245                 250                 255

Gly Gly Gly Gly Ser Gly Gly Gly Gly Ser Gly Gly Gly Gly Ser Gln
                260                 265                 270

Val Gln Leu Val Gln Ser Gly Ala Glu Val Lys Lys Pro Gly Ser Ser
            275                 280                 285

Val Lys Val Ser Cys Lys Ala Ser Gly Gly Thr Phe Ser Gly Tyr Thr
            290                 295                 300

Met Asn Trp Val Arg Gln Ala Pro Gly Gln Gly Leu Glu Trp Met Gly
305                 310                 315                 320

Leu Ile Asn Pro Tyr Lys Gly Val Ser Thr Tyr Asn Gly Lys Phe Lys
                325                 330                 335

Asp Arg Val Thr Ile Thr Ala Asp Lys Ser Thr Ser Thr Ala Tyr Met
            340                 345                 350

Glu Leu Ser Ser Leu Arg Ser Glu Asp Thr Ala Val Tyr Tyr Cys Ala
            355                 360                 365

Arg Ser Gly Tyr Tyr Gly Asp Ser Asp Trp Tyr Phe Asp Val Trp Gly
        370                 375                 380

Gln Gly Thr Leu Val Thr Val Ser Ser Gly Gly Gly Gly Ser Gln Ala
385                 390                 395                 400

Gly Leu Thr Gln Pro Pro Ala Val Ser Val Ala Pro Gly Gln Thr Ala
                405                 410                 415

Ser Ile Thr Cys Gly Arg Asp Asn Ile Gly Ser Arg Ser Val His Trp
            420                 425                 430

Tyr Gln Gln Lys Pro Gly Gln Ala Pro Val Leu Val Val Tyr Asp Asp
            435                 440                 445
```

```
Ser Asp Arg Pro Ala Gly Ile Pro Glu Arg Phe Ser Gly Ser Asn Tyr
    450                 455                 460

Glu Asn Thr Ala Thr Leu Thr Ile Ser Arg Val Glu Ala Gly Asp Glu
465                 470                 475                 480

Ala Asp Tyr Tyr Cys Gln Val Trp Gly Ile Thr Ser Asp His Val Val
                485                 490                 495

Phe Gly Gly Thr Lys Leu Thr Val Leu Ala Ala Ala His His His His
            500                 505                 510

His His His
        515

<210> SEQ ID NO 13
<211> LENGTH: 776
<212> TYPE: PRT
<213> ORGANISM: Artificial Sequence
<220> FEATURE:
<223> OTHER INFORMATION: IgK leader - scDb 3-43xCD3-scFv 3-43 - His

<400> SEQUENCE: 13

Met Glu Thr Asp Thr Leu Leu Leu Trp Val Leu Leu Leu Trp Val Pro
1               5                   10                  15

Gly Ser Thr Gly Gln Val Gln Leu Gln Gln Ser Gly Pro Gly Leu Val
            20                  25                  30

Lys Pro Ser Gln Thr Leu Ser Leu Thr Cys Ala Ile Ser Gly Asp Ser
        35                  40                  45

Val Ser Ser Asn Arg Ala Ala Trp Asn Trp Ile Arg Gln Ser Pro Ser
50                  55                  60

Arg Gly Leu Glu Trp Leu Gly Arg Thr Tyr Tyr Arg Ser Lys Trp Tyr
65                  70                  75                  80

Asn Asp Tyr Ala Gln Ser Leu Lys Ser Arg Ile Thr Ile Asn Pro Asp
                85                  90                  95

Thr Pro Lys Asn Gln Phe Ser Leu Gln Leu Asn Ser Val Thr Pro Glu
            100                 105                 110

Asp Thr Ala Val Tyr Tyr Cys Ala Arg Asp Gly Gln Leu Gly Leu Asp
        115                 120                 125

Ala Leu Asp Ile Trp Gly Gln Gly Thr Met Val Thr Val Ser Ser Gly
130                 135                 140

Gly Gly Gly Ser Asp Ile Gln Met Thr Gln Ser Pro Ser Ser Leu Ser
145                 150                 155                 160

Ala Ser Val Gly Asp Arg Val Thr Ile Thr Cys Arg Ala Ser Gln Asp
                165                 170                 175

Ile Arg Asn Tyr Leu Asn Trp Tyr Gln Gln Lys Pro Gly Lys Ala Pro
            180                 185                 190

Lys Leu Leu Ile Tyr Tyr Thr Ser Arg Leu His Ser Gly Val Pro Ser
        195                 200                 205

Arg Phe Ser Gly Ser Gly Ser Gly Thr Asp Phe Thr Phe Thr Ile Ser
210                 215                 220

Ser Leu Gln Pro Glu Asp Ile Ala Thr Tyr Tyr Cys Gln Gln Gly Asn
225                 230                 235                 240

Thr Leu Pro Trp Thr Phe Gly Gln Gly Thr Lys Leu Glu Ile Lys Arg
                245                 250                 255

Gly Gly Gly Gly Ser Gly Gly Gly Ser Gly Gly Gly Ser Gln
            260                 265                 270

Val Gln Leu Val Gln Ser Gly Ala Glu Val Lys Lys Pro Gly Ser Ser
        275                 280                 285
```

```
Val Lys Val Ser Cys Lys Ala Ser Gly Gly Thr Phe Ser Gly Tyr Thr
        290                 295                 300
Met Asn Trp Val Arg Gln Ala Pro Gly Gln Gly Leu Glu Trp Met Gly
305                 310                 315                 320
Leu Ile Asn Pro Tyr Lys Gly Val Ser Thr Tyr Asn Gly Lys Phe Lys
                325                 330                 335
Asp Arg Val Thr Ile Thr Ala Asp Lys Ser Thr Ser Thr Ala Tyr Met
                340                 345                 350
Glu Leu Ser Ser Leu Arg Ser Glu Asp Thr Ala Val Tyr Tyr Cys Ala
        355                 360                 365
Arg Ser Gly Tyr Tyr Gly Asp Ser Asp Trp Tyr Phe Asp Val Trp Gly
    370                 375                 380
Gln Gly Thr Leu Val Thr Val Ser Ser Gly Gly Gly Ser Gln Ala
385                 390                 395                 400
Gly Leu Thr Gln Pro Pro Ala Val Ser Val Ala Pro Gly Gln Thr Ala
                405                 410                 415
Ser Ile Thr Cys Gly Arg Asp Asn Ile Gly Ser Arg Ser Val His Trp
                420                 425                 430
Tyr Gln Gln Lys Pro Gly Gln Ala Pro Val Leu Val Val Tyr Asp Asp
        435                 440                 445
Ser Asp Arg Pro Ala Gly Ile Pro Glu Arg Phe Ser Gly Ser Asn Tyr
    450                 455                 460
Glu Asn Thr Ala Thr Leu Thr Ile Ser Arg Val Glu Ala Gly Asp Glu
465                 470                 475                 480
Ala Asp Tyr Tyr Cys Gln Val Trp Gly Ile Thr Ser Asp His Val Val
                485                 490                 495
Phe Gly Gly Gly Thr Lys Leu Thr Val Leu Ala Ala Gly Gly Ser
                500                 505                 510
Gly Gly Gly Gly Ser Gly Gly Gly Thr Gln Val Gln Leu Gln Gln Ser
        515                 520                 525
Gly Pro Gly Leu Val Lys Pro Ser Gln Thr Leu Ser Leu Thr Cys Ala
    530                 535                 540
Ile Ser Gly Asp Ser Val Ser Ser Asn Arg Ala Ala Trp Asn Trp Ile
545                 550                 555                 560
Arg Gln Ser Pro Ser Arg Gly Leu Glu Trp Leu Gly Arg Thr Tyr Tyr
                565                 570                 575
Arg Ser Lys Trp Tyr Asn Asp Tyr Ala Gln Ser Leu Lys Ser Arg Ile
                580                 585                 590
Thr Ile Asn Pro Asp Thr Pro Lys Asn Gln Phe Ser Leu Gln Leu Asn
        595                 600                 605
Ser Val Thr Pro Glu Asp Thr Ala Val Tyr Tyr Cys Ala Arg Asp Gly
    610                 615                 620
Gln Leu Gly Leu Asp Ala Leu Asp Ile Trp Gly Gln Gly Thr Met Val
625                 630                 635                 640
Thr Val Ser Ser Gly Gly Gly Gly Ser Gly Gly Gly Gly Ser Gly Gly
                645                 650                 655
Gly Gly Ser Gln Ala Gly Leu Thr Gln Pro Pro Ala Val Ser Val Ala
                660                 665                 670
Pro Gly Gln Thr Ala Ser Ile Thr Cys Gly Arg Asp Asn Ile Gly Ser
        675                 680                 685
Arg Ser Val His Trp Tyr Gln Gln Lys Pro Gly Gln Ala Pro Val Leu
    690                 695                 700
```

```
Val Val Tyr Asp Asp Ser Asp Arg Pro Ala Gly Ile Pro Glu Arg Phe
705                 710                 715                 720

Ser Gly Ser Asn Tyr Glu Asn Thr Ala Thr Leu Thr Ile Ser Arg Val
                725                 730                 735

Glu Ala Gly Asp Glu Ala Asp Tyr Tyr Cys Gln Val Trp Gly Ile Thr
                740                 745                 750

Ser Asp His Val Val Phe Gly Gly Gly Thr Lys Leu Thr Val Leu Gly
            755                 760                 765

Ser Leu His His His His His His
    770                 775

<210> SEQ ID NO 14
<211> LENGTH: 5
<212> TYPE: PRT
<213> ORGANISM: Artificial Sequence
<220> FEATURE:
<223> OTHER INFORMATION: peptide linker 1

<400> SEQUENCE: 14

Gly Gly Gly Gly Ser
1               5

<210> SEQ ID NO 15
<211> LENGTH: 10
<212> TYPE: PRT
<213> ORGANISM: Artificial Sequence
<220> FEATURE:
<223> OTHER INFORMATION: peptide linker 2

<400> SEQUENCE: 15

Gly Gly Gly Gly Ser Gly Gly Gly Gly Ser
1               5                   10

<210> SEQ ID NO 16
<211> LENGTH: 15
<212> TYPE: PRT
<213> ORGANISM: Artificial Sequence
<220> FEATURE:
<223> OTHER INFORMATION: peptide linker 3

<400> SEQUENCE: 16

Gly Gly Gly Gly Ser Gly Gly Gly Gly Ser Gly Gly Gly Gly Ser
1               5                   10                  15

<210> SEQ ID NO 17
<211> LENGTH: 8
<212> TYPE: PRT
<213> ORGANISM: Artificial Sequence
<220> FEATURE:
<223> OTHER INFORMATION: peptide linker 4

<400> SEQUENCE: 17

Gly Ser Leu Gly Gly Ser Gly Gly
1               5

<210> SEQ ID NO 18
<211> LENGTH: 8
<212> TYPE: PRT
<213> ORGANISM: Artificial Sequence
<220> FEATURE:
<223> OTHER INFORMATION: peptide linker 5

<400> SEQUENCE: 18

Gly Gly Gly Ser Gly Gly Gly Thr
1               5
```

```
<210> SEQ ID NO 19
<211> LENGTH: 10
<212> TYPE: PRT
<213> ORGANISM: Artificial Sequence
<220> FEATURE:
<223> OTHER INFORMATION: peptide linker 6

<400> SEQUENCE: 19

Gly Gly Gly Ser Gly Gly Gly Thr Gly Ser
1               5                   10

<210> SEQ ID NO 20
<211> LENGTH: 12
<212> TYPE: PRT
<213> ORGANISM: Artificial Sequence
<220> FEATURE:
<223> OTHER INFORMATION: peptide linker 7

<400> SEQUENCE: 20

Gly Gly Gly Ser Gly Gly Gly Thr Gly Ser Gly Gly
1               5                   10

<210> SEQ ID NO 21
<211> LENGTH: 20
<212> TYPE: PRT
<213> ORGANISM: Artificial Sequence
<220> FEATURE:
<223> OTHER INFORMATION: peptide linker 8

<400> SEQUENCE: 21

Gly Gly Gly Gly Ser Gly Gly Arg Ala Ser Gly Gly Gly Ser Gly
1               5                   10                  15

Gly Gly Gly Ser
            20

<210> SEQ ID NO 22
<211> LENGTH: 8
<212> TYPE: PRT
<213> ORGANISM: Artificial Sequence
<220> FEATURE:
<223> OTHER INFORMATION: peptide linker 9

<400> SEQUENCE: 22

Gly Gly Gly Ser Gly Gly Gly Ser
1               5

<210> SEQ ID NO 23
<211> LENGTH: 5
<212> TYPE: PRT
<213> ORGANISM: Artificial Sequence
<220> FEATURE:
<223> OTHER INFORMATION: peptide linker 10

<400> SEQUENCE: 23

Glu Phe Thr Arg Gly
1               5

<210> SEQ ID NO 24
<211> LENGTH: 3
<212> TYPE: PRT
<213> ORGANISM: Artificial Sequence
<220> FEATURE:
<223> OTHER INFORMATION: peptide linker 11

<400> SEQUENCE: 24
```

```
Ala Ala Ala
  1

<210> SEQ ID NO 25
<211> LENGTH: 8
<212> TYPE: PRT
<213> ORGANISM: Artificial Sequence
<220> FEATURE:
<223> OTHER INFORMATION: FLAG-tag

<400> SEQUENCE: 25

Asp Tyr Lys Asp Asp Asp Asp Lys
  1               5

<210> SEQ ID NO 26
<211> LENGTH: 6
<212> TYPE: PRT
<213> ORGANISM: Artificial Sequence
<220> FEATURE:
<223> OTHER INFORMATION: His-tag

<400> SEQUENCE: 26

His His His His His His
  1               5

<210> SEQ ID NO 27
<211> LENGTH: 10
<212> TYPE: PRT
<213> ORGANISM: Artificial Sequence
<220> FEATURE:
<223> OTHER INFORMATION: Myc-tag

<400> SEQUENCE: 27

Glu Gln Lys Leu Ile Ser Glu Glu Asp Leu
  1               5                  10

<210> SEQ ID NO 28
<211> LENGTH: 22
<212> TYPE: PRT
<213> ORGANISM: Artificial Sequence
<220> FEATURE:
<223> OTHER INFORMATION: PelB leader sequence

<400> SEQUENCE: 28

Met Lys Tyr Leu Leu Pro Thr Ala Ala Ala Gly Leu Leu Leu Leu Ala
  1               5                  10                  15

Ala Gln Pro Ala Met Ala
             20

<210> SEQ ID NO 29
<211> LENGTH: 20
<212> TYPE: PRT
<213> ORGANISM: Artificial Sequence
<220> FEATURE:
<223> OTHER INFORMATION: IgK leader sequence

<400> SEQUENCE: 29

Met Glu Thr Asp Thr Leu Leu Leu Trp Val Leu Leu Leu Trp Val Pro
  1               5                  10                  15

Gly Ser Thr Gly
             20

<210> SEQ ID NO 30
<211> LENGTH: 20
<212> TYPE: PRT
<213> ORGANISM: Artificial Sequence
```

```
<220> FEATURE:
<223> OTHER INFORMATION: IL-2 leader sequence

<400> SEQUENCE: 30

Met Tyr Arg Met Gln Leu Leu Ser Cys Ile Ala Leu Ser Leu Ala Leu
1               5                   10                  15

Val Thr Asn Ser
            20

<210> SEQ ID NO 31
<211> LENGTH: 342
<212> TYPE: PRT
<213> ORGANISM: Artificial Sequence
<220> FEATURE:
<223> OTHER INFORMATION: VH3-43xVLhu225-CL

<400> SEQUENCE: 31

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Arg Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Gln Ser Leu Lys Ser Arg Ile Thr Ile Asn Pro Asp Thr Pro Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Gly Gln Leu Gly Leu Asp Ala Leu Asp Ile
            100                 105                 110

Trp Gly Gln Gly Thr Met Val Thr Val Ser Ser Gly Gly Gly Gly Ser
        115                 120                 125

Asp Ile Gln Leu Thr Gln Ser Pro Ser Phe Leu Ser Ala Ser Val Gly
    130                 135                 140

Asp Arg Val Thr Ile Thr Cys Arg Ala Ser Gln Ser Ile Gly Thr Asn
145                 150                 155                 160

Ile His Trp Tyr Gln Gln Lys Pro Gly Lys Ala Pro Lys Leu Leu Ile
                165                 170                 175

Lys Tyr Ala Ser Glu Ser Ile Ser Gly Val Pro Ser Arg Phe Ser Gly
            180                 185                 190

Ser Gly Ser Gly Thr Glu Phe Thr Leu Thr Ile Ser Ser Leu Gln Pro
        195                 200                 205

Glu Asp Phe Ala Thr Tyr Tyr Cys Gln Gln Asn Asn Asn Trp Pro Thr
    210                 215                 220

Thr Phe Gly Ala Gly Thr Lys Leu Glu Ile Lys Arg Thr Val Ala Ala
225                 230                 235                 240

Pro Ser Val Phe Ile Phe Pro Pro Ser Asp Glu Gln Leu Lys Ser Gly
                245                 250                 255

Thr Ala Ser Val Val Cys Leu Leu Asn Asn Phe Tyr Pro Arg Glu Ala
            260                 265                 270

Lys Val Gln Trp Lys Val Asp Asn Ala Leu Gln Ser Gly Asn Ser Gln
        275                 280                 285

Glu Ser Val Thr Glu Gln Asp Ser Lys Asp Ser Thr Tyr Ser Leu Ser
    290                 295                 300

Ser Thr Leu Thr Leu Ser Lys Ala Asp Tyr Glu Lys His Lys Val Tyr
```

```
305              310              315              320
Ala Cys Glu Val Thr His Gln Gly Leu Ser Ser Pro Val Thr Lys Ser
                325              330              335

Phe Asn Arg Gly Glu Cys
            340

<210> SEQ ID NO 32
<211> LENGTH: 561
<212> TYPE: PRT
<213> ORGANISM: Artificial Sequence
<220> FEATURE:
<223> OTHER INFORMATION: VHhu225xVLhu3-43-CH1-CH2-CH3

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asn Tyr
            20                  25                  30

Gly Val His Trp Val Arg Gln Ala Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Thr Val Thr Val Ser Ser Gly Gly Gly Gly Ser Gln Ala Gly Leu
        115                 120                 125

Thr Gln Pro Pro Ala Val Ser Val Ala Pro Gly Gln Thr Ala Ser Ile
130                 135                 140

Thr Cys Gly Arg Asp Asn Ile Gly Ser Arg Ser Val His Trp Tyr Gln
145                 150                 155                 160

Gln Lys Pro Gly Gln Ala Pro Val Leu Val Val Tyr Asp Asp Ser Asp
                165                 170                 175

Arg Pro Ala Gly Ile Pro Glu Arg Phe Ser Gly Ser Asn Tyr Glu Asn
            180                 185                 190

Thr Ala Thr Leu Thr Ile Ser Arg Val Glu Ala Gly Asp Glu Ala Asp
        195                 200                 205

Tyr Tyr Cys Gln Val Trp Gly Ile Thr Ser Asp His Val Val Phe Gly
    210                 215                 220

Gly Gly Thr Lys Leu Thr Val Leu Ala Ser Thr Lys Gly Pro Ser Val
225                 230                 235                 240

Phe Pro Leu Ala Pro Ser Ser Lys Ser Thr Ser Gly Gly Thr Ala Ala
                245                 250                 255

Leu Gly Cys Leu Val Lys Asp Tyr Phe Pro Glu Pro Val Thr Val Ser
            260                 265                 270

Trp Asn Ser Gly Ala Leu Thr Ser Gly Val His Thr Phe Pro Ala Val
        275                 280                 285

Leu Gln Ser Ser Gly Leu Tyr Ser Leu Ser Ser Val Val Thr Val Pro
    290                 295                 300

Ser Ser Ser Leu Gly Thr Gln Thr Tyr Ile Cys Asn Val Asn His Lys
305                 310                 315                 320

Pro Ser Asn Thr Lys Val Asp Lys Lys Val Glu Pro Lys Ser Cys Asp
```

Lys Thr His Thr Cys Pro Pro Cys Pro Ala Pro Pro Val Ala Gly Pro
              325                 330                 335
              340                 345                 350

Ser Val Phe Leu Phe Pro Pro Lys Pro Lys Asp Thr Leu Met Ile Ser
              355                 360                 365

Arg Thr Pro Glu Val Thr Cys Val Val Val Asp Val Ser His Glu Asp
              370                 375                 380

Pro Glu Val Lys Phe Asn Trp Tyr Val Asp Gly Val Glu Val His Asn
385                 390                 395                 400

Ala Lys Thr Lys Pro Arg Glu Glu Gln Tyr Asn Ser Thr Tyr Arg Val
              405                 410                 415

Val Ser Val Leu Thr Val Leu His Gln Asp Trp Leu Asn Gly Lys Glu
              420                 425                 430

Tyr Lys Cys Lys Val Ser Asn Lys Gly Leu Pro Ser Ser Ile Glu Lys
              435                 440                 445

Thr Ile Ser Lys Ala Lys Gly Gln Pro Arg Glu Pro Gln Val Tyr Thr
              450                 455                 460

Leu Pro Pro Ser Arg Asp Glu Leu Thr Lys Asn Gln Val Ser Leu Thr
465                 470                 475                 480

Cys Leu Val Lys Gly Phe Tyr Pro Ser Asp Ile Ala Val Glu Trp Glu
              485                 490                 495

Ser Asn Gly Gln Pro Glu Asn Asn Tyr Lys Thr Thr Pro Pro Val Leu
              500                 505                 510

Asp Ser Asp Gly Ser Phe Phe Leu Tyr Ser Lys Leu Thr Val Asp Lys
              515                 520                 525

Ser Arg Trp Gln Gln Gly Asn Val Phe Ser Cys Ser Val Met His Glu
              530                 535                 540

Ala Leu His Asn His Tyr Thr Gln Lys Ser Leu Ser Leu Ser Pro Gly
545                 550                 555                 560

Lys

<210> SEQ ID NO 33
<211> LENGTH: 738
<212> TYPE: PRT
<213> ORGANISM: Artificial Sequence
<220> FEATURE:
<223> OTHER INFORMATION: scDbhu225x3-43-Fc(GGGGS)

<400> SEQUENCE: 33

Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Leu Val
              20                  25                  30

Gln Pro Gly Gly Ser Leu Arg Leu Ser Cys Ala Ala Ser Gly Phe Ser
              35                  40                  45

Leu Thr Asn Tyr Gly Val His Trp Val Arg Gln Ala Pro Gly Lys Gly
              50                  55                  60

Leu Glu Trp Leu Gly Val Ile Trp Ser Gly Gly Asn Thr Asp Tyr Asn
65                  70                  75                  80

Thr Pro Phe Thr Ser Arg Phe Thr Ile Ser Arg Asp Asn Ser Lys Asn
              85                  90                  95

Thr Leu Tyr Leu Gln Met Asn Ser Leu Arg Ala Glu Asp Thr Ala Val
              100                 105                 110

Tyr Tyr Cys Ala Arg Ala Leu Thr Tyr Tyr Asp Tyr Glu Phe Ala Tyr
              115                 120                 125

-continued

Trp Gly Gln Gly Thr Thr Val Thr Val Ser Ser Gly Gly Gly Ser
       130                 135                 140

Gln Ala Gly Leu Thr Gln Pro Pro Ala Val Ser Val Ala Pro Gly Gln
145                 150                 155                 160

Thr Ala Ser Ile Thr Cys Gly Arg Asp Asn Ile Gly Ser Arg Ser Val
                165                 170                 175

His Trp Tyr Gln Gln Lys Pro Gly Gln Ala Pro Val Leu Val Val Tyr
            180                 185                 190

Asp Asp Ser Asp Arg Pro Ala Gly Ile Pro Glu Arg Phe Ser Gly Ser
        195                 200                 205

Asn Tyr Glu Asn Thr Ala Thr Leu Thr Ile Ser Arg Val Glu Ala Gly
    210                 215                 220

Asp Glu Ala Asp Tyr Tyr Cys Gln Val Trp Gly Ile Thr Ser Asp His
225                 230                 235                 240

Val Val Phe Gly Gly Gly Thr Lys Leu Thr Val Leu Gly Gly Gly Gly
                245                 250                 255

Ser Gly Gly Gly Gly Ser Gly Gly Gly Ser Gln Val Gln Leu Gln
                260                 265                 270

Gln Ser Gly Pro Gly Leu Val Lys Pro Ser Gln Thr Leu Ser Leu Thr
        275                 280                 285

Cys Ala Ile Ser Gly Asp Ser Val Ser Ser Asn Arg Ala Ala Trp Asn
290                 295                 300

Trp Ile Arg Gln Ser Pro Ser Arg Gly Leu Glu Trp Leu Gly Arg Thr
305                 310                 315                 320

Tyr Tyr Arg Ser Lys Trp Tyr Asn Asp Tyr Ala Gln Ser Leu Lys Ser
                325                 330                 335

Arg Ile Thr Ile Asn Pro Asp Thr Pro Lys Asn Gln Phe Ser Leu Gln
            340                 345                 350

Leu Asn Ser Val Thr Pro Glu Asp Thr Ala Val Tyr Tyr Cys Ala Arg
        355                 360                 365

Asp Gly Gln Leu Gly Leu Asp Ala Leu Asp Ile Trp Gly Gln Gly Thr
    370                 375                 380

Met Val Thr Val Ser Ser Gly Gly Gly Ser Asp Ile Gln Leu Thr
385                 390                 395                 400

Gln Ser Pro Ser Phe Leu Ser Ala Ser Val Gly Asp Arg Val Thr Ile
                405                 410                 415

Thr Cys Arg Ala Ser Gln Ser Ile Gly Thr Asn Ile His Trp Tyr Gln
            420                 425                 430

Gln Lys Pro Gly Lys Ala Pro Lys Leu Leu Ile Lys Tyr Ala Ser Glu
        435                 440                 445

Ser Ile Ser Gly Val Pro Ser Arg Phe Ser Gly Ser Gly Ser Gly Thr
    450                 455                 460

Glu Phe Thr Leu Thr Ile Ser Ser Leu Gln Pro Glu Asp Phe Ala Thr
465                 470                 475                 480

Tyr Tyr Cys Gln Gln Asn Asn Asn Trp Pro Thr Thr Phe Gly Ala Gly
                485                 490                 495

Thr Lys Leu Glu Ile Lys Arg Ala Ala Ala Gly Gly Ser Gly Gly Asp
            500                 505                 510

Lys Thr His Thr Cys Pro Pro Cys Pro Ala Pro Glu Leu Leu Gly Gly
        515                 520                 525

Pro Ser Val Phe Leu Phe Pro Pro Lys Pro Lys Asp Thr Leu Met Ile
530                 535                 540

```
Ser Arg Thr Pro Glu Val Thr Cys Val Val Val Asp Val Ser His Glu
545                 550                 555                 560

Asp Pro Glu Val Lys Phe Asn Trp Tyr Val Asp Gly Val Glu Val His
                565                 570                 575

Asn Ala Lys Thr Lys Pro Arg Glu Glu Gln Tyr Asn Ser Thr Tyr Arg
            580                 585                 590

Val Val Ser Val Leu Thr Val Leu His Gln Asp Trp Leu Asn Gly Lys
        595                 600                 605

Glu Tyr Lys Cys Lys Val Ser Asn Lys Ala Leu Pro Ala Pro Ile Glu
    610                 615                 620

Lys Thr Ile Ser Lys Ala Lys Gly Gln Pro Arg Glu Pro Gln Val Tyr
625                 630                 635                 640

Thr Leu Pro Pro Ser Arg Asp Glu Leu Thr Lys Asn Gln Val Ser Leu
                645                 650                 655

Thr Cys Leu Val Lys Gly Phe Tyr Pro Ser Asp Ile Ala Val Glu Trp
            660                 665                 670

Glu Ser Asn Gly Gln Pro Glu Asn Asn Tyr Lys Thr Thr Pro Pro Val
        675                 680                 685

Leu Asp Ser Asp Gly Ser Phe Phe Leu Tyr Ser Lys Leu Thr Val Asp
    690                 695                 700

Lys Ser Arg Trp Gln Gln Gly Asn Val Phe Ser Cys Ser Val Met His
705                 710                 715                 720

Glu Ala Leu His Asn His Tyr Thr Gln Lys Ser Leu Ser Leu Ser Pro
                725                 730                 735

Gly Lys

<210> SEQ ID NO 34
<211> LENGTH: 519
<212> TYPE: PRT
<213> ORGANISM: Artificial Sequence
<220> FEATURE:
<223> OTHER INFORMATION: scDb4D5x3-43-LL

<400> SEQUENCE: 34

Met Glu Thr Asp Thr Leu Leu Leu Trp Val Leu Leu Leu Trp Val Pro
1               5                   10                  15

Gly Ser Thr Gly Asp Ala Ala Gln Pro Ala Met Ala Glu Val Gln Leu
            20                  25                  30

Val Glu Ser Gly Gly Gly Leu Val Gln Pro Gly Gly Ser Leu Arg Leu
        35                  40                  45

Ser Cys Ala Ala Ser Gly Phe Asn Ile Lys Asp Thr Tyr Ile His Trp
    50                  55                  60

Val Arg Gln Ala Pro Gly Lys Gly Leu Glu Trp Val Ala Arg Ile Tyr
65                  70                  75                  80

Pro Thr Asn Gly Tyr Thr Arg Tyr Ala Asp Ser Val Lys Gly Arg Phe
                85                  90                  95

Thr Ile Ser Ala Asp Thr Ser Lys Asn Thr Ala Tyr Leu Gln Met Asn
            100                 105                 110

Ser Leu Arg Ala Glu Asp Thr Ala Val Tyr Tyr Cys Ser Arg Trp Gly
        115                 120                 125

Gly Asp Gly Phe Tyr Ala Met Asp Tyr Trp Gly Gln Gly Thr Leu Val
    130                 135                 140

Thr Val Ser Ser Gly Gly Gly Ser Gln Ala Gly Leu Thr Gln Pro
145                 150                 155                 160

Pro Ala Val Ser Val Ala Pro Gly Gln Thr Ala Ser Ile Thr Cys Gly
```

165                 170                 175
Arg Asp Asn Ile Gly Ser Arg Ser Val His Trp Tyr Gln Gln Lys Pro
                180                 185                 190
Gly Gln Ala Pro Val Leu Val Val Tyr Asp Asp Ser Asp Arg Pro Ala
            195                 200                 205
Gly Ile Pro Glu Arg Phe Ser Gly Ser Asn Tyr Glu Asn Thr Ala Thr
        210                 215                 220
Leu Thr Ile Ser Arg Val Glu Ala Gly Asp Glu Ala Asp Tyr Tyr Cys
225                 230                 235                 240
Gln Val Trp Gly Ile Thr Ser Asp His Val Val Phe Gly Gly Gly Thr
                245                 250                 255
Lys Leu Thr Val Leu Gly Gly Gly Gly Ser Gly Gly Arg Ala Ser Gly
            260                 265                 270
Gly Gly Gly Ser Gly Gly Gly Ser Gln Val Gln Leu Gln Gln Ser
        275                 280                 285
Gly Pro Gly Leu Val Lys Pro Ser Gln Thr Leu Ser Leu Thr Cys Ala
290                 295                 300
Ile Ser Gly Asp Ser Val Ser Ser Asn Arg Ala Ala Trp Asn Trp Ile
305                 310                 315                 320
Arg Gln Ser Pro Ser Arg Gly Leu Glu Trp Leu Gly Arg Thr Tyr Tyr
                325                 330                 335
Arg Ser Lys Trp Tyr Asn Asp Tyr Ala Gln Ser Leu Lys Ser Arg Ile
            340                 345                 350
Thr Ile Asn Pro Asp Thr Pro Lys Asn Gln Phe Ser Leu Gln Leu Asn
        355                 360                 365
Ser Val Thr Pro Glu Asp Thr Ala Val Tyr Tyr Cys Ala Arg Asp Gly
370                 375                 380
Gln Leu Gly Leu Asp Ala Leu Asp Ile Trp Gly Gln Gly Thr Met Val
385                 390                 395                 400
Thr Val Ser Ser Gly Gly Gly Ser Asp Ile Gln Met Thr Gln Ser
                405                 410                 415
Pro Ser Ser Leu Ser Ala Ser Val Gly Asp Arg Val Thr Ile Thr Cys
            420                 425                 430
Arg Ala Ser Gln Asp Val Asn Thr Ala Val Ala Trp Tyr Gln Gln Lys
        435                 440                 445
Pro Gly Lys Ala Pro Lys Leu Leu Ile Tyr Ser Ala Ser Phe Leu Tyr
450                 455                 460
Ser Gly Val Pro Ser Arg Phe Ser Gly Ser Arg Ser Gly Thr Asp Phe
465                 470                 475                 480
Thr Leu Thr Ile Ser Ser Leu Gln Pro Glu Asp Phe Ala Thr Tyr Tyr
                485                 490                 495
Cys Gln Gln His Tyr Thr Thr Pro Pro Thr Phe Gly Gly Gly Thr Lys
            500                 505                 510
Val Glu Ile Lys Arg Ala Ala
        515

<210> SEQ ID NO 35
<211> LENGTH: 770
<212> TYPE: PRT
<213> ORGANISM: Artificial Sequence
<220> FEATURE:
<223> OTHER INFORMATION: scFv3-43-scDb3-43xhuU3-scFv3-43

<400> SEQUENCE: 35

Met Glu Thr Asp Thr Leu Leu Leu Trp Val Leu Leu Leu Trp Val Pro

-continued

```
1               5                   10                  15
Gly Ser Thr Gly Gln Val Gln Leu Gln Gln Ser Gly Pro Gly Leu Val
            20                  25                  30
Lys Pro Ser Gln Thr Leu Ser Leu Thr Cys Ala Ile Ser Gly Asp Ser
            35                  40                  45
Val Ser Ser Asn Arg Ala Ala Trp Asn Trp Ile Arg Gln Ser Pro Ser
50                      55                  60
Arg Gly Leu Glu Trp Leu Gly Arg Thr Tyr Tyr Arg Ser Lys Trp Tyr
65                  70                  75                  80
Asn Asp Tyr Ala Gln Ser Leu Lys Ser Arg Ile Thr Ile Asn Pro Asp
                85                  90                  95
Thr Pro Lys Asn Gln Phe Ser Leu Gln Leu Asn Ser Val Thr Pro Glu
            100                 105                 110
Asp Thr Ala Val Tyr Tyr Cys Ala Arg Asp Gly Gln Leu Gly Leu Asp
            115                 120                 125
Ala Leu Asp Ile Trp Gly Gln Gly Thr Met Val Thr Val Ser Ser Gly
            130                 135                 140
Gly Gly Gly Ser Asp Ile Gln Met Thr Gln Ser Pro Ser Ser Leu Ser
145                 150                 155                 160
Ala Ser Val Gly Asp Arg Val Thr Ile Thr Cys Arg Ala Ser Gln Asp
                165                 170                 175
Ile Arg Asn Tyr Leu Asn Trp Tyr Gln Gln Lys Pro Gly Lys Ala Pro
                180                 185                 190
Lys Leu Leu Ile Tyr Tyr Thr Ser Arg Leu His Ser Gly Val Pro Ser
            195                 200                 205
Arg Phe Ser Gly Ser Gly Ser Gly Thr Asp Phe Thr Phe Thr Ile Ser
            210                 215                 220
Ser Leu Gln Pro Glu Asp Ile Ala Thr Tyr Tyr Cys Gln Gln Gly Asn
225                 230                 235                 240
Thr Leu Pro Trp Thr Phe Gly Gln Gly Thr Lys Leu Glu Ile Lys Arg
                245                 250                 255
Gly Gly Gly Gly Ser Gly Gly Gly Ser Gly Gly Gly Gly Ser Gln
            260                 265                 270
Val Gln Leu Val Gln Ser Gly Ala Glu Val Lys Lys Pro Gly Ser Ser
            275                 280                 285
Val Lys Val Ser Cys Lys Ala Ser Gly Gly Thr Phe Ser Gly Tyr Thr
            290                 295                 300
Met Asn Trp Val Arg Gln Ala Pro Gly Gln Gly Leu Glu Trp Met Gly
305                 310                 315                 320
Leu Ile Asn Pro Tyr Lys Gly Val Ser Thr Tyr Asn Gly Lys Phe Lys
                325                 330                 335
Asp Arg Val Thr Ile Thr Ala Asp Lys Ser Thr Ser Thr Ala Tyr Met
                340                 345                 350
Glu Leu Ser Ser Leu Arg Ser Glu Asp Thr Ala Val Tyr Tyr Cys Ala
            355                 360                 365
Arg Ser Gly Tyr Tyr Gly Asp Ser Asp Trp Tyr Phe Asp Val Trp Gly
            370                 375                 380
Gln Gly Thr Leu Val Thr Val Ser Ser Gly Gly Gly Gly Ser Gln Ala
385                 390                 395                 400
Gly Leu Thr Gln Pro Pro Ala Val Ser Val Ala Pro Gly Gln Thr Ala
                405                 410                 415
Ser Ile Thr Cys Gly Arg Asp Asn Ile Gly Ser Arg Ser Val His Trp
                420                 425                 430
```

```
Tyr Gln Gln Lys Pro Gly Gln Ala Pro Val Leu Val Val Tyr Asp Asp
        435                 440                 445
Ser Asp Arg Pro Ala Gly Ile Pro Glu Arg Phe Ser Gly Ser Asn Tyr
    450                 455                 460
Glu Asn Thr Ala Thr Leu Thr Ile Ser Arg Val Glu Ala Gly Asp Glu
465                 470                 475                 480
Ala Asp Tyr Tyr Cys Gln Val Trp Gly Ile Thr Ser Asp His Val Val
            485                 490                 495
Phe Gly Gly Gly Thr Lys Leu Thr Val Leu Ala Ala Ala Gly Gly Ser
            500                 505                 510
Gly Gly Gly Gly Ser Gly Gly Gly Thr Gln Val Gln Leu Gln Gln Ser
            515                 520                 525
Gly Pro Gly Leu Val Lys Pro Ser Gln Thr Leu Ser Leu Thr Cys Ala
        530                 535                 540
Ile Ser Gly Asp Ser Val Ser Ser Asn Arg Ala Ala Trp Asn Trp Ile
545                 550                 555                 560
Arg Gln Ser Pro Ser Arg Gly Leu Glu Trp Leu Gly Arg Thr Tyr Tyr
                565                 570                 575
Arg Ser Lys Trp Tyr Asn Asp Tyr Ala Gln Ser Leu Lys Ser Arg Ile
            580                 585                 590
Thr Ile Asn Pro Asp Thr Pro Lys Asn Gln Phe Ser Leu Gln Leu Asn
        595                 600                 605
Ser Val Thr Pro Glu Asp Thr Ala Val Tyr Tyr Cys Ala Arg Asp Gly
        610                 615                 620
Gln Leu Gly Leu Asp Ala Leu Asp Ile Trp Gly Gln Gly Thr Met Val
625                 630                 635                 640
Thr Val Ser Ser Gly Gly Gly Ser Gly Gly Gly Gly Ser Gly Gly Gly
                645                 650                 655
Gly Gly Ser Gln Ala Gly Leu Thr Gln Pro Pro Ala Val Ser Val Ala
            660                 665                 670
Pro Gly Gln Thr Ala Ser Ile Thr Cys Gly Arg Asp Asn Ile Gly Ser
        675                 680                 685
Arg Ser Val His Trp Tyr Gln Gln Lys Pro Gly Gln Ala Pro Val Leu
        690                 695                 700
Val Val Tyr Asp Asp Ser Asp Arg Pro Ala Gly Ile Pro Glu Arg Phe
705                 710                 715                 720
Ser Gly Ser Asn Tyr Glu Asn Thr Ala Thr Leu Thr Ile Ser Arg Val
                725                 730                 735
Glu Ala Gly Asp Glu Ala Asp Tyr Tyr Cys Gln Val Trp Gly Ile Thr
            740                 745                 750
Ser Asp His Val Val Phe Gly Gly Gly Thr Lys Leu Thr Val Leu Gly
        755                 760                 765
Ser Leu
    770
```

ANTIGEN BINDING PROTEIN AGAINST HER3

CROSS-REFERENCE TO RELATED APPLICATION

This application is a U.S. national phase of International Application No. PCT/EP2017/073328, filed Sep. 15, 2017, which claims priority to European Patent Application No. 16188871.4, filed Sep. 15, 2016, both of which are incorporated by reference herein in their entirety.

The present invention provides an antigen-binding protein that specifically binds to a conformational epitope formed by domain III & IV of human epidermal growth factor receptor 3 (HER3) and antigen-binding proteins which compete therewith for binding, as well as fusion protein or conjugate comprising these. The present invention also provides nucleic acid molecule comprising a sequence encoding said antigen binding proteins, vectors comprising the nucleic acid, and cells and pharmaceuticals comprising the antigen binding protein, the fusion protein, the nucleic acid, or the vector. The present invention also provides the antigen binding protein, the fusion protein or conjugate, the nucleic acid, the vector, the cell, or the pharmaceutical for use as a medicament. The present invention further provides a method of inhibiting tumor growth or treating cancer, comprising administering a therapeutically effective amount of the antigen binding protein, the fusion protein or conjugate, the nucleic acid, the vector, the cell, or the pharmaceutical.

BACKGROUND

The complex signaling network of the ErbB family members is tightly regulated in normal human tissue. However, dysregulation of ErbB family members by receptor overexpression, alteration of receptor functions by mutations or aberrant stimulation by ligands is often associated with the development and propagation of cancer. EGFR is frequently overexpressed in colorectal cancer, ovarian cancer, head and neck squamous cell carcinoma and other cancer types and EGFR overexpression has been linked to poor prognosis. HER2 is particularly associated with human breast cancer, where it is amplified and/or overexpressed in up to 30%. It has previously been shown that also HER3 is mutated in ~11% of colon and gastric cancers which promotes oncogenic signaling in presence of HER2 (Jaiswal et al., 2013, Oncogenic ErbB3 mutations in human cancers. Cancer Cell 23, 603-617). Moreover, HER3 gained special interest due to its potent activation of the PI3K/Akt pathway which has been reported to be responsible for resistance mechanisms against ErbB targeted therapies (Holbro et al., 2003, The ErbB2/ErbB3 heterodimer functions as an oncogenic unit: ErbB2 requires ErbB3 to drive breast tumor cell proliferation. Proc. Natl. Acad. Sci. USA 100:8933-8938). The role of HER4 in cancer development has been discussed controversially, but more and more studies have revealed that HER4 is associated with tumorigenesis especially concerning acquired resistance (Canfield et al., 2014, Receptor tyrosine kinase ErbB4 mediates acquired resistance to ErbB2 inhibitors in breast cancer cells. Cell Cycle 14: 648-655).

Oncogenic mutations have been identified in HER3, e.g. in about 11% of colon and gastric cancers (Jaiswal et al., 2013). These mutations were shown to transform colonic and breast epithelial cells in a ligand-independent manner (Jaiswal et al., 2013, Oncogenic ErbB3 mutations in human cancers. Cancer Cell 23, 603-617). Mutations in the extracellular region have been localized in domain I, II and III, with many hot spots in domain II (A232V, P262H/S, G284R, D297Y, G325R), one in domain I (V104M) and one in domain III (T355A/I) (Gaborit et al. 2015, Emerging anticancer antibodies and combination therapies targeting HER3/ErbB3. Hum. Vaccin. Immunother. 12: 576-592).

ErbB family members can be targeted with antibodies. They can inhibit ligand binding and/or receptor dimerization. Furthermore, antibodies can induce receptor internalization and degradation by receptor crosslinking (Friedman et al., 2005, Synergistic down-regulation of receptor tyrosine kinases by combinations of mAbs: implications for cancer therapy. Proc. Natl. Acad. Sci. USA 102:1915-1920; Roepstorff et al., 2008, Endocytic downregulation of ErbB receptors: mechanisms and relevance in cancer. Histochem Cell Biol. 129:563-578; Moody et al., 2015, receptor crosslinking—a general method to trigger internalization and lysosomal targeting of therapeutic receptor:ligand complexes. Mol. Therapy 23:1888-1898). Additionally, antibodies containing an Fc part can mediate cancer cell killing through effector functions like antibody-dependent cellular cytotoxicity (ADCC) and complement-dependent cytotoxicity (CDC). Antibodies can also be used as delivery system for cytotoxic agents to cancer cells. Because of its emerging role as heterodimerization partner involved in propagating tumorigenesis and the development of resistance to therapy, HER3 has become a target for antibody therapy. Various antibodies directed against HER3 have been developed (Gaborit et al. 2015, Emerging anti-cancer antibodies and combination therapies targeting HER3/ErbB3. Hum. Vaccin. Immunother. 12: 576-592; Dey et al. 2015, A critical role of HER3 in HER2-amplified and non-amplified breast cancers: function of a kinase-dead RTK. Am. J. Transl. Res. 7: 733-750; Aurisicchio et al. 2012, The promise of anti-ErbB3 monoclonals as new cancer therapeutics. Oncotarget 3, 744-758; Baselga & Swain 2009, Novel anticancer targets: revisiting ErbB2 and discovering ErbB3. Nat. Rev. Cancer 9: 463-475; Gala & Chandariapaty 2014, Molecular pathways: HER3 targeted therapy. Clin. Cancer Res. 20: 1410-1416; Kol et al. 2014, HER3, serious partner in crime: therapeutic approaches and potential biomarkers for effect of HER3-targeting. Pharmacol. Ther. 143: 1-11; Zhang et al. 2016, HER3/ErbB3, an emerging cancer therapeutic target. Acta Biochim. Biophys. Sin. 48: 39-48), several of them being either directed against domain I or III involved ligand binding, others directed against domain II and/or IV, involved in receptor dimerization. One antibody, KTN3379, was described to bind between domain II and III locking the receptor in an inactive conformation (Lee et al., 2015, Inhibition of ErbB3 by a monoclonal antibody that locks the extracellular domain in an inactive configuration. Proc. Natl. Acad. Sci. USA 112: 13225-13230).

However, as the domains targeted by these antibodies may comprise one or more oncogenetic mutations, they may not be reactive against wild-type HER3, or against an oncogenic mutated HER3 which is mutated in another position than targeted by the respective antibody. There is thus, a need in the art for an antagonistic molecule which is reactive with both wild-type and mutated HER3. Furthermore, in order to inhibit ligand-independent and ligand-dependent HER3 activation, there is a need for an antagonistic molecule which binds HER3 in a way to inhibit heterodimerization as well as inhibit ligand binding.

To solve above problem, we have identified a human anti-HER3 (ErbB3) antibody, 3-43, which recognizes a unique epitope on HER3 formed by domain III and IV, which is conserved between human and mouse HER3. This antibody binds as an IgG molecule with $EC_{50}$ values below 0.1 nM to HER3-expressing tumor cells, efficiently inhibits ligand-independent and ligand-dependent receptor activation and downstream signaling, and leads to rapid and efficient receptor internalization and degradation.

SUMMARY OF THE INVENTION

In a first aspect, the present invention provides an antigen binding protein that specifically binds to a conformational epitope formed by domain III & IV of human epidermal growth factor receptor 3 (HER3).

In a second aspect the present invention provides an antigen-binding protein, which competes with the antigen-binding protein of the first aspect.

In a third aspect the present invention provides a fusion protein or conjugate comprising the antigen binding protein of the first or second aspect.

In a fourth aspect the present invention a nucleic acid molecule comprising a sequence encoding the antigen binding protein of the first or second aspect or the fusion protein of the third aspect.

In a fifth aspect the present invention provides a vector comprising the nucleic acid of the fourth aspect.

In a sixth aspect the present invention provides a cell comprising the antigen binding protein of the first or second aspect, the fusion protein of the third aspect, the nucleic acid of the fourth aspect, or the vector of the fifth aspect.

In a seventh aspect, the present invention provides a pharmaceutical composition comprising the antigen binding protein of the first or second aspect, the fusion protein of the third aspect, the nucleic acid of the fourth aspect, or the vector of the fifth aspect.

In an eighth aspect, the present invention provides the antigen binding protein of the first or second aspect, the fusion protein or conjugate of the third aspect, the nucleic acid of the fourth aspect, or the vector of the fifth aspect, the cell of the sixth aspect, or the pharmaceutical of the seventh aspect for use as a medicament.

In a ninth aspect, the present invention provides a method of inhibiting tumor growth or treating cancer, comprising administering a therapeutically effective amount of the antigen binding protein of the first or second aspect, the fusion protein or conjugate of the third aspect, the nucleic acid of the fourth aspect, or the vector of the fifth aspect, the cell of the sixth aspect, or the pharmaceutical of the seventh aspect.

LIST OF FIGURES

FIG. 1: Biochemical characterization and binding studies of IgG 3-43. A) SDS-PAGE analysis (Coomassie stained) under reducing (R) and non-reducing (NR) conditions. B) HPLC Size exclusion chromatography of IgG 3-43. C) Binding to HER3 was analyzed by ELISA. An Fc fusion protein of the extracellular domain of HER3 was used as antigen. Data are represented as mean±S.D. of three independent experiments. D) Quartz crystal microbalance experiment was performed using the Attana system. IgG 3-43 was immobilized on a carboxyl chip and frequency changes representing weight gain or loss through binding of the his-tagged extracellular domain of HER3 were measured.

Figure 2:
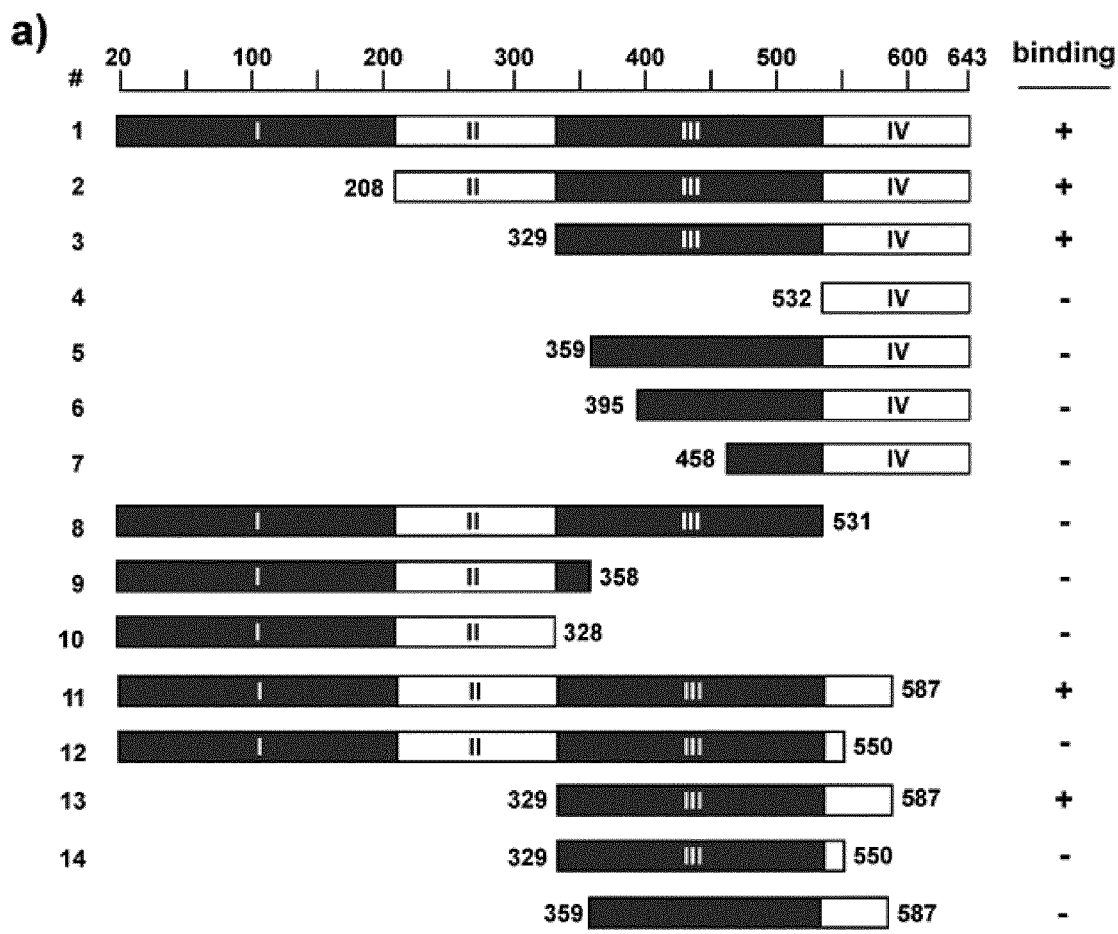
Figure 2:
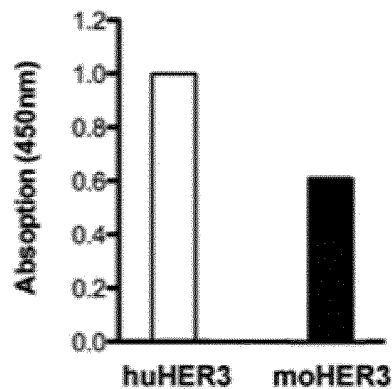

FIG. 2: Epitope mapping and cross-reactivity with mouse HER3 A) Epitope mapping: Sequences encoding for truncated forms of the HER3 extracellular domain were fused to the IgG1 Fc-part sequence. The resulting constructs were transfected and expressed in HEK293 cells and the proteins were purified from the supernatant via protein A affinity chromatography. The Fc-fusion proteins were used as antigens in an ELISA assay and binding IgG 3-43 was detected with an HRP-conjugated anti-Fab antibody. B) Cross-reactivity of 3-43 with human and mouse HER3 using the extracellular region of human and mouse HER3 fused to a human Fc region. Binding of the scFv 3-43 to immobilized HER3-fusion protein was detected with an anti-His-tag antibody.

Figure 3:
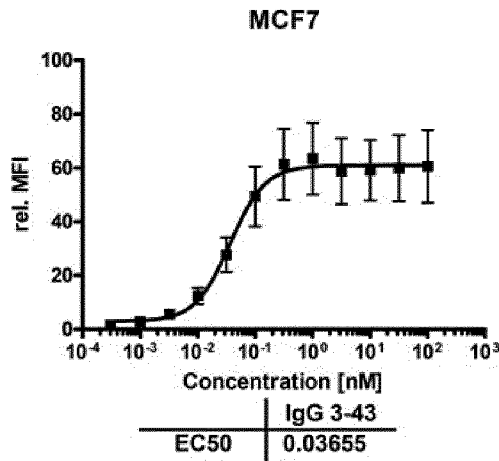
Figure 3:
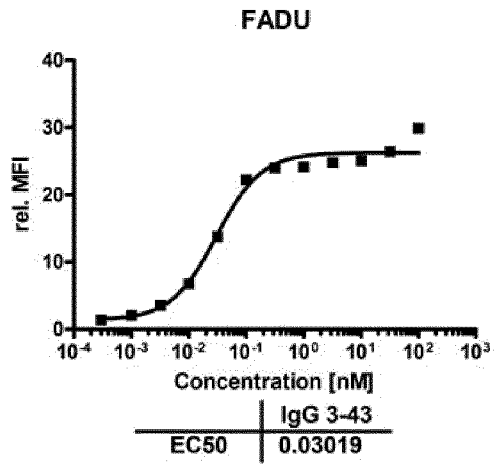
Figure 3:
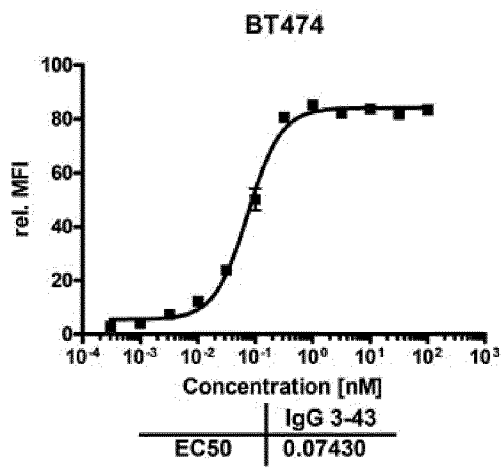
Figure 3:
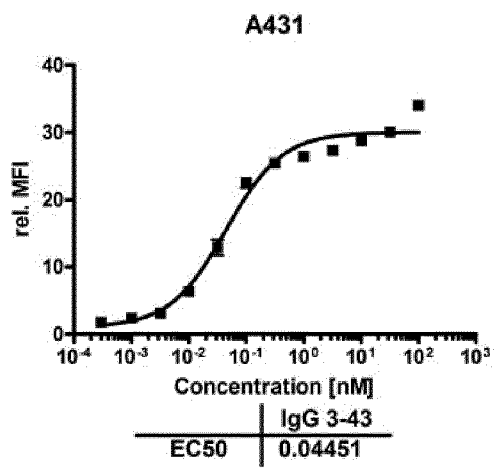
Figure 3:
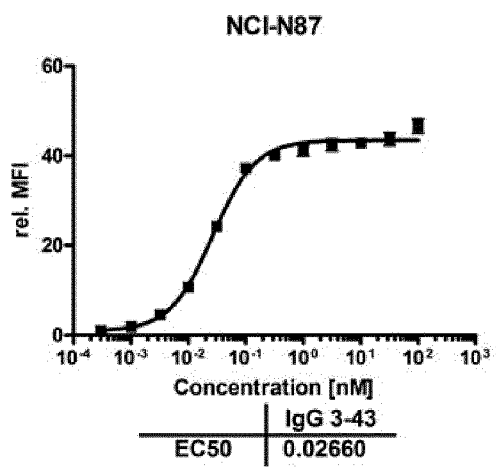
Figure 3:
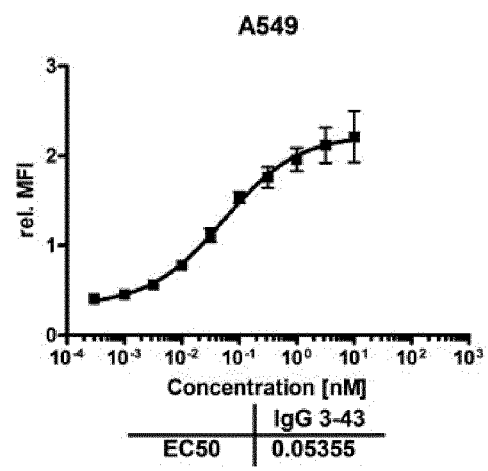

FIG. 3: Binding of IgG 3-43 to HER3-expressing tumor cell lines. Various tumor cell lines (as indicated) were incubated with varying concentrations of IgG 3-43 and bound antibody was detected with a PE-labeled secondary antibody. Cells were analyzed using a Miltenyi MACSquant. $EC_{50}$ values were calculated from n=1 to 3 experiments.

Figure 4:
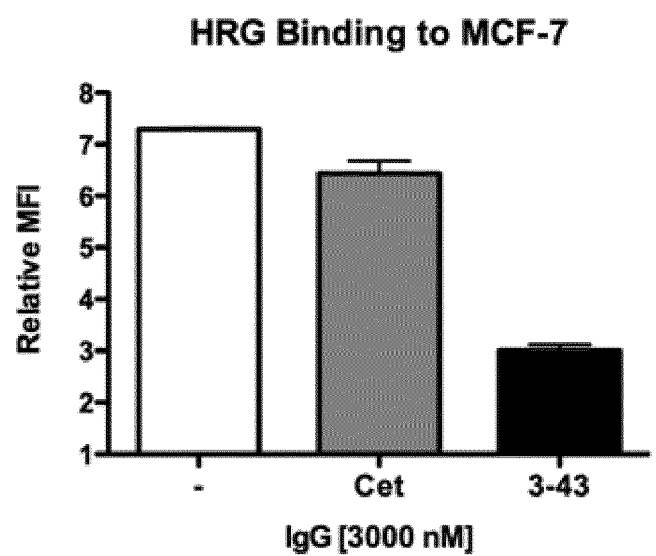

FIG. 4: IgG 3-43 competes with HRG for binding to HER3 expressing cells. Binding of his tagged recombinant human heregulin-β1 was measured by flow cytometry via PE conjugated anti-His antibody. Preincubation with excess of IgG 3-43 potently reduced the signal by more than 60%, whereas the anti-EGFR antibody Cetuximab did not show the same effect.

Figure 5:
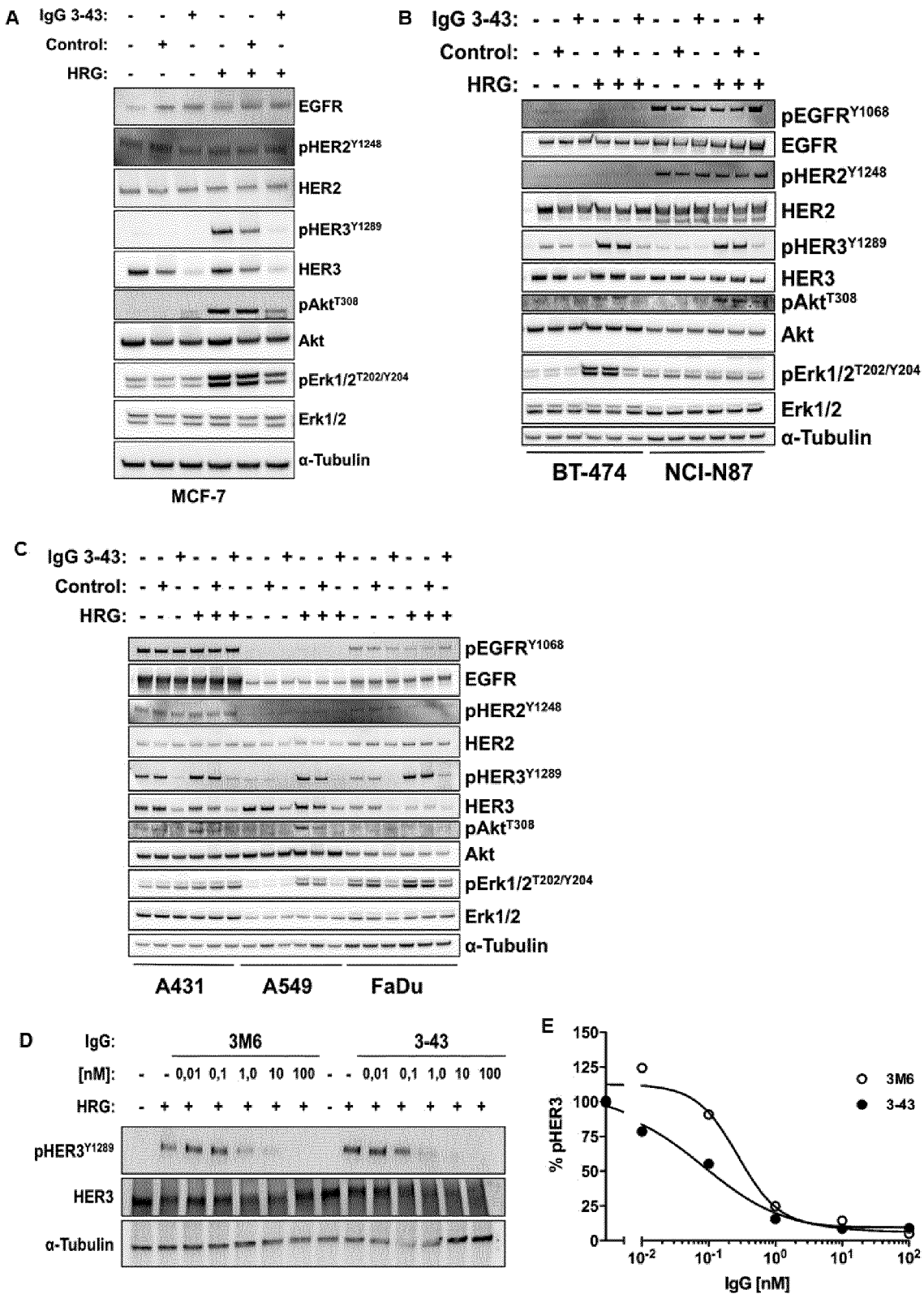

FIG. 5: IgG 3-43 inhibits HRG-induced phosphorylation of HER3 and downstream targets. Indicated cells were seeded in 6 well plates to be semi confluent on the day of experiment. After attachment, cells were serum starved over night and incubated for one hour with 100 nM IgG 3-43 or control (Rituximab) IgG (A, B, C) or with different concentrations of IgG 3-43 or IgG 3M6 (D, E). IgG treated and untreated cells were stimulated with 50 ng/ml human heregulin-β1. Subsequently, cells were lysed with RIPA buffer containing protease inhibitors and cell lysates were analyzed by western blot using the indicated antibodies.

Figure 6:
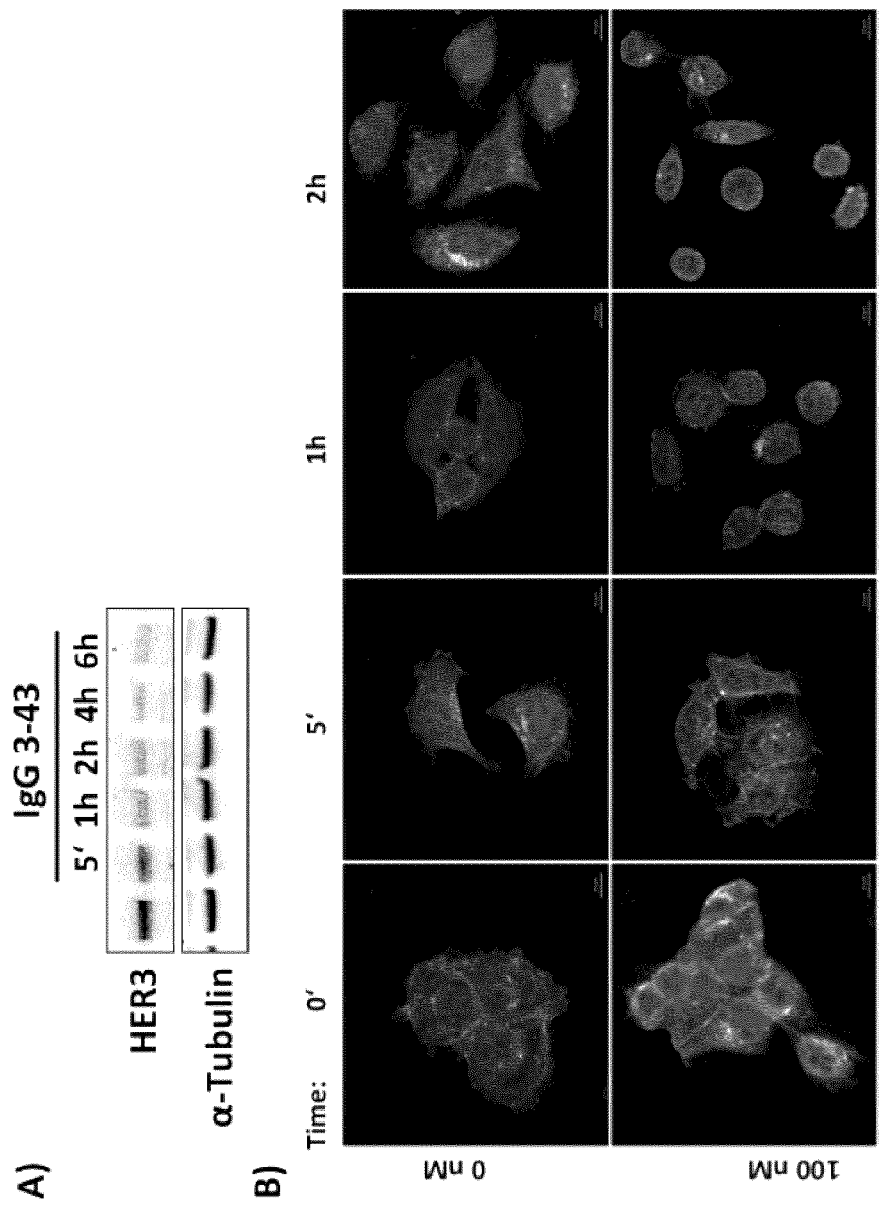

FIG. 6: IgG 3-43 is internalized into cancer cells and leads to reduction of cellular HER3 levels. A) MCF-7 cells were incubated with 100 nM IgG 3-43 for the indicated timepoints and HER3 levels were analyzed by western blot. The HER32 signal rapidly decreased, with a reduction already seen after 5 minutes of incubation time. B) Cy5 labeled IgG 3-43 was incubated with MCF-7 cells at 37° C. for the indicated timepoints. Cellular membranes were stained with Concanavalin-A and cells were fixed with 4% paraformaldehyde. Pictures of treated and control cells were taken with a spinning disk microscope. Blue: Dapi nuclei staining; green: Con A membrane staining; purple: Cy5-labeled IgG 3-43.

Figure 7:
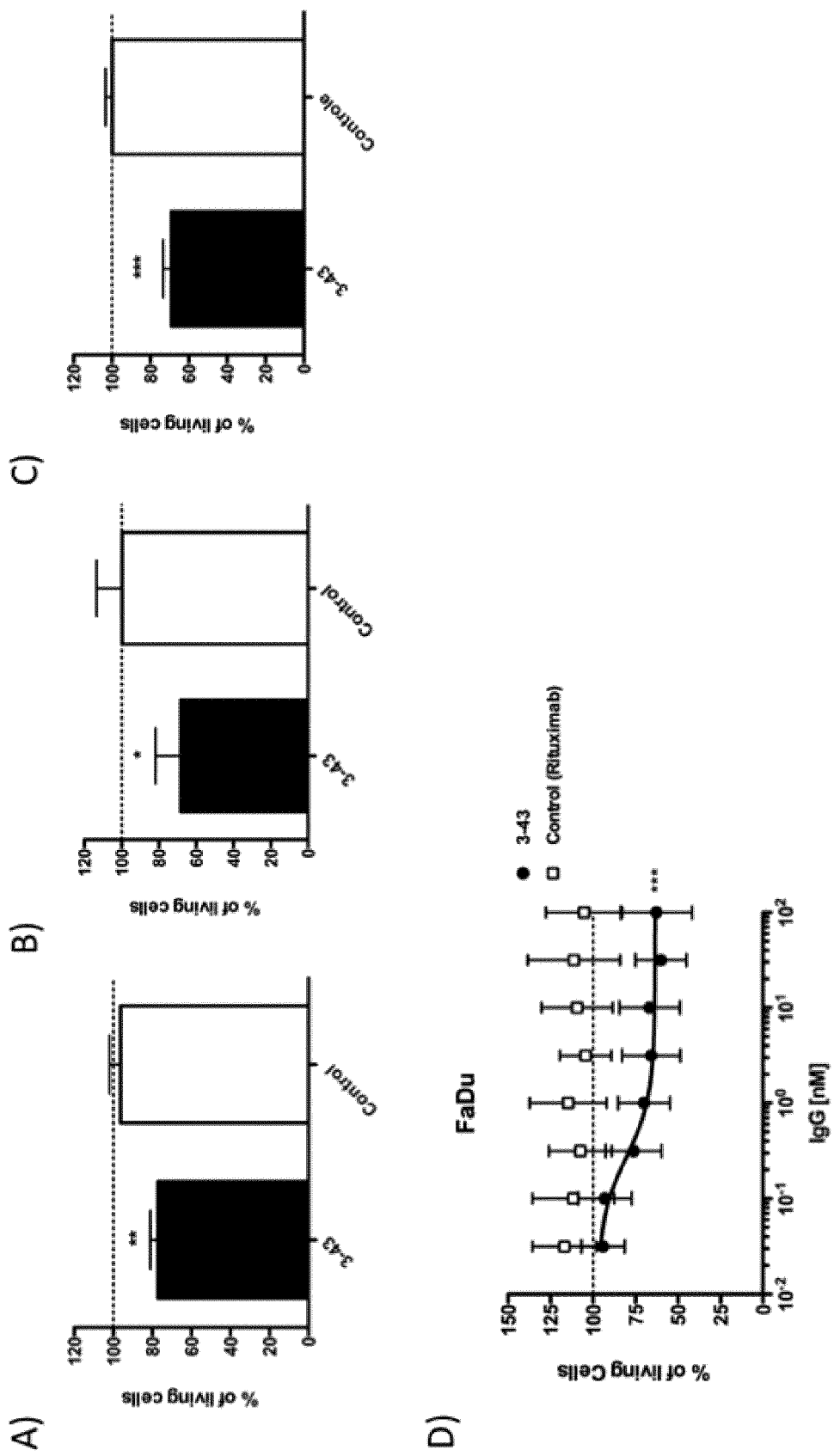

FIG. 7: IgG 3-43 reduces HRG-mediated cancer cell proliferation in vitro. NCI-N87 (A), BT-474 (B) and MCF-7 (C) cells were seeded at low densities in 96 well plates, let adhere over night, and were incubated for one week under low (0.2%) serum concentrations and in the presence of 10 ng/ml heregulin with 10 μg IgG 3-43 or Rituximab as control. D) FaDu cells were known to produce heregulin in an autocrine manner and were subjected to the same proliferation assay but in the absence of ambient heregulin. Titration of IgG 3-43 revealed a potent growth inhibiting effect even at low nanomolar concentrations.

Figure 8:
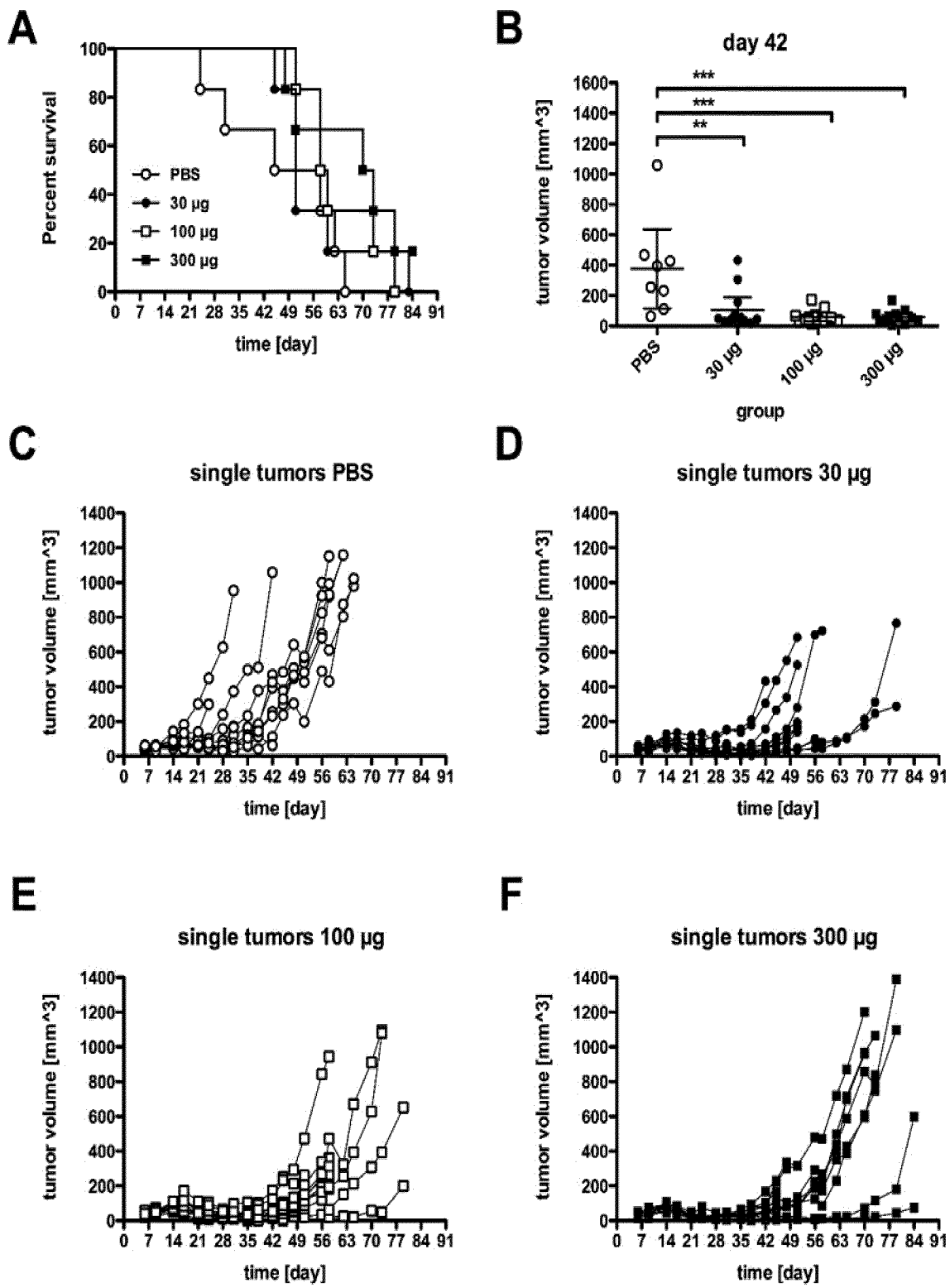

FIG. 8: IgG 3-43 inhibits growth of s.c. xenograft FaDu tumor model in SCID mice. Mice were treated when tumors reached a size of approx. 100 $mm^3$ (2 weekly injections for 3 weeks, see lines) at the indicated doses. A) Kaplan-Mayer blot of survival. B) Tumor volumes at day 42. C)-F) Growths of individual tumors in mice treated with PBS (C), 30 μg of IgG 3-43 (D), 100 μg IgG 3-43 (E), or 300 μg IgG 3-43 (F).

Figure 9:
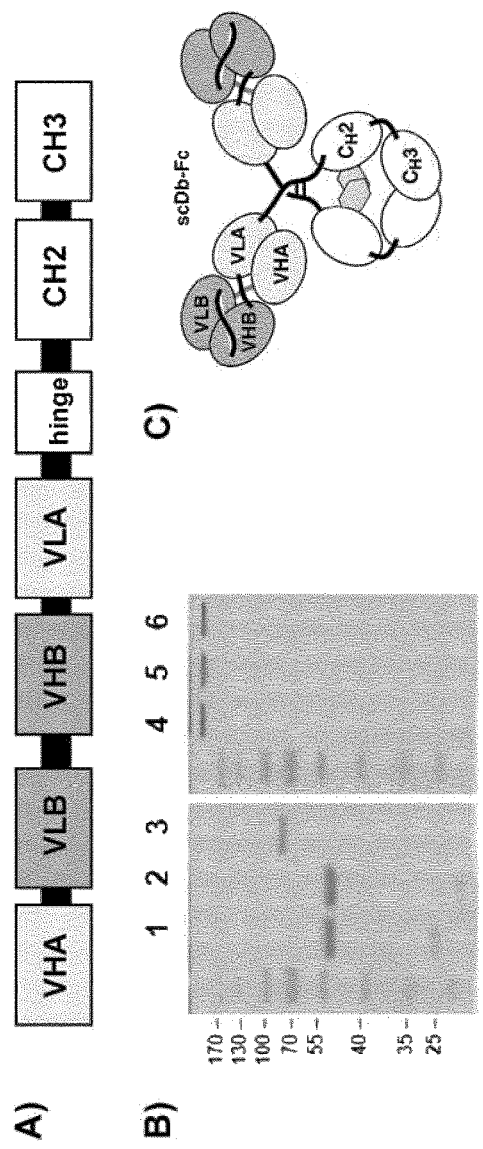
Figure 9:
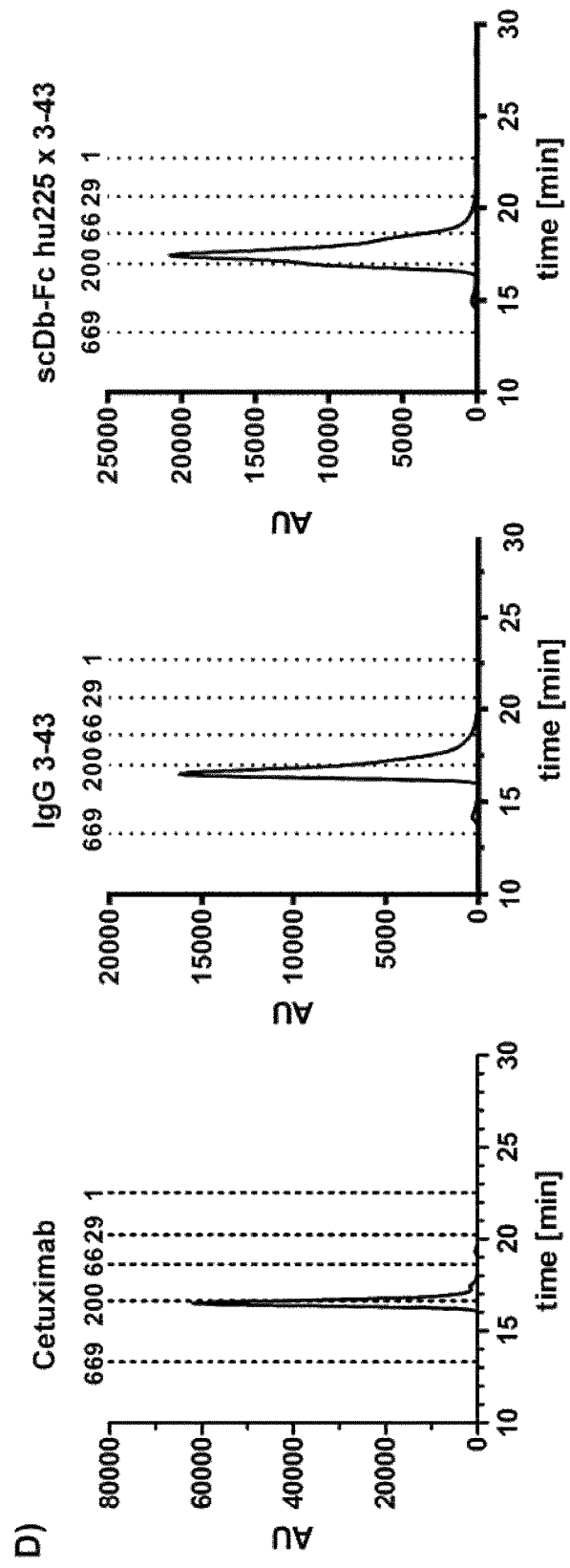

FIG. 9: Biochemical characterization of scDb hu225x3-43-Fc. A) Schematic arrangement of variable and constant domains in a scDb-Fc fusion protein. B) SDS-PAGE analysis (10% PAA, Coomassie stained) of cetuximab (lane 1, 4), IgG 3-43 (lane 2, 5) and scDb hu225x3-43-Fc (lane 3, 6) under reducing (lane 1-3) and non-reducing (lane 4-6) conditions. C) Schematic structure of a dimeric scDb-Fc fusion protein. D) Size exclusion chromatography of cetuximab, IgG 3-43 and scDb hu225x3-43-Fc.

Figure 10:
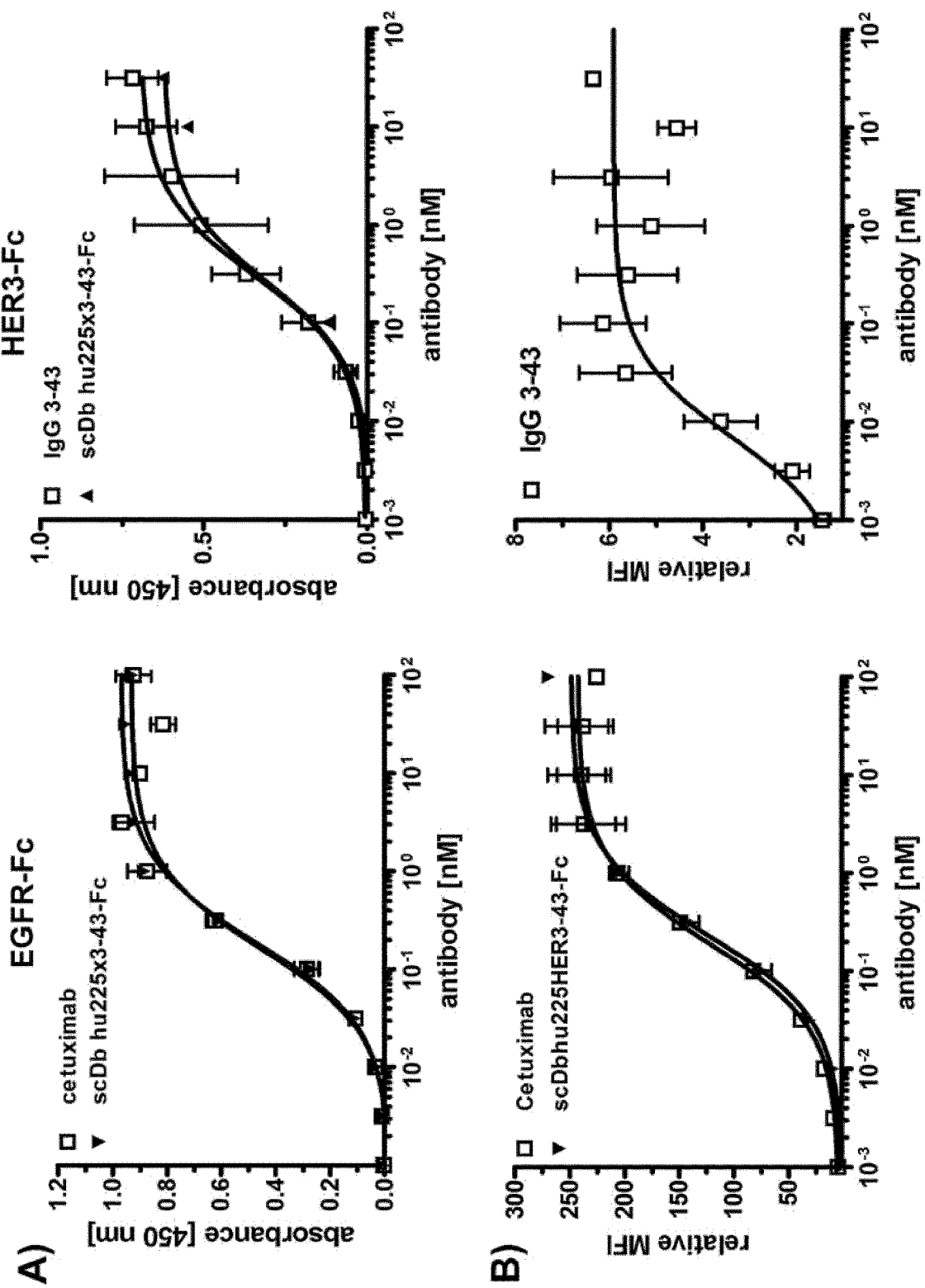

FIG. 10: Binding studies of scDb hu225x3-43-Fc. A) Binding of scDb hu225x3-43-Fc in comparison to cetuximab and IgG 3-43 to immobilized receptor-ECD proteins (0.2 µg/well) was analyzed by ELISA. Antibodies were detected with HRP-conjugated anti-human IgG (Fc specific) antibody. Optical density was measured at 450 nm. Data are represented as mean±S.D. of three independent experiments. B) Binding to FaDu cells was analyzed by flow cytometry. All antibodies were detected with PE-conjugated anti-human Fc antibody. Data are represented as mean±S.D. of three independent experiments.

Figure 11:
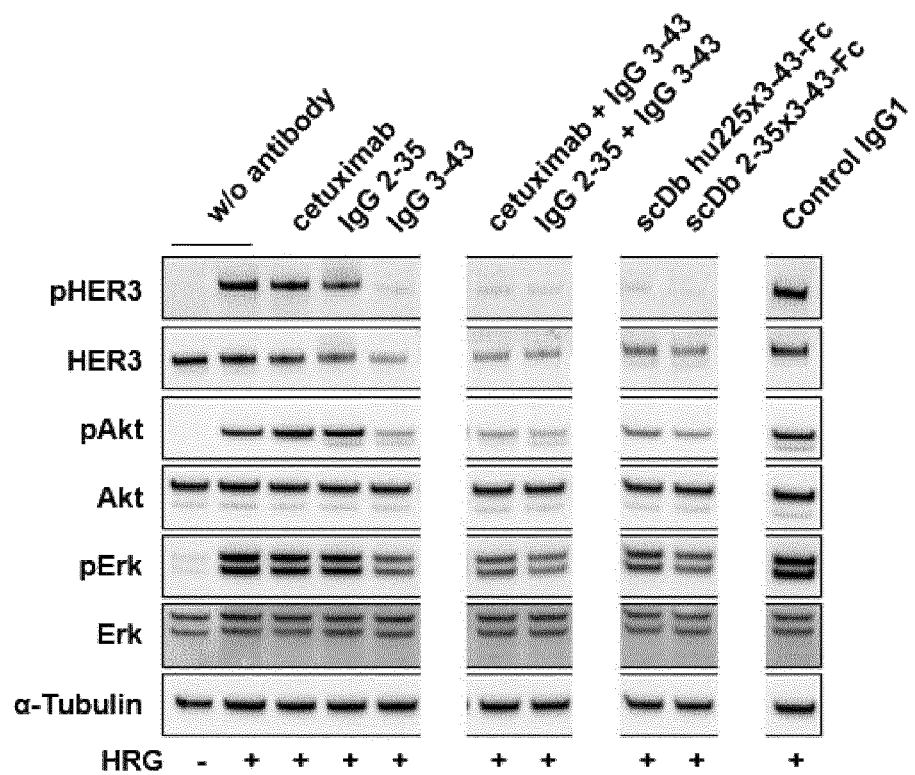

FIG. 11: Inhibition of HER3 signaling in MCF-7 cells. Cells (grown in RPMI 1640, 0.2% serum) were treated with 75 nM of the parental IgG molecules or the scDb-Fc molecules and 37.5 nM of each parental antibody for the combinational treatment for 1 h at 37° C. An irrelevant IgG1 was used as control. Cells were stimulated with heregulin (50 ng/ml) for 15 min at 37° C., before being lysed using RIPA buffer (50 mM Tris pH 7.5, 150 mM NaCl, 10 mM NaF, 20 mM β-glycerophosphate, 1 mM EDTA, 1% NP-40, 1 mM $Na_3VO_4$, 0.5 mM PMSF, 0.25% DOC, 0.1% SDS) containing a protease inhibitor cocktail at 4° C. Cell lysates were analyzed by immunoblotting using antibodies against HER3, phospho-HER3 (Tyr1289), Akt, phospho-Akt (Thr308), Erk½, phospho-Erk½ (Thr202/204) and α-Tubulin. Data shown are representative of two independent experiments.

Figure 12:
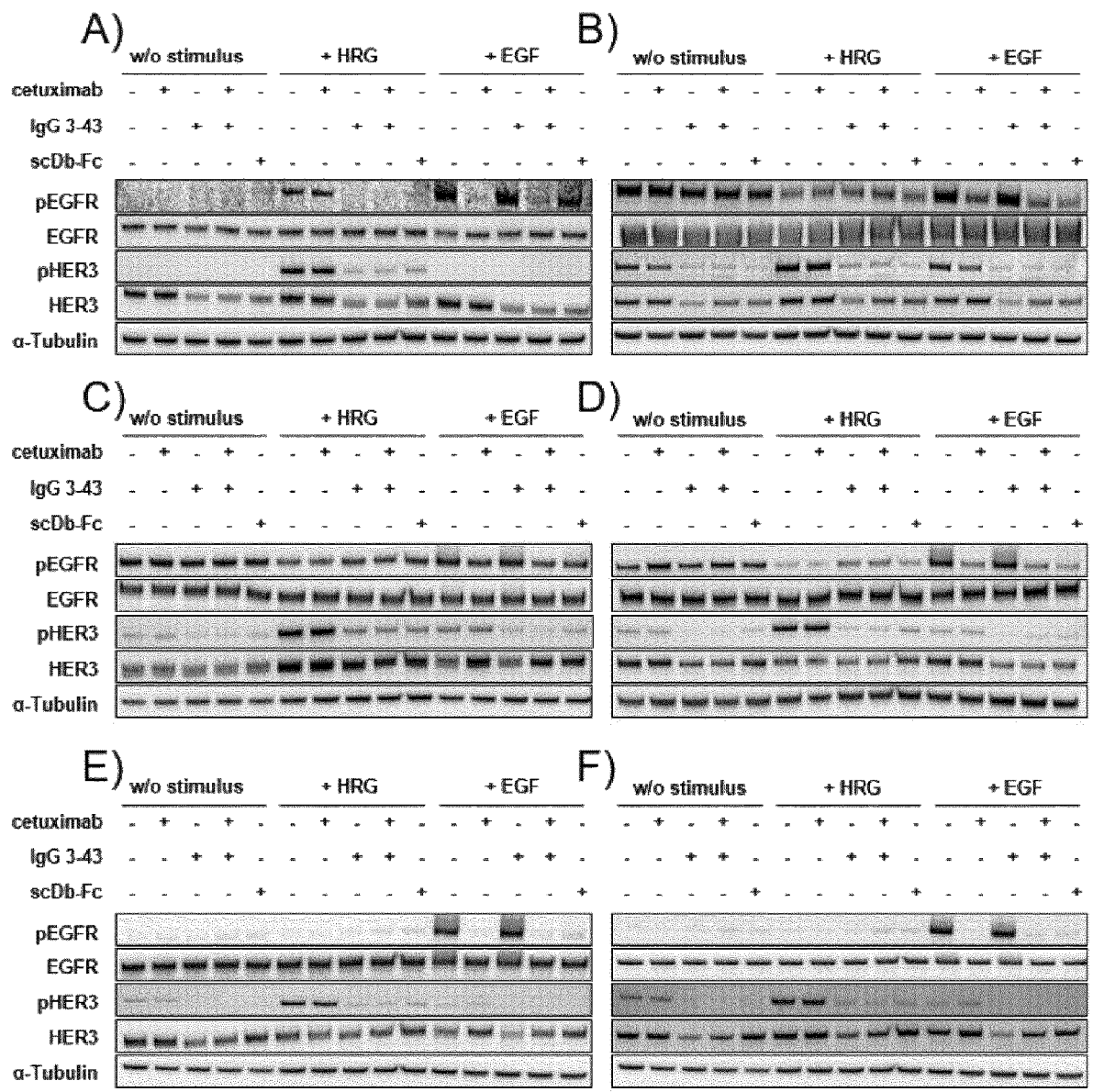
Figure 13:
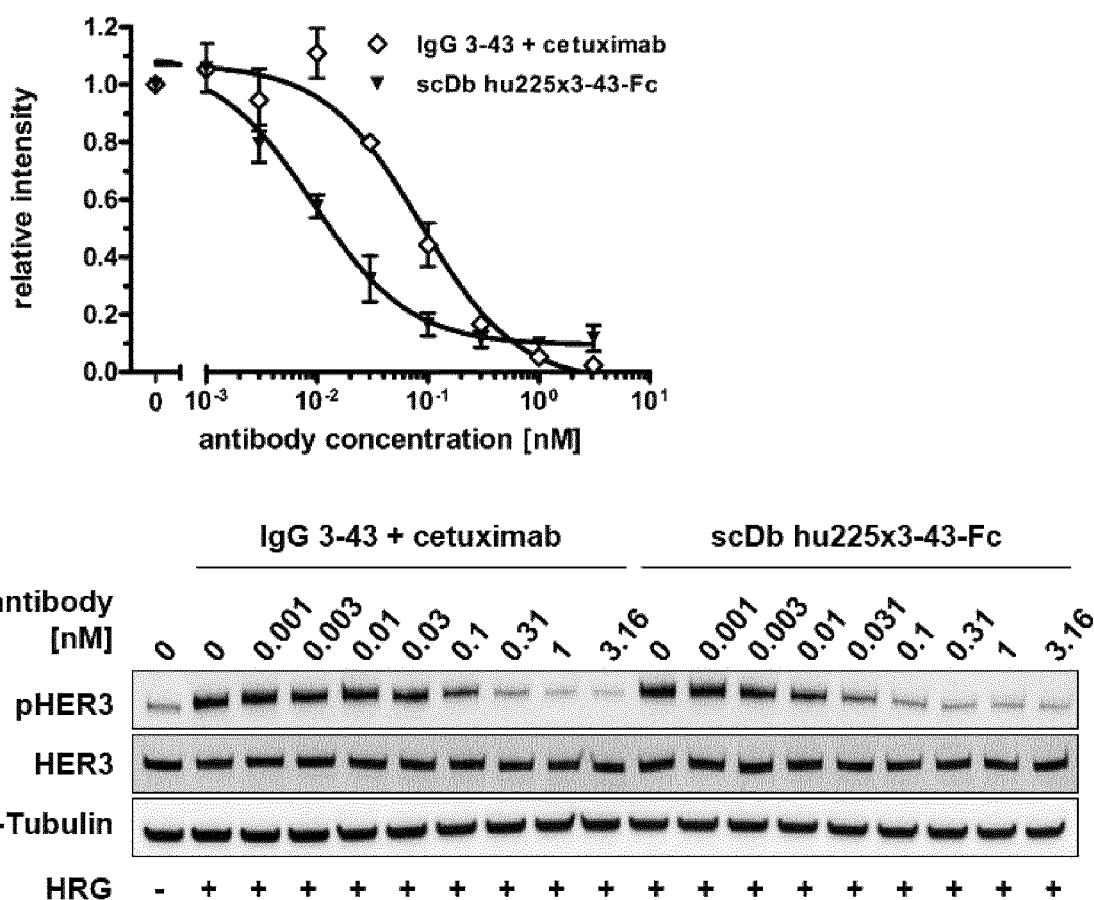

FIG. 12: Inhibition of receptor phosphorylation in different ErbB-overexpressing cell lines. Different cell lines (A; MCF-7; B, A-431; C, NCI-N87; D, SK-BR-3; E, FaDu; F, A549) were treated with 50 nM cetuximab, IgG 3-43 or scDb hu225x3-43-Fc for 1 h at 37° C. prior to stimulation with heregulin (50 ng/ml) or EGF (50 ng/ml) for 15 min. Cells were lysed using RIPA buffer (50 mM Tris pH 7.5, 150 mM NaCl, 10 mM NaF, 20 mM β-Glycerophosphate, 1 mM EDTA, 1% NP-40, 1 mM $Na_3VO_4$, 0.5 mM PMSF, 0.25% DOC, 0.1% SDS) containing a protease inhibitor cocktail and cell lysates were analyzed by immunoblotting using antibodies against EGFR, phospho-EGFR (Tyr1068), HER3, phospho-HER3 (Tyr1289) and α-Tubulin FIG. 13: Inhibition of receptor phosphorylation in FaDu cells. Cells were treated with serial dilutions of scDb hu225x3-43-Fc and IgG 3-43 combined with cetuximab for 1 h at 37° C. prior to stimulation with heregulin (50 ng/ml). Cells were lysed using RIPA buffer (50 mM Tris pH 7.5, 150 mM NaCl, 10 mM NaF, 20 mM β-Glycerophosphate, 1 mM EDTA, 1% NP-40, 1 mM $Na_3VO_4$, 0.5 mM PMSF, 0.25% DOC, 0.1% SDS) containing a protease inhibitor cocktail and lysates were analyzed by immunoblotting using antibodies against HER3, phospho-HER3 (Tyr1289) and α-Tubulin. Levels of phospho-HER3 were quantified relative to the loading control α-Tubulin and normalized to the control without antibody. Data shown are representative of at least two independent experiments with error bars representing the mean±SD values. A, quantified data. B, representative images.

Figure 14:
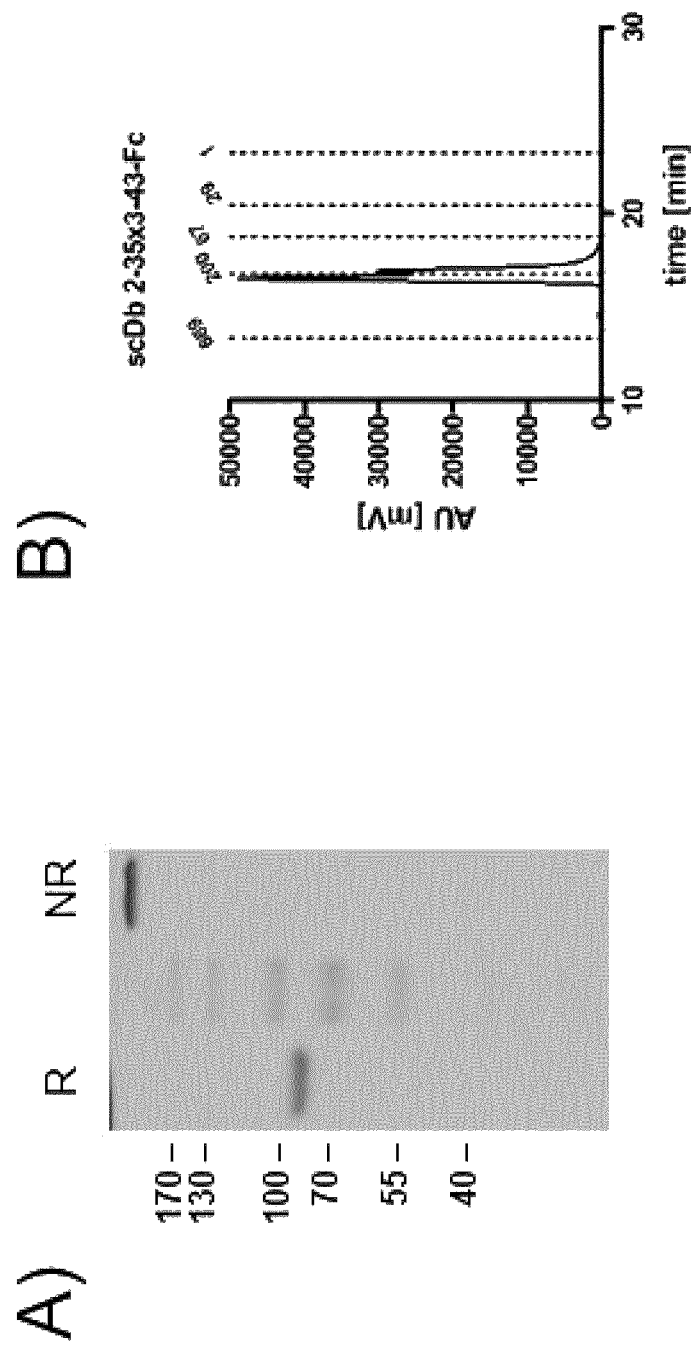

FIG. 14: Biochemical characterization of scDb 2-35x3-43-Fc. A) SDS-PAGE analysis (10% PAA, Coomassie stained) of scDb 2-35x3-43-Fc under reducing (R) and non-reducing (NR) conditions. B) Size exclusion chromatography of scDb 2-35x3-43-Fc.

Figure 15:
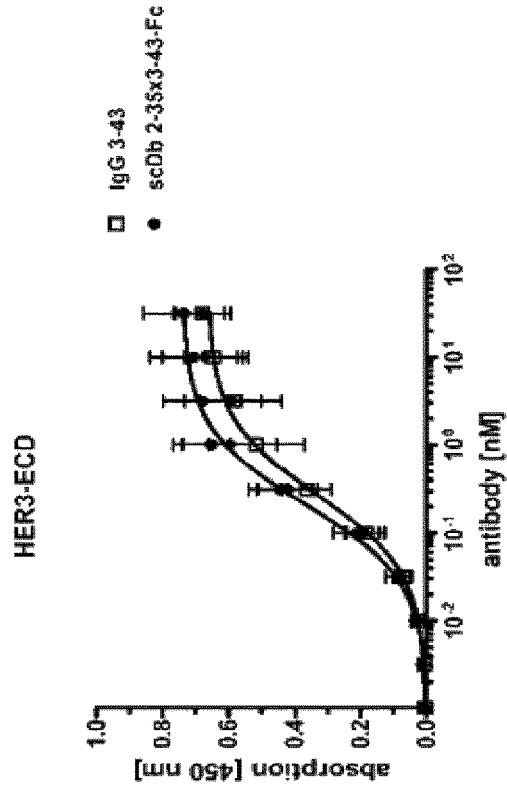
Figure 15:
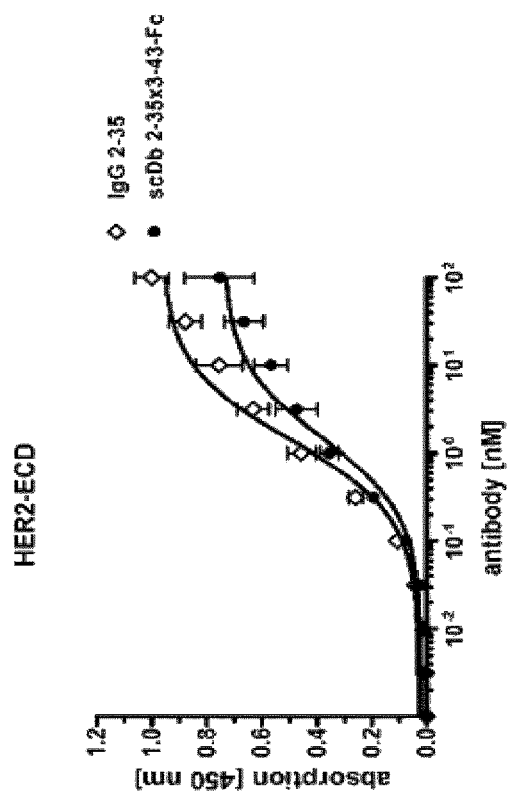
Figure 16:
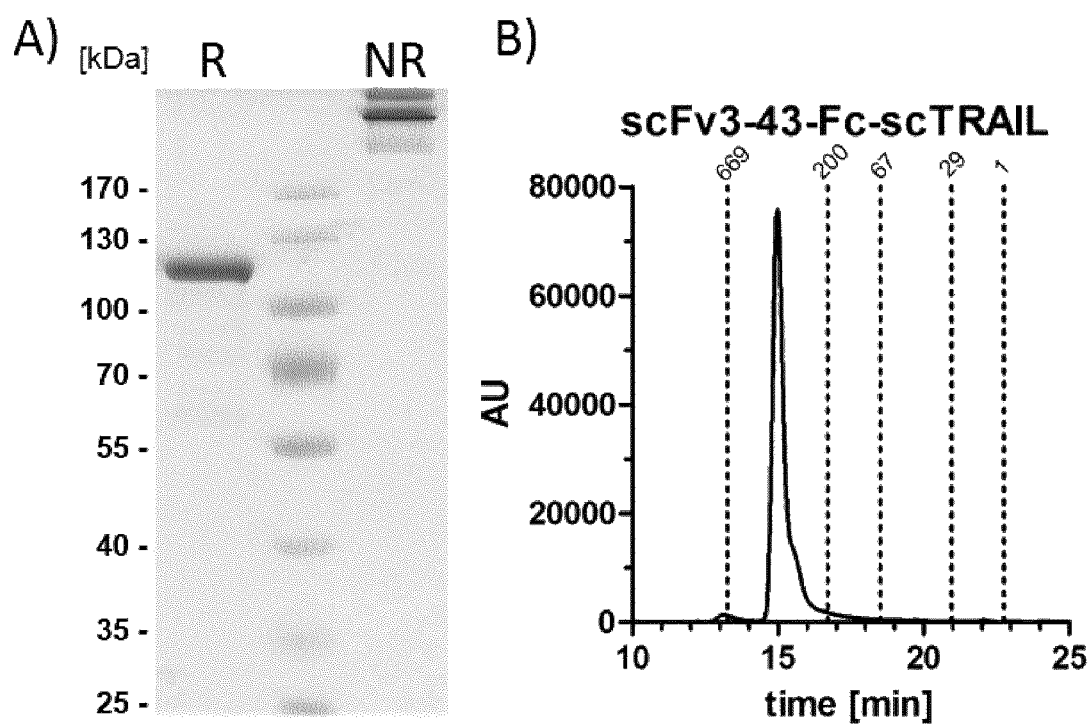
Figure 17:
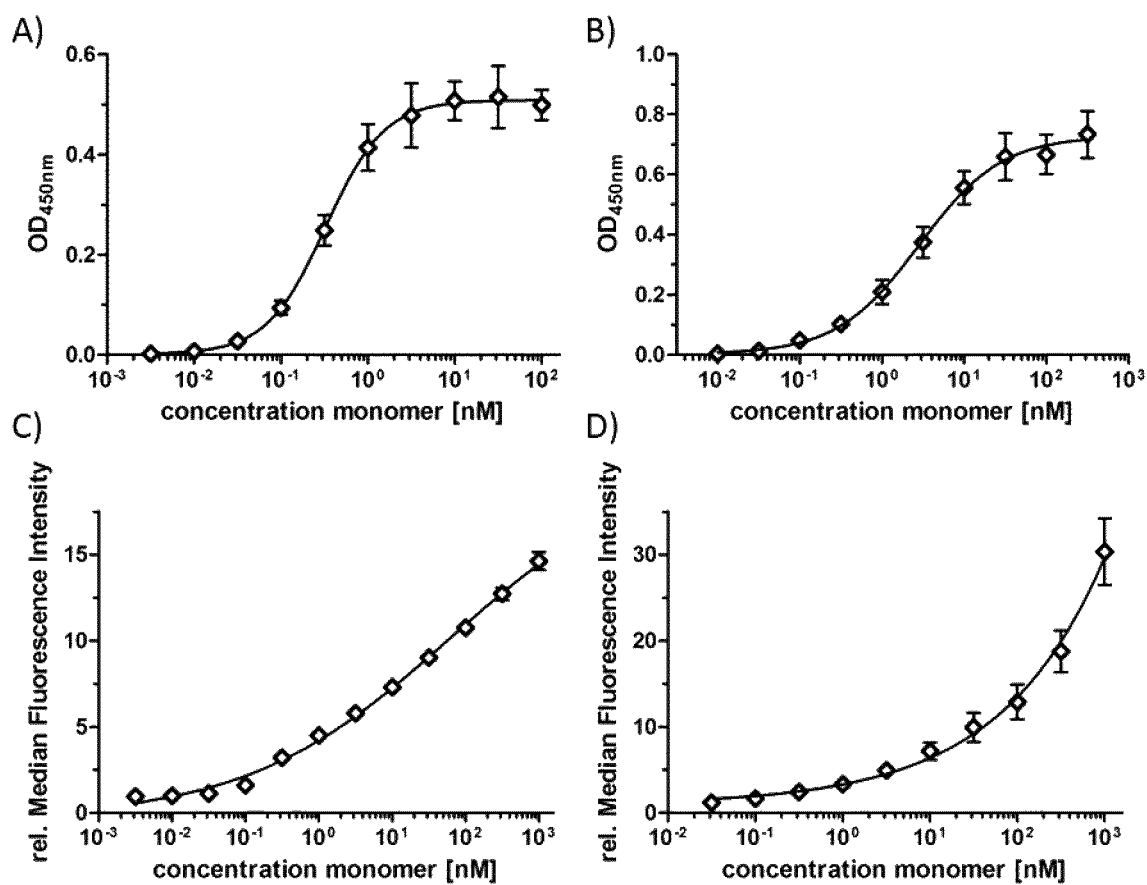

FIG. 15: Binding studies of scDb 2-35x3-43-Fc. Binding of scDb 2-35x3-43-Fc in comparison to IgG 2-35 and IgG 3-43 to immobilized receptor-ECD proteins (0.2 µg/well) was analyzed by ELISA. Antibodies were detected with HRP-conjugated anti-human IgG (Fc specific) antibody. Optical density was measured at 450 nm. Data are represented as mean±S.D. of three independent experiments FIG. 16: Biochemical characterization of scFv3-43-Fc-scTRAIL. A) SDS-PAGE analysis (10% PAA, Coomassie stained) under reducing (R) and non-reducing (NR) conditions. B) Size exclusion chromatography of scFv-3-43-Fc-scTRAIL FIG. 17: Binding studies of scFv3-43-Fc-scTRAIL. Binding to HER3 (A) and human TRAIL-R2 (B) was analyzed by ELISA. Fc fusion proteins of the extracellular domains of HER3 or human TRAIL-R2 were used as antigens. Optical density was measured at 450 nm. Binding to Colo205 (C) and HCT-116 cells (D) was analyzed by flow cytometry. Data are represented as mean±S.D. of at least three independent experiments.

Figure 18:
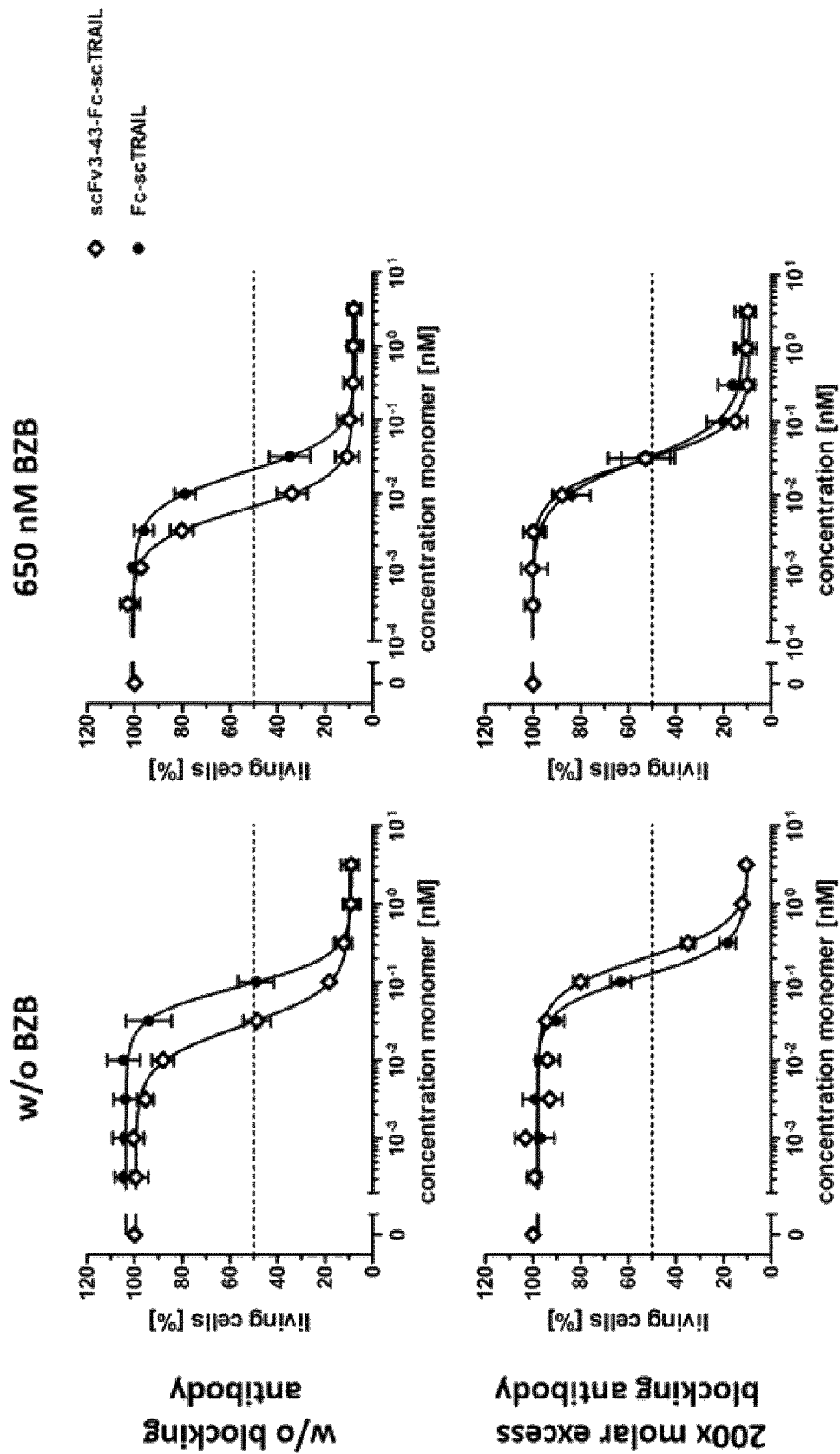

FIG. 18: Induction of cell death compared to a non-targeted construct. Induction of cell death of scFv3-43-Fc-scTRAIL was analyzed in comparison to the corresponding non-targeted fusion proteins Fc-scTRAIL. Effects on Colo205 were investigated after preincubation with medium or bortezomib (650 nM) to sensitize the cells for TRAIL-induced apoptosis. To confirm targeting effects of scFv3-43-Fc-scTRAIL, experiments were additionally performed in the presence of 200-fold molar excess of scFv3-43-Fc. Data are represented as mean±S.D. of three independent experiments.

Figure 19:
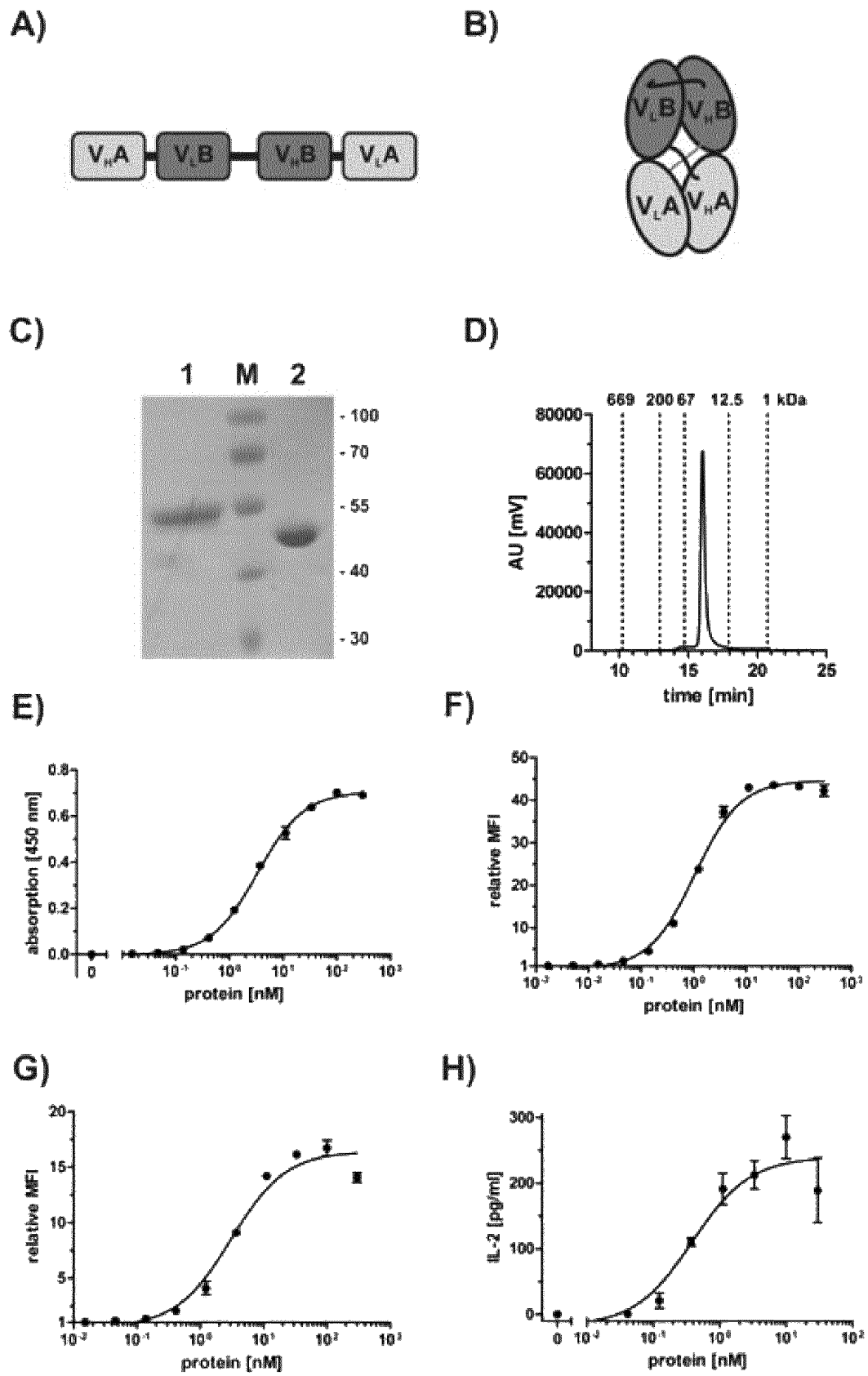

FIG. 19: Biochemical characterization, binding and IL-2 assay of scDb 3-43xCD3. A) Schematic arrangement of variable and constant domains in a scDb construct. B) Schematic structure of a scDb construct. C) SDS-PAGE analysis (12% PAA, Coomassie stained) of scDb 3-43xCD3 under reducing (1) and non-reducing (2) conditions. D) Size exclusion chromatography of scDb 3-43xCD3. E) Binding of scDb 3-43xCD3 was analyzed by ELISA using a Fc fusion protein of the extracellular domain of HER3 as antigen. Protein was detected with HRP-conjugated anti-His antibody. Optical density was measured at 450 nm. F and G) Binding to HER3-expressing MCF-7 (F) and CD3-expressing Jurkat cells (G) was analyzed by flow cytometry. Bound protein was detected with PE-conjugated anti-His antibody. H) IL-2 release of activated PBMC by scDb 3-43xCD3 bound to HER3-expressing Colo205 cells. Concentration of IL-2 in the supernatant was determined by ELISA according to the instructions supplied by the manufacturer (human IL-2 kit, R&D). Data are represented as mean±S.D.

Figure 20:
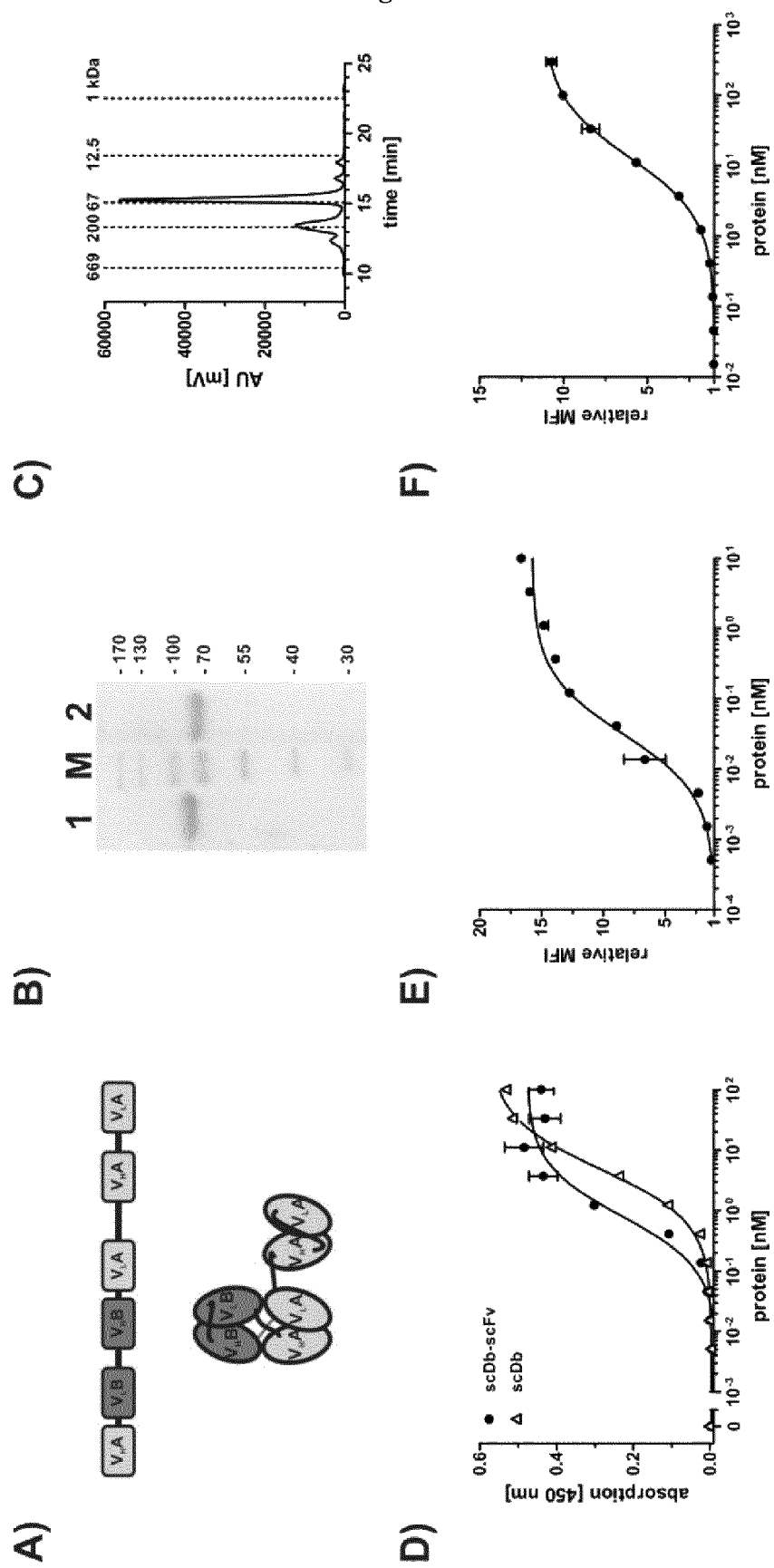

FIG. 20: Biochemical characterization and binding of a trivalent, bispecific scDb3-43xCD3-scFv3-43 fusion protein. A) Schematic arrangement and structure of variable domains in a scDb-scFv construct. B) SDS-PAGE analysis (10% PAA, Coomassie stained) of scDb3-43xCD3-scFv3-43 under reducing (1) and non-reducing (2) conditions. C) Size exclusion chromatography of scDb3-43xCD3-scFv3-43. D) Binding of scDb3-43xCD3-scFv3-43 was analyzed by ELISA using a Fc fusion protein of the extracellular domain of HER3 as antigen. Protein was detected with HRP-conjugated anti-His antibody. Binding of scDb3-43xCD3 was used as monovalent (for HER3) control. Optical density was measured at 450 nm. E) and F) Binding to HER3-expressing MCF-7 (E) and CD3-expressing Jurkat cells (F) was analyzed by flow cytometry. Bound protein was detected with PE-conjugated anti-His antibody. Data are represented as mean±S.D.

Figure 21:
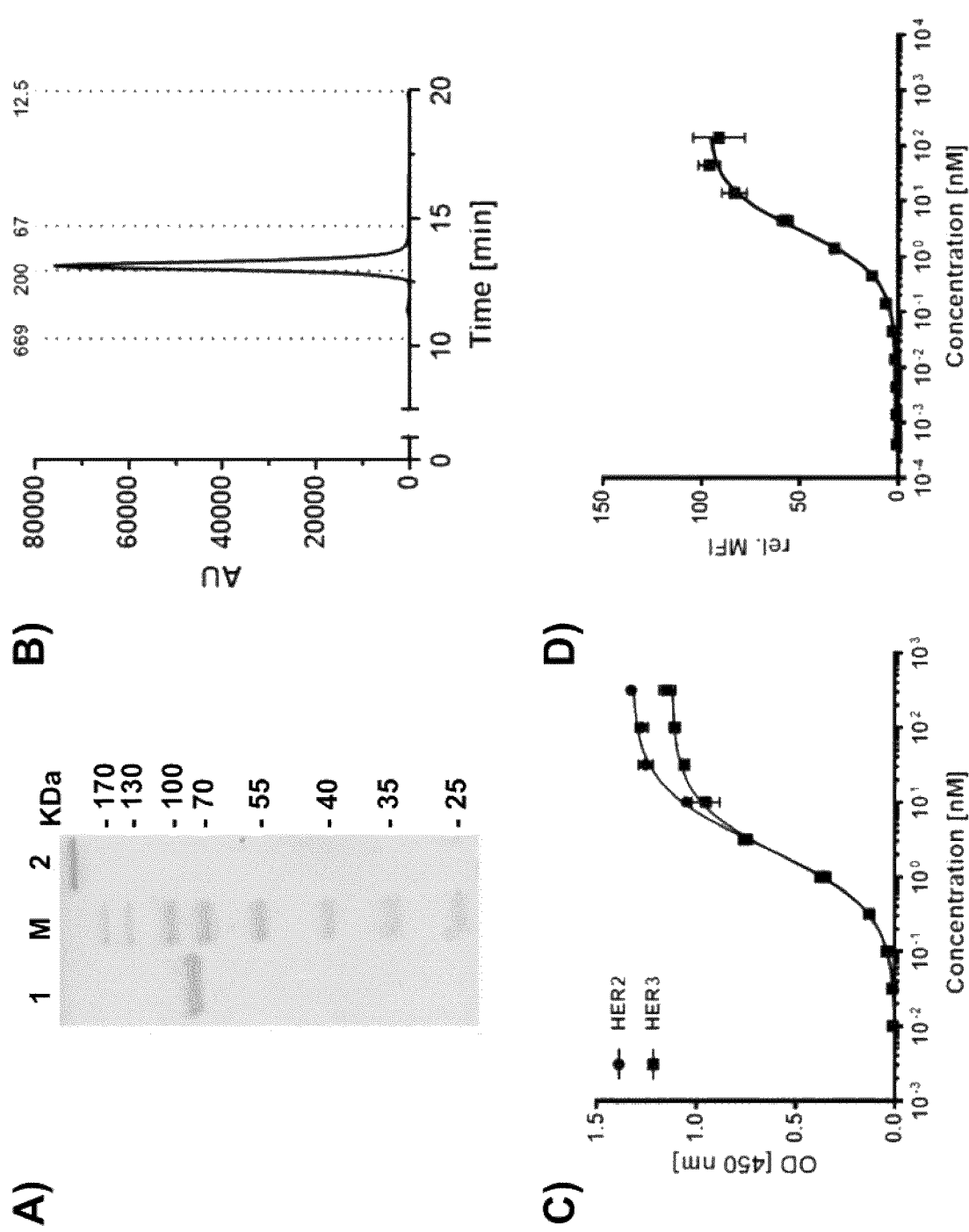

FIG. 21: Characterization of a bispecific scDb 4D5x3-43-Fc targeting HER2 and HER3. A) SDS-PAGE analysis (10% PAA, Coomassie stained) of scDb 4D5x3-43-Fc under reducing (1) and non-reducing (2) conditions. B) Size exclusion chromatography of scDb 4D5x3-43-Fc. C) Binding of scDb 4D5x3-43-Fc was analyzed by ELISA using His-tagged proteins of the extracellular domains of HER2 or HER3 as antigens. Bound protein was detected with HRP-conjugated anti-human Fc antibody. Optical density was measured at 450 nm. D) Binding to HER2- and HER3-expressing FaDu cells was analyzed by flow cytometry. Bound protein was detected with PE-conjugated anti-human Fc antibody. Data are represented as mean±S.D.

Figure 22:
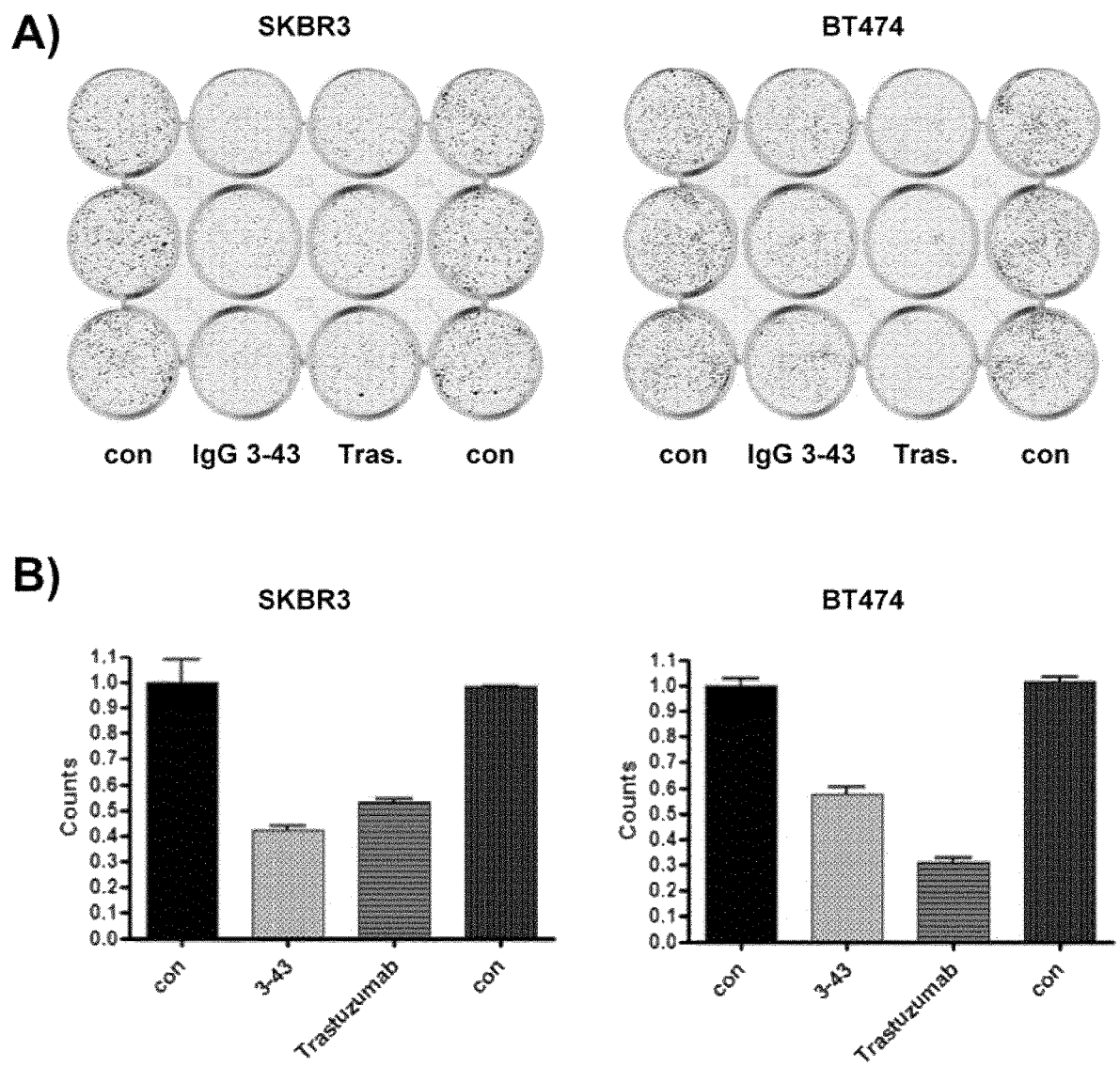

FIG. 22: IgG 3-43 inhibits ligand-independent colony formation of SKBR3 and BT474. A) Colony formation assay with SKBR3 and BT474 incubated for 12 days with IgG 3-43 (50 nM). Untreated cells (con), and cells treated with trastuzumab (Tras., directed against HER2) were included as further controls. Shown are triplicates. B) Quantification of formed colonies of SKBR3 and BT474 cells incubated as described in A).

Figure 23:
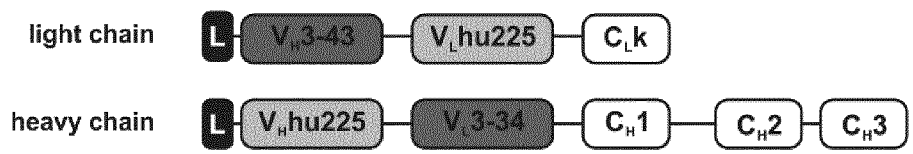
Figure 23:
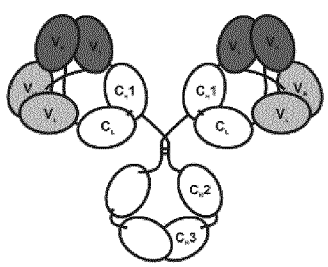
Figure 23:
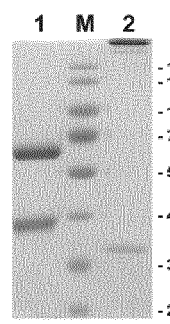
Figure 23:
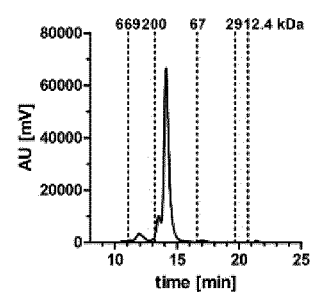
Figure 23:
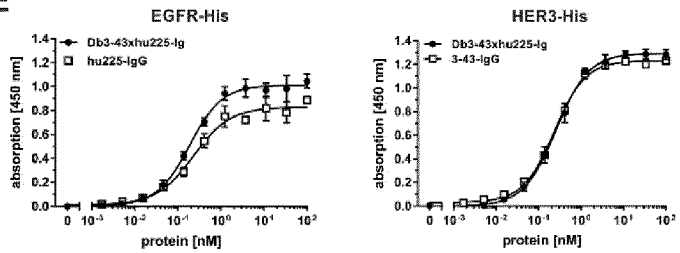
Figure 23:
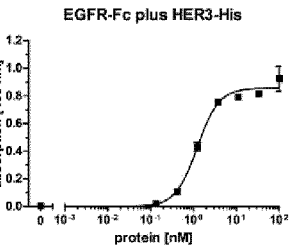
Figure 23:
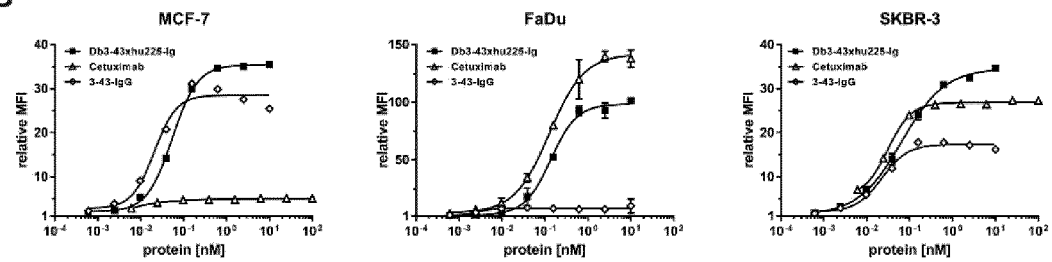

FIG. 23: Biochemical characterization and binding of Db3-43xhu225-Ig. A) Schematic illustration of the light and the heavy chain of the Db3-43xhu225-Ig fusion protein. B) Schematic structure of the domains in the Db3-43xhu225-Ig fusion protein. C) SDS-PAGE analysis (10% PAA; Coomassie stained) of the Db3-43xhu225-Ig fusion protein under reducing (1) and non-reducing (2) conditions (M: marker). D) Size exclusion chromatography of Db3-43xhu225-Ig fusion protein. E) Binding of the bispecific, tetravalent Db3-43xhu225-Ig was analyzed by ELISA using His-tagged fusion proteins of the extracellular domain of EGFR or HER3 as antigen. Bound protein was detected with an HRP-conjugated anti-human Fc antibody. Parenteral antibodies (Cetuximab and 3-43-IgG) were used as control. Optical density was measured at 450 nm. F) Simultaneous binding of the bispecific Db3-43xhu25-Ig fusion protein was analyzed via ELISA using a Fc fusion protein of the extracellular domain of EGFR as first antigen. Serial dilution of Db3-43xhu225-Ig was added to the wells. Finally, the second antigen, HER3-His, was added to the wells. Bound HER3-His was detected using a HRP-conjugated anti-His antibody. Optical density was measured at 450 nm. G) Binding of Db3-43xhu225-Ig to cells was analyzed via flow cytometry. Different tumor cell lines (MCF-7, SKBR-3, and FaDu) were incubated with a serial dilution of bispecific Db3-43xhu225-Ig or the parental monoclonal antibodies (cetuximab and 3-43-IgG). Bound antibody was detected via PE-labeled anti-human Fc secondary antibody. Cells were analyzed using a Miltenyi MACSquant.

Figure 24:
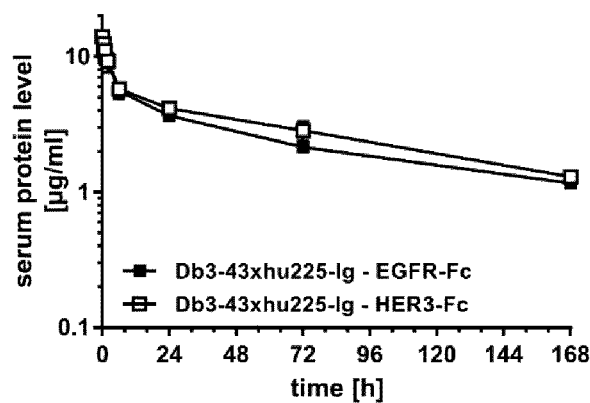

FIG. 24: Pharmacokinetic of Db3-43xhu225-Ig in SWISS mice. Pharmacokinetic profile of Db3-43xhu225-Ig was determined in female SWISS mice (3 mice). 25 µg protein were injected intravenously into the tail vein. Concentrations of serum samples collected after indicated time intervals were determined via ELISA using either EGFR-Fc or HER3-Fc fusion protein as coated antigen. Bound Db3-43xhu225-Ig molecules were detected using an HRP-conjugated anti-human Fab antibody.

Figure 25:
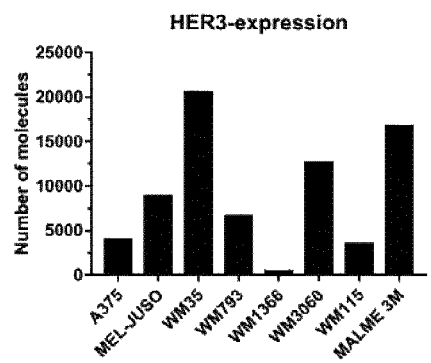
Figure 25:
Figure 25:
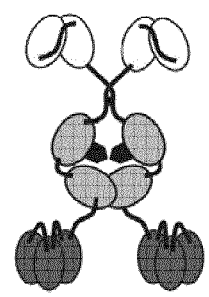
Figure 25:
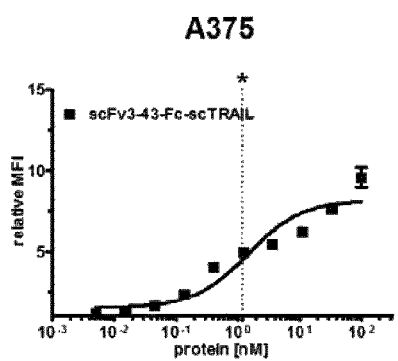
Figure 25:
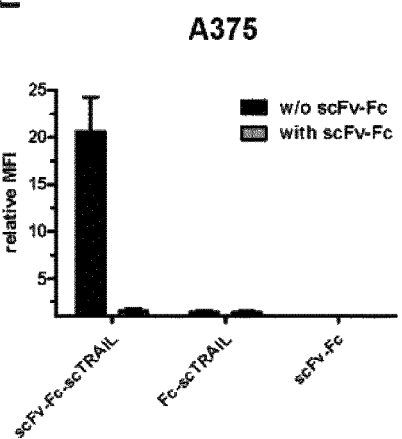

FIG. 25: A scFv3-43-Fc-scTRAIL fusion protein targeting HER3. A) HER3-expression of melanoma cells was analyzed via flow cytometry analysis and quantified via QIFIKIT. B) Schematic composition of scFv3-43-Fc-scTRAIL polypeptide. C) Schematic composition of the dimeric scFv-Fc-scTRAIL fusion protein. D) Binding of scFv3-43-Fc-scTRAIL fusion protein to the HER3-positive cell line A375 was evaluated by flow cytometry. Cell bound protein was detected by anti-human IgG (γ-chain specific) R-PE. $EC_{50}$ values are indicated as dotted lines. Significances of the $EC_{50}$-value were calculated compared to that of the Fc-scTRAIL on the respective cell line. E) Competitive inhibition with the scFv3-43-Fc (inhibitor) was done on the cell line A375. The cells were treated with 200× molar excess of inhibitor before they were treated with the protein (10 nM). Cell bound protein was detected via anti-human TRAIL-PE.

Figure 26:
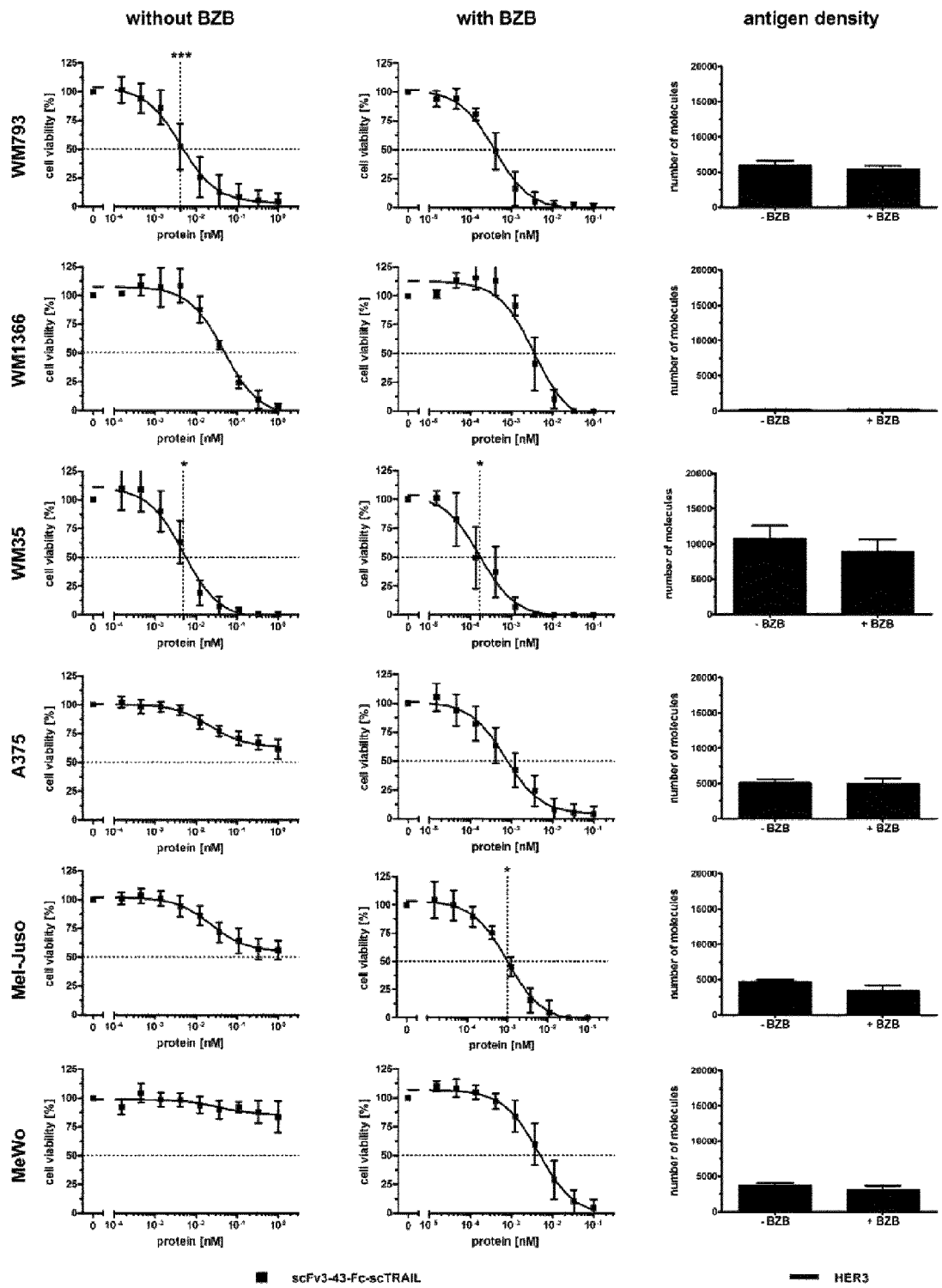

FIG. 26: Cell death induction of scFv3-43-Fc-scTRAIL targeting HER3 and quantitative analysis of HER3 antigen density on the cell surface in presence or absence of bortezomib (BZB). For the cell death induction assays the cells were preincubated with medium or bortezomib for 30 min before they were treated with the a serial dilution of scFv3-43-Fc-scTRAIL for 16 h. Cell viability was analyzed by crystal violet staining. For statistical analysis, the $EC_{50}$ values of scFv3-43-Fc-scTRAIL were compared with Fc-scTRAIL. $EC_{50}$ values are indicated as dotted lines if the target effect is significant. Antigen density of HER3 was determined using the QIFIKIT. Therefore, the cells were treated with the same bortezomib concentration as was used for the cell death induction assays. Statistical analysis was performed by using the unpaired t-test (two-tailed, p<0.05*, p<0.01, p<0.001*, p>0.05 ns).

Figure 27:
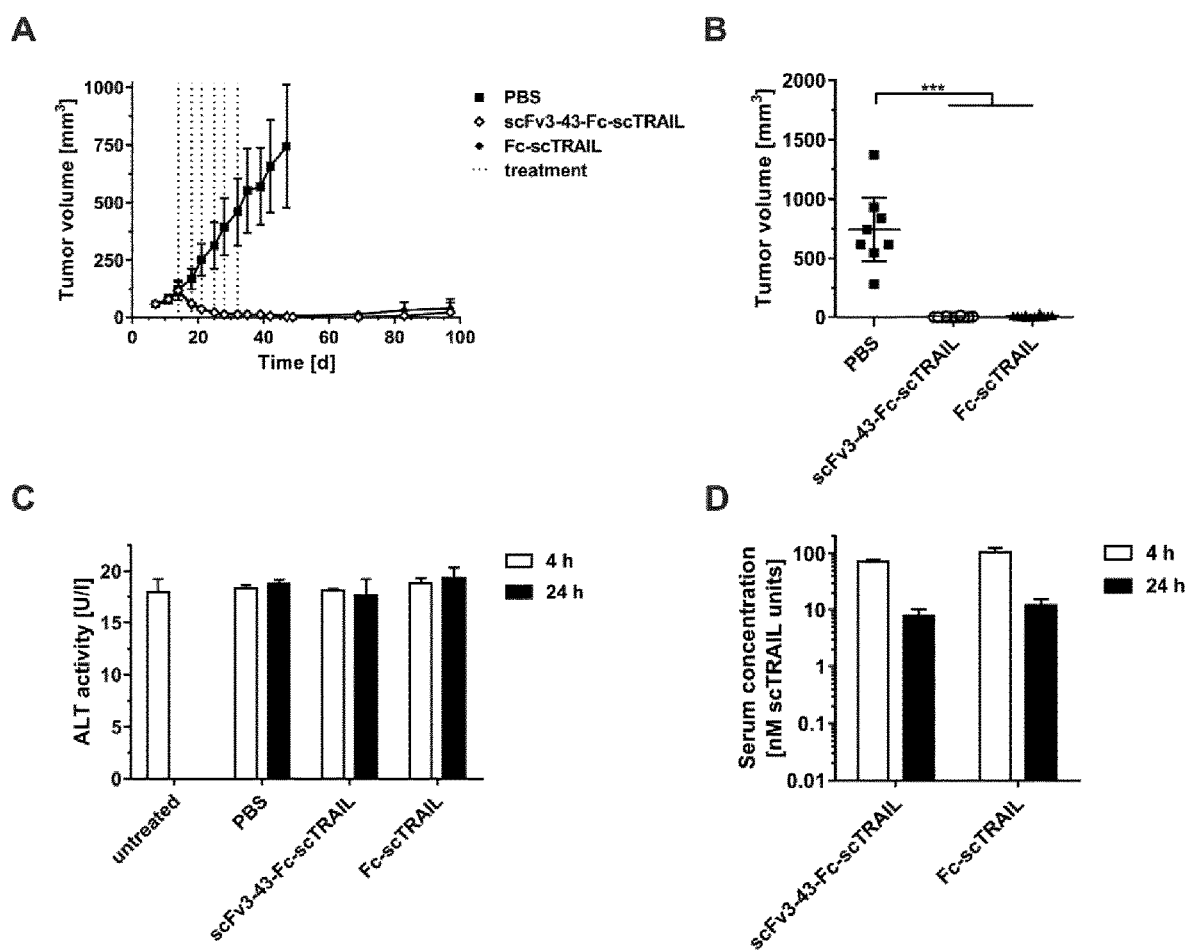

FIG. 27: In vivo activity, tolerability and PK of scFv3-43-Fc-scTRAIL and Fc-scTRAIL. A) NMRI nude mice (6 mice per group) with established Colo205 tumors were treated with 0.2 nmol protein (corresponding to 0.4 nmol scTRAIL units; i.v.) or PBS twice a week for three weeks (days 14, 18, 21, 25, 28, 32). Treatments are indicated with dotted lines. B) Statistical analysis of tumor volumes of the different treated groups at day 47 was performed by One-Way ANOVA, followed by Tukey's post hoc test (*P<0.05; P<0.01; *P<0.001; ns, P>0.05). C) ALT activity and D) serum concentration of the molecules were determined 4 h and 24 h after the last treatment (day 32).

Figure 28:
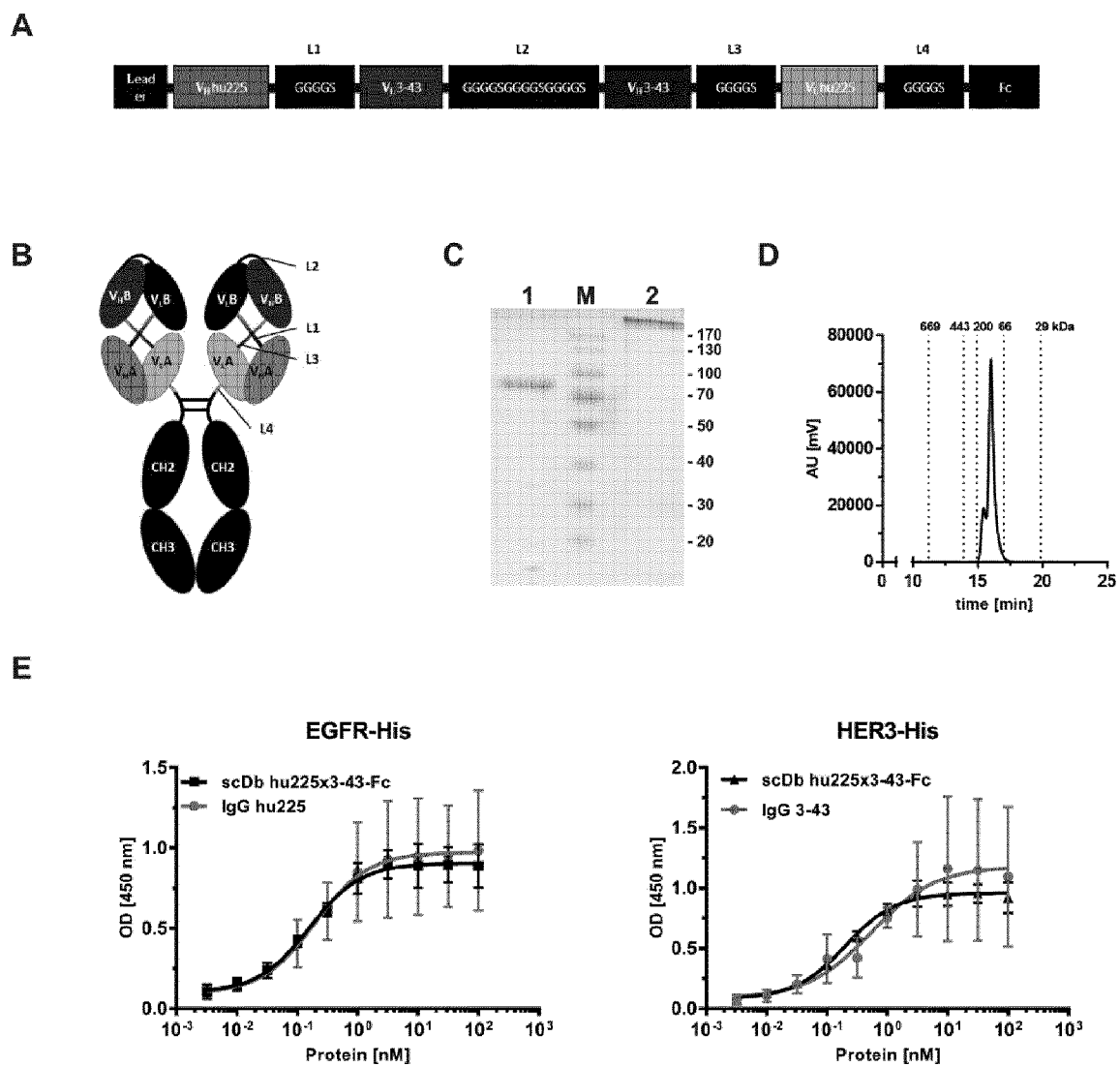

FIG. 28: Biochemical characterization and binding of scDbhu225x3-43-Fc. A) Schematic illustration of scDbhu225x3-43-Fc fusion protein. B) Schematic structure of the domains in the scDbhu225x3-43-Fc fusion protein. C) SDS-PAGE analysis (10% PAA; Coomassie stained) of the scDbhu225x3-43-Fc fusion protein under reducing (1) and non-reducing (2) conditions (M: marker). D) Size exclusion chromatography of scDbhu225x3-43-Fc fusion protein. E) Binding of the bispecific, tetravalent scDbhu225x3-43-Fc fusion protein was analyzed by ELISA using a His-tagged recombinant protein of the extracellular domain of EGFR or HER3 as antigen. Bound protein was detected with an HRP-conjugated anti-human Fc antibody. Parental antibodies (hu225-IgG and 3-43-IgG) were used as control. Optical density was measured at 450 nm.

Figure 29:
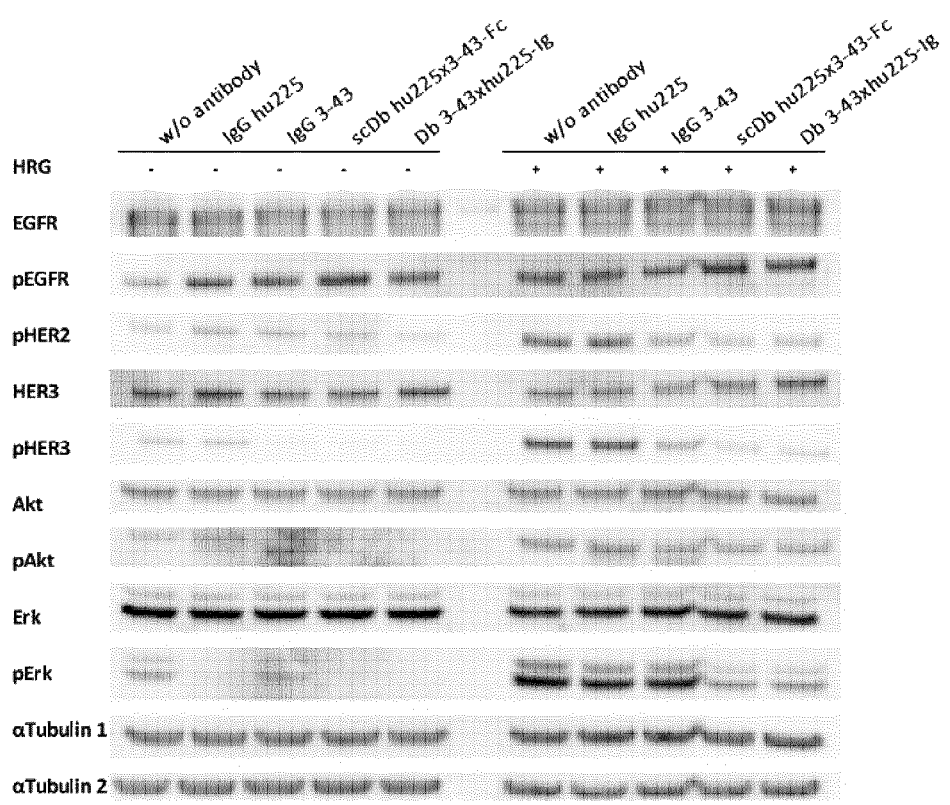

FIG. 29: Receptor signaling inhibition in FaDu cells. Cells were treated with 50 nM of IgG hu225, IgG 3-43, combination of IgG hu225 and IgG 3-43, scDbhu225x3-43-Fc (GGGGS), or Db3-43xhu225-Ig for 1 hour prior to stimulation with heregulin (50 ng/ml) for 15 min at 37° C. Cells were lysed using RIPA buffer (50 mM Tris pH 7.5, 150 mM NaCl, 10 mM NaF, 20 mM β-Glycerophosphate, 1 mM EDTA, 1% NP-40, 1 mM $Na_3VO_4$, 0.5 mM PMSF, 0.25% DOC, 0.1% SDS) containing a protease inhibitor cocktail and lysates were analyzed by immunoblotting using antibodies against EGFR, phosphor-EGFR(Tyr1068), phospho-HER2 (Tyr1221/1222), HER3, phospho-HER3 (Tyr1289), Akt, phosphor-Akt (Thr308), Erk, phosphor-Erk (Thr202/Tyr204) and α-Tubulin. αTubulin1, pHER3, EGFR, Akt and Erk were on membrane 1, αTubulin2, HER3, pEGFR, pHER2, pAkt and pErk were on membrane 2.

Figure 30:
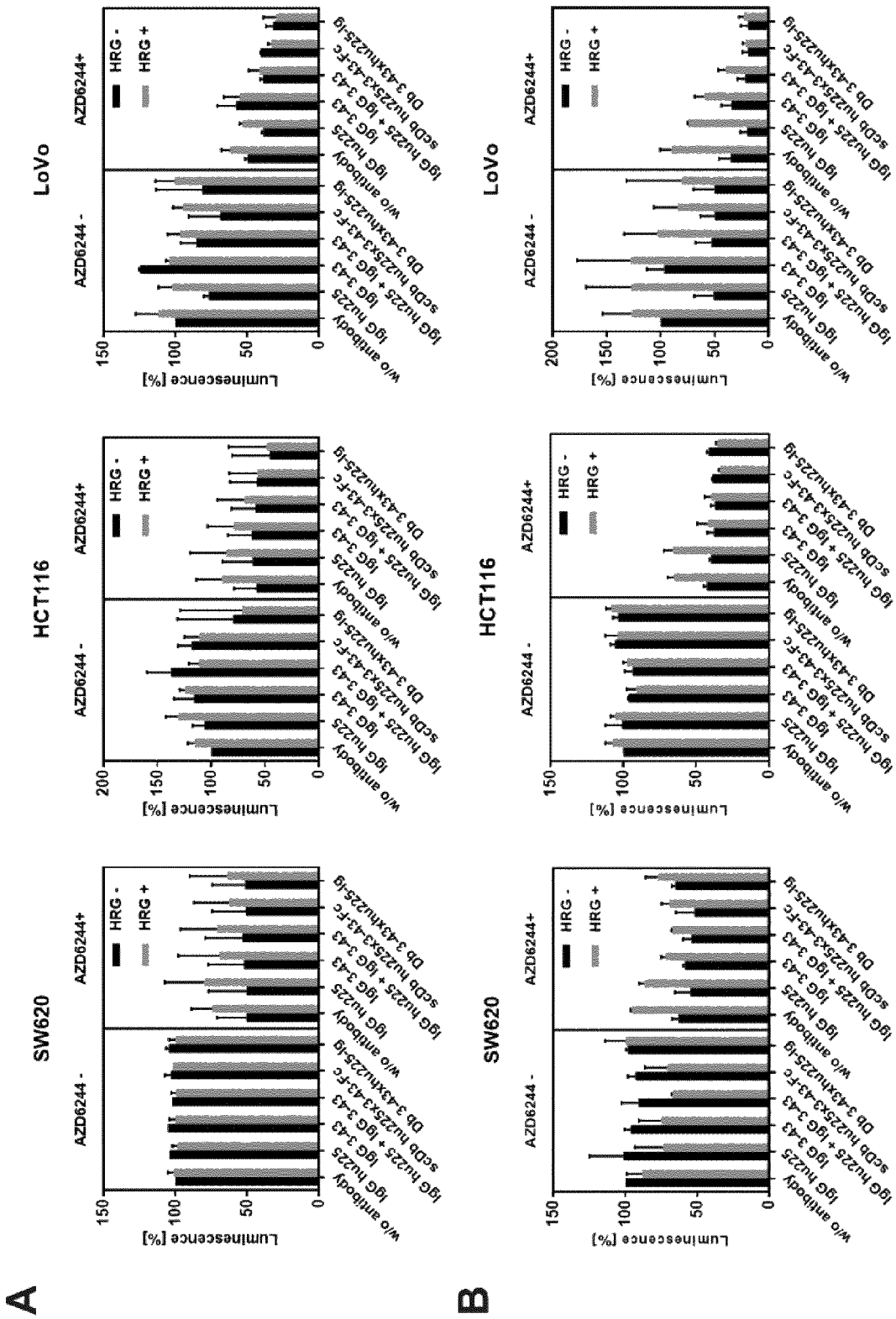

FIG. 30: Proliferation assay using scDbhu225x3-43-Fc or Db3-43xhu225-Ig. SW620, HCT116, and LoVo cells were used for 2D (A) and 3D (B) proliferation assays. 2000 cells/well in a 96-well plate format were cultivated for 24 hours in RPMI medium containing 10% FCS (for 3D culture: 1:2 Matrigel:Kollagen mixture, RPMI or DMEM+ 10% FCS+2% Matrigel). Then, medium was replaced with starvation medium (RPMI medium containing 0.2% FCS and 1% P/S) and after 24 hours of cultivation, cells were treated with the different antibodies (Cetuximab, 3-43-IgG: 50 nM alone or 50 nM each in combination; scDbhu225x3-43-Fc, Db3-43xhu225-Ig: 50 nM) either in the presence of the absence of MEK-inhibitor (AZD6244, Selumetinib; HRG-unstimulated: 5 nM for SW620, 45 nM for HCT116, 35 nM for LoVo; HRG-stimulated: 10 nM for SW620, 300 nM for HCT116, 250 nM for LoVo). After 1 hour of incubation, cells were either stimulated with heregulin (6 ng/well) or kept unstimulated. On day 8 after seeding the cells, plates were analyzed using either CelltiterGlo 2.0 Kit (A) (25 μl of starvation media mixed with 25 μl of CelltiterGlo 2.0 per well) or CelltiterGlo 3D Kit (B) (25 μl of starvation media mixed with 25 μl of CelltiterGlo 3D per well) measuring luminescence. Luminescence of untreated cells (w/o antibody, w/o AZD62244, w/o HRG) was set as 100%; Mean±SD, n=2.

Figure 31:
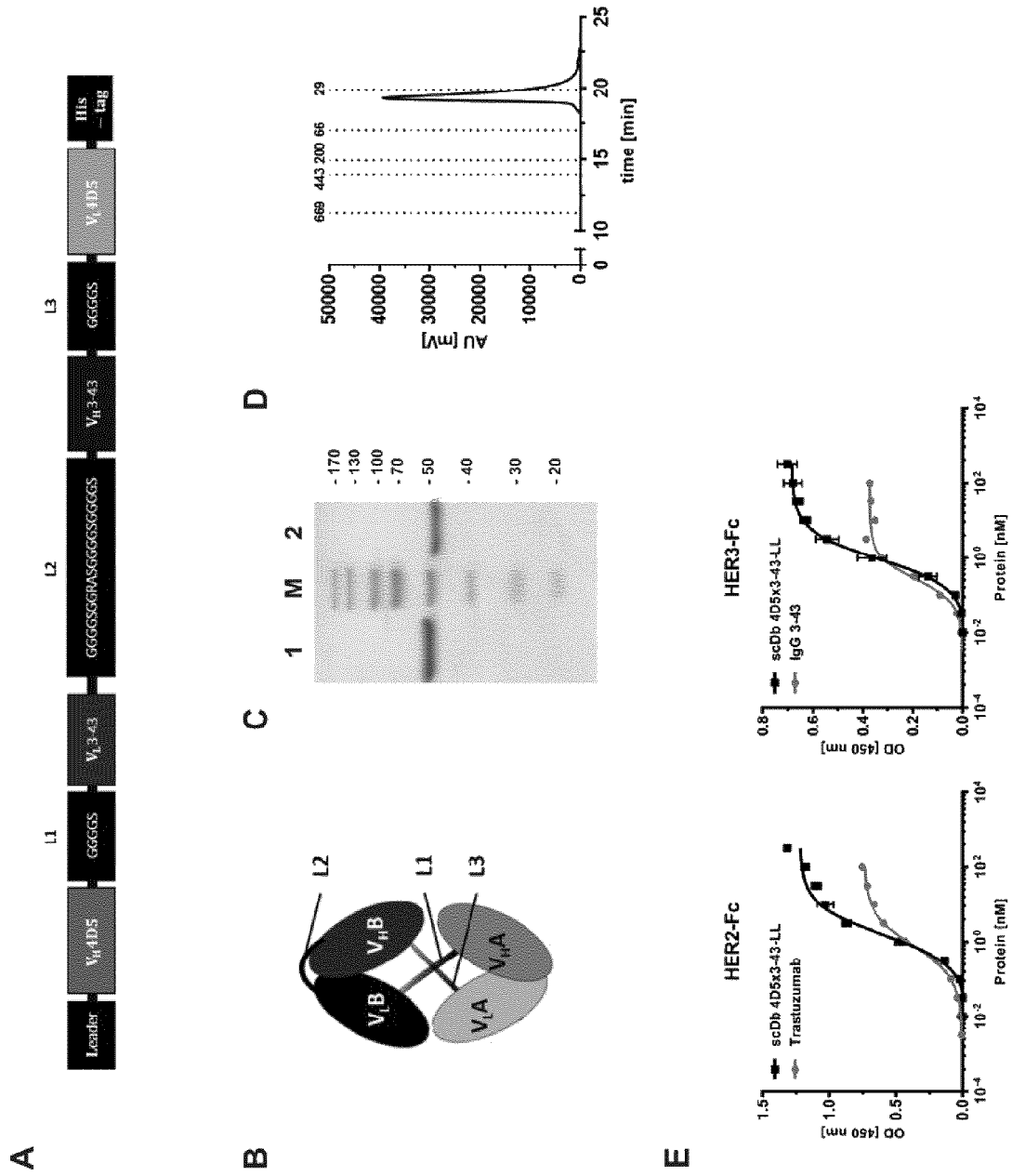

FIG. 31: Biochemical characterization and bioactivity of scDb4D5x3-43-LL. A) Schematic illustration of scDb4D5x3-43-LL fusion protein. B) Schematic structure of the domains in the scDb4D5x3-43-LL fusion protein. C) SDS-PAGE analysis (12% PAA; Coomassie stained) of the scDb4D5x3-43-LL fusion protein under reducing (1) and non-reducing (2) conditions (M: marker). D) Size exclusion chromatography of scDb4D5x3-43-LL fusion protein. E) Binding of the bispecific, bivalent scDb4D5x3-43-LL fusion protein was analyzed by ELISA using a Fc fusion protein of the extracellular domain of HER2 or HER3 as antigen. Bound protein was detected with an HRP-conjugated anti-His antibody. Parenteral antibodies (Trastuzumab and 3-43-IgG) were used as control. Optical density was measured at 450 nm.

Figure 32:
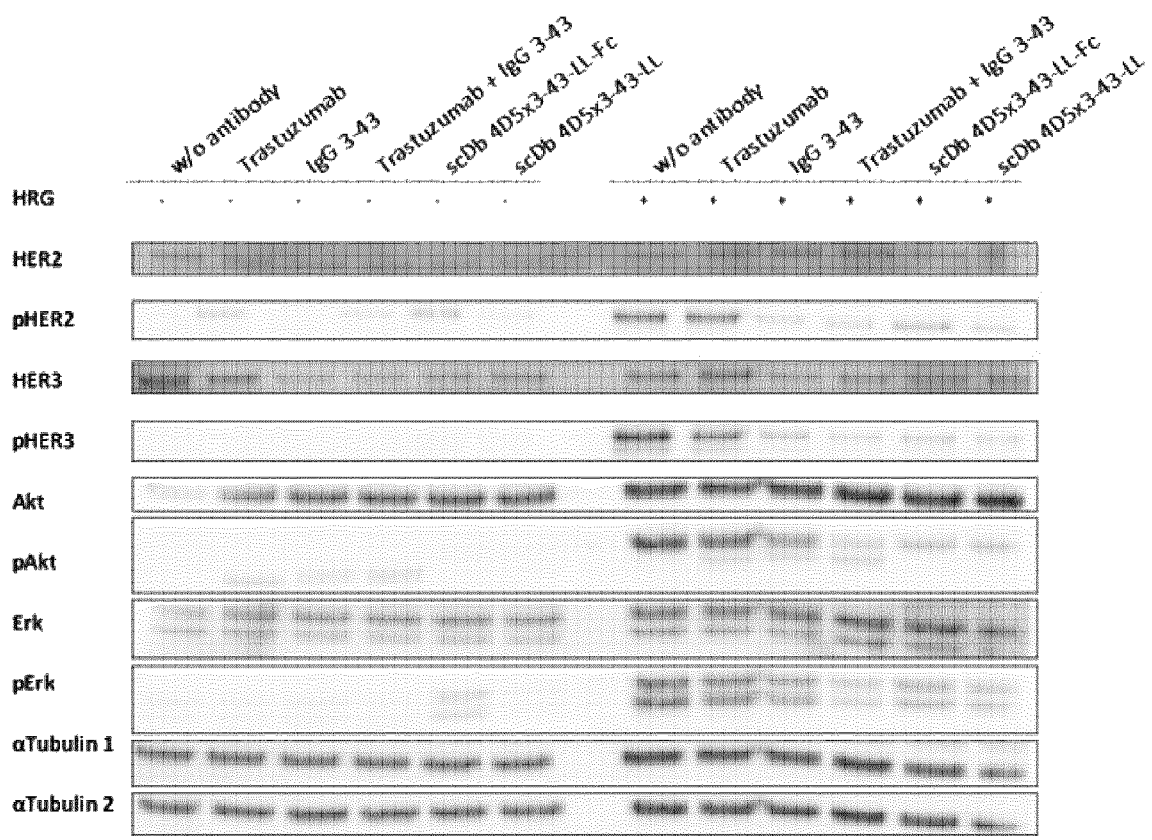

FIG. 32: Receptor signaling inhibition in MCF-7 cells. Cells were treated with 50 nM of Trastuzumab, IgG 3-43, combination of Trastuzumab and IgG 3-43, scDb 4D5x3-43-LL-Fc or scDb 4D5x3-43-LL for 1 h prior to stimulation with heregulin (50 ng/ml) for 15 min at 37° C. Cells were lysed using RIPA buffer (50 mM Tris pH 7.5, 150 mM NaCl, 10 mM NaF, 20 mM β-Glycerophosphate, 1 mM EDTA, 1% NP-40, 1 mM $Na_3VO_4$, 0.5 mM PMSF, 0.25% DOC, 0.1% SDS) containing a protease inhibitor cocktail and lysates were analyzed by immunoblotting using antibodies against EGFR, phosphor-EGFR(Tyr1068), phospho-HER2 (Tyr1221/1222), HER3, phospho-HER3 (Tyr1289), Akt, phosphor-Akt (Thr308), Erk, phosphor-Erk (Thr202/Tyr204) and α-Tubulin. αTubulin1, pHER3, HER2, Akt and Erk were on membrane 1, αTubulin2, HER3, pHER2, pAkt and pErk were on membrane 2.

Figure 33:
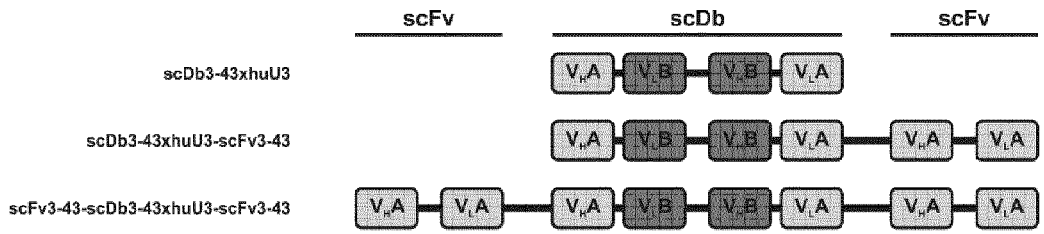
Figure 33:
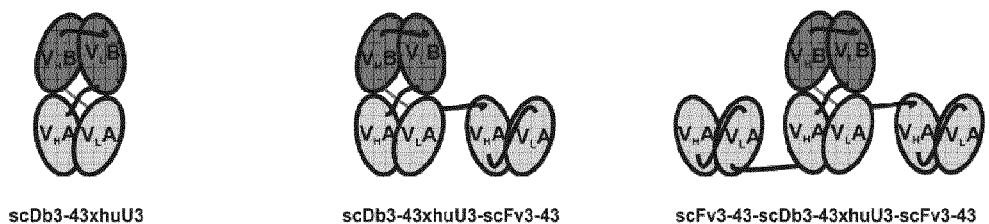
Figure 33:
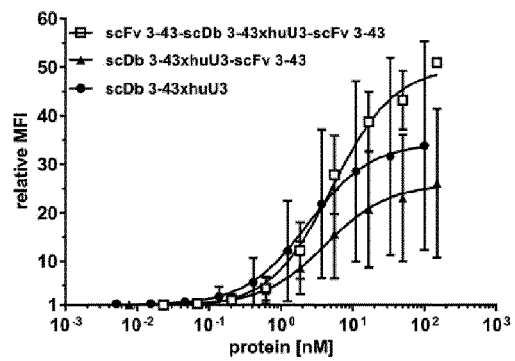
Figure 33:
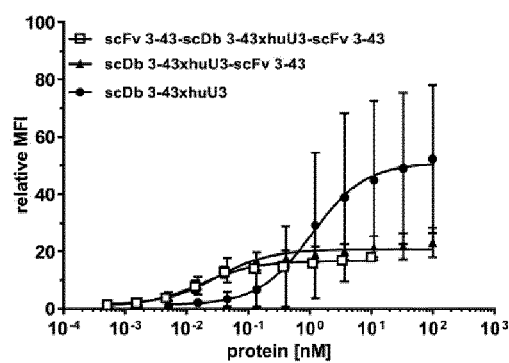
Figure 33:
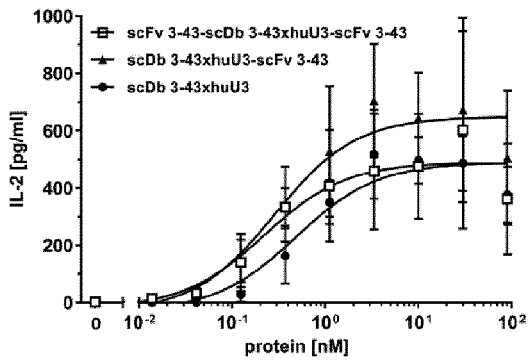
Figure 33:
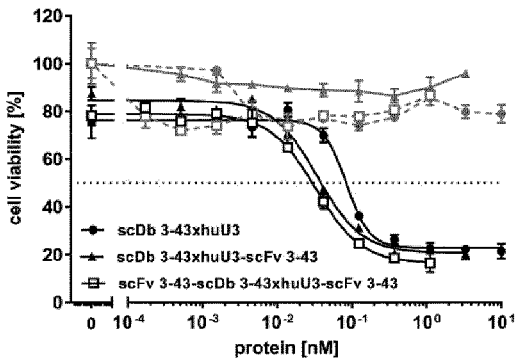

FIG. 33: Biochemical characterization and bioactivity of bispecific, multivalent antibodies directed against HER3 and CD3. (A+B) Schematic illustration (A) and structure (B) of the bispecific, bivalent (scDb3-43xhuU3), trivalent (scDb3-43xhuU3-scFv3-43), or tetravalent (scFv3-43-scDb3-43xhuU3-scFv3-43) fusion protein. (C+D) Binding of the different bispecific fusion proteins to CD3-positive cell lines Jurkat (C) and HER3-positive cell line MCF-7 (D) was analyzed via flow cytometry. A serial dilution of the bispecific antibodies was incubated with the cells for 1 hour at 4° C. Bound antibody was detected via PE-labeled anti-human Fc secondary antibody. Cells were analyzed using a Miltenyi MACSquant. E) IL-2 release of PBMC activated by bispecific, multivalent antibodies bound to HER3-expressing MCF-7 cells. After 24 hours, concentration of IL-2 in the supernatant was determined by ELISA according to the instructions supplied by the manufacture (human IL-2 kit, R&D). F) Bispecific, multivalent antibodies were titrated and incubated with MCF7 as target cells for an hour before human PBMCs were added. Cell viability was determined via MTT-assay after 48 hours of incubation. Additionally, bispecific, multivalent antibodies were titrated and incubated on MCF7 as target cells without addition of PBMCs. Cell viability was determined via MTT-Assay after 48 hours of incubation and indicated with grey symbols and dotted lines for each protein.

Figure 34:
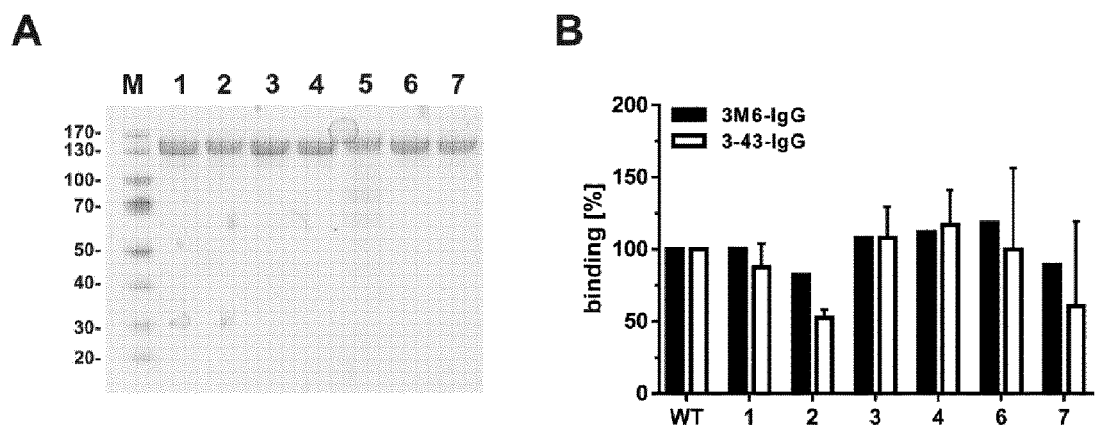

FIG. 34: Analysis of mutated HER3-Fc fusion proteins and binding analysis to 3-43-IgG. A) SDS-PAGE analysis of purified HER3-Fc mutants (1, T335A; 2, T389I; 3, M406K; 4, R453H; 5, Y464C; 6, D492H; 7, K498I) under reducing conditions. Gel was stained with Coomassie Blue. B) Binding of IgG 3-43 to immobilized wild-type HER3-Fc and HER3-Fc mutants using 100 nM of IgG 3-43 detected with a horseradish-peroxidase conjugated anti-human Fab antibody and normalized to the signal obtained for wild-type HER3-Fc fusion protein. Mutant Y464C was not included, because of aggregate formation as revealed by SEC analysis. 3M6-IgG directed against domain I of human HER3 was included as positive control.

LIST OF SEQUENCES—FREE TEXT INFORMATION

SEQ ID NO: 1 Amino acid sequence of Her3 (Expasy Entry No: P21860)
SEQ ID NO: 2 Amino acid sequence of heavy chain variable domain of IgG 3-43
SEQ ID NO: 3 Amino acid sequence of light chain variable domain of IgG 3-43
SEQ ID NO: 4 Amino Acid Sequence of heavy chain of IgG 3-43
SEQ ID NO: 5 Amino acid sequence of light chain of IgG 3-43
SEQ ID NO: 6 Amino acid sequence of scFv 3-43
SEQ ID NO: 7 Amino acid sequence of PelB leader—scFv 3-43-c-myc-his
SEQ ID NO: 8 Amino acid sequence of IgK leader—scDb hu225x3-43-Fc
SEQ ID NO: 9 Amino acid sequence of IgK leader—2-35 x 3-43 scDb-Fc
SEQ ID NO:10 Amino acid sequence of IgK leader—scDb 4D5x3-43-LL-Fc
SEQ ID NO: 11 Amino acid sequence of IgK leader—FLAG-linker-scFv3-43-Fc-scTRAIL
SEQ ID NO: 12 Amino acid sequence of IgK leader—scDb 3-43xCD3-His
SEQ ID NO: 13 Amino acid sequence of IgK leader-scDb 3-43xCD3-scFv 3-43-His
SEQ ID NO: 14 Amino acid sequence of peptide linker 1: GGGGS
SEQ ID NO: 15 Amino acid sequence of peptide linker 2: GGGGSGGGGS
SEQ ID NO: 16 Amino acid sequence of peptide linker 3: GGGGSGGGGSGGGGS
SEQ ID NO: 17 Amino acid sequence of peptide linker 4: GSLGGSGG SEQ ID NO: 18 Amino acid sequence of peptide linker 5: GGGSGGGT SEQ ID NO: 19 Amino acid sequence of peptide linker 6: GGGSGGGTGS SEQ ID NO: 20 Amino acid sequence of peptide linker 7: GGGSGGGTGSGG SEQ ID NO: 21 Amino acid sequence of peptide linker 8: GGGGSGGRASGGGGS GGGGS SEQ ID NO: 22 Amino acid sequence of peptide linker 9: GGGSGGGS SEQ ID NO: 23 Amino acid sequence of peptide linker 10: EFTRG SEQ ID NO: 24 Amino acid sequence of peptide linker 11: AAA SEQ ID NO: 25 Amino acid sequence of FLAG-tag SEQ ID NO: 26 Amino acid sequence of His-tag SEQ ID NO: 27 Amino acid sequence of Myc-tag SEQ ID NO: 28 Amino acid sequence of PelB leader sequence SEQ ID NO: 29 Amino acid sequence of IgK leader sequence SEQ ID NO: 30 Amino acid sequence of IL-2 leader sequence SEQ ID NO: 31 Amino acid sequence of $V_H3$-43x$V_L$hu225-$C_L$ SEQ ID NO: 32 Amino acid sequence of $V_H$hu225x$V_L$hu3-43-$C_H1$-$C_H2$-$C_H3$ SEQ ID NO: 33 Amino acid sequence of scDbhu225x3-43-Fc (GGGGS)

SEQ ID NO: 34 Amino acid sequence of scDb4D5x3-43-LL

SEQ ID NO: 35 Amino acid sequence of scFv3-43-scDb3-43xhuU3-scFv3-43

DETAILED DESCRIPTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

Definitions

The word "comprise", and variations such as "comprises" and "comprising", will be understood to imply the inclusion of a stated integer or step or group of integers or steps but not the exclusion of any other integer or step or group of integers or steps.

As used in this specification and the appended claims, the singular forms "a", "an", and "the" include plural referents, unless the content clearly dictates otherwise.

Concentrations, amounts, and other numerical data may be expressed or presented herein in a "range" format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "150 mg to 600 mg" should be interpreted to include not only the explicitly recited values of 150 mg to 600 mg, but to also include individual values and sub-ranges within the indicated range. Thus, included in this numerical range are individual values such as 150, 160, 170, 180, 190, . . . 580, 590, 600 mg and sub-ranges such as from 150 to 200, 150 to 250, 250 to 300, 350 to 600, etc. This same principle applies to ranges reciting only one numerical value. Furthermore, such an interpretation should apply regardless of the breadth of the range or the characteristics being described.

The term "about" when used in connection with a numerical value is meant to encompass numerical values within a range having a lower limit that is 5% smaller than the indicated numerical value and having an upper limit that is 5% larger than the indicated numerical value.

The term "nucleic acid" and "nucleic acid molecule" are used synonymously herein and are understood as single or double-stranded oligo- or polymers of deoxyribonucleotide or ribonucleotide bases or both. Nucleotide monomers are composed of a nucleobase, a five-carbon sugar (such as but not limited to ribose or 2'-deoxyribose), and one to three phosphate groups. Typically, a nucleic acid is formed through phosphodiester bonds between the individual nucleotide monomers, In the context of the present invention, the term nucleic acid includes but is not limited to ribonucleic acid (RNA) and deoxyribonucleic acid (DNA) molecules but also includes synthetic forms of nucleic acids comprising other linkages (e.g., peptide nucleic acids as described in Nielsen et al. (Science 254:1497-1500, 1991). Typically, nucleic acids are single- or double-stranded molecules and are composed of naturally occurring nucleotides. The depiction of a single strand of a nucleic acid also defines (at least partially) the sequence of the complementary strand. The nucleic acid may be single or double stranded, or may contain portions of both double and single stranded sequences. Exemplified, double-stranded nucleic acid molecules can have 3' or 5' overhangs and as such are not required or assumed to be completely double-stranded over their entire length. The nucleic acid may be obtained by biological, biochemical or chemical synthesis methods or any of the methods known in the art, including but not limited to methods of amplification, and reverse transcription of RNA. The term nucleic acid comprises chromosomes or chromosomal segments, vectors (e.g., expression vectors), expression cassettes, naked DNA or RNA polymer, primers, probes, cDNA, genomic DNA, recombinant DNA, cRNA, mRNA, tRNA, microRNA (miRNA) or small interfering RNA (siRNA). A nucleic acid can be, e.g., single-stranded, double-stranded, or triple-stranded and is not limited to any particular length. Unless otherwise indicated, a particular nucleic acid sequence comprises or encodes complementary sequences, in addition to any sequence explicitly indicated.

Nucleic acids may be degraded by endonucleases or exonucleases, in particular by DNases and RNases which can be found in the cell. It may, therefore, be advantageous to modify the nucleic acids in order to stabilize them against degradation, thereby ensuring that a high concentration of the nucleic acid is maintained in the cell over a long period of time. Typically, such stabilization can be obtained by introducing one or more internucleotide phosphorus groups or by introducing one or more non-phosphorus internucleotides. Accordingly, nucleic acids can be composed of non-naturally occurring nucleotides and/or modifications to naturally occurring nucleotides, and/or changes to the backbone of the molecule. Modified internucleotide phosphate radicals and/or non-phosphorus bridges in a nucleic acid include but are not limited to methyl phosphonate, phosphorothioate, phosphoramidate, phosphorodithioate and/or phosphate esters, whereas non-phosphorus internucleotide analogues include but are not limited to, siloxane bridges, carbonate bridges, carboxymethyl esters, acetamidate bridges and/or thioether bridges. Further examples of nucleotide modifications include but are not limited to: phosphorylation of 5' or 3' nucleotides to allow for ligation or prevention of exonuclease degradation/polymerase extension, respectively; amino, thiol, alkyne, or biotinyl modifications for covalent and near covalent attachments; fluorophores and quenchers; and modified bases such as deoxyInosine (dI), 5-Bromo-deoxyuridine (5-Bromo-dU), deoxyUridine, 2-Aminopurine, 2,6-Diaminopurine, inverted dT, inverted Dideoxy-T, dideoxyCytidine (ddC 5-Methyl deoxyCytidine (5-Methyl dC), locked nucleic acids (LNA's), 5-Nitroindole, Iso-dC and -dG bases, 2'-O-Methyl RNA bases, Hydroxmethyl dC, 5-hydroxybutynl-2'-deoxyuridine, 8-aza-7-deazaguanosine and Fluorine Modified Bases. Thus, the nucleic acid can also be an artificial nucleic acid which includes but is not limited to polyamide or peptide nucleic acid (PNA), morpholino and locked nucleic acid (LNA), as well as glycol nucleic acid (GNA) and threose nucleic acid (TNA).

A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation.

In the context of the present invention, the term "oligonucleotide" refers to a nucleic acid sequence of up to about 50 nucleotides, e.g. 2 to about 50 nucleotides in length. The term "polynucleotide" when used in the context of the present invention, refers to a nucleic acid of more than about 50 nucleotides in length, e.g. 51 or more nucleotides in length.

Oligonucleotides and polypeptides are prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (Meth. Enzymol. 68:90-99, 1979); the phosphodiester method of Brown et al. (Meth. Enzymol. 68:109-151, 1979); the diethylphosphoramidite method of Beaucage et al. (Tetrahedron Lett. 22:1859-1862, 1981); the triester method of Matteucci et al. (J. Am. Chem. Soc. 103:3185-3191, 1981); automated synthesis methods; or the solid support method of U.S. Pat. No. 4,458,066, or other methods known to those skilled in the art.

As used herein, the term "vector" refers to a protein or a polynucleotide or a mixture thereof which is capable of being introduced or of introducing proteins and/or nucleic acids comprised therein into a cell. Examples of vectors include but are not limited to plasmids, cosmids, phages, viruses or artificial chromosomes. In particular, a vector is used to transport a gene product of interest, such as e.g. foreign or heterologous DNA into a suitable host cell.

Vectors may contain "replicon" polynucleotide sequences that facilitate the autonomous replication of the vector in a host cell. Foreign DNA is defined as heterologous DNA, which is DNA not naturally found in the host cell, which, for example, replicates the vector molecule, encodes a selectable or screenable marker, or encodes a transgene. Once in the host cell, the vector can replicate independently of or coincidental with the host chromosomal DNA, and several copies of the vector and its inserted DNA can be generated. In addition, the vector can also contain the necessary elements that permit transcription of the inserted DNA into an mRNA molecule or otherwise cause replication of the inserted DNA into multiple copies of RNA. Vectors may further encompass "expression control sequences" that regulate the expression of the gene of interest. Typically, expression control sequences are polypeptides or polynucleotides such as but not limited to promoters, enhancers, silencers, insulators, or repressors. In a vector comprising more than one polynucleotide encoding for one or more gene products of interest, the expression may be controlled together or separately by one or more expression control sequences. More specifically, each polynucleotide comprised on the vector may be control by a separate expression control sequence or all polynucleotides comprised on the vector may be controlled by a single expression control sequence. Polynucleotides comprised on a single vector controlled by a single expression control sequence may form an open reading frame. Some expression vectors additionally contain sequence elements adjacent to the inserted DNA that increase the half-life of the expressed mRNA and/or allow translation of the mRNA into a protein molecule. Many molecules of mRNA and polypeptide encoded by the inserted DNA can thus be rapidly synthesized.

The term "amino acid" generally refers to any monomer unit that comprises a substituted or unsubstituted amino group, a substituted or unsubstituted carboxy group, and one or more side chains or groups, or analogs of any of these groups. Exemplary side chains include, e.g., thiol, seleno, sulfonyl, alkyl, aryl, acyl, keto, azido, hydroxyl, hydrazine, cyano, halo, hydrazide, alkenyl, alkynyl, ether, borate, boronate, phospho, phosphono, phosphine, heterocyclic, enone, imine, aldehyde, ester, thioacid, hydroxylamine, or any combination of these groups. Other representative amino acids include, but are not limited to, amino acids comprising photoactivatable cross-linkers, metal binding amino acids, spin-labeled amino acids, fluorescent amino acids, metal-containing amino acids, amino acids with novel functional groups, amino acids that covalently or noncovalently interact with other molecules, photocaged and/or photoisomerizable amino acids, radioactive amino acids, amino acids comprising biotin or a biotin analog, glycosylated amino acids, other carbohydrate modified amino acids, amino acids comprising polyethylene glycol or polyether, heavy atom substituted amino acids, chemically cleavable and/or photocleavable amino acids, carbon-linked sugar-containing amino acids, redox-active amino acids, amino thioacid containing amino acids, and amino acids comprising one or more toxic moieties. As used herein, the term "amino acid" includes the following twenty natural or genetically encoded alpha-amino acids: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). In cases where "X" residues are undefined, these should be defined as "any amino acid." The structures of these twenty natural amino acids are shown in, e.g., Stryer et al., Biochemistry, 5th ed., Freeman and Company (2002). Additional amino acids, such as selenocysteine and pyrrolysine, can also be genetically coded for (Stadtman (1996) "Selenocysteine," Annu Rev Biochem. 65:83-100 and Ibba et al. (2002) "Genetic code: introducing pyrrolysine," Curr Biol. 12(13):R464-R466). The term "amino acid" also includes unnatural amino acids, modified amino acids (e.g., having modified side chains and/or backbones), and amino acid analogs. See, e.g., Zhang et al. (2004) "Selective incorporation of 5-hydroxytryptophan into proteins in mammalian cells," Proc. Natl. Acad. Sci. U.S.A. 101(24):8882-8887, Anderson et al. (2004) "An expanded genetic code with a functional quadruplet codon" Proc. Natl. Acad. Sci. U.S.A. 101(20):7566-7571, Ikeda et al. (2003) "Synthesis of a novel histidine analogue and its efficient incorporation into a protein in vivo," Protein Eng. Des. Sel. 16(9):699-706, Chin et al. (2003) "An Expanded Eukaryotic Genetic Code," Science 301(5635):964-967, James et al. (2001) "Kinetic characterization of ribonuclease S mutants containing photoisomerizable phenylazophenylalanine residues," Protein Eng. Des. Sel. 14(12):983-991, Kohrer et al. (2001) "Import of amber and ochre suppressor tRNAs into mammalian cells: A general approach to site-specific insertion of amino acid analogues into proteins," Proc. Natl. Acad. Sci. U.S.A. 98(25): 14310-14315, Bacher et al. (2001) "Selection and Characterization of *Escherichia coli* Variants Capable of Growth on an Otherwise Toxic Tryptophan Analogue," J. Bacteriol. 183(18):5414-5425, Hamano-Takaku et al. (2000) "A Mutant *Escherichia coli* Tyrosyl-tRNA Synthetase Utilizes the Unnatural Amino Acid Azatyrosine More Efficiently than Tyrosine," J. Biol. Chem. 275(51):40324-40328, and Budisa et al. (2001) "Proteins with {beta}-(thienopyrrolyl) alanines as alternative chromophores and pharmaceutically active amino acids," Protein Sci. 10(7): 1281-1292. Amino acids can be merged into peptides, polypeptides, or proteins.

In the context of the present invention, the term "peptide" refers to a short polymer of amino acids linked by peptide bonds. It has the same chemical (peptide) bonds as proteins, but is commonly shorter in length. The shortest peptide is a dipeptide, consisting of two amino acids joined by a single peptide bond. There can also be a tripeptide, tetrapeptide, pentapeptide, etc. Typically, a peptide has a length of up to 8, 10, 12, 15, 18 or 20 amino acids. A peptide has an amino end and a carboxyl end, unless it is a cyclic peptide.

In the context of the present invention, the term "polypeptide" refers to a single linear chain of amino acids bonded together by peptide bonds and typically comprises at least about 21 amino acids. A polypeptide can be one chain of a protein that is composed of more than one chain or it can be the protein itself if the protein is composed of one chain.

In the context of present invention, the "primary structure" of a protein or polypeptide is the sequence of amino acids in the polypeptide chain. The "secondary structure" in a protein is the general three-dimensional form of local segments of the protein. It does not, however, describe specific atomic positions in three-dimensional space, which are considered to be tertiary structure. In proteins, the secondary structure is defined by patterns of hydrogen bonds between backbone amide and carboxyl groups. The "tertiary structure" of a protein is the three-dimensional structure of the protein determined by the atomic coordinates. The "quaternary structure" is the arrangement of multiple folded or coiled protein or polypeptide molecules molecules in a multi-subunit complex.

The term "folding" or "protein folding" as used herein refers to the process by which a protein assumes its three-dimensional shape or conformation, i.e. whereby the protein is directed to form a specific three-dimensional shape through non-covalent interactions, such as but not limited to hydrogen bonding, metal coordination, hydrophobic forces, van der Waals forces, pi-pi interactions, and/or electrostatic effects. The term "folded protein" thus, refers to a protein its three-dimensional shape, such as its secondary, tertiary, or quaternary structure.

The term "fragment" used herein refers to naturally occurring fragments (e.g. splice variants) as well as artificially constructed fragments, in particular to those obtained by gene-technological means. Typically, a fragment has a deletion of up to 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, or 300 amino acids at its N-terminus and/or at its C-terminus and/or internally as compared to the parent polypeptide, preferably at its N-terminus, at its N- and C-terminus, or at its C-terminus.

An "epitope", also known as antigenic determinant, is the segment of a macromolecule that is recognized by the immune system, specifically by antibodies, B cells, or T cells. Such epitope is that part or segment of a macromolecule capable of binding to an antibody or antigen-binding fragment thereof. In this context, the term "binding" preferably relates to a specific binding. In the context of the present invention it is preferred that the term "epitope" refers to the segment of protein or polyprotein that is recognized by the immune system. Epitopes usually consist of chemically active surface groupings of molecules such as amino acids or sugar side chains and usually have specific three-dimensional structural characteristics, as well as specific charge characteristics. Conformational and non-conformational epitopes are distinguished in that the binding to the former but not the latter is lost in the presence of denaturing solvents.

As used herein, a "conformational epitope" refers to an epitope of a linear macromolecule (e.g. a polypeptide) that is formed by the three-dimensional structure of said macromolecule. In the context of the present application, a "conformational epitope" is a "discontinuous epitope", i.e. the conformational epitope on the macromolecule (e.g. a polypeptide) which is formed from at least two separate regions in the primary sequence of the macromolecule (e.g. the amino acid sequence of a polypeptide). In other words, an epitope is considered to be a "conformational epitope" in the context of the present invention, if the epitope consists of at least two separate regions in the primary sequence to which a binding moiety of the invention (e.g. an antibody or an antigen-binding fragment thereof) binds simultaneously, wherein these at least two separate regions are interrupted by one more region in the primary sequence to which a binding moiety of the invention does not bind. In particular, such a "conformational epitope" is present on a polypeptide, and the two separate regions in the primary sequence are two separate amino acid sequences to which a binding moiety of the invention (e.g. an antibody or an antigen-binding fragment thereof) binds, wherein these at least two separate amino acid sequences are interrupted by one more amino acid sequences in the primary sequence to which a binding moiety of the invention does not bind. In particular, the interrupting amino acid sequence is a contiguous amino acid sequence comprising two or more amino acids to which the binding moiety does not bind. The at least two separate amino acid sequences to which a binding moiety of the invention binds are not particularly limited with regard to their length. Such a separate amino acid sequence may consists of only one amino acid as long as the total number of amino acids within said at least two separate amino acid sequences is sufficiently large to effect specific binding between the binding moiety and the conformational epitope.

A "paratope" is the part of an antibody that recognizes the epitope. In the context of the present invention, a "paratope" is the part of a binding moiety (e.g. an antibody or antigen-binding fragment thereof) as described herein that recognizes the epitope.

A "peptide linker" in the context of the present invention refers to an amino acid sequence which sterically separates two parts or moieties of a complex, e.g. two peptides or proteins. Typically such linker consists of between 1 and 100 amino acids having a minimum length of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids, and a maximum length of at least 100, 95, 90, 85, 80, 75, 70, 65, 60, 55, 50, 45, 40, 35, 34, 33, 32, 31, 30, 29, 28, 27, 26, 25, 24, 23, 22, 21, 20, 19, 18, 17, 16, or 15 amino acids or less. The indicated preferred minimum and maximum lengths of the peptide linker according to the present invention may be combined, if such a combination makes mathematically sense, e.g. such linker may consist of 1-15, or 12-40, or 25-75, or 1-100 amino acids. Peptide linkers may also provide flexibility among the two moieties that are linked together. Such flexibility is generally increased if the amino acids are small. Accordingly, flexible peptide linkers comprise an increased content of small amino acids, in particular of glycines and/or alanines, and/or hydrophilic amino acids such as serines, threonines, asparagines and glutamines. Preferably, more than 20%, 30%, 40%, 50%, 60% or more of the amino acids of the peptide linker are small amino acids.

As used herein, the term "variant" is to be understood as a polypeptide or polynucleotide which differs in comparison to the polypeptide or polynucleotide from which it is derived by one or more changes in its length or sequence. The polypeptide or polynucleotide from which a polypeptide or polynucleotide variant is derived is also known as the parent polypeptide or polynucleotide. The term "variant" comprises "fragments" or "derivatives" of the parent molecule. Typically, "fragments" are smaller in length or size than the parent molecule, whilst "derivatives" exhibit one or more differences in their sequence in comparison to the parent molecule. Also encompassed are modified molecules such as but not limited to post-translationally modified proteins (e.g. glycosylated, biotinylated, phosphorylated, ubiquitinated, palmitoylated, or proteolytically cleaved proteins) and modified nucleic acids such as methylated DNA. Also mixtures of different molecules such as but not limited to RNA-DNA hybrids, are encompassed by the term "variant". Typically, a variant is constructed artificially, preferably by gene-technological means, whilst the parent protein or polynucleotide is a wild-type protein or polynucleotide, or a consensus sequence thereof. However, also naturally occurring variants are to be understood to be encompassed by the term "variant" as used herein. Further, the variants usable in the present invention may also be derived from homologs, orthologs, or paralogs of the parent molecule or from artificially constructed variant, provided that the variant exhibits at least one biological activity of the parent molecule, i.e. is functionally active.

In particular, the term "peptide variant", "polypeptide variant", "protein variant" is to be understood as a peptide, polypeptide, or protein which differs in comparison to the peptide, polypeptide, or protein from which it is derived by one or more changes in the amino acid sequence. The peptide, polypeptide, or protein, from which a peptide, polypeptide, or protein variant is derived, is also known as the parent peptide, polypeptide, or protein. Further, the variants usable in the present invention may also be derived from homologs, orthologs, or paralogs of the parent peptide, polypeptide, or protein or from artificially constructed variant, provided that the variant exhibits at least one biological activity of the parent peptide, polypeptide, or protein. The changes in the amino acid sequence may be amino acid exchanges, insertions, deletions, N-terminal truncations, or C-terminal truncations, or any combination of these changes, which may occur at one or several sites. A peptide, polypeptide, or protein variant may exhibit a total number of up to 200 (up to 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200) changes in the amino acid sequence (i.e. exchanges, insertions, deletions, N-terminal truncations, and/or C-terminal truncations). The amino acid exchanges may be conservative and/or non-conservative. Alternatively or additionally, a "variant" as used herein, can be characterized by a certain degree of sequence identity to the parent peptide, polypeptide, or protein from which it is derived. More precisely, a peptide, polypeptide, or protein variant in the context of the present invention exhibits at least 80% sequence identity to its parent peptide, polypeptide, or protein. The sequence identity of peptide, polypeptide, or protein variants is over a continuous stretch of 20, 30, 40, 45, 50, 60, 70, 80, 90, 100 or more amino acids.

The "percentage of sequences identity" is determined by comparing two optimally aligned sequences over a comparison window, wherein the portion of the sequence in the comparison window can comprise additions or deletions (i.e. gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "identical" in the context of two or more nucleic acids or polypeptide sequences, refers to two or more sequences or subsequences that are the same, i.e. comprise the same sequence of nucleotides or amino acids. Sequences are "substantially identical" to each other if they have a specified percentage of nucleotides or amino acid residues that are the same (e.g., at least 20%, at least 25%, at least 30%, at least 35%, at least 40%, at least 45%, at least 50%, at least 55%, at least 60%, at least 65%, at least 70%, at least 75%, at least 80, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity over a specified region), when compared and aligned for maximum correspondence over a comparison window, or designated region as measured using one of the following sequence comparison algorithms or by manual alignment and visual inspection. These definitions also refer to the complement of a test sequence. Accordingly, the term "at least 80% sequence identity" is used throughout the specification with regard to polypeptide and polynucleotide sequence comparisons. This expression preferably refers to a sequence identity of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide.

For term "sequence comparison" refers to the process wherein one sequence acts as a reference sequence, to which test sequences are compared. When using a sequence comparison algorithm, test and reference sequences are entered into a computer, if necessary subsequence coordinates are designated, and sequence algorithm program parameters are designated. Default program parameters are commonly used, or alternative parameters can be designated. The sequence comparison algorithm then calculates the percent sequence identities or similarities for the test sequences relative to the reference sequence, based on the program parameters. In case where two sequences are compared and the reference sequence is not specified in comparison to which the sequence identity percentage is to be calculated, the sequence identity is to be calculated with reference to the longer of the two sequences to be compared, if not specifically indicated otherwise. If the reference sequence is indicated, the sequence identity is determined on the basis of the full length of the reference sequence indicated by SEQ ID, if not specifically indicated otherwise.

In a sequence alignment, the term "comparison window" refers to those stretches of contiguous positions of a sequence which are compared to a reference stretch of contiguous positions of a sequence having the same number of positions. The number of contiguous positions selected may range from 10 to 1000, i.e. may comprise 20, 30, 40, 50, 60, 70, 80, 90, 100, 150, 200, 250, 300, 350, 400, 450, 500, 550, 600, 650, 700, 750, 800, 850, 900, 950, or 1000 contiguous positions. Typically, the number of contiguous positions ranges from about 20 to 800 contiguous positions, from about 20 to 600 contiguous positions, from about 50 to 400 contiguous positions, from about 50 to about 200 contiguous positions, from about 100 to about 150 contiguous positions.

Methods of alignment of sequences for comparison are well known in the art. Optimal alignment of sequences for comparison can be conducted, for example, by the local homology algorithm of Smith and Waterman (Adv. Appl. Math. 2:482, 1970), by the homology alignment algorithm of Needleman and Wunsch (J. Mol. Biol. 48:443, 1970), by the search for similarity method of Pearson and Lipman (Proc. Natl. Acad. Sci. USA 85:2444, 1988), by computerized implementations of these algorithms (e.g., GAP, BEST-FIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)). Algorithms suitable for determining percent sequence identity and sequence similarity are the BLAST and BLAST 2.0 algorithms, which are described in Altschul et al. (Nuc. Acids Res. 25:3389-402, 1977), and Altschul et al. (J. Mol. Biol. 215:403-10, 1990), respectively. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4, and a comparison of both strands. The BLAST algorithm also performs a statistical analysis of the similarity between two sequences (see, e.g., Karlin and Altschul, Proc. Natl. Acad. Sci. USA 90:5873-87, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, typically less than about 0.01, and more typically less than about 0.001.

Semi-conservative and especially conservative amino acid substitutions, wherein an amino acid is substituted with a chemically related amino acid are preferred. Typical substitutions are among the aliphatic amino acids, among the amino acids having aliphatic hydroxyl side chain, among the amino acids having acidic residues, among the amide derivatives, among the amino acids with basic residues, or the amino acids having aromatic residues. Typical semi-conservative and conservative substitutions are:

| Amino | Conservative | Semi-conservative |
| --- | --- | --- |
| A | G; S; T | N; V; C |
| C | A; V; L | M; I; F; G |
| D | E; N; Q | A; S; T; K; R; H |
| E | D; Q; N | A; S; T; K; R; H |
| F | W; Y; L; M; H | I; V; A |
| G | A | S; N; T; D; E; N; Q |
| H | Y; F; K; R | L; M; A |
| I | V; L; M; A | F; Y; W; G |
| K | R; H | D; E; N; Q; S; T; A |

| Amino | Conservative | Semi-conservative |
|---|---|---|
| L | M; I; V; A | F; Y; W; H; C |
| M | L; I; V; A | F; Y; W; C |
| N | Q | D; E; S; T; A; G; K; R |
| P | V; I | L; A; M; W; Y; S; T; C; F |
| Q | N | D; E; A; S; T; L; M; K; R |
| R | K; H | N; Q; S; T; D; E; A |
| S | A; T; G; N | D; E; R; K |
| T | A; S; G; N; V | D; E; R; K; I |
| V | A; L; I | M; T; C; N |
| W | F; Y; H | L; M; I; V; C |
| Y | F; W; H | L; M; I; V; C |

Changing from A, F, H, I, L, M, P, V, W or Y to C is semi-conservative if the new cysteine remains as a free thiol. Furthermore, the skilled person will appreciate that glycines at sterically demanding positions should not be substituted and that P should not be introduced into parts of the protein which have an alpha-helical or a beta-sheet structure.

The EGF receptor family comprises four members, EGFR (erbB1, HER1), ErbB2 (HER2), ErbB3 (HER3), and ErbB4 (HER4). The receptors consists of an extracellular region composed of four domains (I-IV), a transmembrane region, and an intracellular region composed of a tyrosine kinase domain and a carboxyterminal tail containing tyrosine residues (Baselga & Swain 2009, Novel anticancer targets: revisiting ErbB2 and discovering ErbB3. Nat. Rev. Cancer 9: 463-475). The extracellular domains I and III are involved in ligand binding, domains II and IV in receptor dimerization. Domain II mediates receptor-receptor contacts via a dimerization loop, the so-called dimerization arm (Garrett et al., 2002, Combination of antibody that inhibits ligand-independent HER3 dimerization and a p110 alpha inhibitor potently blocks PI3K signaling and growth of HER2+ breast cancers. Cancer Res. 73: 6013-6023). Various ligands, which belong to the EGF ligand family, can bind to the receptor. EGF, transforming growth factor-α (TGF-alpha) and amphiregulin bind specifically to EGFR/ErbB1. Beta-cellulin (BTC), heparin-binding EGF (HB-EGF) and epiregulin (EPR) show dual specificity, binding both EGFR/ErbB1 and ErbB4. Neuregulins (NRGs) form two subgroups based on their capacity to bind ErbB3 and ErbB4 (NRG-1 and NRG-2) or only ErbB4 (NRG-3 and NRG-4). None of the ligands binds to ErbB2, but ErbB2 is the preferred dimerization partner for all the other ErbB receptors. ErbB3 has impaired kinase activity and only acquires signaling potential when it is dimerized with another member of ErbB receptor family. Ligand binding to ErbB receptors induces a large conformational change leading to the formation of receptor homo- and heterodimers and the activation of the intrinsic kinase domain, resulting in phosphorylation of specific tyrosine residues within the cytoplasmic tail. These phosphorylated residues serve as docking sites for intracellular signaling molecules. The ligand determines the tyrosine residues that are phosphorylated and hence the signaling molecules recruited. Three main pathways that can be stimulated upon activation of ErbBs: the mitogen-activated protein kinase (MAPK), the phosphatidylinositol 3-kinase (PI3K)-AKT and the Janus Kinase (JAK-STAT) pathway, all responsible for the regulation of cellular metabolism, growth and survival (Hervent & De Keulenaer, 2012, Molecular mechanisms of cardiotoxicity induced by ErbB receptor inhibitor cancer therapeutics. Int. J. Mol. Sci. 13: 12268-12286).

A tag (or marker or label) is any kind of substance which is able to indicate the presence of another substance or complex of substances. The marker can be a substance that is linked to or introduced in the substance to be detected. Detectable markers are used in molecular biology and biotechnology to detect e.g. a protein, a product of an enzymatic reaction, a second messenger, DNA, interactions of molecules etc. Examples of suitable tags or labels include fluorophores, chromophores, radiolabels, metal colloids, enzymes, or chemiluminescent or bioluminescent molecules. In the context of the present invention suitable tags are preferably protein tags whose peptide sequences is genetically grafted into or onto a recombinant protein. Protein tags may e.g. encompass affinity tags, solubilization tags, chromatography tags, epitope tags, or Fluorescence tags.

"Affinity tags" are appended to proteins so that the protein can be purified from its crude biological source using an affinity technique. These include chitin binding protein (CBP), maltose binding protein (MBP), and glutathione-S-transferase (GST). The poly(His) tag is a widely used protein tag which binds to metal matrices.

"Solubilization tags" are used, especially for recombinant proteins expressed in chaperone-deficient species to assist in the proper folding in proteins and keep them from precipitating. These include thioredoxin (TRX) and poly(NANP). Some affinity tags have a dual role as a solubilization agent, such as MBP, and GST.

"Chromatography tags" are used to alter chromatographic properties of the protein to afford different resolution across a particular separation technique. Often, these consist of polyanionic amino acids, such as FLAG-tag.

"Epitope tags" are short peptide sequences which are chosen because high-affinity antibodies can be reliably produced in many different species. These are usually derived from viral genes, which explain their high immunoreactivity. Epitope tags include V5-tag, Myc-tag, and HA-tag. These tags are particularly useful for western blotting, immunofluorescence and immunoprecipitation experiments, although they also find use in antibody purification.

"Fluorescence tags" are used to give visual readout on a protein. GFP and its variants are the most commonly used fluorescence tags. More advanced applications of GFP include using it as a folding reporter (fluorescent if folded, colourless if not). Further examples of fluorophores include fluorescein, rhodamine, and sulfoindocyanine dye Cy5.

The term "antigen-binding protein", as used herein, refers to immunoglobulin molecules and immunologically active portions of immunoglobulin molecules, i.e. molecules that contain an antigen-binding site that immunospecifically binds an antigen. Also comprised are immunoglobulin-like proteins that are selected through techniques including, for example, phage display to specifically bind to a target molecule or target epitope. In assessing the binding and/or specificity of an antigen binding protein, e.g., an antibody or immunologically functional fragment thereof, an antibody or fragment can substantially inhibit binding of a ligand to its binding partner when an excess of antibody reduces the quantity of binding partner bound to the ligand by at least about 1-20, 20-30%, 30-40%, 40-50%, 50-60%, 60-70%, 70-80%, 80-85%, 85-90%, 90-95%, 95-97%, 97-98%, 98-99% or more (e.g. as measured in an in vitro competitive binding assay). The neutralizing ability may be described in terms of an $IC_{50}$ or $EC_{50}$ value.

The "$IC_{50}$" value refers to the half maximal inhibitory concentration of a substance and is thus a measure of the effectiveness of a substance in inhibiting a specific biological or biochemical function. The values are typically expressed as molar concentration. The $IC_{50}$ of a drug can be determined in functional antagonistic assays by constructing a dose-response curve and examining the inhibitory effect of the examined substance at different concentrations. Alternatively, competition binding assays may be performed in order to determine the $IC_{50}$ value. Typically, inhibitory antibodies exhibit an $IC_{50}$ value of between 50 nM-1 pM, i.e. 50 nM, 10 nM, 1 nM, 900 pM, 800 pM, 700 pM, 600 pM, 500 pM, 400 pM, 300 pM, 200 pM, 100 pM, 50 pM, 1 pM.

The "$EC_{50}$" value refers to half maximal effective concentration of a substance and is thus a measure of the concentration of said substance which induces a response halfway between the baseline and maximum after a specified exposure time. It is commonly used as a measure of drug's potency. The $EC_{50}$ of a graded dose response curve therefore represents the concentration of a substance where 50% of its maximal effect is observed. The $EC_{50}$ of a quantal dose response curve represents the concentration of a compound where 50% of the population exhibit a response, after a specified exposure duration. Typically, inhibitory antibodies exhibit an $EC_{50}$ value of between 50 nM-1 pM, i.e. 50 nM, 10 nM, 1 nM, 900 pM, 800 pM, 700 pM, 600 pM, 500 pM, 400 pM, 300 pM, 200 pM, 100 pM, 50 pM, or 1 pM.

The term "binding" according to the invention preferably relates to a specific binding. The term "binding affinity" generally refers to the strength of the sum total of noncovalent interactions between a single binding site of a molecule (e.g., an antibody) and its binding partner (e.g., target or antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). "Specific binding" means that a binding moiety (e.g. an antibody) binds stronger to a target such as an epitope for which it is specific compared to the binding to another target. A binding moiety binds stronger to a first target compared to a second target if it binds to the first target with a dissociation constant ($K_d$) which is lower than the dissociation constant for the second target. The dissociation constant ($K_d$) for the target to which the binding moiety binds specifically is more than 10-fold, preferably more than 20-fold, more preferably more than 50-fold, even more preferably more than 100-fold, 200-fold, 500-fold or 1000-fold lower than the dissociation constant ($K_d$) for the target to which the binding moiety does not bind specifically.

Accordingly, the term "$K_d$" (measured in "mol/L", sometimes abbreviated as "M") is intended to refer to the dissociation equilibrium constant of the particular interaction between a binding moiety (e.g. an antibody or fragment thereof) and a target molecule (e.g. an antigen or epitope thereof). Affinity can be measured by common methods known in the art, including but not limited to surface plasmon resonance based assay (such as the BIAcore assay); quartz crystal microbalance assays (such as Attana assay); enzyme-linked immunoabsorbent assay (ELISA); and competition assays (e.g. RIA's). Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

Typically, antibodies bind with a sufficient binding affinity to their target, for example, with a Kd value of between 500 nM-1 pM, i.e. 500 nM, 450 nM, 400 nM, 350 nM, 300 nM, 250 nM, 200 nM, 150 nM, 100 nM, 50 nM, 10 nM, 1 nM, 900 pM, 800 pM, 700 pM, 600 pM, 500 pM, 400 pM, 300 pM, 200 pM, 100 pM, 50 pM, or 1 pM.

The term "compete" when used in the context of antigen binding proteins (e.g., neutralizing antigen binding proteins or neutralizing antibodies) that compete for the same epitope means competition between antigen binding proteins as determined by an assay in which the antigen binding protein (e.g., antibody or immunologically functional fragment thereof) being tested prevents or inhibits (e.g., reduces) specific binding of a reference antigen binding protein (e.g., a ligand, or a reference antibody) to a common antigen. Numerous types of competitive binding assays can be used to determine if one antigen binding protein competes with another, for example: solid phase direct or indirect radioimmunoassay (RIA), solid phase direct or indirect enzyme immunoassay (EIA), sandwich competition assay (see, e.g., Stahli et al., 1983, Methods in Enzymology 2:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using I-125 label (see, e.g., Morel et al., 1988, Molec. Jmmunol. 25:7-15); solid phase direct biotinavidin EIA (see, e.g., Cheung, et al., 1990, Virology 176:546-552); and direct labeled RIA (Moldenhauer et al., 1990, Scand. J Immunol. 32:77-82). Typically, such an assay involves the use of purified antigen bound to a solid surface or cells bearing either of these, an unlabeled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Additional details regarding methods for determining competitive binding are provided in the examples herein. Usually, when a competing antigen binding protein is present in excess, it will inhibit (e.g., reduce) specific binding of a reference antigen binding protein to a common antigen by at least 40-45%, 45-50%, 50-55%, 55-60%, 60-65%, 65-70%, 70-75% or 75% or more. In some instances, binding is inhibited by at least 80-85%, 85-90%, 90-95%, 95-97%, or 97% or more. The term "immunoglobulin (Ig)" as used herein refers to immunity conferring glycoproteins of the immunoglobulin superfamily. "Surface immunoglobulins" are attached to the membrane of effector cells by their transmembrane region and encompass molecules such as but not limited to B-cell receptors, T-cell receptors, class I and II major histocompatibility complex (MHC) proteins, beta-2 microglobulin (β2M), CD3, CD4 and CD8.

Typically, the term "antibody" as used herein refers to secreted immunoglobulins which lack the transmembrane region and can thus, be released into the bloodstream and body cavities. Human antibodies are grouped into different isotypes based on the heavy chain they possess. There are five types of human Ig heavy chains denoted by the Greek letters: α, γ, δ, ε, and μ. The type of heavy chain present defines the class of antibody, i.e. these chains are found in IgA, IgD, IgE, IgG, and IgM antibodies, respectively, each performing different roles, and directing the appropriate immune response against different types of antigens. Distinct heavy chains differ in size and composition; and may comprise approximately 450 amino acids (Janeway et al.

(2001) Immunobiology, Garland Science). IgA is found in mucosal areas, such as the gut, respiratory tract and urogenital tract, as well as in saliva, tears, and breast milk and prevents colonization by pathogens (Underdown & Schiff (1986) Annu. Rev. Immunol. 4:389-417). IgD mainly functions as an antigen receptor on B cells that have not been exposed to antigens and is involved in activating basophils and mast cells to produce antimicrobial factors (Geisberger et al. (2006) Immunology 118:429-437; Chen et al. (2009) Nat. Immunol. 10:889-898). IgE is involved in allergic reactions via its binding to allergens triggering the release of histamine from mast cells and basophils. IgE is also involved in protecting against parasitic worms (Pier et al. (2004) Immunology, Infection, and Immunity, ASM Press). IgG provides the majority of antibody-based immunity against invading pathogens and is the only antibody isotype capable of crossing the placenta to give passive immunity to fetus (Pier et al. (2004) Immunology, Infection, and Immunity, ASM Press). In humans there are four different IgG subclasses (IgG1, 2, 3, and 4), named in order of their abundance in serum with IgG1 being the most abundant (~66%), followed by IgG2 (~23%), IgG3 (~7%) and IgG (~4%). The biological profile of the different IgG classes is determined by the structure of the respective hinge region. IgM is expressed on the surface of B cells in a monomeric form and in a secreted pentameric form with very high avidity. IgM is involved in eliminating pathogens in the early stages of B cell mediated (humoral) immunity before sufficient IgG is produced (Geisberger et al. (2006) Immunology 118:429-437). Antibodies are not only found as monomers but are also known to form dimers of two Ig units (e.g. IgA), tetramers of four Ig units (e.g. IgM of teleost fish), or pentamers of five Ig units (e.g. mammalian IgM). Antibodies are typically made of four polypeptide chains comprising two identical heavy chains and identical two light chains which are connected via disulfide bonds and resemble a "Y"-shaped macro-molecule. Each of the chains comprises a number of immunoglobulin domains out of which some are constant domains and others are variable domains. Immunoglobulin domains consist of a 2-layer sandwich of between 7 and 9 antiparallel ~-strands arranged in two ~-sheets. Typically, the heavy chain of an antibody comprises four Ig domains with three of them being constant (CH domains: CHI. CH2. CH3) domains and one of the being a variable domain (VH). The light chain typically comprises one constant Ig domain (CL) and one variable Ig domain (V L). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding fragment" of an antibody (or simply "binding portion"), as used herein, refers to one or more fragments of an antibody that retain the ability to specifically bind to an antigen. It has been shown that the antigen-binding function of an antibody can be performed by fragments of a full-length antibody.

As used herein, "human antibodies" include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). Human antibodies of the invention include antibodies isolated from human immunoglobulin libraries or from animals transgenic for one or more human immunoglobulin and that do not express endogenous immunoglobulins, as described for example in U.S. Pat. No. 5,939,598 by Kucherlapati & Jakobovits.

The term "monoclonal antibody" as used herein refers to a preparation of antibody molecules of single molecular composition. A monoclonal antibody displays a single binding specificity and affinity for a particular epitope. In one embodiment, the monoclonal antibodies are produced by a hybridoma which includes a B cell obtained from a non-human animal, e.g. mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g. from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another species or class. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human is less likely to elicit an immune response from a human subject when the antibodies are injected than would the constant region from a non-human source. However, the definition is not limited to this particular example.

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen-binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

Different methods for humanizing antibodies are known to the skilled person, as reviewed by Almagro & Fransson, 2008, the content of which is herein incorporated by reference in its entirety. The review article by Almagro & Fransson is briefly summarized in the following. Almagro & Fransson distinguish between rational approaches and empirical approaches. Rational approaches are characterized by generating few variants of the engineered antibody and assessing their binding or any other property of interest. If the designed variants do not produce the expected results, a new cycle of design and binding assessment is initiated. Rational approaches include CDR grafting, Resurfacing, Superhumanization, and Human String Content Optimization. In contrast, empirical approaches are based on the generation of large libraries of humanized variants and selection of the best clones using enrichment technologies or high-throughput screening. Accordingly, empirical approaches are dependent on a reliable selection and/or screening system that is able to search through a vast space of antibody variants. In vitro display technologies, such as phage display and ribosome display fulfill these requirements and are well-known to the skilled person. Empirical approaches include FR libraries, Guided selection, Framework-shuffling, and Humaneering.

A "bivalent antibody" comprises two antigen binding sites. Bivalent antibodies may be monospecific or bispecific. In case, the bivalent antibody is monospecific, the two binding sites of the antibody have the same antigen specificities. A "bispecific" or "bifunctional" antigen binding protein or antibody is a hybrid antigen binding protein or antibody, respectively, having two different antigen binding sites. The two binding sites of a bispecific antigen binding protein or antibody bind to two different epitopes residing either on the same or on different antigens. Bispecific antigen binding proteins and antibodies are a species of multispecific antigen binding protein antibody and can be produced by a variety of methods including, but not limited to, fusion of hybridomas, chemical linking of IgG or IgG fragments such as Fab', or by genetic means. See, e.g., Songsivilai and Lachmann, 1990, Clin. Exp. Immunol. 79:315-321; Kostelny et al., 1992, J. Immunol. 148:1547-1553; Kontermann, 2014, MAbs 4:182-197.

A "trifunctional antibody" is a type of bispecific antibody which comprises the two binding sites targeting different antigens as well as an intact Fc-part which can bind to an Fc receptor on accessory cells (e.g. monocytes/macrophages, natural killer cells, dendritic cells or other). For example, a trifunctional antibody may comprise a binding site targeting an epitope on the surface of a cancer cell, the second binding site may target an epitope on the surface of a T cell (e.g. CD3) and the Fc-part may bind to the Fc receptor on the surface of a macrophage. Such trifunctional antibody is thus able to link T cells and macrophages to the tumor cells, leading to their destruction.

Papain digestion of antibodies produces two identical antigen binding fragments, called "Fab fragments" (also referred to as "Fab portion" or "Fab region") each with a single antigen binding site, and a residual "Fe fragment" (also referred to as "Fe portion" or "Fe region") whose name reflects its ability to crystallize readily. The crystal structure of the human IgG Fe region has been determined (Deisenhofer (1981) Biochemistry 20:2361-2370). In IgG, IgA and IgD isotypes, the Fe region is composed of two identical protein fragments, derived from the CH2 and CH3 domains of the antibody's two heavy chains; in IgM and IgE isotypes, the Fe regions contain three heavy chain constant domains (CH2-4) in each polypeptide chain. In addition, smaller immunoglobulin molecules exist naturally or have been constructed artificially. The term "Fab' fragment" refers to a Fab fragment additionally comprise the hinge region of an Ig molecule whilst "F(ab')2 fragments" are understood to comprise two Fab' fragments being either chemically linked or connected via a disulfide bond. Whilst "single domain antibodies (sdAb)" (Desmyter et al. (1996) Nat. Structure Biol. 3:803-811) and "Nanobodies" only comprise a single VH domain, "single chain Fv (scFv)" fragments comprise the heavy chain variable domain joined via a short linker peptide to the light chain variable domain (Huston et al. (1988) Proc. Natl. Acad. Sci. USA 85, 5879-5883). Divalent single-chain variable fragments (di-scFvs) can be engineered by linking two scFvs (scFvA-scFvB). This can be done by producing a single peptide chain with two VH and two VL regions, yielding "tandem scFvs" ($V_H$A-$V_L$A-$V_H$B-$V_L$B). Another possibility is the creation of scFvs with linkers that are too short for the two variable regions to fold together, forcing scFvs to dimerize. Usually linkers with a length of 5 residues are used to generate these dimers. This type is known as "diabodies". Still shorter linkers (one or two amino acids) between a $V_H$ and $V_L$ domain lead to the formation of monospecific trimers, so-called "triabodies" or "tribadies". Bispecific diabodies are formed by expressing to chains with the arrangement $V_H$A-$V_L$B and $V_H$B-$V_L$A or $V_L$A-VHB and $V_L$B-$V_H$A, respectively. Single-chain diabodies (scDb) comprise a $V_H$A-$V_L$B and a $V_H$B-$V_L$A fragment which are linked by a linker peptide (P) of 12-20 amino acids, preferably 14 amino acids, ($V_H$A-$V_L$B-P-$V_H$B-$V_L$A). "Bi-specific T-cell engagers (BiTEs)" are fusion proteins consisting of two scFvs of different antibodies wherein one of the scFvs binds to T cells via the CD3 receptor, and the other to a tumor cell via a tumor specific molecule (Kufer et al. (2004) Trends Biotechnol. 22:238-244). Dual affinity retargeting molecules ("DART" molecules) are diabodies additionally stabilized through a C-terminal disulfide bridge. Divalent single-chain variable fragments may be linked to one or more homo or heterodimerization domains to create tetravalent, hexavalent, octavalent molecules or molecules of even higher valency. Depending on the respective specificities of the single-chain variable fragments linked through the one or more homo- or heterodimerization domains the resulting dimeric or multimeric proteins will have two, three, four or more specificities.

The antibodies described herein are preferably isolated. An "isolated antibody" as used herein, is intended to refer to an antibody which is substantially free of other antibodies having different antigenic specificities. Moreover, an isolated antibody may be substantially free of other cellular material and/or chemicals. In one embodiment of the invention, a combination of "isolated" monoclonal antibodies relates to antibodies having different specificities and being combined in a well defined composition.

As used herein, the term "antibody-like protein" refers to a protein that has been engineered (e.g. by mutagenesis of loops) to specifically bind to a target molecule. Typically, such an antibody-like protein comprises at least one variable peptide loop attached at both ends to a protein scaffold. This double structural constraint greatly increases the binding affinity of the antibody-like protein to levels comparable to that of an antibody. The length of the variable peptide loop typically consists of 10 to 20 amino acids. The scaffold protein may be any protein having good solubility properties. Preferably, the scaffold protein is a small globular protein. Antibody-like proteins include without limitation affibodies, anticalins, and designed ankyrin repeat proteins (for review see: Binz H. K. et al. (2005) Engineering novel binding proteins from nonimmunoglobulin domains. Nat. Biotechnol. 23(10):1257-1268). Antibody-like proteins can be derived from large libraries of mutants, e.g. be panned from large phage display libraries and can be isolated in analogy to regular antibodies. Also, antibody-like binding proteins can be obtained by combinatorial mutagenesis of surface-exposed residues in globular proteins. Antibody-like proteins are sometimes referred to as "peptide aptamers".

As used herein, a "peptidomimetic" is a small protein-like chain designed to mimic a peptide. Peptidomimetics typically arise from modification of an existing peptide in order to alter the molecule's properties. For example, they may arise from modifications to change the molecule's stability or biological activity. This can have a role in the development of drug-like compounds from existing peptides. These modifications involve changes to the peptide that will not occur naturally (such as altered backbones and the incorporation of nonnatural amino acids).

The term "target" refers to a molecule or a portion of a molecule capable of being bound by an antigen binding protein. In certain embodiments, a target can have one or more epitopes. In certain embodiments, a target is an antigen. The use of "antigen" in the phrase "antigen binding protein" simply denotes that the protein sequence that comprises the antigen can be bound by an antibody. In this context, it does not require that the protein be foreign or that it be capable of inducing an immune response.

The term "recombinant" refers to an amino acid sequence or a nucleotide sequence that is intentionally modified by recombinant methods. The term "recombinant nucleic acid" as used herein refers to a nucleic acid which is formed in vitro, and optionally further manipulated by endonucleases to form a nucleic acid molecule not normally found in nature. Exemplified, recombinant nucleic acids include cDNA, in a linear form, as well as vectors formed in vitro by ligating DNA molecules that are not normally joined. It is understood that once a recombinant nucleic acid is made and introduced into a host cell, it will replicate non-recombinantly, i.e. using the in vivo cellular machinery of the host cell rather than in vitro manipulations. Accordingly, nucleic acids which were produced recombinantly, may be replicated subsequently non-recombinantly. A "recombinant protein" is a protein made using recombinant techniques, e.g. through the expression of a recombinant nucleic acid as depicted above. The term "recombinant vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

The term "host cell" refers to a cell that harbours a vector (e.g. a plasmid or virus). Such host cell may either be a prokaryotic (e.g. a bacterial cell) or a eukaryotic cell (e.g. a fungal, plant or animal cell). Host cells include both single-cellular prokaryote and eukaryote organisms (e.g., bacteria, yeast, and actinomycetes) as well as single cells from higher order plants or animals when being grown in cell culture. "Recombinant host cell", as used herein, refers to a host cell that comprises a polynucleotide that codes for a polypeptide fragment of interest, i.e., the fragment of the viral PA subunit or variants thereof according to the invention. This polynucleotide may be found inside the host cell (i) freely dispersed as such, (ii) incorporated in a recombinant vector, or (iii) integrated into the host cell genome or mitochondrial DNA. The recombinant cell can be used for expression of a polynucleotide of interest or for amplification of the polynucleotide or the recombinant vector of the invention. The term "recombinant host cell" includes the progeny of the original cell which has been transformed, transfected, or infected with the polynucleotide or the recombinant vector of the invention. A recombinant host cell may be a bacterial cell such as an *E. coli* cell, a yeast cell such as Saccharomyces cerevisiae or Pichia pastoris, a plant cell, an insect cell such as SF9 or High Five cells, or a mammalian cell. Preferred examples of mammalian cells are Chinese hamster ovary (CHO) cells, green African monkey kidney (COS) cells, human embryonic kidney (HEK293) cells, HELA cells, and the like.

The terms "individual", "subject", or "patient" are used interchangeably herein and refer to any mammal, reptile or bird that may benefit from the present invention. In particular, an individual is selected from the group consisting of laboratory animals (e.g. mouse, rat or rabbit), domestic animals (including e.g. guinea pig, rabbit, horse, donkey, cow, sheep, goat, pig, chicken, duck, camel, cat, dog, turtle, tortoise, snake, or lizard), or primates including chimpanzees, bonobos, gorillas and human beings. In particular, the "individual" is a human being.

The term "disease" and "disorder" are used interchangeably herein, referring to an abnormal condition, especially an abnormal medical condition such as an illness or injury, wherein a tissue, an organ or an individual is not able to efficiently fulfil its function anymore. Typically, but not necessarily, a disease is associated with specific symptoms or signs indicating the presence of such disease. The presence of such symptoms or signs may thus, be indicative for a tissue, an organ or an individual suffering from a disease. An alteration of these symptoms or signs may be indicative for the progression of such a disease. A progression of a disease is typically characterised by an increase or decrease of such symptoms or signs which may indicate a "worsening" or "bettering" of the disease. The "worsening" of a disease is characterised by a decreasing ability of a tissue, organ or organism to fulfil its function efficiently, whereas the "bettering" of a disease is typically characterised by an increase in the ability of a tissue, an organ or an individual to fulfil its function efficiently. A tissue, an organ or an individual being at "risk of developing" a disease is in a healthy state but shows potential of a disease emerging. Typically, the risk of developing a disease is associated with early or weak signs or symptoms of such disease. In such case, the onset of the disease may still be prevented by treatment. Examples of a disease include but are not limited to infectious diseases, traumatic diseases, inflammatory diseases, cutaneous conditions, endocrine diseases, intestinal diseases, neurological disorders, joint diseases, genetic disorders, autoimmune diseases, and various types of cancer.

By "tumor" is meant an abnormal group of cells or tissue that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign or malignant.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

"Symptoms" of a disease or disorder are implication of the disease or disorder noticeable by the tissue, organ or organism having such disease or disorder and include but are not limited to pain, weakness, tenderness, strain, stiffness, and spasm of the tissue, an organ or an individual as well as the presence, absence, increase, decrease, of specific indicators such as biomarkers or molecular markers. The term "disease" and "disorder" as used herein, refer to an abnormal condition, especially an abnormal medical condition such as an illness or injury, wherein a tissue, an organ or an individual is not able to efficiently fulfil its function anymore. Typically, but not necessarily, a disease or disorder is associated with specific symptoms or signs indicating the presence of such disease or disorder. Diseases or disorders include but are not limited to autoimmune diseases, allergic diseases, cancer type diseases, cutaneous conditions, endocrine diseases, blood diseases and disorders, eye diseases and disorders, genetic disorders, inflammatory diseases, infectious diseases, intestinal diseases, neurological disorders, and mental illness. Exemplified, cancer type diseases include but are not limited to Basal cell carcinoma, Bladder cancer, Bone cancer, Brain tumor, Breast cancer, Burkitt lymphoma, Cervical cancer, Colon Cancer, Cutaneous T-cell lymphoma, Esophageal cancer, Retinoblastoma, Gastric (Stomach) cancer, Gastrointestinal stromal tumor, Glioma, Hodgkin lymphoma, Kaposi sarcoma, Leukemias, Lymphomas, Melanoma, Oropharyngeal cancer, Ovarian cancer, Pancreatic cancer, Pleuropulmonary blastoma, Prostate cancer, Throat cancer, Thyroid cancer, and Urethral cancer.

As used herein, "treat", "treating", "treatment" or "therapy" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in an individual that has previously had the disorder(s); and (e) limiting or preventing recurrence of symptoms in individuals that were previously symptomatic for the disorder(s). Accordingly, a moiety having a therapeutic effect treats the symptoms of a disease or disorder by accomplishing one or more of above named effects (a)-(e).

As used herein, "prevent", "preventing", "prevention", or "prophylaxis" of a disease or disorder means preventing that such disease or disorder occurs in patient.

"Pharmaceutically acceptable" means approved by a regulatory agency of the Federal or a state government or listed in the U.S. Pharmacopeia or other generally recognized pharmacopeia for use in animals, and more particularly in humans.

The term "pharmaceutically active moiety" as used herein, is understood to refer to a part or moiety of a macromolecule or complex, i.e. a polypeptide, polynucleotide or complex thereof, which mediates a pharmaceutical effect including but not limited to prophylactic, therapeutic, and/or diagnostic effects. Pharmaceutically active moieties typically comprises a biological and/or chemical pharmaceutical, e.g. ligands, effector molecules, half-life extension modules and imaging molecules. The term "ligand" refers to a chemical or biological substance that forms a complex with another molecule to fulfil a specific biological function. Ligands include but are not limited to substrates, inhibitors, and activators, such as antigen-binding molecules, scaffold proteins, natural ligands, ligand-binding receptor fragments, and apatamers. The term "effector molecule" typically refers to small molecules, peptides or polypeptides that bind to a protein and thereby alter the activity of that protein. They include but are not limited to cytokines, chemokines, immuno(co)-stimulatory molecules, immunosuppressive molecules, death ligands, apoptosis-inducing proteins, kinases, prodrug-converting enzymes, RNases, agonistic antibody or antibody fragment, antagonistic antibody or antibody fragment, toxins, growth factors, hormone, coagulation factor, fibrinolytic protein, peptides mimicking these, and fragments, fusion proteins or derivatives thereof "Half-life extension modules" prolong the half-life, e.g. the "plasma half-life" or the "serum half-life", of a chemical or biological substance. Imaging molecules are those binding to specific target molecules thereby, allowing the visualization of the location of that molecule.

The terms "pharmaceutical", "medicament" and "drug" are used interchangeably herein, referring to a substance and/or a combination of substances being used for the identification, prevention or treatment of a disease or disorder.

The terms "preparation" and "composition" are intended to include the formulation of the active compound with encapsulating material as a carrier providing a capsule in which the active component with or without other carriers, is surrounded by a carrier, which is thus in association with the active compound.

"Chemical pharmaceuticals" are typically understood to refer to chemical compounds synthesized artificially which are effective in the prevention, treatment or diagnosis of disorders or diseases.

"Biologicals" are typically understood to refer to medical drugs produced using biotechnological means and are used for prophylactic, therapeutic, and/or in vivo diagnostic purposes. Biologicals include but are not limited to peptides, polypeptides, proteins and nucleic acids (e.g. DNA, RNA, or hybrids thereof). Approved therapeutic biologicals include but are not limited to hormones (e.g. insulin, hGH, FSH, Glucagon-like peptide 1, parathyroid hormone, calcitonin, lutropin, glucagon), growth factors (e.g. erythropoietin, G-CSF/GM-CSF, IGF-1), interferons (e.g. IFN-α, IFN-β, IFN-γ), interleukins (e.g. IL-2, IL-11, IL-1Ra), coagulation factors (e.g. factor VIII, factor IX, factor VIIa, thrombin), thrombolytics and anti-coagulants (e.g. t-PA, hirudin, activated protein C), enzymes (e.g. α-glucosidase, glucocerebrosidase, iduronate-2-sulfatase, galactosidase, urate oxidase, DNase), antigen-binding molecule such as antibodies and antibody fragments (e.g. IgG, Fab), and fusion proteins thereof (e.g. TNFR2-Fc, TMP-Fc, CTLA-4-Fc, IL-1R-Fc, LFA-3-Fc, IL-2-DT).

The term "active ingredient" refers to the substance in a pharmaceutical composition or formulation that is biologically active, i.e. that provides pharmaceutical value. A pharmaceutical composition may comprise one or more active ingredients which may act in conjunction with or independently of each other. The active ingredient can be formulated as neutral or salt forms. Pharmaceutically acceptable salts include those formed with free amino groups such as but not limited to those derived from hydrochloric, phosphoric, acetic, oxalic, tartaric acids, etc., and those formed with free carboxyl groups such as but not limited to those derived from sodium, potassium, ammonium, calcium, ferric hydroxides, isopropylamine, triethylamine, 2-ethylamino ethanol, histidine, procaine, and the like.

The term "carrier", as used herein, refers to a pharmacologically inactive substance such as but not limited to a diluent, excipient, surfactants, stabilizers, physiological buffer solutions or vehicles with which the therapeutically active ingredient is administered. Such pharmaceutical carriers can be liquid or solid. Liquid carrier include but are not limited to sterile liquids, such as saline solutions in water and oils, including but not limited to those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. A saline solution is a preferred carrier when the pharmaceutical composition is administered intravenously. Examples of suitable pharmaceutical carriers are described in "Remington's Pharmaceutical Sciences" by E. W. Martin.

Suitable pharmaceutical "excipients" include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like.

"Surfactants" include anionic, cationic, and non-ionic surfactants such as but not limited to sodium deoxycholate, sodium dodecylsulfate, Triton X-100, and polysorbates such as polysorbate 20, polysorbate 40, polysorbate 60, polysorbate 65 and polysorbate 80.

"Stabilizers" include but are not limited to mannitol, sucrose, trehalose, albumin, as well as protease and/or nuclease antagonists.

"Physiological buffer solution" include but are not limited to sodium chloride solution, demineralized water, as well as suitable organic or inorganic buffer solutions such as but not limited to phosphate buffer, citrate buffer, tris buffer (tris (hydroxymethyl)aminomethane), HEPES buffer ([4 (2 hydroxyethyl)piperazino]ethanesulphonic acid) or MOPS buffer (3 morpholino-1 propanesulphonic acid). The choice of the respective buffer in general depends on the desired buffer molarity. Phosphate buffer are suitable, for example, for injection and infusion solutions.

The term "adjuvant" refers to agents that augment, stimulate, activate, potentiate, or modulate the immune response to the active ingredient of the composition at either the cellular or humoral level, e.g. immunologic adjuvants stimulate the response of the immune system to the actual antigen, but have no immunological effect themselves. Examples of such adjuvants include but are not limited to inorganic adjuvants (e.g. inorganic metal salts such as aluminium phosphate or aluminium hydroxide), organic adjuvants (e.g. saponins or squalene), oil-based adjuvants (e.g. Freund's complete adjuvant and Freund's incomplete adjuvant), cytokines (e.g. IL-1β, IL-2, IL-7, IL-12, IL-18, GM-CFS, and INF-γ) particulate adjuvants (e.g. immunostimulatory complexes (ISCOMS), liposomes, or biodegradable microspheres), virosomes, bacterial adjuvants (e.g. monophosphoryl lipid A, or muramyl peptides), synthetic adjuvants (e.g. non-ionic block copolymers, muramyl peptide analogues, or synthetic lipid A), or synthetic polynucleotides adjuvants (e.g. polyarginine or polylysine).

An "effective amount" or "therapeutically effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

Embodiments

In a first aspect the present invention provides an antigen binding protein that specifically binds to a conformational epitope formed by domain III and IV of human epidermal growth factor receptor 3 (HER3). The phrase "conformational epitope formed by domain III and IV" means that at least one amino acid of domain III and at least one amino acid of domain IV is bound by the antigen binding protein. Thus, it does not imply that all amino acids of domain III and IV are part of the conformational epitope but that amino acid(s) in both domains are bound. Typically the epitope of an antibody comprises between 12 to 20 amino acids and thus in a particular embodiment between 1 to 19 amino acids of domain III and between 1 and 19 amino acids of domain IV are bound by the antigen binding protein, preferably between 3 to 17 amino acids of domain III and between 3 and 17 amino acids of domain IV are bound by the antigen binding protein. In each case it is preferred that the epitope bound comprises between 12 to 20 amino acids.

In embodiments, the conformational epitope is formed by the complete domain III and the complete domain IV of HER3. In alternative embodiments, the conformational epitope is formed by the complete domain III and a fragment of domain IV of HER3. In alternative embodiments, the conformational epitope is formed by a fragment of domain III and the complete domain IV of HER3. In alternative embodiments, the conformational epitope is formed by a fragment of domain III and a fragment of domain IV of HER3.

In particular embodiments, the domain III consists of amino acids 329 to 531 of HER3 according to SEQ ID NO: 1.

In particular embodiments, the fragment of domain IV comprises or consists of amino acids 532-587 of HER3 according to SEQ ID NO: 1.

In particular embodiments, the domain IV consists of amino acids 532-643 of HER3 according to SEQ ID NO: 1

Thus, in particular embodiments, the present invention provides an antigen binding protein that specifically binds to a conformational epitope formed by domain III & IV of HER3, wherein domain III consists of amino acids 329 to 531 of HER3 according to SEQ ID NO: 1, and wherein a fragment of domain IV comprises or consists of amino acids 532-587 of HER3 according to SEQ ID NO: 1.

In particular embodiments, the present invention provides an antigen binding protein that specifically binds to a conformational epitope formed by domain III & IV of HER3, wherein domain III consists of amino acids 329 to 531 of HER3 according to SEQ ID NO: 1, and wherein domain IV consists of amino acids 532 to 643 of HER3 according to SEQ ID NO: 1.

In a second aspect, the present invention provides an antigen-binding protein, which competes with the antigen-binding protein of the first aspect of the present invention for binding to HER3.

In particular embodiments, the present invention provides an antigen-binding protein, which competes with the antigen-binding protein that specifically binds to a conformational epitope formed by domain III & IV of human epidermal growth factor receptor 3 (HER3).

In embodiments, the conformational epitope is formed by the complete domain III and the complete domain IV of HER3. In alternative embodiments, the conformational epitope is formed by the complete domain III and a fragment of domain IV of HER3. In alternative embodiments, the conformational epitope is formed by a fragment of domain III and the complete domain IV of HER3. In alternative embodiments, the conformational epitope is formed by a fragment of domain III and a fragment of domain IV of HER3.

In particular embodiments, the domain III consists of amino acids 329 to 531 of HER3 according to SEQ ID NO: 1.

In particular embodiments, the fragment of domain IV comprises or consists of amino acids 532-587 of HER3 according to SEQ ID NO: 1.

In particular embodiments, the domain IV consists of amino acids 532-643 of HER3 according to SEQ ID NO: 1

Thus, in particular embodiments, the present invention provides an antigen binding protein which competes with the antigen-binding protein that specifically binds to a conformational epitope formed by domain III & IV of HER3, wherein domain III consists of amino acids 329 to 531 of HER3 according to SEQ ID NO: 1, and wherein a fragment of domain IV comprises or consists of amino acids 532-587 of HER3 according to SEQ ID NO: 1.

In particular embodiments, the present invention provides an antigen binding protein which competes with the antigen-binding protein that specifically binds to a conformational epitope formed by domain III and IV of HER3, wherein domain III consists of amino acids 329 to 531 of HER3 according to SEQ ID NO: 1, and wherein domain IV consists of amino acids 532 to 643 of HER3 according to SEQ ID NO: 1.

In particular embodiment, said antigen binding protein of the second aspects competes with the antigen binding protein of the first aspect for its binding to the conformational epitope formed by domain III and IV of HER3.

In particular embodiments, the antigen binding protein of the second aspects competes for the binding to the conformational epitope formed by domain III and IV of HER3 by exhibiting a greater affinity to the epitope than the antigen binding protein of the first aspect.

In further embodiments, the antigen binding protein of the second aspects competes with the binding to the conformational epitope formed by domain III and IV of HER3 by sterically hindering the binding of the antigen binding protein of the first aspect. In embodiments, the antigen binding protein of the second aspects sterically hinders the binding with the antigen binding protein of the first aspects by binding to the identical epitope or by binding to an adjacent epitope such that the antigen binding protein of the first aspects is not able to bind to the conformational epitope formed by domain III and IV of HER3.

In particular embodiments of the first or second aspect of the present invention, the antigen binding protein exhibits one or more of the following characteristics:

(a) The antigen-binding protein binds to HER3 with an $EC_{50}$ value below 15 nM (in particular as analyzed by flow cytometry on HER3-expressing cells). In particular, the antigen-binding protein binds to HER3 with an $EC_{50}$ value of below 10 nM, below 5 nM, below 1 nM, below 500 pM, below 100 pM, below 50 pM, or below 30 pM.

(b) The antigen-binding protein binds to monomeric HER3 with a $K_D$ of below 100 nM (in particular as analyzed by quartz crystal microbalance measurements, surface plasmon resonance, optical interferometry (Octet), or competitive ELISA). In particular, the antigen-binding protein binds to monomeric HER3 with a $K_D$ value of below 50 nM, below 30 nM, or below 20 nM.

(c) The antigen-binding protein inhibits heregulin-induced HER3 phosphorylation with an $IC_{50}$ value below 10 nM. In particular, the antigen-binding protein inhibits its heregulin-induced HER3 phosphorylation with an $IC_{50}$ value of below 5 nM, below 1 nM, below 500 pM, below 300 pM, below 200 pM or below 100 pM. In particular, the antigen-binding protein inhibits heregulin-induced HER3 phosphorylation with an $IC_{50}$ value of 80 pM.

Accordingly, in particular embodiments of the first or second aspect of the present invention, the antigen binding protein:

(a) binds to HER3 with an $EC_{50}$ value below 15 nM (as analyzed by flow cytometry on HER3-expressing cells), in particular with an $EC_{50}$ value of below 10 nM, below 5 nM, below 1 nM, below 500 pM, below 100 pM, below 50 pM, or below 30 pM; and/or (b) binds to an monomeric HER3 with a $K_D$ of below 100 nM (as analyzed by quartz crystal microbalance measurements), in particular with a $K_D$ value of below 50 nM, below 30 nM, or below 20 nM; and/or (c) inhibits heregulin-induced HER3 phosphorylation HER3 with an $IC_{50}$ value below 10 nM, in particular with an $IC_{50}$ value of below 5 nM, below 1 nM, below 500 pM, below 300 pM, below 200 pM or below 100 pM, in particular, with an $IC_{50}$ value of 80 pM.

In particular embodiments of the first or second aspect of the present invention, the antigen binding protein inhibits one or more of the following:

(i) binding of HER3 to its ligand,
(ii) receptor activation and/or signaling,
(iii) induces HER3 internalization,
(iv) inhibits cell proliferation, and/or
(v) inhibits tumor growth.

In particular embodiments of the first or second aspect of the present invention, the antigen binding protein is selected from the group consisting of a) an antibody or an antigen-binding fragment thereof,
b) antibody-like protein, and
c) a peptidomimetic.

In particular embodiments of the first or second aspect of the present invention, the antigen binding protein is an antibody which is selected from the group consisting of a polyclonal antibody, a monoclonal antibody, monovalent antibodies, bispecific antibody, heteroconjugate antibodies, multispecific antibodies, deimmunized antibodies a chimeric antibody, a humanized antibody, and a human antibody (in particular a human IgG1 antibody).

In particular embodiments, the antigen-binding fragment of the antibody is selected from the group consisting of a Fab fragment, a Fab' fragment, a F(ab')2 fragment, a Fd fragment, a Fv fragment, a disulfide-linked Fv (dsFv), a single domain antibody, a single chain Fv (scFv) antibody, and a single domain antibody (VH, VL, VHH, Nanobody, VNAR).

In particular embodiments, the antibody-like protein is selected from the group consisting of lipoprotein-associated coagulation inhibitor (LACI-D1); affilins, e.g. human-γ B crystalline or human ubiquitin; cystatin; Sac7D from *Sulfolobus acidocaldarius*; lipocalin and anticalins derived from lipocalins; designed ankyrin repeat domains (DARPins); SH3 domain of Fyn; Kunits domain of protease inhibitors; monobodies, e.g. the $10^{th}$ type III domain of fibronectin; adnectins; cysteine knot miniproteins; atrimers; evibodies, e.g. CTLA4-based binders, affibodies, e.g. three-helix bundle from Z-domain of protein A from *Staphylococcus aureus*; Trans-bodies, e.g. human transferrin; tetranectins, e.g. monomeric or trimeric human C-type lectin domain; microbodies, e.g. trypsin-inhibitor-II; affilins; armadillo repeat proteins.

In particular embodiments of the first or second aspect of the present invention, the antigen binding protein is monospecific, bispecific or multispecific. In particular embodiments, the bispecific or multispecific antigen binding protein specifically binds to a second cellular target. In particular embodiments, the second cellular target is selected from the group consisting of a protein expressed on the surface of an immune cell, preferably CD3, a protein expressed on the surface of tumor cells, in particular the extracellular region of a growth receptor, in particular epidermal growth factor receptor (EGFR), human epidermal growth factor receptor 2 (HER2), human epidermal growth factor receptor (HER4), insulin-like growth factor 1-receptor (IGF-1R), hepatocyte growth factor receptor (HGFR, c-MET), and derivatives thereof, in particular EGFR or HER2.

In particular embodiments of the first or second aspect of the present invention, the antigen binding protein is tri- or tetravalent. In particular embodiments, the antigen binding protein comprises an effector domain which is in particular bound by Fc receptors, neonatal Fc receptor (FcRn) or the complement system. In particular embodiments, the Fc domain is an domain bound by Fc gamma receptors, in particular by CD 16, CD32, and/or CD64. In particular embodiments, the Fc domain is a domain activating the complement system, in particular by binding to C1q of the complement system.

In a preferred embodiment of the present invention, the antigen binding protein is bivalent. Unless indicated otherwise the configurations of the antigen binding protein embodiments below are written from N-terminus on the left to C-terminus on the right. It is further preferred that the antigen binding protein is bivalent and bispecific. In a further preferred embodiment the bivalent and bispecific antigen binding protein is a diabody. The bispecific diabody comprises two chains, each comprising a VH and VL domain from different antibodies. The two variable domains VH and VL are preferably connected by a short linker of 3 to 5 residues.

The diabody may be a two-chain diabody (Db) or a single-chain diabody (scDb). For the two-chain diabody, the two chains may have the configuration VHA-VLB and VHB-VLA or VLA-VHB and VLB-VHA, wherein A and B represent the two different specificities. For the single-chain diabody, the first chain, VHA-VLB or VLA-VHB, and the second chain, VHB-VLA or VLB-VHA, are covalently connected. Preferably, the first and second chain are connected by a peptide linker with a length of 10 to 15 amino acids. Preferably, the bispecific diabody is a scDb. Preferably, the antigen binding protein has the configuration (VHA-VLB-VHB-VLA)$_{scDb}$. In a particularly preferred embodiment the antigen binding protein comprises or consists of the amino acid sequence of SEQ ID NO: 12 or of SEQ ID NO: 34.

In a further preferred embodiment, the antigen binding protein is a bispecific Db or bispecific scDb, preferably a bispecific scDb, connected to one or more scFvs, preferably to one or two scFvs. Two or more scFvs may be connected in tandem. A scFv comprises the VH and VL domain of the same antibody, preferably connected with peptide linker of about 10 to 25 amino acids. An scFv may have the configuration VH-VL or VL-VH. Preferably, the one or more scFvs have one or both of the specificities of the bispecific Db or bispecific scDb. Thus, the scFvs preferably have the configuration VHA-VLA or VLA-VHA or preferably have the configuration VHB-VLB or VLB-VHB. In a further preferred embodiment, the one ore more scFvs may have a specificity different to the specificities of the bispecific Db or bispecific scDb. Accordingly, the one or more scFvs may have the configurations VHC-VLC or VLC-VHC, or VHD-VLD or VLD-VHD, and so on. In a preferred embodiment, the antigen binding protein is a bispecific trivalent antigen binding protein. Preferably the antigen binding protein has the configuration (VHA-VLB-VHB-VLA)$_{scDb}$-(VHA-VLA)$_{scFv}$. In a particularly preferred embodiment, the antigen binding protein comprises or consists of the amino acid sequence of SEQ ID NO: 13. In a preferred embodiment, the antigen binding protein is a bispecific tetravalent antigen binding protein. In a preferred embodiment, the antigen binding protein has the configuration (VHA-VLA)$_{scFv}$-(VHA-VLB-VHB-VLA)$_{scDb}$-(VHA-VLA)$_{scFv}$. In a particularly preferred embodiment the antigen binding protein comprises or consists of the amino acid sequence of SEQ ID NO: 35.

In a further preferred embodiment, the antigen binding protein is comprised of two bispecific Dbs or bispecific scDbs, preferably bispecific scDbs, each connected to an Fc region, wherein the Fc region serves as homodimerization domain. In a preferred embodiment, the antigen binding protein comprises two moieties of the configuration (VHA-VLB-VHB-VLA)$_{scDb}$-Fc. The two moieties may be covalently or non-covalently bound. In a particularly preferred embodiment, the antigen binding protein comprises two moieties comprising or consisting of the amino acid sequence of SEQ ID NO: 8, SEQ ID NO: 9, SEQ ID NO: 10, or SEQ ID NO: 33.

In a further preferred embodiment of a bispecific antigen binding protein, an additional VH domain and VL domain of a second specificity is connected to a light chain and a heavy chain, respectively, wherein the Fc region of the heavy chain serves as dimerization domain. The two VH domains and the two VL domains of different speficities may be connected in various combinations to the light chain and heavy chain, respectively, resulting in different configurations. In a preferred embodiment of the antigen binding protein, the light chain has the configuration VHA-VHB-CLk and the heavy chain has the configuration VLA-VLB-CH1-CH2-CH3. Certain configurations allow a crossover pairing of the VH and VL domains. In a preferred embodiment the light chain has the configuration VHA-VLB-CLk and the heavy chain has the configuration VHB-VLA-CH1-CH2-CH3. In a preferred embodiment, the light chain has the configuration VLA-VLB-CLk and the heavy chain has the configuration VHB-VHA-CH1-CH2-CH3. In a particularly preferred embodiment, the antigen binding protein comprises a chain of SEQ ID NO: 31 and a chain of SEQ ID NO: 32.

In each of above examples the letters "A", "B", "C" and "D" symbolize an antigen specificity of the antigen binding proteins of the present invention. At least one out of "A", "B", "C" and "D" within each antigen binding protein of the invention specifically binds to a conformational epitope formed by domain III and IV of human epidermal growth factor receptor 3 (HER3). The other specificities may be the same or different. Preferred second and further specificities are outlined below.

Further examples for bispecific antibodies are described in Brinkmann U & Kontermann RE, MABS, 2017, 9(2), 182-212 and are specifically incorporated herein.

In a particular embodiment the antigen binding proteins of the present invention comprise multimerization domains. Preferred examples are dimerization domains, trimerization domains or a tetramerization domains. If two proteins chains are bound to each comprises at least one dimerization domain capable of binding to at least one dimerization domain in the other protein. Accordingly, if the antigen biding protein comprises three protein chains, each comprises at least one treimization domain capable of interacting with the respective other trimerization domain. In a particular embodiment the dimerization domains are selected from the group consisting of heavy chain domain 2 (CH2) of IgM (MHD2) or IgE (EHD2), immunoglobulin Fc region, heavy chain domain 3 (CH3) of IgG or IgA, heavy chain domain 4 (CH$_4$) of IgM or IgE, Fab, Fab2, leucine zipper motifs, barnase-barstar dimers, miniantibodies, and ZIP miniantibodies; the trimerization domain is selected from the group consisting of tenascin C (TNC), the trimerization region of the C-terminal noncollagenous domain (NC1) of collagen XVIII, Fab3 like molecules, and TriBi-minibodies; or tetramerization domains are selected from the group consisting of the tetramerization domain of p53, the tetramerization domain of the general control protein 4 (GCN4), the tetramerization domain of VASP (vasodilator stimulated phosphoprotein), tandem diabodies, and di-diabodies. In some embodiments the use of heterodimerization domains is preferred, in particular if two protein chains with different antigen specificities are to be used.

In particular embodiments of the first or second aspect of the present invention, the antigen binding protein comprises an ADCC-improved heavy chain sequence.

In particular embodiments of the first or second aspect of the present invention, the antigen binding protein comprises
  (a) a CDRH1 comprising amino acids 32-37 according to SEQ ID NO: 2 and variants thereof comprising one amino acid exchange, a CDRH2 comprising amino acids 52-69 according to SEQ ID NO: 2 and variants thereof comprising one amino acid exchange, and a CDRH3 comprising amino acids 102-112 according to SEQ ID NO: 2 and variants thereof comprising one amino acid exchange, and/or
  (b) a CDRL1 comprising amino acids 23-33 according to SEQ ID NO: 3 and variants thereof comprising one amino acid exchange, a CDRL2 and variants thereof comprising one amino acid exchange comprising amino acids 49-55 according to SEQ ID NO: 3, and a CDR3L comprising amino acids 88-98 according to SEQ ID NO: 3 and variants thereof comprising one amino acid exchange.

In particular embodiments of the first or second aspect of the present invention, the antigen binding protein comprises
  (a) a FRH1 comprising amino acids 1-31 according to SEQ ID NO: 2 and variants thereof comprising at least 80%, preferably 90%, more preferably at least 95% sequence identity, a FRH2 comprising amino acids 38-51 and variants thereof comprising at least 80%, preferably 90%, more preferably at least 95% sequence identity, a FRH3 comprising amino acids 70-101 and variants thereof comprising at least 80%, preferably 90%, more preferably at least 95% sequence identity, and a FRH4 comprising amino acids 113-123 and variants thereof comprising at least 80%, preferably 90%, more preferably at least 95% sequence identity, and/or
  (b) a FRL1 comprising amino acids 1-22 according to SEQ ID NO: 3 and variants thereof comprising at least 80%, preferably 90%, more preferably at least 95% sequence identity, a FRL2 comprising amino acids 34-48 according to SEQ ID NO: 3 and variants thereof comprising at least 80%, preferably 90%, more preferably at least 95% sequence identity, a FRL3 comprising amino acids 56-87 according to SEQ ID NO: 3 and variants thereof comprising at least 80%, preferably 90%, more preferably at least 95% sequence identity, and a FRL4 comprising amino acids 99-109 according to SEQ ID NO: 3 and variants thereof comprising at least 80%, preferably 90%, more preferably at least 95% sequence identity.

In particular embodiments of the first or second aspect of the present invention, the antigen binding protein comprises
  (a) a heavy chain comprising CDRH1 consisting of amino acids 32-37 according to SEQ ID NO: 2 and variants thereof comprising one amino acid exchange, a CDRH2 consisting of amino acids 52-69 according to SEQ ID NO: 2 and variants thereof comprising one amino acid exchange, and a CDRH3 consisting of amino acids 102-112 according to SEQ ID NO: 2 and variants thereof comprising one amino acid exchange, a FRH1 consisting of amino acids 1-31 according to SEQ ID NO: 2 and variants thereof comprising at least 80%, preferably 90%, more preferably at least 95% sequence identity, a FRH2 comprising amino acids 38-51 according to SEQ ID NO: 2 and variants thereof at least 80%, preferably 90%, more preferably at least 95% sequence identity, a FRH3 comprising amino acids 70-101 according to SEQ ID NO: 2 and variants thereof at least 80%, preferably 90%, more preferably at least 95% sequence identity, and a FRH4 comprising amino acids 113-123 according to SEQ ID NO: 2 and variants thereof comprising at least 80%, preferably 90%, more preferably at least 95% sequence identity
  (b) a light chain comprising CDRL1 consisting of amino acids 23-33 according to SEQ ID NO: 3 and variants thereof comprising one amino acid exchange, a CDRL2 comprising amino acids 49-55 according to SEQ ID NO: 3 and variants thereof comprising one amino acid exchange, and a CDR3L comprising amino acids 88-98 according to SEQ ID NO: 3 and variants thereof comprising one amino acid exchange, a FRL1 comprising amino acids 1-22 according to SEQ ID NO: 3 and variants thereof comprising at least 80%, preferably 90%, more preferably at least 95% sequence identity, a FRL2 comprising amino acids 34-48 according to SEQ ID NO: 3 and variants thereof comprising at least 80%, preferably 90%, more preferably at least 95% sequence identity, a FR3L comprising amino acids 56-87 according to SEQ ID NO: 3 and variants thereof comprising at least 80%, preferably 90%, more preferably at least 95% sequence identity, and a FR4L comprising amino acids 99-109 according to SEQ ID NO: 3 and variants thereof comprising at least 80%, preferably 90%, more preferably at least 95% sequence identity.

In particular embodiments of the first or second aspect of the present invention, the antigen binding protein comprises a variable domain comprising a heavy chain according to amino acids 1-123 according to SEQ ID NO: 2 or variants thereof having at least 80%, preferably 90%, more preferably at least 95% identity to amino acid sequence according to SEQ ID NO: 2.

In particular embodiments of the first or second aspect of the present invention, the antigen binding protein comprises a variable domain comprising a light chain according to amino acids 1-109 according to SEQ ID NO: 3 or variants thereof having at least 80%, preferably 90%, more preferably at least 95% identity to amino acid sequence according to SEQ ID NO: 3.

In particular embodiments of the first or second aspect of the present invention, the antigen binding protein comprises a variable domain comprising a heavy chain according to amino acids 1-123 according to SEQ ID NO: 2 and a light chain according to amino acids 1-109 according to SEQ ID NO: 3 or variants thereof having at least 80%, preferably 90%, more preferably at least 95% identity to amino acid sequence according to SEQ ID NO: 3.

In particular embodiments of the first or second aspect of the present invention, the antigen binding protein comprises a heavy chain comprising or consisting of amino acids 1-453 according to SEQ ID NO 4 or variants thereof having at least 80%, preferably 90%, more preferably at least 95% identity to amino acid sequence according to SEQ ID NO: 4.

In particular embodiments of the first or second aspect of the present invention, the antigen binding protein comprises a light chain comprising or consisting of amino acids 1-215 according to SEQ ID NO 5 or variants thereof having at least 80%, preferably 90%, more preferably at least 95% identity to amino acid sequence according to SEQ ID NO: 5.

In particular embodiments of the first or second aspect of the present invention, the antigen binding protein comprises a heavy chain comprising or consisting of amino acids 1-453 according to SEQ ID NO 4 or variants thereof having at least 80%, preferably 90%, more preferably at least 95% identity to amino acid sequence according to SEQ ID NO: 4, and a light chain comprising or consisting of amino acids 1-215 according to SEQ ID NO 5 or variants thereof having at least 80%, preferably 90%, more preferably at least 95% identity to amino acid sequence according to SEQ ID NO: 5

In particular embodiments, the antigen binding protein further comprises a linker, in particular a peptide linker. In particular embodiments, peptide linkers have a length between 5 and 40 amino acids (i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29 30, 31, 32, 33, 34 35, 36, 37, 38, 39, 40 amino acids), in particular between 5 and 20 amino acids (i.e. 1, 2, 3, 4, 5, 6, 7, 8, 9, 10, 11, 12, 13, 14, 15, 16, 17, 18, 19, 20 amino acids), in particular 8 to 15 amino acids (i.e. 8, 9, 10, 11, 12, 13, 14, 15 amino acids).

Particularly preferred are flexible peptide linkers. Flexible linkers are composed of amino acids without bulky side chains that impede rotation or bending of the amino acid chain. Flexible linkers preferably comprise G, S, T, and A residues. In particular embodiments, at least 50% of the amino acids of the flexible linker peptide consists of amino acids selected from the group consisting of G, S, T, and A. In particular embodiments, at least 60%, 70%, 80%, 90%, 95% or 100% of the amino acids of the linker consists of amino acids selected from the group consisting of G, S, T, and A. A large number of peptide linkers are described in the art (Robinson & Sauer, 1998; Völkel et al., 2001; Kavoosi et al., 2007; Watanabe et al., 2011). In particular embodiments, peptide linkers include but are not limited to linker peptide 1: GGGGS (SEQ ID NO: 14), linker peptide 2: GGGGSGGGGS (SEQ ID NO: 15), linker peptide 3: GGGGSGGGGSGGGGS (SEQ ID NO: 16), linker peptide 4: GSLGGSGG (SEQ ID NO: 17), linker peptide 5: GGGSGGGT (SEQ ID NO: 18), linker peptide 6: GGGSGGGTGS (SEQ ID NO: 19), linker peptide 7: GGGSGGGTGSGG (SEQ ID NO: 20), linker peptide 8: GGGGSGGRASGGGGSGGGGS (SEQ ID NO: 21), linker peptide 9: GGGSGGGS (SEQ ID NO: 22), linker peptide 10: EFTRG (SEQ ID NO: 23), and linker peptide 11: AAA (SEQ ID NO: 24), or multimers, derivatives and fragments thereof.

In particular embodiments of the first or second aspect of the present invention, the antigen binding protein comprises a variable domain comprising a heavy chain according to amino acids 1-123 according to SEQ ID NO: 2, a light chain according to amino acids 1-109 according to SEQ ID NO: 3 or variants thereof having at least 80% identity to amino acid sequence, and a peptide linker, in particular a peptide linker according to SEQ ID NO: 16.

In particular embodiments, the peptide linker is position between the heavy chain and the light chain of the variable domain.

In particular embodiments of the first or second aspect of the present invention, the antigen binding protein comprises or consists of the scFv according to SEQ ID NO: 6.

In further preferred embodiments the one or more linkers comprise one or more cleavage sites, i.e. one or more sequence areas wherein the linker sequence may be chemically or enzymatically cleaved by division of one or more peptide-bonds. Enzymatic cleavage may be attained by proteolytic enzymes including but not limited to restriction endonuclease (e.g. type I, type II, type II, type IV or artificial restriction enzymes) and endo- or exo-peptidases or -proteases (e.g. serine-proteases, cysteine-proteases, metalloproteases, threonine proteases, aspartate proteases, glutamic acid proteases). In particularly preferred embodiments the one or more cleavage sites comprise one or more endopeptidase cleavage sites, i.e. wherein the sequence is cleaved or is cleavable by an endopeptidase such as but not limited to trypsin, pepsin, elastase, thrombin, collagenase, furin, thermolysin, endopeptidase V8, and/or cathepsins.

In particular embodiments of the first or second aspect of the present invention, the antigen binding protein further comprises one or more tags. In particular embodiments, the one or more tags is selected from the group consisting of affinity tag, solubilization tag, chromatography tag, epitope tag, and fluorescence tag. In particular embodiments, the tag is selected from the FLAG-tag (SEQ ID NO: 25), His-tag (SEQ ID NO: 26) and Myc-tag (SEQ ID NO: 27).

In particular embodiments of the first or second aspect of the present invention, the antigen binding protein further comprises a leader sequences. In particular embodiments, the leader sequence may be a PelB leader sequence (in particular according to SEQ ID NO: 28) for bacterial expression, an IgK leader sequence (in particular according to SEQ ID NO: 29) or an IL-2 leader sequence (SEQ ID NO: 30) for expression in mammalian cells.

In particular embodiment of the first or second aspect of the present invention, the antigen binding protein comprises the scFv according to SEQ ID NO: 6, a Myc-tag and a His-tag. In particular embodiments of the first or second aspect of the present invention, the antigen binding protein comprises or consists of amino acids 23-310 according to SEQ ID NO: 7.

In particular embodiment of the first or second aspect of the present invention, the antigen binding protein comprises the scFv according to SEQ ID NO: 6, a Myc-tag, a His-tag and a leader sequence, in particular a PelB, a IgGK, or IL-2 leader sequence. In particular embodiments, the antigen binding protein comprises or consists of amino acids 1-310 according to SEQ ID NO: 7.

In embodiments of the first or second aspect of the present invention, the antigen binding protein is a bispecific antigen binding protein directed against the conformational epitope formed by domain III and IV of HER3 and EGFR. In particular embodiments, the antigen binding protein is a single-chain diabody wherein one antigen binding site is directed against the conformational epitope formed by domain III and IV of HER3 as described in detail above, and the second antigen binding site is directed against EGFR. In particular embodiments, the second antigen binding site is directed against EGFR is derived from the EGFR specific humanized antibody hu225, i.e. the humanized version of C225 (cetuximab, Erbitux). In further embodiments, the antigen binding protein is trifunctional and further comprises a Fc domain, in particular an Fc domain recognized by the Fc gamma receptors, in particular CD16, CD32, and/or CD64. In particular embodiments, the antigen binding protein comprises or consist of an amino acid sequence according to amino acids 23-738 of SEQ ID NO: 8. In further embodiments, the antigen binding protein further comprises a leader sequence, in particular an IgK leader sequence. In particular embodiments, the antigen binding protein comprises or consist of an amino acid sequence according to amino acids 1-738 of SEQ ID NO: 8.

In embodiments of the first or second aspect of the present invention, the antigen binding protein is a bispecific antigen binding protein directed against the conformational epitope formed by domain III and IV of HER3 and HER2. In particular embodiments, the antigen binding protein is a single-chain diabody wherein one antigen binding site is directed against the conformational epitope formed by domain III and IV of HER3 as described in detail above, and the second antigen binding site is directed against HER2. In particular embodiments, the second antigen binding site is from the HER2 specific antibody 2-35. In further embodiments, the antigen binding protein is trifunctional and further comprises a Fc domain, in particular an Fc domain recognized by the Fc gamma receptors, in particular CD16, CD32, and/or CD64. In particular embodiments, the antigen binding protein comprises or consist of an amino acid sequence according to amino acids 23-744 of SEQ ID NO: 9. In further embodiments, the antigen binding protein further comprises a leader sequence, in particular an IgK leader sequence. In particular embodiments, the antigen binding protein comprises or consist of an amino acid sequence according to amino acids 1-744 of SEQ ID NO: 9.

In embodiments of the first or second aspect of the present invention, the antigen binding protein comprises a bispecific antigen binding protein directed against the conformational epitope formed by domain III and IV of HER3 and HER2. In particular embodiments, the antigen binding protein is a single chain diabody wherein one antigen binding site is directed against the conformational epitope formed by domain III and IV of HER3 as described in detail above, and the second antigen binding site is directed against HER2. In particular embodiments, the second antigen binding site is directed against HER2 is derived from the HER2 specific antibody 4D5 (trastuzumab, Herceptin). In further embodiments, the antigen binding protein is trifunctional and further comprises a Fc domain, in particular an Fc domain recognized by Fc gamma receptors, in particular CD16, CD32, and/or CD64. In particular embodiments, the antigen binding protein comprises or consist of an amino acid sequence according to amino acids 23-477 of SEQ ID NO: 10. In further embodiments, the antigen binding protein further comprises a leader sequence, in particular a IgK leader sequence. In particular embodiments, the antigen binding protein comprises or consist of an amino acid sequence according to amino acids 1-477 of SEQ ID NO: 10.

In embodiments of the first or second aspect of the present invention, the antigen binding protein comprises an antigen binding site directed against the conformational epitope formed by domain III and IV of HER3 and further comprises a single chain TRAIL (scTRAIL) domain. In particular embodiments, the antigen binding protein comprises an antigen binding site against the conformational epitope formed by domain III and IV of HER3 as described in detail above. In particular embodiments, the antigen binding protein further comprises scFv 3-43, in particular according to SEQ ID NO: 6. In particular embodiments, the antigen binding protein further comprises a Flag-tag. In particular embodiments, the antigen binding protein comprises or consist of an amino acid sequence according to amino acids 23-1020 of SEQ ID NO: 11. In further embodiments, the antigen binding protein further comprises a leader sequence, in particular a IgK leader sequence. In particular embodiments, the antigen binding protein comprises or consist of an amino acid sequence according to amino acids 1-1020 of SEQ ID NO: 11.

In embodiments of the first or second aspect of the present invention, the antigen binding protein comprises a bispecific antigen binding site directed against the conformational epitope formed by domain III and IV of HER3 and CD3. In particular embodiments, the antigen binding protein is a single chain diabody wherein one antigen binding site is directed against the conformational epitope formed by domain III and IV of HER3 as described in detail above, and the second antigen binding site is directed against CD3. In particular embodiments, the second antigen binding site is directed against CD3 is derived from the CD3 specific humanized version of UCHT1. In particular embodiments, the antigen binding protein further comprises a His-tag. In particular embodiments, the antigen binding protein comprises or consist of an amino acid sequence according to amino acids 23-515 of SEQ ID NO: 12. In further embodiments, the antigen binding protein further comprises a leader sequence, in particular an IgK leader sequence. In particular embodiments, the antigen binding protein comprises or consist of an amino acid sequence according to amino acids 1-515 of SEQ ID NO: 12.

In particular embodiments, the antigen binding protein further comprises scFv 3-43, in particular according to SEQ ID NO: 6. In particular embodiments, the antigen binding protein comprises or consist of an amino acid sequence according to amino acids 23-776 of SEQ ID NO: 13. In further embodiments, the antigen binding protein further comprises a leader sequence, in particular a IgK leader sequence. In particular embodiments, the antigen binding protein comprises or consist of an amino acid sequence according to amino acids 1-776 of SEQ ID NO: 13.

In particular embodiments, the antigen binding protein comprises or consists of amino acids sequence selected from the group consisting of SEQ ID NO: 6, amino acids 23-310 of SEQ ID NO: 7, amino acids 23-738 of SEQ ID NO: 8, amino acids 23-724 of SEQ ID NO: 9, amino acids 23-744 of SEQ ID NO: 10, amino acids 23-1020 of SEQ ID NO: 11, amino acids 23-515 of SEQ ID NO: 12, and amino acids 23-776 of SEQ ID NO: 13.

In particular embodiments, the antigen binding protein comprises or consists of amino acids sequence selected from the group consisting of SEQ ID NO: 6, SEQ ID NO: 7, SEQ ID NO: 8, SEQ ID NO: 9, SEQ ID NO: 10, SEQ ID NO: 11, SEQ ID NO: 12, and SEQ ID NO: 13.

It will be appreciated by those skilled in the art that in particular the sequences of the CDR, hypervariable and variable regions can be modified without losing the ability to bind HER3. For example, CDR regions will be either identical or highly homologous to the regions specified herein. By "highly homologous" it is contemplated that from 1 to 5, preferably from 1 to 4, such as 1 to 3 or 1 or 2 substitutions, deletions, or additions may be made in the CDRs. In addition, the hypervariable and variable regions may be modified so that they show substantial homology with the regions specifically disclosed herein.

Furthermore, it may be desired according to the present invention to modify the amino acid sequences described herein, in particular those of human heavy chain constant regions to adapt the sequence to a desired allotype, e.g. an allotype found in the Caucasian population.

The present invention further comprises antibodies in which alterations have been made in the Fc region in order to change the functional or pharmacokinetic properties of the antibodies. Such alterations may result in a decrease or increase of C1q binding and CDC or of FcγR binding and ADCC. Substitutions can, for example, be made in one or more of the amino acid residues of the heavy chain constant region, thereby causing an alteration in an effector function while retaining the ability to bind to the antigen as compared with the modified antibody, cf. U.S. Pat. Nos. 5,624,821 and 5,648,260.

The in vivo half-life of antibodies can be improved by modifying the salvage receptor epitope of the Ig constant domain or an Ig-like constant domain such that the molecule does not comprise an intact CH2 domain or an intact Ig Fc region, cf. U.S. Pat. Nos. 6,121,022 6,194,551. The in vivo half-life can furthermore be increased by making mutations in the Fc region, e.g., by substituting threonine for leucine at position 252, by substituting threonine for serine at position 254, or by substituting threonine for phenylalanine at position 256, cf. U.S. Pat. No. 6,277,375.

Furthermore, the glycosylation pattern of antibodies can be modified in order to change the effector function of the antibodies. For example, the antibodies can be expressed in a transfectoma which does not add the fucose unit normally attached to Asn at position 297 of the Fc region in order to enhance the affinity of the Fc region for Fc-Receptors which, in turn, will result in an increased ADCC of the antibodies in the presence of NK cells, cf. Shield et al. (2002) JBC, 277: 26733. Furthermore, modification of galactosylation can be made in order to modify CDC.

Accordingly, in particular embodiments of the first or second aspect of the present invention, the variant exhibits a sequence identity of at least 85% to the given amino acid sequence. In particular embodiments, the variant exhibits at least 90%. 95%, or 98% sequence identity to the given amino acid sequence.

In a third aspect, the present invention provides a fusion protein comprising the antigen binding protein according to the first and/or second aspect of the present invention as described in detail above and further comprising at least one pharmaceutically active moiety.

In particular embodiments, the at least one pharmaceutically active moiety is a chemical pharmaceutical or a biological. In embodiments, wherein the at least one pharmaceutically active moiety is a biological it is preferred that such biological is a peptide, polypeptide, protein and/or nucleic acid (e.g. DNA, RNA, or hybrids thereof). In particular embodiments, such biological is selected from the group consisting of hormones (e.g. insulin, hGH, FSH, Glucagon-like peptide 1, parathyroid hormone, calcitonin, lutropin, glucagon); growth factors (e.g. erythropoietin, thrombopoietin, G-CSF/GM-CSF, IGF-1); cytokines (e.g. TNF, TRAIL, FasL, TGF-β) such as interferons (e.g. IFN-α, IFN-β, IFN-γ) and interleukins (e.g. IL-2, IL-11, IL-1Ra); costimulatory and immunostimulatory ligands (e.g. 4-1BBL, CD40L, CD27L, OX40L, GITRL, LIGHT); coagulation factors (e.g. factor VIII, factor IX, factor VIIa, thrombin); thrombolytics and anti-coagulants (e.g. t-PA, hirudin, activated protein C); enzymes (e.g. α-glucosidase, glucocerebrosidase, iduronate-2-sulfatase, galactosidase, urate oxidase, DNase); antigen-binding molecule such as antibodies and antibody fragments (e.g. IgG, Fab, Fc); and fusion proteins thereof (e.g. TNFR2-Fc, TMP-Fc, CTLA-4-Fc, IL-1R-Fc, LFA-3-Fc, IL-2-DT).

In particular embodiments, the at least one pharmaceutically active moiety is selected from the group consisting of ligands, effector molecules, half-life extension modules, and imaging molecules.

In particular embodiments, ligands are any chemical or biological substance that forms a complex with another molecule to fulfil a specific biological function such as substrates, inhibitors, and activators. In particular, ligands include but are not limited to antigen-binding molecules, scaffold proteins, natural ligands (e.g. EGF, VEGF, PDGF, FGF, EPO, TPO, TGF-β, TNF, TRAIL), ligand-binding receptor fragments (e.g. TNFR1, TNFR2, VEGFR, CTLA-4, LFA-3, BR3, CD95R, IL-1R, FGFR1), and apatamers (e.g. anti-Thrombin, anti-FIXa, anti-C3b, anti-VEGF, anti-CD40L). Scaffold proteins are regulators of key signalling pathways including but not limited to KSR, MEKK1, BCL-10, MAPK, AHNAK-1, HOMER, Pellino, NLRP, DLG1, Spinophilin, Plant FLU regulatory protein.

In particular embodiments, the antigen-binding molecule is selected from the group consisting of an antibody fragment, a Fab fragment (excluding those from IgM or IgE), a Fab' fragment (excluding those from IgM or IgE), a heavy chain antibody, a single-domain antibody (sdAb), variable domain of a heavy chain antibody, VHH, Nanobodies, a single-chain variable fragment (scFv), a tandem scFv, a bispecific T-cell engager (BITEs), a diabody, a single-chain diabody, a DART molecule, a triple body, a nanoantibody, an alternative scaffold protein (e.g. DARPins, Anticalins, Affibody molecules, Microbodies, Monobodies, Fynomers, Adnetins, Tetranectins, Kunitz domains, Affilins, Avimers), and a fusion protein thereof. It is preferred that the antigen-binding molecule binds to an antigen that is pharmaceutically relevant, i.e. which is suitable to prevent, diagnose and/or treat a disease or the symptoms of a disease or disorder. In preferred embodiment the disease is a cancer type disease. Preferably, the antigen-binding molecule recognises a tumor-associated antigen such as but not limited to EGFR, HER2, HER4, carcinoembryonic antigen (CEA), alphafetoprotein (AFP), CA-125, epithelial tumor antigen (ETA), tyrosinase, melanoma-associated antigen (MAGE), and abnormal products of ras and p53, estrogen receptors, 5-alpha-reductase, prostaglandin-endoperoxide synthase 2, VEGFRs, integrin receptor family, fibroblast activation protein, galectin, EpCAM, CEA, CD44, CD44v, CD2, CDS, CD7, CD19, CD20, CD21, CD22, CD24, CD25, CD30, CD33, CD38, CD40, CD52, CD56, CD71, CD72, CD73, CD105, CD117, CD123, claudins, c-Met, PDGFR, IGF1-R, HMW-MAA, TAG-72, GD2, GD3, GM2, folate receptor, Leg, MUC-1, MUC-2, PSMA, PSCA and uPAR. In preferred embodiments the antigen-binding molecule is envisaged not to be a Fab or Fc fragment from IgM or IgE.

In particular embodiments, the antigen-binding molecule is a scFv, preferably an anti-HER2 scFv or an anti-EGFR scFv.

In particular embodiments, effector molecules, i.e. small molecules, peptides or polypeptides that bind to a protein and thereby alter the activity of that protein, include but are not limited to cytokines, chemokines, immuno(co)-stimulatory molecules, immunosuppressive molecules, death ligands, apoptosis-inducing proteins, enzymes (e.g. kinases) prodrug-converting enzymes, RNases, agonistic antibody or antibody fragment, antagonistic antibody or antibody fragment, toxins, growth factors, hormone, coagulation factor, fibrinolytic protein, peptides mimicking these, and fragments, fusion proteins or derivatives thereof.

In particular embodiments, cytokines are interleukins and/or interferons. Interleukins (IL) include but are not limited to Interleukin-1, Interleukin-2, Interleukin-3, Interleukin-4, Interleukin-5, Interleukin-6, Interleukin-7, Interleukin-8, Interleukin-9, Interleukin-10, Interleukin-11, Interleukin 12, Interleukin-13, Interleukin-14, Interleukin-15, Interleukin-16, Interleukin-17, Interleukin-18, Interleukin-19, Interleukin-20, Interleukin-21, Interleukin-22, Interleukin-23, Interleukin-24, Interleukin-25, Interleukin-26 Interleukin-27, Interleukin-28, Interleukin-29, Interleukin-30, Interleukin-31, Interleukin-32, Interleukin-33, Interleukin-34 and Interleukin-35. Interferons (IFN) include but are not limited to interferon type I (e.g. IFN-α, IFN-β and IFN-ω), interferon type II (e.g. IFN-γ), and interferon type III. In particular included are interferon A1, interferon A2, interferon A4, interferon A5, interferon A6, interferon A7, interferon A8, interferon A10, interferon A13, interferon A14, interferon A16, interferon A17, interferon A21, interferon B1, TNF, TRAIL, and FasL.

In particular embodiments, chemokines include but are not limited to CC chemokines, CXC chemokines, C chemokines, and CX3C chemokines. In particular chemokine include but are not limited to CCL1, CCL2, CCL3, CCL4, CCLS, CCL6, CCL7, CCL8, CCL9/CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17, XCL1, XCL2, and CX3CL1.

In particular embodiments, immuno-(co)stimulatory proteins include but are not limited to B7.1, B7.2, 4-1BBL, LIGHT, ICOSL, GITRL, CD40L, OX40L, and CD70.

Immuno-suppressive proteins may be selected from the group consisting of IL1-Ra, IL-10, CTLA-4, PD-L1, and PD-L2. Toxins may be selected from the group consisting of Pseudomonas exotoxin A, Diphtheria toxin and ricin.

In particular embodiments, apoptosis-inducing proteins may be selected from the group consisting of Bid, Bik, Puma, and Bim, and proapoptotic cytokines (death ligands) such as but not limited to TNF, scTNF, TRAIL, scTRAIL, and FasL. In particular embodiments, the cytokine is TNF. In further embodiments, the cytokine is TRAIL or scTRAIL.

In particular embodiments, enzymes may be selected from the group consisting of oxidoreductases, transferases, hydrolases, lyases, isomerases, ligases. Kinases include but are not limited to AGC kinases such as PKA, PKC and PKG, CaM kinases such as calcium/calmodulin-dependent protein kinases and serine/threonine protein kinases (e.g. DAPK2), CK1 such as the casein kinase 1 group, CMGC such as CDK, MAPK, GSK3 and CLK kinases, STE such as homologs of yeast Sterile 7, Sterile 11, and Sterile 20 kinases, tyrosine kinases (TK), the tyrosine-kinase like group of kinases (TKL), receptor-associated tyrosine kinases, MAP kinases, and histidine kinases.

Pro-drug-converting enzymes may be selected from the group consisting of esterases such as but not limited to acetylesterase, thiolester hydrolases, phosphoric monoester hydrolases, phosphoric diester hydrolases, triphosphoric monoester hydrolases, sulfuric ester hydrolases (sulfatases), diphosphoric monoester hydrolases, and phosphoric triester hydrolases; phosphatases such as but not limited to tyrosine-specific phosphatases, serine/threonine specific phosphatases, dual specificity phosphatases, histidine phosphatase, and lipid phosphatase; and reductases such as but not limited to 5-alpha reductase, dihydrofolate reductase, HMG-CoA reductase, methemoglobin reductase, ribonucleotide reductase, thioredoxin reductase, *E. coli* nitroreductase, methylenetetrahydrofolate reductase, and carboxypeptidase G2, cytosine deaminase, nitroreductase, thymidine kinase.

RNAses include endoribonucleases, in particular selected from the group consisting of RNase A, RNase H, RNase I, RNase III, RNase L, RNase P, RNase PhyM, RNase T1, RNase T2, RNase U2, RNase V1, and RNase V, and exoribonucleases such as but not limited to Polynucleotide Phosphorylase (PNPase), RNase PH, RNase II, RNase R, RNase D, RNase T, Oligoribonuclease Exoribonuclease I, and Exoribonuclease II.

Agonistic antibodies or antibody fragments include those that cause an action in a tissue, organ or individual such as but not limited to receptor-signalling, gene expression, protein synthesis, and protein degradation, e.g. directed against TRAIL receptors, anti-glucocorticoid-induced tumor necrosis factor family receptor (GITR), and CD40. Agonistic antibody or antibody fragment act by binding to the active site or to allosteric sites of a receptor molecule thereby, triggering a specific reaction.

Antagonistic antibodies or antibody fragments include those blocking the action of an agonist. Typically, antagonistic antibodies or antibody fragments act by binding to the active site or to allosteric sites of a receptor molecule, or interact with unique binding sites not normally involved in the regulation of the activity of the receptor, e.g. anti-CTLA-4, anti-TNFR1, anti-VEGFR, anti-PDGFR, anti-EGFR, anti-Her2. Typically, an antagonistic antibody or antibody fragment competes with the agonist at structurally-defined binding sites or alters the binding site of the agonist in a manner that the agonist is not able to cause the action it would normally cause due to its binding.

In particular embodiments growth factors may be selected from the group consisting of to Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor Myostatin (GDF-8), Nerve growth factor (NGF) and other neurotrophins, Platelet-derived growth factor (PDGF), Thrombopoietin (TPO), Transforming growth factor alpha (TGF-α), Transforming growth factor beta (TGF-β), Vascular endothelial growth factor (VEGF), Wnt Signaling Pathway, and placental growth factor (P1GF).

In particular embodiments, coagulation factors may be selected from the group consisting of Thrombin, Factor V, Factor VII, Factor VIII, Factor IX, Factor X, Factor XI, Factor XII and Factor XIII, and active fragments thereof.

In particular embodiments, fibrinolytic proteins may be selected from the group consisting of plasmin, urokinase, plasminogen, α2-antiplasmin, tissue-plasminogen activator (t-PA), and plasminogen activator inhibitor-1 (PAI-1).

Mimicking peptides and proteins include peptides and proteins which mimic activities of other peptides or proteins, in particular of peptides or proteins named herein above or below, in particular thrombopoietin-mimetic peptides, erythropoietin-mimetic peptides.

In further embodiments, half-life extension modules are chemical or biological substances that alter the half-life, e.g. the "plasma half-life" or the "serum half-life", of the polypeptide of the present invention. In particular, the half-life extension module is selected from the group consisting of immunoglobulin binding domains (IgBD), albumin, albumin-binding domains (ABD), peptides, small molecules, fatty acids, antibody fragments, single-domain antibodies, VHH, scaffold proteins, and natural ligands exhibiting affinity for a long-circulating plasma protein, either of which are optionally PEGylated, HESylated, Polysialylated, N-glycosylated, O-glycosylated, or PEG-mimicking polypeptides. Preferably, an IgBD may bind to any of the domains of an Ig molecule, i.e. to the variable domains VH or VL and/or to the constant domains CH1, CH2, CH3 CH4 and/or CL of an Ig molecule. IGBDs include but are not limited to domains derived from protein A (SpA) of *Staphylococcus aureus*, streptococcal protein G (SpG), protein L (PpL) from *peptostreptococcus magnus*, protein Eib from *Escherichia coli*, protein Sbi from *Staphylococcus*, and streptococcal proteins MAG, MIG, H, M and ZAG.

In further embodiments, imaging molecules are those binding to specific target molecules thereby, allowing the visualization of the location of that molecule. In particular, the imaging molecule is selected from the group consisting of bioluminescent reagents, chemiluminescent reagents, fluorescent imaging reagents, photosensitizers, chelating reagents, and radioactive moieties.

Imaging molecule include bioluminescent, chemiluminescent and fluorescent imaging reagent such as but not limited to luciferase from *Renilla reniformis* and/or *Metridia longa*, peroxalate, polymethines (e.g. cyanine dyes such as Cy3, Cy5, Cy5.5, Cy7) squaraine derivatives, phthalocyanine, porphyrin derivatives, and BODIPY analogous (BODIPY FL, BODIPY R6G, BODIPY TR, BODIPY TMR, BODIPY 581/591, BODIPY 630/650, BODIPY 650/665), as well as fluorescent proteins such as but not limited to GFP, EGPF, CFP, BFP, YFP, DsRED (Chudakov et al. (2010) Physiol. Rev. 90:1103-1163).

Chelating reagents are capable of binding at least one metal ion, such as but not limited to calcium, magnesium, iron, aluminium, zinc, copper, arsenic, lead, thallium, and mercury ions, by chelation. Such chelating reagents may comprise ethylenediamine tetraacetic acid (EDTA), ethylenediamine tetraacetic acid (calcium disodium versante) (CaNa2-EDTA), dimercaprol (BAL), dimercaptosuccinic acid (DMSA), dimercapto-propane sulfonate (DMPS), ferritin, deferoxamine and deferasirox, deferiprone (1,2-dimethyl-3-hydroxyl-4-pyridinone), DOTA, DTPA, DADT, DADS, DO3A, N2S2MAMA, Triamidethiol, phosphonates, organic gadolinium complexes, penicillamine, and antibiotic drugs of the tetracycline family.

In particular embodiments, the radioactive moiety comprises a radionuclide. The radioactive moiety may be an isotope of F, Br, Mn, Co, Ga, As, Zr, P, C, S, H, I, In, Lu, Cu, Rh, Bi, At, Y, Re, Ac, Tc, or Hg atom. The radioactive moiety labels polypeptide of the present invention radioactively allowing for its detection, e.g in the human body, rendering it not only useful for diagnostic approaches (radioimmunodetection: RAID) but also suitable in therapeutic applications (radioimmunotherapy: RAIT).

Photosensitizers are chemical compounds capable of light emission or formation of free radicals and singlet oxygen after being excited by light of a specific wavelength. Photosensitizers are used e.g. for photodynamic therapy. In preferred embodiments photosensitizers include but are not limited to compounds of the porphyrin family, texaphyrin family, the chlorin family and the phthalocyanine family, in particular including HpD, ALA, M-ALA, Vertiporfin, Lutexaphyrin, Temoporfin, Talaporfin, HPPH, Phthalocyanine, and Napthalocyanine.

In a fourth aspect, the present invention provides a nucleic acid molecule comprising a sequence encoding the antigen-binding protein of the first or second aspect of the present invention and/or the fusion protein of the third aspect of the present invention. In particular embodiments, such nucleic acid molecule comprises a DNA and/or RNA molecule.

In a fifth aspect the present invention provides a vector comprising the nucleic acid molecule of the fourth aspect of the present invention. In particular embodiments, the vector selected from the group consisting of plasmids, cosmids, phages, viruses and/or artificial chromosomes.

In a sixth aspect the present invention provides a recombinant host cell comprising the antigen-binding protein of the first or second aspect of the present invention, the fusion protein of the third aspect of the present invention, the nucleic acid of the fourth aspect of the present invention, and/or a vector of the fifth aspect of the present invention. In particular embodiments, the host cell is a HEK293, CHO, BHK, or PerC6 cells.

In a seventh aspect the present invention provides a pharmaceutical composition comprising the antigen-binding protein of the first or second aspect of the present invention, the fusion protein of the third aspect of the present invention, the nucleic acid of the fourth aspect of the present invention, and/or a vector of the fifth aspect of the present invention, and further comprising one or more pharmaceutically acceptable carriers, diluents, excipients, fillers, binders, lubricants, glidants, disintegrants, adsorbents, and/or preservatives.

In particular embodiments, the composition of the seventh aspect contains a therapeutically effective amount of the active ingredient, i.e. the antigen-binding protein of the first or second aspect of the present invention, the fusion protein of the third aspect of the present invention, the nucleic acid of the fourth aspect of the present invention, and/or a vector of the fifth aspect of the present invention, preferably in purified form, together with a suitable amount of carrier and/or excipient so as to provide the form for proper administration to the patient. The formulation should suit the mode of administration.

The pharmaceutical compositions can take the form of solutions, suspensions, emulsion, tablets, pills, capsules, powders, sustained-release formulations and the like. The pharmaceutical composition can be formulated as a suppository, with traditional binders and carriers such as triglycerides.

For preparing pharmaceutical compositions of the present invention, pharmaceutically acceptable carriers can be either solid or liquid. Solid form compositions include powders, tablets, pills, capsules, lozenges, cachets, suppositories, and dispersible granules. A solid excipient can be one or more substances, which may also act as diluents, flavoring agents, binders, preservatives, tablet disintegrating agents, or an encapsulating material. In powders, the excipient is preferably a finely divided solid, which is in a mixture with the finely divided inhibitor of the present invention. In tablets, the active ingredient is mixed with the carrier having the necessary binding properties in suitable proportions and compacted in the shape and size desired. Suitable excipients are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. For preparing suppositories, a low melting wax, such as a mixture of fatty acid glycerides or cocoa butter, is first melted and the active component is dispersed homogeneously therein, as by stirring. The molten homogeneous mixture is then poured into convenient sized moulds, allowed to cool, and thereby to solidify. Tablets, powders, capsules, pills, cachets, and lozenges can be used as solid dosage forms suitable for oral administration.

Liquid form compositions include solutions, suspensions, and emulsions, for example, water, saline solutions, aqueous dextrose, glycerol solutions or water/propylene glycol solutions. For parenteral injections (e.g. intravenous, intraarterial, intraosseous infusion, intramuscular, subcutaneous, intraperitoneal, intradermal, and intrathecal injections), liquid preparations can be formulated in solution in, e.g. aqueous polyethylene glycol solution. A saline solution is a preferred carrier when the pharmaceutical composition is administered intravenously.

In particular embodiments, the pharmaceutical composition is in unit dosage form. In such form the composition may be subdivided into unit doses containing appropriate quantities of the active component. The unit dosage form can be a packaged composition, the package containing discrete quantities of the composition, such as packaged tablets, capsules, and powders in vials or ampoules. Also, the unit dosage form can be a capsule, an injection vial, a tablet, a cachet, or a lozenge itself, or it can be the appropriate number of any of these in packaged form.

The composition, if desired, can also contain minor amounts of wetting or emulsifying agents, or pH buffering agents.

Furthermore, such pharmaceutical composition may also comprise other pharmacologically active substance such as but not limited to adjuvants and/or additional active ingredients. Adjuvants in the context of the present invention include but are not limited to inorganic adjuvants, organic adjuvants, oil-based adjuvants, cytokines, particulate adjuvants, virosomes, bacterial adjuvants, synthetic adjuvants, or synthetic polynucleotides adjuvants.

In an eighth aspect, the present invention provides the antigen-binding protein of the first or second aspect of the present invention, the fusion protein of the third aspect of the present invention, the nucleic acid of the fourth aspect of the present invention, the vector of the fifth aspect of the present invention, or the pharmaceutical composition of the seventh aspect of the present invention, for use in medicine. In particular embodiments the use in medicine is the use in the prophylaxis, treatment or diagnosis of a disorder or disease, in particular in the prophylaxis, treatment or diagnosis of proliferative disorders or diseases.

In particular embodiments, the antigen-binding protein of the first or second aspect of the present invention, the fusion protein of the third aspect of the present invention, the nucleic acid of the fourth aspect of the present invention, the vector of the fifth aspect of the present invention, or the pharmaceutical composition of the seventh aspect of the present invention is for use in inhibiting tumor growth or treating cancer.

Proliferative disorders or disorders include but are not limited to Basal cell carcinoma, Bladder cancer, Bone cancer, Brain tumor, Breast cancer, Burkitt lymphoma, Cervical cancer, Colon Cancer, Cutaneous T-cell lymphoma, Esophageal cancer, Retinoblastoma, Gastric (Stomach) cancer, Gastrointestinal stromal tumor, Glioma, Hodgkin lymphoma, Kaposi sarcoma, Leukemias, Lymphomas, Melanoma, Oropharyngeal cancer, Ovarian cancer, Pancreatic cancer, Pleuropulmonary blastoma, Prostate cancer, Throat cancer, Thyroid cancer, and Urethral cancer.

In a ninth aspect the present invention provides a method of inhibiting tumor growth or treating cancer, comprising administering a therapeutically effective amount of antigen-binding protein of the first or second aspect of the present invention, the fusion protein of the third aspect of the present invention, the nucleic acid of the fourth aspect of the present invention, the vector of the fifth aspect of the present invention, or the pharmaceutical composition of the seventh aspect of the present invention to a patient in need thereof.

In the practice of any aspect of the present invention, a pharmaceutical composition as described above or a binding moiety (e.g. an antibody or antigen-binding fragment thereof) may be administered to a patient by any route established in the art which provides a sufficient level of the binding moiety in the patient. It can be administered systemically or locally. Such administration may be parenterally, transmucosally, e.g., orally, nasally, rectally, intravaginally, sublingually, submucosally, transdermally, or by inhalation. Preferably, administration is parenteral, e.g., via intravenous or intraperitoneal injection, and also including, but is not limited to, intra-arterial, intramuscular, intradermal and subcutaneous administration. If the pharmaceutical composition of the present invention is administered locally it can be injected directly into the organ or tissue to be treated, e.g. into the organ afflicted by a tumour.

Pharmaceutical compositions adapted for oral administration may be provided as capsules or tablets; as powders or granules; as solutions, syrups or suspensions (in aqueous or non-aqueous liquids); as edible foams or whips; or as emulsions. Tablets or hard gelatine capsules may comprise lactose, starch or derivatives thereof, magnesium stearate, sodium saccharine, cellulose, magnesium carbonate, stearic acid or salts thereof. Soft gelatine capsules may comprise vegetable oils, waxes, fats, semi-solid, or liquid polyols etc. Solutions and syrups may comprise water, polyols and sugars.

An active agent intended for oral administration may be coated with or admixed with a material that delays disintegration and/or absorption of the active agent in the gastrointestinal tract (e.g., glyceryl monostearate or glyceryl distearate may be used). Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

Pharmaceutical compositions adapted for transdermal administration may be provided as discrete patches intended to remain in intimate contact with the epidermis of the recipient for a prolonged period of time. Pharmaceutical compositions adapted for topical administration may be provided as ointments, creams, suspensions, lotions, powders, solutions, pastes, gels, sprays, aerosols or oils. For topical administration to the skin, mouth, eye or other external tissues a topical ointment or cream is preferably used. When formulated in an ointment, the active ingredient may be employed with either a paraffinic or a water-miscible ointment base. Alternatively, the active ingredient may be formulated in a cream with an oil-in-water base or a water-in-oil base. Pharmaceutical compositions adapted for topical administration to the eye include eye drops. In these compositions, the active ingredient can be dissolved or suspended in a suitable carrier, e.g., in an aqueous solvent. Pharmaceutical compositions adapted for topical administration in the mouth include lozenges, pastilles and mouthwashes.

Pharmaceutical compositions adapted for nasal administration may comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, compositions adopted for nasal administration may comprise liquid carriers, e.g., nasal sprays or nasal drops. These compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient. In a preferred embodiment, pharmaceutical compositions of the invention are administered via the nasal cavity to the lungs.

Pharmaceutical compositions adapted for rectal administration may be provided as suppositories or enemas. Pharmaceutical compositions adapted for vaginal administration may be provided as pessaries, tampons, creams, gels, pastes, foams or spray formulations.

Pharmaceutical compositions adapted for parenteral administration include aqueous and non-aqueous sterile injectable solutions or suspensions, which may contain antioxidants, buffers, bacteriostats and solutes that render the compositions substantially isotonic with the blood of an intended recipient. Other components that may be present in such compositions include water, alcohols, polyols, glycerine and vegetable oils, for example. Compositions adapted for parenteral administration may be presented in unit-dose or multi-dose containers, for example sealed ampules and vials, and may be stored in a freeze-dried (lyophilized) condition requiring only the addition of a sterile liquid carrier, e.g., sterile saline solution for injections, immediately prior to use. Extemporaneous injection solutions and suspensions may be prepared from sterile powders, granules and tablets.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically-sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile saline can be provided so that the ingredients may be mixed prior to administration.

In another embodiment, for example, an inhibitor of chemoattraction can be delivered in a controlled-release system. For example, the inhibitor may be administered using intravenous infusion, an implantable osmotic pump, a transdermal patch, liposomes, or other modes of administration. In one embodiment, a pump may be used (see Sefton (1987) *CRC Crit. Ref Biomed. Eng.* 14: 201; Buchwald et al. (1980) Surgery 88:507; Saudek et al. (1989) N. Eng. J. Med. 321: 574). In another embodiment, the compound can be delivered in a vesicle, in particular a liposome (see Langer (1990) Science 249:1527-1533; Treat et al. (1989) in Liposomes in the Therapy of Infectious Disease and Cancer, Lopez-Berestein and Fidler (eds.), Liss, N.Y., 353-365; WO 91/04014; U.S. Pat. No. 4,704,355). In another embodiment, polymeric materials can be used (see Medical Applications of Controlled Release (1974) Langer and Wise (eds.), CRC Press: Boca Raton, Fla.; Controlled Drug Bioavailability, Drug Product Design and Performance, (1984) Smolen and Ball (eds.), Wiley: N.Y.; Ranger and Peppas (1953) J. Macromol. Sci. Rev. Macromol. Chem. 23: 61; see also Levy et al. (1985) Science 228:190; During et al. (1989) Ann. Neurol. 25: 351; Howard et al. (1989) J. Neurosurg. 71: 105).

In yet another embodiment, a controlled release system can be placed in proximity of the therapeutic target, i.e., the target cells, tissue or organ, thus requiring only a fraction of the systemic dose (see, e.g., Goodson (1984) 115-138 in Medical Applications of Controlled Release, vol. 2). Other controlled release systems are discussed in the review by Langer (1990, Science 249: 1527-1533).

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers.

Selection of the preferred effective dose will be determined by a skilled artisan based upon considering several factors which will be known to one of ordinary skill in the art. Such factors include the particular form of the pharmaceutical composition, e.g. polypeptide or vector, and its pharmacokinetic parameters such as bioavailability, metabolism, half-life, etc., which will have been established during the usual development procedures typically employed in obtaining regulatory approval for a pharmaceutical compound. Further factors in considering the dose include the condition or disease to be prevented and or treated or the benefit to be achieved in a normal individual, the body mass of the patient, the route of administration, whether administration is acute or chronic, concomitant medications, and other factors well known to affect the efficacy of administered pharmaceutical agents. Thus the precise dosage should be decided according to the judgment of the practitioner and each patient's circumstances, e.g., depending upon the condition and the immune status of the individual patient, and according to standard clinical techniques.

The following examples are merely illustrative of the present invention and should not be construed to limit the scope of the invention as indicated by the appended claims in any way.

EXAMPLES

Example 1: Binding and Epitope Specificity of Anti-HER3 Antibody 3-43

A fully human IgG1 molecule (IgG 3-43) comprising the 3-43 variable domain sequence optimized for eukaryotic expression was cloned and expressed in suspension culture adapted HEK 293-6E cells. The protein was purified from the supernatant of transiently transfected cells by protein-A affinity chromatography. SDS-PAGE analysis and size exclusion chromatography confirmed the integrity of the protein. SDS-PAGE analysis of purified IgG 3-43 showed a single band under non-reducing conditions with a molecular mass of intact IgG (approximately 150 kDa) and two bands under nonreducing conditions corresponding to the heavy chain (50 kDa) and the light chain (25 kDa) (FIG. 1A). Size exclusion chromatography confirmed purity of IgG 3-43 (FIG. 1B). Antigen binding of IgG 3-43 was analyzed in ELISA using immobilized HER3-Fc fusion comprising the extracellular domain (aa 27-599) of human HER3. The HER3-Fc fusion protein was coated onto polystyrene microtiter plates at 3 µg/ml in PBS. Remaining binding sites were blocked with PBS, 2% skimmed milk (MPBS). Plates were then incubated with a serial dilution of IgG 3-43 in MPBS. After washing, bound antibody was detected with an HRP-conjugated anti-human Fc antibody and TMB, $H_2O_2$ as substrate. IgG 3-43 showed specific, concentration-dependent binding to HER3 with an $EC_{50}$ value in the subnanomolar range (0.4±0.2 nM) (FIG. 1C). Affinity of IgG 3-43 for the monomeric receptor HER3 was determined via quartz crystal microbalance measurements using an Attana 200 cell instrument. IgG 3-43 was immobilized on the surface of a low nonspecific-binding carboxyl chip by amine coupling, in a density that resulted in a frequency change of about 90 Hz. The measurement was performed at 25° C. with a flow-rate of 25 µl/min of PBST (0.1% Tween) pH7.4. Regeneration of the binding was performed twice with 3M $MgCl_2$ for 15 sec. After every second measurement a buffer injection was performed to determine the baseline, which was subsequently subtracted from the neighboring measurements. Soluble His-tagged HER3 was injected in a two-fold dilution series in PBST in random order, with concentrations between 2.5 to 20 nM (FIG. 1D). A Kd value of 11 nM was determined (Table 1).

Example 2: Epitope Mapping and Cross-Reactivity of Anti-HER3 Antibody 3-43

To localize the epitope of the antibody, full length (aa 20-643) and truncated forms of the human HER3 extracellular domain (DII-DIV aa 208-643, DIII-DIV aa 329-643, DIV aa 532-643) were cloned and produced as Fc fusion proteins in transfected HEK293 cells. SDS-PAGE of the protein-A chromatography-purified fusion proteins under non-reducing and reducing conditions confirmed correct size and dimeric assembly of the fusion proteins. The ability of binding of IgG 3-43 to the different domain-deleted HER3 fusion proteins was assessed in ELISA and immunoblotting experiments under non-reducing conditions (summarized in FIG. 2A). For ELISA, the HER3-Fc fusion proteins were coated onto polystyrene microtiter plates at 10 µg/ml in PBS. Remaining binding sites were blocked with PBS, 2% skimmed milk (MPBS). Plates were then incubated with a serial dilution of IgG 3-43 in MPBS. After washing, bound antibody was detected with an HRP-conjugated anti-human Fab antibody and TMB, $H_2O_2$ as substrate. Binding was detected for the full-length HER3-Fc fusion protein (aa 20-643) as well as the DII-DIV (aa 208-643) Fc and DIII-DIV (aa 329-643) Fc fusion proteins but not with DIV-Fc (aa 532-643). This finding indicates that the epitope of IgG 3-43 resides in domain III of HER3. Fragments comprising part of DIII and the entire DIV (aa 359-643, 395-643, aa 458-643) showed no binding, indicating that the entire DIII domain is required for antibody binding. Surprisingly, when testing a Fc fusion protein containing DI-DIII (aa 20-531; lacking DIV) or DI-DII and a short part of DIII (aa 20-358), no binding was observed. This finding indicates that DIV is also required for antibody binding. Testing fragments comprising DI-III plus parts of DIV (aa 20-587, 20-550) showed binding of 3-43 to aa 20-587 but not to aa 20-550, indicating that the epitope resides in and requires at least aa 328-587. This was confirmed using a fragment composed of aa 329-587, which showed binding in ELISA. In contrast, fragments composed of aa 359-587 or aa 329-550 showed no binding, thus confirming that the epitope resides in and requires aa 329-587.

IgG 3-43 was not able to detect the denatured and reduced HER3-Fc fusion proteins in immunoblotting experiments, while binding was seen with denatured but non-reduced fragments, indicating an epitope for IgG 3-43 sensitive to reduction, i.e. stabilized by disulfide bonds.

Furthermore, we analyzed binding to human and mouse HER3-Fc fusion proteins in ELISA (FIG. 2B). Binding to both HER3-Fc fusion proteins was detected demonstrating that IgG 3-43 is cross-reactive with HER3, thus the epitope of IgG 3-43 is conserved in these two species.

Example 3: Binding of Anti-HER3 Antibody 3-43 to HER3-Expressing Tumor Cell Lines Flow cytometry studies were performed with HER3-expressing MCF-7, FaDu, BT474, A431, NCI-N87, and A549 cells (FIG. 3). Cells were shortly trypsinized at 37° C. Trypsin was quenched with FCS-containing medium and removed by centrifugation and 200.000 cells per probe were seeded. Then, cells were incubated with varying concentrations of IgG 3-43 for at least one hour at 4° C. Washing was performed twice with PBA (2% (v/v) FCS, 0.02% (w/v) $NaN_3$ in 1×PBS). PE-labeled anti-human Fc antibody from mouse was incubated for another hour to visualize bound antibody molecules. After two further washing steps, fluorescence was measured with a MACSQuant® Analyzer 10 and median fluorescence intensities relative to unstained cells were calculated using the FlowJo software. These experiments demonstrated binding of IgG 3-43 to the cellular receptor with surprisingly low $EC_{50}$ values in a range between 26 to 74 pM.

Example 4: IgG 3-43 Inhibits Heregulin Ligand Binding

Recombinant his-tagged human HRG-β1 was incubated with MCF-7 cells and bound protein was detected via PE conjugated anti-his antibody. Preincubation with excess amounts of IgG 3-43 (3 µM) strongly reduced the fluorescence intensity of the cells, indicating blocking of HRG binding, whereas preincubation with Cetuximab as a negative control did not have the same effect (FIG. 4).

Example 5: Inhibition of Heregulin-Induced HER3 Phosphorylation and Signal Transduction by Anti-HER3 Antibody 3-43

IgG 3-43 was further analyzed for its capacity of preventing HRG-induced phosphorylation of HER3. Semi-confluent cells were incubated with IgG 3-43 for one hour, followed by 15 minutes stimulation with HRG (50 ng/ml). Western blot analyses of the cell lysates revealed efficient blockade of HER3 phosphorylation as well as repression of HRG-induced Erk and Akt phosphorylation in different cell lines (MCF-7, BT-474, NCI-N87, A431, A549, FaDu) (FIG. 5). Titration of IgG 3-43 further revealed an $IC_{50}$ value in the low picomolar range for blockade of HRG induced HER3 phosphorylation. Density of the bands was analyzed with the Fusion Solo S software (Vilber) and the relative values to tubulin loading control were used to calculate the $IC_{50}$ values. For MCF-7 cells an $IC_{50}$ value of 80 pM was determined. A comparison with anti-HER3 IgG 3M6, which comprises the same variable domain as seribantumab, on MCF-7 cells, demonstrated superior activity of IgG 3-43. Here, 3M6 inhibited HER3 phosphorylation with an $IC_{50}$ value of 270 pM.

Example 6: HER3 Internalization Induced by Anti-HER3 IgG 3-43

Cellular HER3 expression levels and IgG localization after incubation of IgG 3-43 were analyzed by western blot and immuno-fluorescence microscopy, respectively. For Western blot analysis, MCF-7 cells were seeded in 6 well plates two days before, to be semi confluent on the day of the experiment. Cells were serum starved for one night and incubated with 100 nM IgG 3-43 for the indicated time points. HER3 levels were analyzed by western blot. Density of the bands was analyzed with the Fusion Solo S software (Vilber). The values were corrected for loading differences by reactivation to tubulin loading control and normalized to the relative values of untreated probes. IgG 3-43 rapidly leads to a reduction of HER3 levels in MCF-7 cells (FIG. 6). Furthermore, Cy5-labeled IgG 3-43 was rapidly internalized into MCF-7 cells as shown by confocal microscopy (not shown). After one hour, a strong intracellular accumulation of IgG 3-43 was detectable.

Example 7: Inhibition of Cell Proliferation by Anti-HER3 IgG 3-43

IgG 3-43 was further evaluated concerning its ability to reduce tumor cell proliferation in vitro. To monitor this effect, various human cancer cell lines (MCF-7, BT-474, NCI-N87, FaDu) were seeded at low density in 96 well plates, let adhere for one night, and were afterwards incubated under low serum concentration with IgG 3-43 or other antibodies as control. Proliferation was determined after 1 week of incubation. For all four cell lines a reduction on proliferation compared to control antibody was observed (FIG. 7). For FaDu, an $IC_{50}$ value of 273 pM was determined under these conditions.

Example 8: IgG 3-43 Efficiently Inhibits Growth of s.c. Xenograft FaDu Tumors in SCID Mice The antitumor activity of IgG 3-43 was tested in a subcutaneous FaDu xenograft model in SCID mice. $5\times10^6$ cells were injected into both flanks of the mice and treatment was started when tumors reached a volume of approximately 80 mm$^3$ (14 days after tumor cell inoculation). Mice received twice weekly intravenous injections for 3 weeks at doses of 30, 100, and 300 µg, including PBS as negative control. Antitumor effects were observed for all three dosing regiments of IgG 3-43 with increased survival (increased median survival only for the two higher concentrations) and a significant tumor growth inhibition (FIG. 8).

Example 9: A Bispecific Single-Chain Diabody-Fc Fusion Protein Targeting EGFR and HER3 Induces Potent Inhibition of EGFR and HER3 Activation We generated a bispecific antibody targeting EGFR and HER3 in the single-chain diabody-Fc format (FIG. 9A, C) comprising the antibody moieties of hu225 (humanized version of C225 (cetuximab, Erbitux)) and 3-43. The scDb-Fc fusion protein was produced in HEK293-6E suspension cells and purified from cell culture supernatant by protein A affinity purification. SDS-PAGE analysis of the scDb hu225x3-43-Fc revealed single bands at an apparent molecular mass of approximately 82 kDa under reducing conditions and 200 kDa under non-reducing conditions corresponding to the monomeric and dimeric assembly of the construct (FIG. 9B). In contrast, cetuximab and IgG 3-43 showed two bands under reducing conditions representing the heavy and light chains. Purity was confirmed by size exclusion chromatography (FIG. 9C). The binding activity of the scDb-Fc to its antigens and to cells expressing ErbB receptors was assessed by ELISA and flow cytometry, respectively. ELISA analysis revealed that the binding activity of the parental antibodies to the extracellular domain (ECD) of EGFR and HER3 is retained in the scDb-Fc format (see FIG. 10A). The scDb-Fc molecule and the parental antibodies bound with similar $EC_{50}$ values in the subnanomolar range to their corresponding antigens (Table 3). Flow cytometry analysis showed that cetuximab and the scDb hu225x3-43-Fc bound to FaDu cells with an $EC_{50}$ value of 0.2 nM, whereas IgG 3-43 bound with an $EC_{50}$ value of 0.006 nM (FIG. 10B).

Next, signaling inhibition assays in MCF-7 cells were performed to determine if receptor activation is inhibited by treatment with the scDb hu225x3-43-Fc (FIG. 11). Heregulin induced HER3 phosphorylation and activation of the downstream effectors Akt and Erk1/2. Pretreatment with IgG 3-43 and the combination of IgG 3-43 and cetuximab efficiently blocked HER3 phosphorylation and activation of Akt and Erk1/2 and HER3 was degraded. Treatment with the scDb hu225x3-43-Fc also showed strong inhibition of HER3 signaling and resulted in HER3 degradation. Signaling inhibition assays were also performed in other ErbB-overexpressing cell lines (A-431, A549, FaDu, NCI-N87, SK-BR-3) and inhibition of EGFR stimulated with EGF was additionally evaluated (FIG. 12A-F). The bispecific scDb hu225x3-43-Fc as well as the combination of cetuximab and IgG 3-43 inhibited both phosphorylation of EGFR in the presence of EGF and phosphorylation of HER3 in the presence of heregulin in all cell lines. To further investigate possible differences in HER3 signaling inhibition between the scDb-Fc and the parental antibodies, signaling inhibition assays were performed with serial dilutions of the antibodies in FaDu cells in presence of heregulin (see FIG. 13). The scDb-Fc inhibited HER3 phosphorylation with an $IC_{50}$ value of 0.008 nM, whereas the combination of IgG 3-43 and cetuximab blocked HER3 phosphorylation with an $IC_{50}$ value of 0.081 nM demonstrating that the bispecific antibody has superior inhibitory activity for HER3 phosphorylation in comparison to the combination of the monospecific parental antibodies.

Example 10: A Bispecific Single-Chain Diabody-Fc Fusion Protein Targeting HER2 and HER3 Derived from Antibodies 2-35 and 3-43

We constructed a bispecific antibody targeting HER2 and HER3 in the single-chain diabody-Fc format containing the antibody moieties of antibodies 2-35 and 3-43. The 2-35 moiety was also identified by phage display and is specific for the extracellular domain of HER2. The scDb-Fc fusion protein was produced in HEK293-6E suspension cells and purified from cell culture supernatant by protein A affinity purification. SDS-PAGE analysis of the scDb 2-35x3-43-Fc revealed a single band at an apparent molecular weight of about 82 kDa under reducing conditions and 200 kDa under non-reducing conditions (see FIG. 14A). Purity was confirmed by size exclusion chromatography (see FIG. 14B). Binding of the scDb-Fc to the extracellular domain of HER2 and HER3 in comparison to the parental antibodies IgG 2-35 and IgG 3-43 was determined by ELISA. ELISA analysis revealed that the binding activity of the parental antibodies to the ECD proteins of HER2 and HER3 is retained in the scDb-Fc format (see FIG. 15). The scDb 2-35x3-43-Fc and IgG 2-35 bound with an $EC_{50}$ value of approximately 1.5 nM to the HER2-ECD, whereas the bispecific antibody bound with an $EC_{50}$ value of 0.24 nM and IgG 3-43 bound with an $EC_{50}$ value of 0.33 nM to the HER3-ECD. Signaling inhibition assays in MCF-7 cells showed that IgG 2-35 only slightly decreased HER3 phosphorylation which is likely due to inhibition of HER3 heterodimerization with HER2 (see FIG. 11). The combination of the 2-35 and 3-43 moieties in the bispecific antibody format showed potent inhibition of HER3 signaling. These results demonstrate that the scDb 2-35x3-43-Fc might be a further candidate for blocking compensatory signaling axes and thus preventing tumor escape.

Example 11: Anti-HER3 scTRAIL Fusion Proteins Mediate Target-Dependent Cytotoxicity TNF-related apoptosis-inducing ligand (TRAIL) is considered as a promising effector molecule, due to its selective toxicity on cancer cells. A single-chain version of TRAIL was fused to the C-terminus of a human IgG1 Fc part (Fc-scTRAIL) to induce dimeric assembly, which greatly increases anti-tumor effects. To further improve the bioactivity, scFv 3-43 was fused N-terminally to the Fc part generating scFv3-43-Fc-scTRAIL. The fusion protein was produced in stably transfected HEK293 cells and purified from the supernatant via anti-FLAG affinity chromatography. SDS-PAGE analysis and size exclusion chromatography confirmed purity and integrity of the protein (see FIG. 16).

The new scFv3-43-Fc-scTRAIL fusion protein was evaluated concerning its ability to bind to the corresponding target antigen and human TRAIL-R2 by ELISA as well as by flow cytometry using intact Colo205 and HCT-116 cells. Antigen and TRAIL-receptor binding was analyzed in ELISA using Fc fusion proteins of the corresponding extracellular domains. ScFv3-43-Fc-scTRAIL showed specific, concentration-dependent binding to HER3 with an $EC_{50}$ value in the subnanomolar range (see FIG. 17A, Table 4). Further ELISA studies revealed potent binding to human TRAIL-R2 with an $EC_{50}$ value of 2.84 nM (see Figure M2B, Table M1).

Thus, fusion to scFv3-43 does not hinder TRAIL-R2 binding. The ELISA results were confirmed by flow cytometry studies with antigen- and TRAIL receptor-expressing Colo205 and HCT-116 cells (see FIG. 17C, D). These data show that scFv3-43-Fc-scTRAIL possesses full functionality concerning binding to purified and cell surface expressed HER3 and TRAIL-R2.

Cell death induction of scFv3-43-Fc-scTRAIL was analyzed using Colo205 cells and compared to the non-targeted Fc-scTRAIL. One day before treatment, 50,000 Colo205 cells/well were seeded in 96-well plates. After pretreatment of the cells with the sensitizer bortezomib (650 nM) or medium for 30 min, cells were incubated with serial dilutions of the fusion proteins for 16 h. Cell death was analyzed by crystal violet staining. ScFv3-43-Fc-scTRAIL showed strong induction of cell death on Colo205, which could be further enhanced in the presence of bortezomib (see FIG. 18). Comparison with the non-targeted Fc-scTRAIL revealed better effects of scFv3-43-Fc-scTRAIL in the absence and presence of bortezomib (see FIG. 18, Table 5). To confirm that this superiority is caused by the scFv3-43 targeting moiety, experiments were repeated adding the corresponding blocking antibody scFv3-43-Fc (200-fold molar excess) to the pretreatment of the cells. In the presence of the blocking antibody the effects of scFv3-43-Fc-scTRAIL were reduced to the level of those of the non-targeted Fc-scTRAIL (see FIG. 18, Table 5). This confirms the suitability of the 3-43 antibody moiety for targeting of cytotoxic fusion proteins to improve anti-tumor effects.

Example 12: Anti-HER3× Anti-CD3 Bispecific Antibody for T-Cell Retargeting

A bispecific scDb molecule was generated by combining the binding site of anti-HER3 3-43 with a humanized version of anti-human CD3 antibody UCHT1. Thus, the scDb 3-43xCD3 exhibits one binding site for HER3 and one binding site for CD3 (FIGS. 19A and B). The scDb 3-43xCD3 was produced in HEK293 cells and purified by IMAC. SDS-PAGE analysis of the scDb 3-43xCD3 revealed single bands at an apparent molecular mass of approximately 55 kDa under reducing conditions and 50 kDa under non-reducing conditions (FIG. 19C). Size exclusion chromatography confirmed purity and integrity of the protein with an apparent molecular mass of approximately 50 kDa (hydrodynamic radius: 2.96 nm) (FIG. 19D).

The binding of the novel scDb construct was evaluated by ELISA and flow cytometry.

Antigen binding of scDb 3-43xCD3 was analyzed in ELISA using immobilized HER3-Fc fusion comprising the extracellular domain (aa 27-599) of human HER3. The HER3-Fc fusion protein was coated onto polystyrene microtiter plates at 2 μg/ml in PBS. Remaining binding sites were blocked with PBS, 2% skimmed milk (MPBS). Plates were then incubated with a serial dilution of scDb 3-43xCD3 in MPBS. After washing, bound antibody was detected with an HRP-conjugated anti-His antibody and TMB, $H_2O_2$ as substrate. ScDb 3-43xCD3 showed specific, concentration-dependent binding to HER3 with an $EC_{50}$ value in the lower nanomolar range (3.3 nM) (FIG. 19E).

Flow cytometry studies were performed with HER3-expressing MCF-7 (FIG. 19F) and CD3-expressing Jurkat (FIG. 19G). For the adherent MCF-7, cells were shortly trypsinized at 37° C. and trypsin was quenched with FCS containing medium and removed by centrifugation. For both, MCF-7 and Jurkat, 100,000 cells per well were seeded and incubated with a titration of scDb 3-43xCD3 in PBA (2% (v/v) FCS, 0.02% (w/v) NaN3 in 1×PBS) for one hour at 4° C. Washing was performed twice with PBA. Bound protein was detected using PE-conjugated anti-His antibody incubated for another hour at 4° C. After washing, fluorescence was measured with a MACSQuant® Analyzer 10. Relative median fluorescence intensities (to unstained cells) were calculated using the MACSQuant® software. Similar binding activities were observed for both antigen binding sites in the lower nanomolar range with $EC_{50}$ values of 1.1 nM for MCF-7 and 3.1 nM or Jurkat (FIGS. 19F and G).

Activation of T cells was analyzed in an IL-2 release assay using HER3-expressing Colo205 cells and PBMC. One day before the treatment, 20,000 Colo205 cells were seeded per well in a 96-well plate. The medium was removed and substituted with a titration of the scDb 3-43xCD3 in fresh medium. After 1 hour of incubation at room temperature, 200,000 PBMC per well were added and incubated for additional 24 hours at 37° C. The supernatant was collected and concentration of IL-2 was determined by ELISA (human IL-2 kit, R&D) according to the instructions supplied by the manufacturer. ScDb 3-43xCD3 showed dose-dependent release of IL-2 (activation of T cells) in the subnanomolar range with an $EC_{50}$ value of 0.3 nM (FIG. 19H).

Example 13: Trivalent, Bispecific Anti-HER3×Anti-CD3 Bispecific Antibody for T-Cell Retargeting A trivalent, bispecific scDb3-43xCD3-scFv343 (scDb-scFv) molecule was generated by combining the scDb molecule, specific for HER3 (3-43) and CD3 (humanized version of UCHT1), with an anti-HER3 specific scFv (3-43). Thus, the scDb-scFv exhibits two binding site for HER3 and one binding site for CD3 (FIG. 20A). The scDb-scFv was produced in HEK293E cells and purified by IMAC. SDS-PAGE analysis of the scDb-scFv revealed single bands at an apparent molecular mass of approximately 80 kDa under reducing conditions and 75 kDa under non-reducing conditions (FIG. 20B). Size exclusion chromatography confirmed purity and integrity of the protein with an apparent molecular mass of approximately 62 kDa (hydrodynamic radius: 3.83 nm) (FIG. 20C).

Antigen binding of scDb-scFv was analyzed in ELISA using immobilized HER3-Fc fusion comprising the extracellular domain (aa 27-599) of human HER3. The HER3-Fc fusion protein was coated onto polystyrene microtiter plates at 2 µg/ml in PBS. Remaining binding sites were blocked with PBS, 2% skimmed milk (MPBS). Plates were then incubated with a serial dilution of scDb-scFv and the bivalent and bispecific scDb3-43xCD3 as control in MPBS. After washing, bound antibody was detected with an HRP-conjugated anti-His antibody and TMB, $H_2O_2$ as substrate. ScDb-scFv showed specific, concentration-dependent binding to HER3 with an $EC_{50}$ value in the sub-nanomolar range (0.81 nM), whereas the scDb3-43xCD3 showed an $EC_{50}$ value in the lower nanomolar range (4.87 nM) (FIG. 20D).

Flow cytometry studies were performed with HER3-expressing MCF-7 (FIG. 20E) and CD3-expressing Jurkat (FIG. 20F). For the adherent MCF-7, cells were shortly trypsinized at 37° C. and trypsin was quenched with FCS containing medium and removed by centrifugation. For both, MCF-7 and Jurkat, 100,000 cells per well were seeded and incubated with a titration of scDb-scFv in PBA (2% (v/v) FCS, 0.02% (w/v) NaN3 in 1×PBS) for one hour at 4° C. Washing was performed twice with PBA. Bound protein was detected using PE-conjugated anti-His antibody incubated for another hour at 4° C. After washing, fluorescence was measured with a MACSQuant® Analyzer 10. Relative median fluorescence intensities (to unstained cells) were calculated using the MACSQuant® software. Binding to MCF-7 cells was observed in the picomolar range with an $EC_{50}$ value of 31.6 pM, comparable to the binding properties of the whole IgG3-43 molecule, and binding to Jurkat cells in the nanomolar range with an $EC_{50}$ value of 13.2 nM (FIGS. 20 E and F).

Example 14: A Bispecific Single-Chain Diabody-Fc Fusion Protein Targeting HER2 and HER3 Derived from Antibodies 4D5 and 3-43

We generated a bispecific antibody targeting HER2 and HER3 in the single-chain diabody-Fc format (FIG. 21) comprising the antibody moieties of 4D5 (trastuzumab, Herceptin) and 3-43. The scDb-Fc fusion protein was produced in HEK293-6E suspension cells and purified from cell culture supernatant by protein A affinity purification and following FPLC SEC. SDS-PAGE analysis of the scDb 4D5x3-43-Fc revealed single bands at an apparent molecular mass of approximately 85 kDa under reducing conditions and 200 kDa under non-reducing conditions corresponding to the monomeric and dimeric polypeptide chains of the construct (FIG. 21A). Purity and integrity was confirmed by size exclusion chromatography with an apparent molecular mass of approximately 175 kDa (FIG. 21B). Antigen binding of scDb 4D5x3-43-Fc was analyzed in ELISA using immobilized HER2-His or HER3-His comprising the extracellular domain of human HER2 or HER3. The antigens were coated onto polystyrene microtiter plates at 2 µg/ml in PBS. Remaining binding sites were blocked with PBS, 2% skimmed milk (MPBS).

Plates were then incubated with a serial dilution of scDb-Fc fusion protein in MPBS. After washing, bound antibody was detected with an HRP-conjugated anti-human Fc antibody and TMB, $H_2O_2$ as substrate. ELISA analysis revealed binding in the nanomolar range of the scDb 4D5x3-43-Fc fusion protein with $EC_{50}$ values of 2.5 nM for HER2-His and 1.9 nM for HER3-His (see FIG. 21C).

Flow cytometry studies were performed with HER2- and HER3-expressing FaDu cells (FIG. 21D). FaDu cells were shortly trypsinized at 37° C., trypsin was quenched with FCS-containing medium and removed by centrifugation. 100,000 cells per well were seeded and incubated with a titration of scDb-Fc in PBA (2% (v/v) FCS, 0.02% (w/v) NaN3 in 1×PBS) for one hour at 4° C. Washing was performed twice with PBA. Bound protein was detected using PE-conjugated anti-human Fc antibody incubated for another hour at 4° C. After washing, fluorescence was measured with a MACSQuant® Analyzer 10. Relative median fluorescence intensities (to unstained cells) were calculated using the MACSQuant® software. Binding to FaDu cells was observed in the nanomolar range with an $EC_{50}$ value of 2.9 nM, comparable to the binding properties obtained from the ELISA analysis.

Example 15: Inhibition of Ligand-Independent Colony Formation of SKBR3 and BT474 Tumor Cells Incubated with IgG 3-43

SKBR3 and BT474 express high levels of HER2 and can, thus proliferate in a ligand-independent manner. The potential of IgG 3-43 to inhibited colony formation, as marker for cell proliferation, was analyzed on these two cell lines (FIG. 22). Cells (1,000 cells per well) were seeded into a 12-well plate in RPMI medium. The next day, cells were incubated with antibody (IgG 3-43 or Trastuzumab) at a concentration of 50 nM in RPMI medium containing 2% FCS. After 7 days, medium was removed and fresh medium with antibody at the same concentration was added. At day 12, cells were fixed with Histofix for 10 min at room temperature and cells were stained with crystal violet for 10 min (FIG. 22A). Untreated cells (con) were included as negative control. All incubations were performed in triplicates. Trastuzumab, directed against HER2, was included as positive control. A potent inhibition of colony formation was observed for IgG 3-43 and trastuzumab on both cell lines (FIG. 22B). These findings indicate that HER3 forms signaling competent heterodimers with HER2 even in the absence heregulin, which can be inhibited by IgG 3-43.

Example 16: A Bispecific and Tetravalent Diabody-Ig Fusion Protein (Db-Ig) Targeting EGFR (hu225) and HER3 (3-43)

A tetravalent, bispecific Db3-43xhu225-Ig molecule was generated by combining a Db molecule, specific for EGFR (hu225; humanized version of C225 (cetuximab, Erbitux)) and HER3 (3-43), with the constant domains of an IgG antibody. Thus, the Db3-43xhu225-Ig molecule consists of two different polypeptides, $V_H3\text{-}43\text{x}V_L\text{hu}225\text{-}C_L$ (light chain, SEQ ID NO: 31) and $V_H\text{hu}225\text{x}V_L\text{hu}3\text{-}43\text{-}C_H1\text{-}C_H2\text{-}C_H3$ (heavy chain, SEQ ID NO: 32) (FIG. 23A). The bispecific Db3-43xhu225-Ig exhibits two antigen binding sites for EGFR and two antigen binding sites for HER3 (FIG. 23B). Db3-43xhu225-Ig was expressed in transiently transfected HEK293-6E cells after co-administration of two plasmids encoding for either light chain or heavy chain, using polyethylenimine as transfection reagent. Protein secreted into cell culture supernatant was purified using CH1-CaptureSelect affinity chromatography. SDS-PAGE analysis revealed two bands under reducing conditions at approximately 65 kDa and 35 kDa corresponding to the heavy and light chain, and one major band under non-reducing conditions at approximately 220 kDa corresponding to the bispecific Db-Ig molecule (FIG. 23C). Purity, integrity and homogeneity of the Db3-43xhu225-Ig molecule were confirmed by size exclusion chromatography (FIG. 23D). Binding of the Db3-43xhu225-Ig and the monospecific parental antibodies (Cetuximab (anti-EGFR) and 3-43-IgG (anti-HER3)) to the extracellular domain (ECD) of EGFR (aa 20-643) and HER3 (aa 27-599) was determined by ELISA. The His-tagged EGFR or HER3 fusion protein was coated onto polystyrene microtiter plates at a concentration of 2 µg/ml diluted in PBS. Remaining binding sites were blocked with PBS, 2% skimmed milk (MPBS). Plates were then incubated with serial dilution of the bispecific Db3-43xhu225-Ig or the monospecific parental antibodies. After washing, bound antibodies were detected with an HRP-conjugated anti-human Fc antibody and TMB, $H_2O_2$ as substrate. ELISA analysis revealed that binding activity of the parental antibodies to the extracellular domain of EGFR and HER3 is retained in the Db-Ig format. The bispecific, tetravalent Db3-43xhu225-Ig showed concentration-dependent binding to EGFR and HER3 with an $EC_{50}$ value in the sub-nanomolar range (0.19 nM for EGFR; 0.26 nM for HER3) (FIG. 23E). The parental antibodies bound with similar $EC_{50}$ values to their corresponding antigens (Table 6). Simultaneous binding to both antigens, EGFR and HER3, was confirmed by a second binding ELISA analysis. As first antigen, EGFR-Fc fusion protein was coated onto polystyrene microtiter plates at 2 µg/ml in PBS. Remaining binding sites were blocked with PBS, 2% skimmed milk (MPBS). Plates were then incubated with serial dilution of the bispecific Db3-43xhu225-Ig diluted in MPBS. After washing, the second antigen, HER3-His (HER3 (aa 27-599) of the extracellular domain fused C-terminally with a hexa-histidyl-tag; 300 nM diluted in MPBS), was added to the plates. After washing, bound HER3-His (second antigen) was detected with an HRP-conjugated anti-His-tag antibody and TMB, $H_2O_2$ as substrate. The second antigen was bound to the bispecific Db3-43xhu225-Ig in a concentration-dependent manner with an $EC_{50}$ value in the sub-nanomolar range (0.85 nM) (FIG. 23F) similar as binding of Db3-43xhu225-Ig to coated HER3-Fc. Thus, this result demonstrates the unrestricted accessibility of both antigen binding sites within the Db-Ig molecule.

In addition, binding studies of Db3-43xhu225-Ig and parental monoclonal antibodies (cetuximab and 3-43-IgG) to EGFR- and/or HER3-expressing cells (MCF-7, SKBR-3, and FaDu) (FIG. 23G) were analyzed via flow cytometry. Adherent cells were washed with PBS and shortly trypsinized at 37° C. Trypsin was quenched with FCS containing medium and removed by centrifugation (500×g, 5 minutes). 100,000 cells per well were seeded and incubated with a serial dilution of Db3-43xhu225-Ig or parental monoclonal antibodies diluted in PBA (PBS containing 2% (v/v) FCS, 0.02% (w/v) NaN3) for one hour at 4° C. Cells were washed twice using PBA. Bound antibodies were detected using PE-labeled anti-human Fc secondary antibody, which was incubated for another hour at 4° C. After washing, median fluorescence intensity (MFI) was measured with a Milltenyi MACSQuant® Analyzer 10. Relative MFI (to unstained cells) were calculated by MACSQuant® software and Excel. For the HER3-positive MCF-7 cell line, binding of the bispecific Db3-43xhu225-Ig bound in the sub-nanomolar range with an $EC_{50}$ value of 0.054 nM. As the parental anti-HER3 3-43-IgG bound with similar $EC_{50}$ values (0.021 nM), the binding activity of the parental anti-HER3 antibodies is retained in the Db-Ig format. No binding to MCF-7 cells was observed for the anti-EGFR antibody cetuximab. Regarding the cell line SKBR-3, which expresses EGFR and HER3 in similar ranges, the bispecific Db3-43xhu225-Ig molecule bound with an $EC_{50}$ value of 0.047 nM, similar to the binding of both parental antibodies cetuximab (0.031 nM) and 3-43-IgG (0.022 nM). Concerning binding to FaDu Db3-43xhu225-Ig bound with an $EC_{50}$ values of 0.14 nM. As the parental anti-EGFR antibody cetuximab bound to the cells with a similar $EC_{50}$ value (0.13 nM), the binding activity of the parental antibody cetuximab is also retained in the Db-Ig format. As FaDu cells express very high amount of EGFR and comparatively low amount of HER3, Db3-43xhu225-Ig bound most likely preferential with the hu225 moieties to the cells. However, the parental anti-HER3 3-43-IgG also bound with comparatively low fluorescence signal to the cells with an $EC_{50}$ value of 0.003 nM. (FIG. 23G, Table 1).

The pharmacokinetic profile of the bispecific and tetravalent Db3-43xhu225-Ig molecule was analyzed in SWISS mice. 25 µg of the protein was diluted in 100 µl sterile PBS and injected intravenously into the tail. After different time points (3 minutes, 30 minutes, 1 hour, 2 hours, 6 hours, 1 day, 3 days, and 7 days) blood samples were taken from the tail and incubated on ice for 10 minutes. Clotted blood was centrifuged (16,000×g, 20 minutes, 4° C.) and serum samples were stored at −20° C. Protein serum concentration was determined via ELISA. EGFR-Fc or HER3-Fc fusion protein was coated onto polystyrene microtiter plates at a concentration of 2 µg/ml diluted in PBS. Remaining binding sites were blocked with PBS, 2% skimmed milk (MPBS). Plates were then incubated with serum diluted in MPBS. After washing, bound antibodies were detected with an HRP-conjugated anti-human Fab antibody and TMB, $H_2O_2$ as substrate. Serum concentration of the Db3-43xhu225-Ig molecule was interpolated from a standard curve of purified fusion protein (FIG. 24). No differences were observed for the serum concentrations of Db3-43xhu225-Ig using either EGFR-Fc or HER3-Fc fusion protein as coated antigen. The bispecific Db3-43xhu225-Ig molecule had an initial half-life of approximately 2.7 h and a terminal half-life in the range of 87 to 92 h.

Example 17: Anti-HER3 scFv-Fc-scTRAIL Fusion Proteins Mediate Target-Dependent Cytotoxicity In Vitro Against Various Melanoma Cell Lines A panel of melanoma cell lines was screened by flow cytometry for expression of HER3, which was quantified using a QIFIKIT (Dako) (FIG. 25A). Most of the melanoma cell lines analyzed showed HER3 expression to various extent. A375 with moderate HER3 expression were chosen for analyzing binding of an anti-HER3 scFv-Fc-scTRAIL fusion protein (see example 11; FIG. 25B, C). Binding of scFv3-43-Fc-scTRAIL to HER3-positive cell line A375 was analyzed via flow cytometry. A concentration-dependent binding of scFv3-43-Fc-scTRAIL was observed with an $EC_{50}$ value of 1.19±0.31 nM (FIG. 25D). Competitive inhibition of the scFv3-43-Fc-scTRAIL with scFv3-43-Fc fusion protein was performed to verify that the improved binding of the targeted format resulted from the 3-43 binding domain (FIG. 25E). Therefore, the binding domain of scFv3-43-Fc-scTRAIL was blocked with a 200-fold molar excess of the scFv3-43-Fc (inhibitor). Binding of scFv3-43-Fc-scTRAIL was reduced to the level of the untargeted protein in the presence of the inhibitor, while binding of Fc-scTRAIL itself was not affected. This results confirmed that the targeting moiety (scFv3-43) of the TRAIL fusion protein increases the binding to HER3-positive cells.

The anti-HER3 scFv-Fc-scTRAIL fusion protein was then analyzed in vitro for killing of the different melanoma cell lines in the presence or absence of bortezomib (FIG. 26). One day before treatment, 30,000 to 60,000 cells/well were seeded in 96-well plates. For combination treatment with bortezomib, cells were pretreated with bortezomib at 250 ng/ml (650 nM), except for A375 which were pretreated with 50 ng/ml bortezomib for 30 min. Cells were then incubated with serial dilutions of the fusion proteins for 16 h. Cell viability was analyzed by crystal violet staining.

In the absence of bortezomib, scFv3-43-Fc-scTRAIL showed strong induction of cell death on W793 ($EC_{50}$ value of 4.25 pM), MW1366 ($EC_{50}$ value of 48.2 pM) and WM35 ($EC_{50}$ value of 4.96 pM), and a partial induction of cell death (not reaching 50% killing) on A375, MelJuso and MeWo (see FIG. 26). In contrast, the addition of bortezomib sensitized all tested melanoma cell lines showing killing with $EC_{50}$ values between 0.17 to 4.63 pM (FIG. 26). In comparison with the non-targeted Fc-scTRAIL, $EC_{50}$ values were decreased, both in the absence or presence of bortezomib (Table 7). In addition, HER3 expression of the melanoma cells, which were used in the cell viability assay, were analyzed in the absence or presence of bortezomib via flow cytometry using a QIFIKIT (Dako). Treatment with bortezomib had no or only a marginal effect on the expression of HER3 by the melanoma cells (FIG. 26).

Example 18: Anti-HER3 scFv-Fc-scTRAIL Fusion Protein Shows Potent Antitumoral Activity and is Well Tolerated in an In Vivo Colo205 Xenograft Tumor Model The scFv3-43-Fc-scTRAIL fusion protein (see example 11) was evaluated for its antitumoral activity, safety and pharmacokinetic profile in tumor bearing mice. $3\times10^6$ Colo205 cells (in 100 µl DPBS) were injected subcutaneously into the left and right flank of female NMRI nude mice. Tumor growth was monitored by measuring the length (a) and width (b) of the tumors with a caliper to calculate the tumor volume ($V=a\times b^2/2$). Treatment was started when tumors reached a size of approximately 100 mm³. Injections of fusion proteins (in 150 µl DPBS) were done intravenously. Control animals received respective injections of 150 µl DPBS. Mice (9 or 11 weeks old, 6 mice per group) were treated with 0.2 nmol protein (0.4 nmol scTRAIL units) twice a week for three weeks (days 14, 18, 21, 25, 28, 32). Blood samples were taken 4 h and 24 h after the last treatment to analyze protein concentration and ALT levels.

Complete tumor remission was observed for the treatment with scFv3-43-Fc-scTRAIL and the non-targeted Fc-scTRAIL. Tumor remission was stable over the monitoring period of almost 100 d for scFv3-43-Fc-scTRAIL treated animals, and only marginal regrowth was detected for Fc-scTRAIL at the end of the experiment (FIG. 27A, B). No toxic effects of the liver were observed for TRAIL fusion protein-treated groups, as ALT activity in the serum 4 and 24 hours after the last treatment were similar compared to the untreated or PBS-treated group (FIG. 27C). Serum concentrations of the proteins were determined 4 and 24 hours after the last treatment (FIG. 27D). No differences were observed between scFv3-43-Fc-scTRAIL and Fc-scTRAIL.

Example 19: A Bispecific Single-Chain Diabody-Fc Fusion Protein Containing a $G_4S$-Linker Targeting EGFR and HER3

The linker L2 of the bispecific single-chain diabody-Fc fusion protein targeting EGFR and HER3 linking the $V_L$3-43 with the $V_H$3-43 was modified from the sequence GGGGSGGRASGGGGS (SEQ ID NO: 21) to GGGGSGGGGSGGGGS (SEQ ID NO: 16) (FIG. 28A, B). The modified scDb-Fc fusion protein was produced in HEK293-6E suspension cells and purified from cell culture supernatant by protein A affinity chromatography and fast protein liquid chromatography. SDS-PAGE analysis of the purified scDbhu225x3-43-Fc revealed single bands at an apparent molecular mass of approximately 82 kDa under reducing conditions and 200 kDa under non-reducing conditions corresponding to the monomeric and dimeric assembly of the molecule (FIG. 28C). Purity was confirmed by size exclusion chromatography (FIG. 28D). Binding of the scDb-Fc to the His-tagged extracellular domain of EGFR (aa 20-643) and HER3 (aa 27-599) was assessed by ELISA in comparison to the parental antibodies (hu225-IgG and 3-43-IgG). The EGFR-His or the HER3-His fusion protein was coated onto polystyrene microtiter plates at a concentration of 2 µg/ml diluted in PBS. Remaining binding sites were blocked with PBS, 2% skimmed milk (MPBS). Plates were then incubated with serial dilution of the bispecific scDb-Fc or the monospecific parental antibodies. After washing, bound antibodies were detected with an HRP-conjugated anti-human Fc antibody and TMB, $H_2O_2$ as substrate. ELISA analysis revealed that binding activity of the parental antibodies to the extracellular domain (ECD) of EGFR and HER3 is retained in the modified scDb-Fc format (see FIG. 28E). The scDb-Fc molecule bound with $EC_{50}$ values of 0.16 nM to EGFR and 0.20 nM to HER3, whereas the parental antibodies bound with similar $EC_{50}$ values in the sub-nanomolar range to their corresponding antigens (hu225-IgG: 0.20 nM; 3-43-IgG: 0.54 nM).

Example 20: Comparison of Bispecific Diabody-Ig (Db-Ig) and Bispecific Single-Chain Diabody-Fc Fusion Protein Targeting EGFR and HER3

The two different formats of bispecific and tetravalent antibodies targeting EGFR and HER3, single-chain diabody-Fc (scDb-Fc) (see example 19) and Diabody-Ig (Db-Ig) (example 16), were analyzed for inhibitory activity of EGFR, HER2, HER3, Akt, and Erk. Signal inhibition assays were performed using FaDu cells. Cells were treated with 50 nM of the parental antibodies (alone or in combination (50 nM of each antibody)), the bispecific antibodies (scDbhu225x3-43-Fc (GGGGS) SEQ ID NO: 33, Db3-43xhu225-Ig) for 1 hour prior to stimulation with heregulin (50 ng/ml) for 15 min at 37° C. Cells were lysed using RIPA buffer (50 mM Tris pH 7.5, 150 mM NaCl, 10 mM NaF, 20 mM β-Glycerophosphate, 1 mM EDTA, 1% NP-40, 1 mM $Na_3VO_4$, 0.5 mM PMSF, 0.25% DOC, 0.1% SDS) containing a protease inhibitor cocktail and lysates were analyzed by immunoblotting. Phosphorylation of HER2 and HER3 was inhibited by the bispecific antibodies as well as by 3-43-IgG in the absence of heregulin-stimulation, whereas receptor phosphorylation was more efficiently inhibited in the presence of heregulin by both bispecific antibodies compared to 3-43-IgG. In addition, the bispecific antibodies inhibited efficiently the phosphorylation of Akt and Erk in the absence and in the presence of heregulin (FIG. 29).

Next, proliferation assays in colon cancer cell lines (SW620, HCT116, and LoVo) were performed using the two different bispecific antibody formats or the parental antibodies (hu225-IgG and 3-43-IgG) either alone or in combination. Cells were grown either in 2D or in 3D cultures. 2000 cells/well were seeded in 96-well plates (for 3D culture: 1:2 Matrigel:Collagen mixture, RPMI or DMEM+10% FCS+2% Matrigel). After 24 h medium was discarded and starvation medium (RPMI or DMEM+0.2% FCS+1% P/S) was added. After additional 24 h of incubation, cells were treated with/without MEK-inhibitor (AZD6244, Selumetinib) and/or antibody (50 nM, combination: 50 nM each). After 1 h cells were stimulated with HRG (6 ng/well) or kept unstimulated. On day 8 after seeding the cells, the assay was developed with CelltiterGlo 3D Kit (25 µl of starvation media mixed with 25 µl of CelltiterGlo 2.0 per well) and luminescence measured with plate reader (tecan infinite). For SW620 and HCT116 cells, only marginal differences in proliferation were observed for all antibodies. However, when cells were treated in combination with the MEK inhibitor in presence of heregulin, the bispecific antibodies showed a reduced proliferative effect compared to the other antibodies. For HRG-unstimulated LoVo cells, strong reduced proliferative effects were observed for both bispecific antibodies as well as for hu225-IgG or the combination of both parental antibodies in 3D culture either in the presence of in the absence of MEK-inhibitor. After HRG-stimulation, only the bispecific antibodies were able to reduce efficiently the proliferation of cells either in the presence or in the absence of MEK-inhibitor.

Example 21: A Bispecific, Bivalent Single-Chain Diabody (scDb) Targeting HER2 and HER3

A bispecific scDb molecule was generated by combining the binding site of anti-HER3 3-43 with that of humanized anti-HER2 antibody 4D5 (Trastuzumab). The scDb4D5x3-43-LL exhibits one binding site for HER3 and one binding site for HER2 (FIGS. 31A and B). The linker (L2) that connects the $V_L$3-43 with $V_H$3-43, consists of 20 amino acids (GGGGSGGGRASGGGGSGGGGS, SEQ ID NO: 21). The scDb4D5x3-43-LL (SEQ ID NO: 34) was produced in HEK293E suspension cells and purified by IMAC and fast protein liquid chromatography (FPLC). SDS-PAGE analysis of the purified scDb4D5x3-43-LL revealed a single band at an apparent molecular mass of approximately 53 kDa under reducing conditions and 50 kDa under non-reducing conditions, respectively (FIG. 31C). Size exclusion chromatography confirmed purity and integrity of the protein (FIG. 31D).

Binding of scDb4D5x3-43-LL in comparison to the parental antibodies (Trastuzumab and 3-43 IgG) was evaluated by ELISA using immobilized HER2-Fc or HER3-Fc fusion proteins comprising the extracellular domain (ECD) of human HER2 (aa 23-652) or HER3 (aa 27-599). The ECD-Fc fusion proteins were coated onto polystyrene microtiter plates at 2 µg/ml in PBS. Remaining binding sites were blocked with PBS, 2% skimmed milk (MPBS). Plates were then incubated with a serial dilution of scDb4D5x3-43-LL or the parental antibody in MPBS. After washing, bound antibody was detected either with a HRP-conjugated anti-His antibody in case of the scDb4D5x3-43-LL or with a HRP-conjugated anti-human Fab antibody and TMB, $H_2O_2$ as substrate. The scDb4D5x3-43-LL showed concentration-dependent binding to HER2 and HER3 with $EC_{50}$ values in the low nanomolar range (HER2: 1.54 nM; HER3: 0.93 nM) (FIG. 31E). The parental antibodies showed binding to the respective antigen (Trastuzumab to HER2: 0.80 nM; 3-43-IgG to HER3: 0.27 nM), thus, binding of the scDb4D5x3-43-LL protein is retained.

Signal inhibition assays in MCF-7 cells were performed to determine if receptor activation of HER2, HER3, Akt, and Erk is inhibited by treatment with the bispecific scDb4D5x3-43-LL molecule in comparison to the parental antibodies either as single or as combinatorial treatment. In addition, the bispecific and tetravalent scDb4D5x3-43-Fc fusion protein was also used in this experiment to determine the receptor phosphorylation. Cells were treated with 50 nM of the parental antibodies (alone or in combination (50 nM of each antibody)) or the bispecific scDb4D5x3-43-LL for 1 hour prior to stimulation with heregulin (50 ng/ml) for 15 min at 37° C. Cells were lysed using RIPA buffer (50 mM Tris pH 7.5, 150 mM NaCl, 10 mM NaF, 20 mM β-Glycerophosphate, 1 mM EDTA, 1% NP-40, 1 mM $Na_3VO_4$, 0.5 mM PMSF, 0.25% DOC, 0.1% SDS) containing a protease inhibitor cocktail and lysates were analyzed by immunoblotting. For HRG-unstimulated cells, only the bispecific, bivalent scDb4D5x3-43-LL molecule showed reduced phosphorylation of HER2, Akt, and Erk, whereas activation of Akt was observed for the parental antibodies as single or as combinatorial treatment. In addition, activation of Erk was detected for the bispecific but tetravalent scDb4D5x3-43-Fc fusion protein (FIG. 32). Similar results were observed in HRG-stimulated cells. Again, only the bispecific and bivalent scDb4D5x3-43 molecule showed efficiently reduced phosphorylation of HER2, HER3, Akt, and Erk.

Example 22: Anti-HER3xAnti-CD3 Bispecific Antibodies with Different Valences for T-Cell Retargeting We generated bispecific antibodies, which bind on the one hand monovalent to human CD3 (humanized version of UCHT1), and on the other hand to HER3 either monovalent as scDb3-43xhuU3 (see also Example 12), bivalent as scDb3-43xhuU3-scFv3-43 (see also Example 13), or trivalent as scFv3-43-scDb3-43xhuU3-scFv3-43 (SEQ ID NO: 35, FIG. 33A, B). The bispecific and multivalent antibodies were produced in HEK293E cells and purified by IMAC. The trivalent (scDb3-43xhuU3-scFv3-43) and tetravalent (scFv3-43-scDb3-43xhuU3-scFv3-43) antibodies were further purified via fast protein liquid chromatography resulting in one homogenous population of the antibodies.

Binding of the bispecific antibodies was analyzed by flow cytometry using CD3-expressing Jurkat cell (FIG. 33C) and HER3-expressing MCF-7 cells (FIG. 33D). For the adherent MCF-7, cells were shortly trypsinized at 37° C., trypsin was quenched with FCS containing medium and removed by centrifugation. For both cell lines, Jurkat and MCF-7, 100,000 cells per well were seeded and incubated with a titration of the different bispecific and multivalent antibodies in PBA (2% (v/v) FCS, 0.02% (w/v) NaN$_3$ in 1×PBS) for one hour at 4° C. Washing was performed twice with PBA. Bound protein was detected using PE-conjugated anti-His antibody incubated for another hour at 4° C. After washing, fluorescence was measured with a MACSQuant® Analyzer 10. Relative median fluorescence intensities (to unstained cells) were calculated using the MACSQuant® software. Binding to CD3-positive Jurkat cells was observed in a concentration-dependent manner for all three antibodies resulting in similar $EC_{50}$-values in the nanomolar range (scDb3-43xhuU3: 2.4 nM; scDb3-43xhuU3-scFv3-43: 4.2 nM; scFv3-43-scDb3-43xhuU3-scFv3-43: 5.2 nM). Binding to MCF-7 cells was also observed in a concentration-dependent manner, however, binding of the bispecific antibodies was dependent on the valency of HER3-binding. The $EC_{50}$ value of the monovalent HER3-binder (scDb3-43xhuU3) was determined with 1.1 nM, whereas the bivalent and trivalent HER3-binder showed binding in the picomolar range with $EC_{50}$ values of 31.4 pM for scDb3-43xhuU3-scFv3-43 and 17.3 pM for scFv3-43-scDb3-43xhuU3-scFv3-43.

Activation of T cells was analyzed in an IL-2 release assay using HER3-expressing MCF-7 cells and human PBMCs. One day before the treatment, 20,000 MCF-7 cells were seeded per well in a 96-well plate. The medium was removed and substituted with a titration of the different bispecific antibodies in fresh medium. After 1 hour of incubation at room temperature, 200,000 PBMC per well were added and incubated for additional 24 hours at 37° C. The supernatant was collected and concentration of IL-2 was determined by ELISA (human IL-2 kit, R&D) according to the instructions supplied by the manufacturer. All three bispecific antibodies showed dose-dependent release of IL-2 (activation of T cells) in the subnanomolar range with $EC_{50}$ values of 0.48 nM (scDb3-43xhuU3), 0.29 nM (scDb3-43xhuU3-scFv3-43), and 0.22 nM (scFv3-43-scDb3-43xhuU3-scFv3-43) (FIG. 33E).

Killing of target cells by the different bispecific antibodies was analyzed using HER-3 expressing MCF-7 cells and human PBMCs. One day before the treatment, 20,000 MCF-7 cells were seeded per well in a 96-well plate. The medium was removed and substituted with a titration of the different bispecific and multivalent antibodies in fresh medium. After 1 hour of incubation at room temperature, 200,000 PBMC per well were added and incubated for additional 48 hours at 37° C. Cell viability was measured via MTT-assay. All three bispecific antibodies showed a dose-dependent killing of MCF-7 cells in the picomolar range with $EC_{50}$ values of 84 pM (scDb3-43xhuU3), 34 pM (scDb3-43xhuU3-scFv3-43), and 32 pM (scFv3-43-scDb3-43xhuU3-scFv3-43) (FIG. 33F; black lines). In the absence of PBMCs, no reduced cell viability of MCF-7 cells was observed (FIG. 33F; grey lines).

Example 23: IgG 3-43 Binds to HER3-Fc Fusion Proteins Mutated in Domain III and IV HER3 somatic mutations in domain III and IV were cloned via Q5® site-directed mutagenesis kit (NEB). Besides one hot spot mutation (T335A), six other mutations in domain III and IV (T389I, M406K, R453H, Y464C, D492H, K498I) were expressed as HER3-Fc fusion proteins, which were produced in transiently transfected HEK 293-6E cell and purified via protein A chromatography. SDS-PAGE analysis confirmed purity of the proteins and showed one single band of approximately 140 kDa under reducing conditions (FIG. 34A). The ability of binding of 3-43-IgG to different mutated HER3-Fc fusion proteins was analyzed in ELISA and compared with binding to wild-type (non-mutated) HER3-Fc fusion protein. The different HER3-Fc fusion proteins were coated onto polystyrene microtiter plates at a concentration of 2 μg/ml diluted in PBS. Remaining binding sites were blocked with PBS, 2% skimmed milk (MPBS). Plates were then incubated with serial dilution of the antiHER3 antibodies 3-43-IgG and 3M6-IgG. After washing, bound antibodies were detected with an HRP-conjugated anti-human Fab antibody and TMB, $H_2O_2$ as substrate. IgG 3-43 showed binding to all tested mutations, including the hot spot mutation T335A. IgG 3M6 which binds to domain I of HER3 was included as positive control and showed binding at 100 nM similar to signals observed for wild-type HER3-Fc. Although IgG 3-43 was able to bind all mutant forms of HER3, for some of the mutants a reduced saturation binding was observed in ELISA with immobilized HER3-Fc mutants (FIG. 34B), although $EC_{50}$ values were in a similar range for all HER3 mutants (0.1 to 0.3 nM). Tables:

TABLE 1

Monovalent and bivalent affinity.
KDs were measured using the Attana system.

| Analyte | Bmax (Signal) | ka (1/(M*s)) | kd (1/s) | KD (nM) | BI (Signal) | Chi2 (Signal^2) |
|---|---|---|---|---|---|---|
| HER3-his | 63.55 | 622000 | 0.00696 | 11.2 | 0 | 0.45 |
| HER3-Fc | 237.32 | 468000 | 0.000103 | 0.22 | 0 | 0.14 |

TABLE 2

Cell binding properties of IgG 3-43. The $EC_{50}$ values of binding to the indicated cells were assessed by flow cytometry

| Cell line | $EC_{50}$ value (pM) |
|---|---|
| MCF-7 | 37 |
| FaDu | 30 |
| BT474 | 74 |
| A431 | 45 |
| NCI-N87 | 27 |
| A549 | 53 |

TABLE 3

Binding properties of scDb hu225x3-43-Fc. $EC_{50}$ values [nM dimer] of binding to EGFR-ECD and HER3-ECD proteins were determined by ELISA. The $EC_{50}$ values [nM dimer] of binding to FaDu cells were assessed by flow cytometry.

| | ELISA | | FACS |
|---|---|---|---|
| Construct | EGFR-ECD | HER3-ECD | FaDu |
| cetuximab | 0.18 | — | 0.2 |
| IgG 3-43 | — | 0.33 | 0.30 |
| scDb hu225x3-43-Fc | 0.2 | 0.24 | 0.23 |

TABLE 4

Binding properties of scFv3-43-Fc-scTRAIL. $EC_{50}$ values [nM monomer] of binding to HER3 and human TRAIL-R2 were determined by ELISA. Fc fusion proteins of the extracellular domains of HER3 or human TRAIL-R2 were used as antigens.

| Construct | HER3 | TRAIL-R2 |
|---|---|---|
| scFv3-43-Fc-scTRAIL | 0.33 | 2.84 |

TABLE 5

Cell death induction by scFv3-43-Fc-scTRAIL. $EC_{50}$ values [nM monomer] of cell death induction on Colo205 were determined in the absence and presence of bortezomib (650 nM) in the absence and presence of a blocking antibody (200× molar excess). Effects of scFv3-43-Fc-scTRAIL were compared to the non-targeted Fc-scTRAIL fusion protein.

| | $EC_{50}$ value (pM) w/o blocking antibody | | $EC_{50}$ value (pM) with blocking antibody | |
|---|---|---|---|---|
| Construct | w/o BZB | 650 nM BZB | w/o BZB | 650 nM BZB |
| ScFv3-43-Fc-scTRAIL | 31.0 | 6.7 | 217.5 | 32.6 |
| Fc-scTRAIL | 97.6 | 21.4 | 129.5 | 34.2 |

TABLE 6

Binding properties of Db3-43xhu225-Ig. $EC_{50}$ values [nM] of binding to the extracellular domain (ECD) of EGFR and HER3 fusion proteins were determined by ELISA. The $EC_{50}$ values [nM] of binding to MCF-7, SKBR-3, and FaDu cells were assessed by flow cytometry.

| | ELISA | | Flow cytometry | | |
|---|---|---|---|---|---|
| Construct | EGFR-ECD | HER3-ECD | MCF-7 | SKBR-3 | FaDu |
| Db3-43xhu225-Ig | 0.19 | 0.26 | 0.054 | 0.047 | 0.14 |
| cetuximab | 0.23 | — | — | 0.031 | 0.13 |
| 3-43-IgG | — | 0.23 | 0.021 | 0.022 | 0.003 |

TABLE 7

$EC_{50}$ Values of cell death induction assays of scFv3-43-Fc-scTRAIL and Fc-scTRAIL in presence or absence of bortezomib (BZB). $EC_{50}$ [pM] were determined after the cells were treated for 16 h with the protein alone or in combination with bortezomib. —, less than 50% cell death; mean ± SD

| | scFv3-43-Fc-scTRAIL | | Fc-scTRAIL* | |
|---|---|---|---|---|
| | −BZB | +BZB | −BZB | +BZB |
| WM793 | 4.25 ± 2.40 | 0.39 ± 0.18 | 22.0 ± 1.75 | 2.87 ± 1.51 |
| WM1366 | 48.2 ± 7.29 | 3.58 ± 1.40 | 20.1 ± 4.77 | 4.84 ± 1.00 |
| WM35 | 4.96 ± 1.81 | 0.17 ± 0.17 | 691 ± 342 | 0.64 ± 0.11 |
| A375 | — | 0.72 ± 0.41 | 5003 ± 4376 | 1.06 ± 0.32 |
| Mel-Juso | — | 1.00 ± 0.04 | — | 4.10 ± 1.60 |
| MeWo | — | 4.63 ± 2.89 | — | 4.88 ± 0.87 |

The invention claimed is:

1. An antigen binding protein comprising
    (a) a CDRH1 comprising amino acids 32-37 according to SEQ ID NO: 2, a CDRH2 comprising amino acids 52-69 according to SEQ ID NO: 2, and a CDRH3 comprising amino acids 102-112 according to SEQ ID NO: 2, and
    (b) a CDRL1 comprising amino acids 23-33 according to SEQ ID NO: 3, a CDRL2 comprising amino acids 49-55 according to SEQ ID NO: 3, and a CDRL3 comprising amino acids 88-98 according to SEQ ID NO: 3.

2. The antigen-binding protein of claim 1, wherein the antigen-binding protein specifically binds to a conformational epitope formed by domain III and IV of human epidermal growth factor receptor 3 (HER3).

3. The antigen binding protein according to claim 2, wherein the conformational epitope is formed by amino acids 329 to 531 of domain III of HER3 according to SEQ ID NO: 1 and by amino acids 532 to 587 of domain IV of HER3 according to SEQ ID NO: 1.

4. The antigen binding protein according to claim 2, which:
 (a) binds to HER3-expressing cells with an $EC_{50}$ value below 15 nM; and/or
 (b) binds to a monomeric HER3 with a KD of below 100 nM; and/or
 (c) inhibits heregulin-induced HER3 phosphorylation HER3 with an $IC_{50}$ value below 10 nM.

5. The antigen binding protein according to claim 2, which inhibits (i) binding of HER3 to its ligand, (ii) receptor activation and/or signaling, (iii) induces HER3 internalization, (iv) inhibits cell proliferation, and/or (v) tumor growth.

6. The antigen-binding protein according to claim 1, wherein the antigen binding protein is selected from the group consisting of
 a) an antibody or an antigen-binding fragment thereof,
 b) antibody-like protein, and
 c) a peptidomimetic.

7. The antigen binding protein according to claim 1, wherein the antigen-binding protein is monospecific, bispecific or multispecific.

8. A fusion protein comprising the antigen-binding protein according to claim 1, further comprising at least one pharmaceutically active moiety.

9. A nucleic acid encoding the antigen binding protein according to claim 1, or the fusion protein according to claim 8.

10. A recombinant vector comprising the nucleic acid of claim 9.

11. A recombinant host cell comprising the nucleic acid of claim 9.

12. A pharmaceutical composition comprising the antigen binding protein according to claim 1, and further comprising one or more pharmaceutically acceptable carriers, diluents, excipients, fillers, binders, lubricants, glidants, disintegrants, adsorbents, and/or preservatives.

13. A method comprising administering the antigen binding protein according to claim 1 to a subject.

14. A method of inhibiting HER3-positive tumor growth or treating HER3-positive cancer, comprising administering to a patient in need thereof a therapeutically effective amount of the antigen binding protein according to claim 1 to inhibit HER3-positive tumor growth or treat HER3-positive cancer.

\* \* \* \* \*